United States Patent
Gaeta et al.

(10) Patent No.: US 7,192,955 B2
(45) Date of Patent: Mar. 20, 2007

(54) INHIBITORS OF MACROPHAGE MIGRATION INHIBITORY FACTOR AND METHODS FOR IDENTIFYING THE SAME

(75) Inventors: Federico C. A. Gaeta, Mountain View, CA (US); Andrew Baird, San Diego, CA (US); Jerry Anchin, Del Mar, CA (US); Wenbin Ying, San Diego, CA (US); Robert Florkiewicz, Seattle, WA (US); Jagadish Sircar, San Diego, CA (US); Sunil Kumar K.C., San Diego, CA (US)

(73) Assignee: Avanir Pharmaceuticals, San Diego, CA (US)

( * ) Notice: Subject to any disclaimer, the term of this patent is extended or adjusted under 35 U.S.C. 154(b) by 0 days.

(21) Appl. No.: 11/415,785

(22) Filed: May 2, 2006

(65) Prior Publication Data
US 2006/0194792 A1    Aug. 31, 2006

Related U.S. Application Data

(62) Division of application No. 10/156,650, filed on May 24, 2002, now Pat. No. 7,105,519.

(60) Provisional application No. 60/293,642, filed on May 24, 2001.

(51) Int. Cl.
*A61K 31/551* (2006.01)
*C07D 401/04* (2006.01)

(52) U.S. Cl. .................................. 514/218; 540/575
(58) Field of Classification Search ................. 514/218
See application file for complete search history.

(56) References Cited

U.S. PATENT DOCUMENTS

| | | | |
|---|---|---|---|
| 4,284,768 A | 8/1981 | Santilli | |
| 4,299,814 A | 11/1981 | Brandt et al. | |
| 4,683,202 A | 7/1987 | Mullis | |
| 4,708,937 A | 11/1987 | Remold | |
| 5,246,869 A | 9/1993 | Potter et al. | |
| 5,328,990 A | 7/1994 | Wistow | |
| 5,350,687 A | 9/1994 | Odink et al. | |
| 5,352,660 A | 10/1994 | Pawson | |
| 5,411,882 A | 5/1995 | Odink et al. | |
| 5,530,101 A | 6/1996 | Queen et al. | |
| 5,597,708 A | 1/1997 | Holder et al. | |
| 5,650,295 A | 7/1997 | Li et al. | |
| 5,656,596 A | 8/1997 | Monard et al. | |
| 5,656,737 A | 8/1997 | Wistow | |

(Continued)

FOREIGN PATENT DOCUMENTS

| | | |
|---|---|---|
| AU | 592753 | 5/1985 |
| EP | 0020090 | 12/1980 |
| EP | 0162812 | 5/1985 |
| EP | 0 154 454 A1 | 9/1985 |
| EP | 0 263 072 A2 | 4/1988 |

(Continued)

OTHER PUBLICATIONS

Morand et al. Expert Opin.Ther. Patents, vol. 13, p. 1189-1212 (2003).*
Riedemann et al. J.Clin.Invest. vol. 112, p. 460-467 (2003).*
Atkins, Nephrology, vol. 7, p. S2 (2002) (Abstract).*
Lolis et al. Expert Opin. Ther.Targets, vol. 7, pp. 153-164 (2003).*
Abe et al. 1993. "Induction of Vascular Endothelial Tubular Morphogenesis by Human Giloma Cells." *J. Clin. Invest.* 92:54.

(Continued)

*Primary Examiner*—Emily Bernhardt
(74) *Attorney, Agent, or Firm*—Knobbe Martens Olson & Bear LLP

(57) ABSTRACT

Inhibitors of MIF are provided which have utility in the treatment of a variety of disorders, including the treatment of pathological conditions associated with MIF activity. The inhibitors of MIF have the following structures:

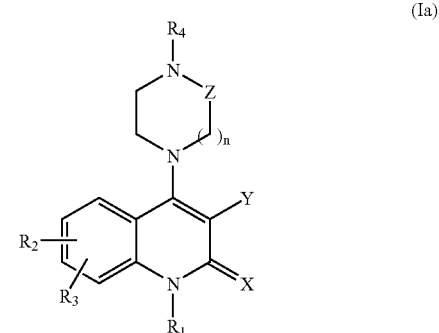

(Ia)

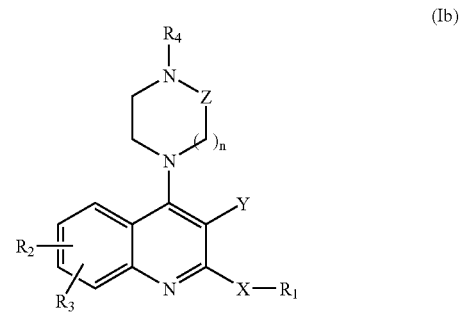

(Ib)

including stereoisomers, prodrugs and pharmaceutically acceptable salts thereof, wherein n, $R_1$, $R_2$, $R_3$, $R_4$, X, Y and Z are as defined herein. Compositions containing an inhibitor of MIF in combination with a pharmaceutically acceptable carrier are also provided, as well as methods for use of the same.

52 Claims, 14 Drawing Sheets

U.S. PATENT DOCUMENTS

| | | | |
|---|---|---|---|
| 5,683,887 | A | 11/1997 | Bucala et al. |
| 5,700,447 | A | 12/1997 | Bucala et al. |
| 5,702,920 | A | 12/1997 | Odink et al. |
| 5,733,524 | A | 3/1998 | Bucala et al. |
| 5,733,546 | A | 3/1998 | Bucala et al. |
| 5,733,933 | A | 3/1998 | Bucala et al. |
| 5,780,615 | A | 7/1998 | Bucala et al. |
| 5,801,200 | A | 9/1998 | Bucala et al. |
| 5,821,336 | A | 10/1998 | Odink et al. |
| 5,869,534 | A | 2/1999 | Bucala et al. |
| 5,883,224 | A | 3/1999 | Kirkpatrick et al. |
| 5,919,815 | A | 7/1999 | Bradley et al. |
| 5,986,060 | A | 11/1999 | Li et al. |
| 6,028,081 | A | 2/2000 | Sada et al. |
| 6,030,615 | A | 2/2000 | Bucala et al. |
| 6,080,407 | A * | 6/2000 | Bucala et al. ............ 424/158.1 |
| 6,214,343 | B1 | 4/2001 | Kink et al. |
| 6,238,874 | B1 | 5/2001 | Jarnagin et al. |
| 6,413,939 | B1 | 7/2002 | Bucala et al. |
| 6,420,188 | B1 | 7/2002 | Bucala et al. |
| 2003/0195194 | A1 | 10/2003 | Gaeta et al. |
| 2004/0019921 | A1 | 1/2004 | Fingerle-Rowson et al. |
| 2004/0204586 | A1 | 10/2004 | Sircar et al. |
| 2005/0124604 | A1 | 6/2005 | Sircar et al. |

FOREIGN PATENT DOCUMENTS

| | | |
|---|---|---|
| EP | 0 263 072 A3 | 4/1988 |
| EP | 0 412 050 A1 | 2/1991 |
| EP | 0 154 454 B1 | 7/1991 |
| EP | 0 263 072 B1 | 3/1994 |
| EP | 0 512 050 B1 | 12/1995 |
| EP | 0900789 | 10/1999 |
| EP | 1424336 | 6/2004 |
| EP | 1500402 A1 | 1/2005 |
| WO | WO 90/11301 | 10/1990 |
| WO | WO 94/20083 | 9/1994 |
| WO | WO 96/09389 | 3/1996 |
| WO | WO 96/15242 | 5/1996 |
| WO | WO 97/29635 | 8/1997 |
| WO | WO 97/39326 A2 | 10/1997 |
| WO | WO 97/40159 | 10/1997 |
| WO | WO 04/26307 | 11/1997 |
| WO | WO 98/17314 | 4/1998 |
| WO | WO 01/32606 | 5/2001 |
| WO | WO 02/07720 A1 | 1/2002 |
| WO | WO 02/067862 A2 | 9/2002 |
| WO | WO 02/079517 | 10/2002 |
| WO | WO 03/065979 A2 | 8/2003 |
| WO | WO 03/104178 | 12/2003 |
| WO | WO 03/104203 | 12/2003 |
| WO | WO 04/060881 | 7/2004 |
| WO | WO 04/076679 | 9/2004 |

OTHER PUBLICATIONS

Abe et al. 2001. "Regulation of the CTL Response by Macrophage Migration Inhibitory Factor." *J. Immunol.* 166:747-753.

Bacher et al. 1998. "MIF Expression in the Rat Brain: Implications for Neuronal Function." *Mol. Med.* 4(4):217-230.

Baugh and Bucala. 2002. "Macrophage migration inhibitory factor." *Crit. Care Med.* 30(1 Suppl.): S27-S35.

Bernhagen et al. 1995. "The emerging role of MIF in septic shock and infection." *Biotherapy* 8(2)123-7.

Bernhagen et al. 1993. "MIF is a pituitary-derived cytokine that potentiates lethal endotoxaemia." *Nature* 365:756-759.

Bernhagen et al. 1994. "Macrophage migration inhibitory factor is a neuroendocrine mediator of endotoxaemia." *Trends Microbiol.* 2:198-201.

Bernhagen et al. 1998. "Regulation of the immune response by macrophage migration inhibitory factor: biological and structural features." *J. Mol. Med.* 76(3-4):151-161.

Bianchi et al. 1999. "Conformational Changes in Human Hepatisis C Virus NS3 Protease upon Binding of Product-Based Inhibitors." *Biochem.* 38(42): 13844-13852.

Blocki et al. 1992. "Rat liver protein linking chemical and immunological detoxification systems." *Nature* 360:269-270.

Blocki et al. 1993. "MIF proteins are theta-class glutathione S-transferase homologs." *Protein Science* 2:2095-2102.

Bone et al. 1987. "A controlled clinical trial of high-dose methylprednisolone in the treatment of severe sepsis and septic shock." *N. Eng. J. Med.* 317:653-658.

Bucala. 1994. "MIF, a Previously Unrecognized Pituitary Hormone and Macrophage Cytokine, Is a Pivotal Mediator in Endotoxic Shock." *Circulatory Shock* 44(1):35-30.

Bucala. 1996. "MIF rediscovered: cytokine, pituitary hormone, and glucocorticoid-induced regulator of the immune response." *FASEB J.* 10:14):1607-1613.

Bucala. 1998. "Neuroimmunomodulation by Macrophage Migration Inhibitory Factor (MIF)." *Ann. N.Y. Acad. Sci.* 840:74-82.

Bucala. 2000. "A most interesting factor." *Nature* 408:146-147.

Calandra and Bucala. 1996. Macrophage Migration Inhibitory Factor: A Counter-Regulator of Glucocorticoid Action and Critical Mediator of Septic Shock.: *J. Inflammation* 47:39-51.

Calandra and Bucala. 1997. "Macrophage Migration Inhibitory Factor (MIF): A Glucocorticoid Counter-Regulator within the Immune System." *Crit. Rev. Immunol.* 17(1):77-88.

Calandra et al. 1994. "The Macrophage Is and Important and Previously Unrecognized Source of Macrophage Migration Inhibitory Factor." *J. Exp. Med.* 179:1895-1902.

Calandra et al. 1995. "MIF as a glucocorticoid-induced modulator of cytokine production." *Nature* 377:68-71.

Calandra et al. 2000. "Protection from septic shock by neutralization of macrophage migration inhibitory factor." *Nature Medicine* 6(2):164-170.

Carceller et al. 1993. "Synthesis and Structure-Activity Relationships of 1-Acyl-4-((2-methyl-3-pyridyl)cyanomethyl)piperaines as PAF Antagonists." *J. Med. Chem.* 36:2984-2997.

Carvajal et al. 1982. "Cell-Mediated Immunity Against Connective Tissue in Experimental Pulmonary Fibrosis." *Lung* 160(3): 131-40.

Chesney et al. 1999. "An Essential Role for Macrophage Migration Inhibitory Factor (MIF) in Angiogenesis and the Growth of a Murine Lymphoma." *Mol. Med.* 5: 181-191.

*Current Protocols in Molecular Biology*. 1987. Ausubel et al.(ed.) John Wiley & Sons. Inc.

Coppola, et al., *Transformation in the 2-Quinolone Series*, Journal of Heterocyclic Chemistry, Aug. 1981, vol. 18, No. 5, pp. 917-920.

Dandliker and Saussure. 1970. "Flourescence polarization in immunochemistry." *Immonochem.* 7:799-828.

Donnelly and Bucala. 1997. "Macrophage migration inhibitory factor: a regulator of glocucorticoid activity with a critical role in inflammatory disease." *Mol. Med. Today* 3(11):502-507.

Donnelly et al. 1997. "Regulatory role for macrophage migration inhibitory factor in acute respiratory distress syndrome." *Nat. Med.* 3(3):320-323.

Durand et al. 1998. "Interaction of methyl green with an oligonucleotide in intramolecular duplex and tripex conformations." *Eur. Biophys. J.* 27(2):147-151.

Ferro et al. 1991. "Antigen induced inhibition of autoimmune response to rat male accessory glands: role of thymocytes on the efferent phase of the suppression." *Autoimmunity* 9(3):193-200.

Florkiewicz et al. 1991. "Basic Fibroblast Growth Factor Gene Expression." *Ann. N.Y. Acad. Sci.* 638:109-126.

Galat et al. 1993. "Purification of macrophage migration inhibitory factor (MIF) from bovine brain cytosol." *Fed. Eur. Biochem. Soc.* 319:233-236.

Goto et al. 1993. "Synergistic Effects of Vascular Endothelial Growth Factor and Basic Fibroblast Growth Factor on the Proliferation and Cord Formulation of Bovine Capillary Endothelial Cells Within Collagen Gels." *Lab. Invest.* 69:508-517.

Harrington and Stastny. 1973. "Macrophage migration from an agarose droplet: development of a micromethod for assay of delayed hypersensitivity." *J. Immunol.* 110:752-759, 1973.

Haugland, 1999. *Handbook of Flourescent Probes and Research Chemicals- Seventh Ed.*, Molecular Probes, Eugene, OR. Not included, substantially cumulative with Ninth Ed., below.

Haugland, 2002. *Handbook of Flourescent Probes and Research Chemicals-Ninth Ed.*, Molecular Probes, Eugene, OR.

Hermanowski-Vosatka et al. 1999. "Enzymatically Inactive Macrophage Migration Inhibitory Factor Monocyte Chemotaxis and Random Migration." *Biochemistry* 38:12841-12849.

Huang et al. 2001. "Macrophage Migration Inhibitory Factor Is an Important Mediator in the Pathogenesis of Gastric Inflammation in Rats." *Gastroenterology* 121:619-630.

Huse et al. 1989, "Generation of a Large Combinatorial Library of the Immunoglobin Repertoire in Phage Lambda." *Science* 246:1275-1281.

Kleifeld et al. 2000. "Spectroscopic Studies of Inhibited Alcohol Dehydrogenase from *Thermoanaerobacter brockii*: Proposed Structure for the Catalytic Intermediate State." *Biochem* 39(26):7702-7711.

Larsen and Wieczorkowska. 1974. "Synthesis and Properties of 3-(3-Carboxyphenyl)pyruvic Acid and 3-(3-Carboxy-4-hydroxyphenyl)pyruvic Acid." *Acta Chem. Scand. B.* 28:92-96.

Leech et al. 1998. "Involvement of macrophage migration inhibitory factor in the evolution of rat adjuvant arthritis." *Arthritis and Rheumatism* 41(5):910-917.

Lundblad et al. 1996. "Flourescense Polarization Analysis of Protein-DNA and Protein-Protein Interactions." *Molec. Endocrinol.* 10:607-612.

Meanwell et al. 1993. "Inhibitors of Blood Platelet cAMP Phosphodieserase. 4. Structural Variation of the Side-Chain Terminus of Water-Soluble 1,3-Dihydro-2H-imidazo[4, 5-b]quinolin-2-one Derivatives." *J. Med. Chem.* 36:3251-3264.

Metz and Bucala. 1997. "Role of Macrophage Migration Inhibitory Factor in Regulation of the Immune Response." *Advances in Immunology* 66:197-2233.

Mitchell et al. 1999. "Sustained Mitogen-activated Protein Kinase (MAPK) and Cytoplasmic Phospholipase A2 Activation by Macrophage Migration Inhibitory Factor (MIF)." *J. Biol. Chem.* 274(25):18100-18106.

Monoclonal Anti-human MIF Antibody. Product Information. R&D Systems. Minneapolis, MN.

Natanson et al. 1994. "Selected Treatment Strategies for Septic Shock Based on Proposed Mechanisms of Pathogenesis." *Annals of Internal Medicine* 120(9):771-783.

Nishihira, Jun. 1998. "Novel pathophysiological aspects of macrophage migration inhibitory factor (Review)." *Int. J. Mol. Med.* 2(1):17-28.

Ogawa et al. 2000. "An antibody for macrophage migration inhibitory factor suppresses tumour growth and inhibits tumour-associates angiogenesis." *Cytokine* 12(4):309-314.

Onodera et al. 2000. "Macrophage Migration Inhibitory Factor Up-regulates Expression of Matrix Metalloproteinases in Synovial Fibroblasts or Rheumatoid Arthritis." *J. Biol. Chem.* 275:444-450.

Perrin. 1926. "Polarisation de la lumiere de fluorescence vie moyenne des molecules dans l'etat excite." J. Phys. Rad. 1:390-401 (English Abstract included).

Petrovsky and Bucala. 2002. "Macrophage Migration Inhibitory Factor: A Critical Neurohhumoral Mediator." *Front Horm Res. Basel, Karger* 29:83-90.

Product Information. 1990. Cortone Acetate Tablets. Physicians'Desk Reference. Edward R. Barhnhart, Publisher. USA p. 1341-1342.

Rosengren et al. 1996. "The Immonoregulatory Mediator Macrophage Migration Inhibitory Factor (MIF) Catalyzes a Tautomerization Reaction." *Mol. Med.* 2:143-149.

Rupreht, et al., *Murine Monoclonal Antibodies directed against Human Recombinant Macrophage Migration Inhibitory Factor*, Pflugers Arch—Eur. J. Physiol. (2000) 440 {Suppl}: R78-R80.

Sakaue et al. 1999. "Regulation of Macrophage Migration Inhibitory Factor (MIF) Expression by Glucose and Insulin in Adipocytes In Vitro." *Mol. Med.* 5:361-371.

Sarver et al. 1999. "Thermodynamic and circular dichroism studies differentiate inhibitor interactions with the stromelysin $S_1$-$S_3$ and $S'_1$-$S'_3$ subsites." *Biochim Biophys Acta* 1434(2):304-316.

Scatchard et al. 1949. "The Attractions of Proteins for Small Molecules and Ions." Ann. N.Y. Acad. Sci. 51-660-672.

Scopes, R. K. 1987. *Protein Purification: Principles and Practice Second Edition*. Springer-Verlag, N.Y.

Sprung et al. 1984. "The effects of high-dose corticosteroids in patients with septic shock." *N. Eng. J. Med.* 311: 1137-1143.

Swope and Lolis. 1999. "Macrophage Migration Inhibitory Factor: Cytokine, Hormone, or Enzyme?" *Rev. Physiol. Biochem. Pharmacol.* 139:1-32.

Swope et al. 1998. "Direct Linik between cytokine activity and catalytic site for macrophage migration inhibitory factor." *EMBO J.* 17(13):3534-3541.

Takahashi et al. 1998. "Involvement of Macrophage Migration Inhibitory Factor (MIF) in the Mechanism of Tumor Cell Growth." *Mol. Med.* 4:707-714.

Takahashi et al. 1999. "Antisense of Macrophage Migration Inhibitory Factor (MIF) Prevents Anti-IgM Mediated Growth Arrest and Apoptosis of a Mature B Cell Line by Regulation Cell Cycle Progression." *Microbiol.. Immunol.* 43(1)61-67.

Urry, D. W. 1969. "Optical Rotation and Biomolecular Conformation." *Spectroscopic Approaches to Biomolecular Conformation*. American Medical Association Press, Chicago, IL, pp. 33-121.

Waeber et al. 1999. "A Role for the Endocrine and Pro-inflammatory Mediator MIF in the Control of Insulin Secretion During Stress." *Diabetes Met. Res. Rev.* 15(1):47-54.

Ward et al. 1989. "Binding activities of a repertoire of a single immunoglobin variable domains secreted from *Escherichia coli*." *Nature* 341:544-546.

Warren et al. 1995. "Regulation by Vascular Endothelial Growth Factor of Human Colon Cancer Tumorgenesis in a Mouse Model of Experimental Liver Metastasis." *J. Clin. Invest.* 95:1789-1797.

Weir, D.M. 1986. *Handbook of Experimental Immunology, Cellular Immunology*. Blackwell Scientific, Boston, MA.

Weiser et al. 1989. "Molecular cloning of a cDNA encoding a human macrophage migration inhibitory factor." *Proc. Natl. Acad. Sci. USA.* 86:7522-7526.

Weiser et al. 1991. "Human recombinant macrophage migration inhibitory factor activates human macrophages to kill *Leishmania donovani*." J. Immunol. 147:2006-2011.

Winder et al. 1993. "The mouse *brown* (b) locus protein has dopachrome tautomerase activity and is located in lysosomes in transfected fibroblasts." *J. Cell. Sci.* 106-153-166.

Winter and Harris. 1993. "Humanized antibodies." *Immunol. Today* 14(6):243-246.

Wistow et al. 1993. "A macrophage migration inhibitory factor is expressed in the differentiating cells of the eye lens." *Proc. Natl. Acad. Sci. USA* 90:1272-1275.

Wu and Brand. 1994. "Resonance Energy Transfer: Methods and Applications." *Analytical Biochem.* 218:1-13.

Yang et al. 1998. "Reversal of Established Rat Crescentic Glumerulonephritis by Blockade of Macrophage Migration Inhibitory Factor (MIF): Potential Role of MIF in Regulatng Glocucorticoid Production." *Mol. Med.* 4(6):413-424.

Zuckerman et al. 1989. "Differential regulation of lipopolysaccharide-induced interleukin 1 and tumour necrosis factor synthesis: effects on endogenous and exogenous glococorticoids and the role of the pituitary-adrenal axis." *Eur. J. Immunol.* 19:310-305.

Supplementary European Search Report for European application EP 02 73 1971—enclosed with EPO Communication dated Sep. 6, 2004.

International Search Report for PCT/US02/16963.

U.S. Appl. No. 11/385,630, filed Mar. 20, 2006, Sircar, et al.

* cited by examiner

Experimental protocol for Inhibition of MIF in RA models

INHIBITORS OF MACROPHAGE MIGRATION INHIBITORY FACTOR AND METHODS FOR IDENTIFYING THE SAME

RELATED APPLICATION

This application is a division of U.S. application Ser. No. 10/156,650, filed May 24, 2002, now U.S. Pat. No. 7,105,519, which claims the benefit of U.S. Provisional Application No. 60/293,642, filed May 24, 2001. All above-referenced prior applications are incorporated by reference herein in their entirety and are hereby made a portion of this specification.

FIELD OF THE INVENTION

This invention relates generally to inhibitors of macrophage migration inhibitory factor (MIF), methods for identifying MIF inhibitors, and to methods of treating MIF-related disorders by administration of such inhibitors.

BACKGROUND OF THE INVENTION

The lymphokine, macrophage migration inhibitory factor (MIF), has been identified as a mediator of the function of macrophages in host defense and its expression correlates with delayed hypersensitivity, immunoregulation, inflammation, and cellular immunity. See Metz and Bucala, *Adv. Immunol.* 66:197–223, 1997. Macrophage migration inhibitory factors (MIFs), which are between 12–13 kilodaltons (kDa) in size, have been identified in several mammalian and avian species; see, for example, Galat et al., *Fed. Eur. Biochem. Soc.* 319:233–236, 1993; Wistow et al., *Proc. Natl. Acad. Sci. USA* 90:1272–1275, 1993; Weiser et al., *Proc. Natl. Acad. Sci. USA* 86:7522–7526, 1989; Bernhagen et al., *Nature* 365:756–759, 1993; Blocki et al., *Protein Science* 2:2095–2102, 1993; and Blocki et al., *Nature* 360:269–270, 1992. Although MIF was first characterized as being able to block macrophage migration, MIF also appears to effect macrophage adherence; induce macrophage to express interleukin-1-beta, interleukin-6, and tumor necrosis factor alpha; up-regulate HLA-DR; increase nitric oxide synthase and nitric oxide concentrations; and activate macrophage to kill *Leishmania donovani* tumor cells and inhibit *Mycoplasma avium* growth, by a mechanism different from that effected by interferon-gamma. In addition to its potential role as an immunoevasive molecule, MIF can act as an immunoadjuvant when given with bovine serum albumin or HIV gp120 in incomplete Freunds or liposomes, eliciting antigen induced proliferation comparable to that of complete Freunds. Also, MIF has been described as a glucocorticoid counter regulator and angiogenic factor. As one of the few proteins that is induced and not inhibited by glucocorticoids, it serves to attenuate the immunosuppressive effects of glucocorticoids. As such, it is viewed as a powerful element that regulates the immunosuppressive effects of glucocorticoids. Hence, when its activities/gene expression are over-induced by the administration of excess exogenous glucocorticoids (for example when clinical indicated to suppress inflammation, immunity and the like), there is significant toxicity because MIF itself exacerbates the inflammatory/immune response. See Buccala et al., *Ann. Rep. Med. Chem.* 33:243–252, 1998.

While MIF is also thought to act on cells through a specific receptor that in turn activates an intracellular cascade that includes erk phosphorylation and MAP kinase and upregulation of matrix metalloproteases, c-jun, c-fos, and IL-1 mRNA (see Onodera et al., *J. Biol. Chem.* 275:444–450, 2000), it also possesses endogenous enzyme activity as exemplified by its ability to tautomerize the appropriate substrates (e.g., dopachrome). Further, it remains unclear whether this enzymatic activity mediates the biological response to MIF and the activities of this protein in vitro and in vivo. While site directed mutagenesis of MIF has generated mutants which possess full intrinsic activity, yet fail to possess enzyme activity (Hermanowski-Vosatka et al., *Biochemistry* 38:12841–12849, 1999), Swope et al. have described a direct link between cytokine activity and the catalytic site for MIF (Swope et al., *EMBO J.* 17(13):3534–3541, 1998). Accordingly, it is unclear that strategies to identify inhibitors of MIF activity through inhibition of dopachrome tautomerase alone yields inhibitors of MIF activity of clinical value. The ability to evaluate the inhibition of MIF to its cell surface receptor is also limited since no high affinity receptor is currently known.

The interest in developing MIF inhibitors derives from the observation that MIF is known for its cytokine activity concentrating macrophages at sites of infection, and cell-mediated immunity. Moreover, MIF is known as a mediator of macrophage adherence, phagocytosis, and tumoricidal activity. See Weiser et al., *J. Immunol.* 147:2006–2011, 1991. Hence, the inhibition of MIF results in the indirect inhibition of cytokines, growth factors, chemokines and lymphokines that the macrophage may otherwise bring to a site of inflammation. Human MIF cDNA has been isolated from a T-cell line, and encodes a protein having a molecular mass of about 12.4 kDa with 115 amino acid residues that form a homotrimer as the active form (Weiser et al., *Proc. Natl. Acad. Sci. USA* 86:7522–7526, 1989). While MIF was originally observed in activated T-cells, it has now been reported in a variety of tissues including the liver, lung, eye lens, ovary, brain, heart, spleen, kidney, muscle, and others. See Takahashi et al., *Microbiol. Immunol.* 43(1):61–67, 1999. Another characteristic of MIF is its lack of a traditional leader sequence (i.e., a leaderless protein) to direct classical secretion through the ER/Golgi pathway.

A MIF inhibitor (and a method to identify MIF inhibitors) that act by neutralizing the cytokine activity of MIF presents significant advantages over other types of inhibitors. For example, the link between tautomerase activity alone and the inflammatory response is controversial. Furthermore, inhibitors that act intracellularly are often toxic by virtue of their action on related targets or the activities of the target inside cells. Small molecule inhibitors of the ligand receptor complex are difficult to identify let alone optimize and develop. The ideal inhibitor of a cytokine like MIF is one that alters MIF itself so that when released from the cell it is effectively neutralized. A small molecule with this activity is superior to antibodies because of the fundamental difference between proteins and chemicals as drugs.

SUMMARY OF THE INVENTION

As MIF has been identified in a variety of tissues and has been associated with numerous pathological events, there exists a need in the art to identify inhibitors of MIF. There is also a need for pharmaceutical compositions containing such inhibitors, as well as methods relating to the use thereof to treat, for example, immune related disorders or other MIF induced pathological events, such as tumor associated angiogenesis. The preferred embodiments may fulfill these needs, and provide other advantages as well.

In preferred embodiments, inhibitors of MIF are provided that have the following general structures (Ia) and (Ib):

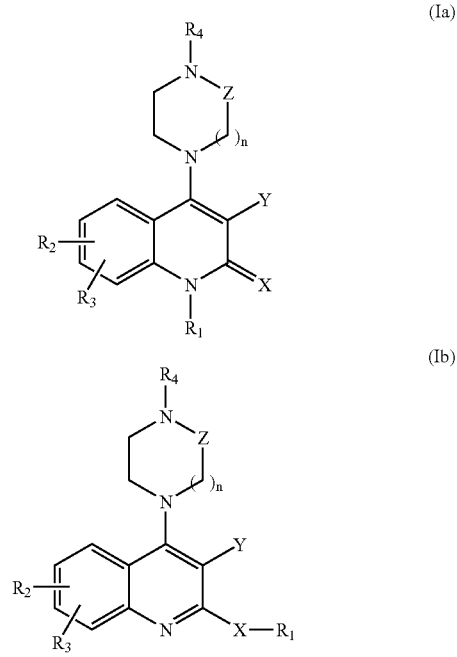

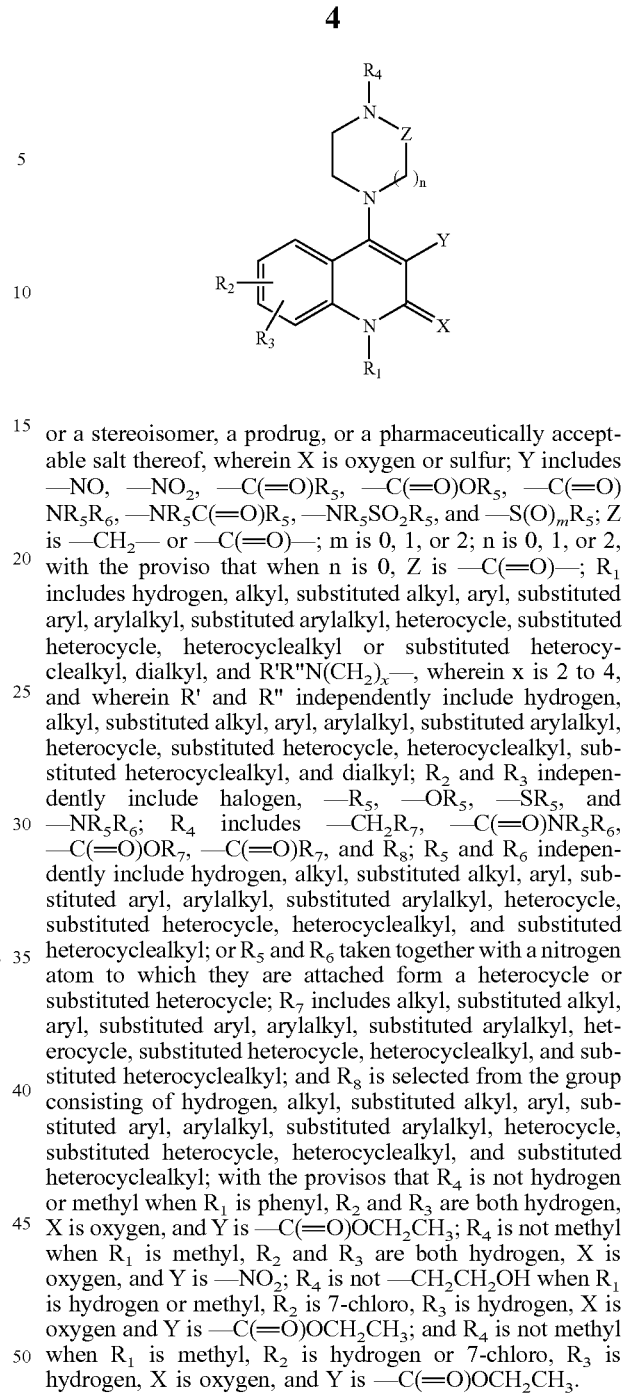

including stereoisomers, prodrugs, and pharmaceutically acceptable salts thereof, wherein n, $R_1$, $R_2$, $R_3$, $R_4$, X, Y and Z are as defined below.

The MIF inhibitors of preferred embodiments have utility over a wide range of therapeutic applications, and may be employed to treat a variety of disorders, illnesses, or pathological conditions including, but not limited to, a variety of immune related responses, tumor growth (e.g., prostate cancer, etc.), glomerulonephritis, inflammation, malarial anemia, septic shock, tumor associated angiogenesis, vitreoretinopathy, psoriasis, graft versus host disease (tissue rejection), atopic dermatitis, rheumatoid arthritis, inflammatory bowel disease, otitis media, Crohn's disease, acute respiratory distress syndrome, delayed-type hypersensitivity, and others. See, e.g., Metz and Bucala (supra); Swope and Lolis, *Rev. Physiol. Biochem. Pharmacol* 139:1–32, 1999; Waeber et al., *Diabetes M. Res. Rev.* 15(1):47–54, 1999; Nishihira, *Int. J. Mol. Med.* 2(1):17–28, 1998; Bucala, *Ann. N.Y. Acad. Sci.* 840:74–82, 1998; Bernhagen et al., *J. Mol. Med.* 76(3–4):151–161, 1998; Donnelly and Bucala, *Mol. Med. Today* 3(11):502–507, 1997; Bucala et al., *FASEB J.* 10(14): 1607–1613, 1996. Such methods include administering an effective amount of one or more inhibitors of MIF as provided by the preferred embodiments, preferably in the form of a pharmaceutical composition, to an animal in need thereof. Accordingly, in another embodiment, pharmaceutical compositions are provided containing one or more inhibitors of MIF of preferred embodiments in combination with a pharmaceutically acceptable carrier and/or diluent.

One strategy of a preferred embodiment characterizes molecules that interact with MIF so as to induce a conformational change in MIF and as such a loss of immunoreactivity to a monoclonal antibody. This change, when identified by screening, identifies small molecule inhibitors of MIF. This particular aspect may be extended to any bioactive polypeptide where loss of immunoreactivity may act as a surrogate for activity (e.g., cytokine activity, enzymatic activity, co-factor activity, or the like).

In a first embodiment, a compound is provided having a structure:

or a stereoisomer, a prodrug, or a pharmaceutically acceptable salt thereof, wherein X is oxygen or sulfur; Y includes —NO, —$NO_2$, —C(=O)$R_5$, —C(=O)O$R_5$, —C(=O)N$R_5R_6$, —N$R_5$C(=O)$R_5$, —N$R_5SO_2R_5$, and —S(O)$_m R_5$; Z is —$CH_2$— or —C(=O)—; m is 0, 1, or 2; n is 0, 1, or 2, with the proviso that when n is 0, Z is —C(=O)—; $R_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; $R_2$ and $R_3$ independently include halogen, —$R_5$, —O$R_5$, —S$R_5$, and —N$R_5R_6$; $R_4$ includes —$CH_2R_7$, —C(=O)N$R_5R_6$, —C(=O)O$R_7$, —C(=O)$R_7$, and $R_8$; $R_5$ and $R_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or $R_5$ and $R_6$ taken together with a nitrogen atom to which they are attached form a heterocycle or substituted heterocycle; $R_7$ includes alkyl, substituted alkyl, aryl, substituted aryl, arylalkyl, substituted arylalkyl, heterocycle, substituted heterocycle, heterocyclealkyl, and substituted heterocyclealkyl; and $R_8$ is selected from the group consisting of hydrogen, alkyl, substituted alkyl, aryl, substituted aryl, arylalkyl, substituted arylalkyl, heterocycle, substituted heterocycle, heterocyclealkyl, and substituted heterocyclealkyl; with the provisos that $R_4$ is not hydrogen or methyl when $R_1$ is phenyl, $R_2$ and $R_3$ are both hydrogen, X is oxygen, and Y is —C(=O)OCH$_2$CH$_3$; $R_4$ is not methyl when $R_1$ is methyl, $R_2$ and $R_3$ are both hydrogen, X is oxygen, and Y is —NO$_2$; $R_4$ is not —CH$_2$CH$_2$OH when $R_1$ is hydrogen or methyl, $R_2$ is 7-chloro, $R_3$ is hydrogen, X is oxygen and Y is —C(=O)OCH$_2$CH$_3$; and $R_4$ is not methyl when $R_1$ is methyl, $R_2$ is hydrogen or 7-chloro, $R_3$ is hydrogen, X is oxygen, and Y is —C(=O)OCH$_2$CH$_3$.

In a second embodiment, a compound is provided having a structure:

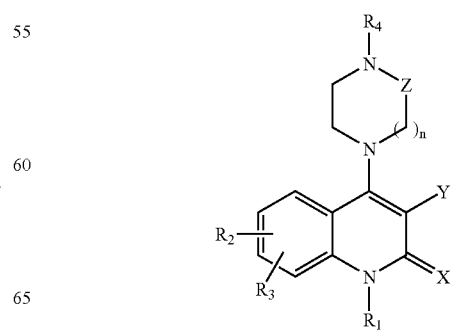

or a stereoisomer, a prodrug, or a pharmaceutically acceptable salt thereof, wherein X is oxygen or sulfur; Y includes —NO, —NO$_2$, —C(=O)R$_5$, —C(=O)OR$_5$, —C(=O)NR$_5$R$_6$, —NR$_5$C(=O)R$_5$, —NR$_5$SO$_2$R$_5$, and —S(O)$_m$R$_5$; Z is —CH$_2$—; m is 0, 1, or 2; n is 1; R$_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; R$_2$ and R$_3$ independently include halogen, —R$_5$, —OR$_5$, —SR$_5$, and —NR$_5$R$_6$; R$_4$ includes —CH$_2$R$_7$, —C(=O)NR$_5$R$_6$, —C(=O)OR$_7$, —C(=O)R$_7$, and R$_8$; R$_5$ and R$_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R$_5$ and R$_6$ taken together with a nitrogen atom to which they are attached form a heterocycle or substituted heterocycle; R$_7$ includes alkyl, substituted alkyl, aryl, substituted aryl, arylalkyl, substituted arylalkyl, heterocycle, substituted heterocycle, heterocyclealkyl, and substituted heterocyclealkyl; and R$_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the provisos that R$_4$ is not hydrogen or methyl when R$_1$ is phenyl, R$_2$ and R$_3$ are both hydrogen, X is oxygen, and Y is —C(=O)OCH$_2$CH$_3$; R$_4$ is not methyl when R$_1$ is methyl, R$_2$ and R$_3$ are both hydrogen, X is oxygen, and Y is —NO$_2$; R$_4$ is not —CH$_2$CH$_2$OH when R$_1$ is hydrogen or methyl, R$_2$ is 7-chloro, R$_3$ is hydrogen, X is oxygen and Y is —C(=O)OCH$_2$CH$_3$; and R$_4$ is not methyl when R$_1$ is methyl, R$_2$ is hydrogen or 7-chloro, R$_3$ is hydrogen, X is oxygen, and Y is —C(=O)OCH$_2$CH$_3$.

In aspects of the second embodiment, X is oxygen; or Y is —C(=O)OCH$_2$CH$_3$; or Y is —NO$_2$; or R$_4$ is

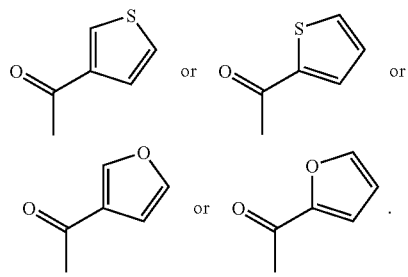

In a third embodiment, a compound is provided having a structure:

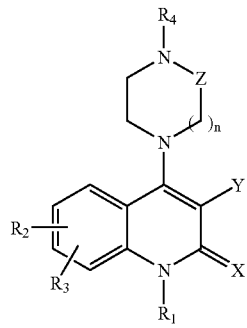

or a stereoisomer, a prodrug, or a pharmaceutically acceptable salt thereof, wherein X is oxygen or sulfur; Y is —NO$_2$; Z is —CH$_2$— or —C(=O)—; m is 0, 1, or 2; n is 0, 1, or 2, with the proviso that when n is 0, Z is —C(=O)—; R$_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; R$_2$ and R$_3$ independently include halogen, —R$_5$, —OR$_5$, —SR$_5$, and —NR$_5$R$_6$; R$_4$ includes —CH$_2$R$_7$, —C(=O)NR$_5$R$_6$, —C(=O)OR$_7$, —C(=O)R$_7$, and R$_8$; R$_5$ and R$_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R$_5$ and R$_6$ taken together with a nitrogen atom to which they are attached form a heterocycle or substituted heterocycle; R$_7$ includes alkyl, substituted alkyl, aryl, substituted aryl, arylalkyl, substituted arylalkyl, heterocycle, substituted heterocycle, heterocyclealkyl, and substituted heterocyclealkyl; and R$_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the proviso that R$_4$ is not methyl when R$_1$ is methyl, R$_2$ and R$_3$ are both hydrogen, X is oxygen, and Y is —NO$_2$.

In aspects of the third embodiment, X is oxygen; or Z is —CH$_2$— and n is 1; or R$_4$ is

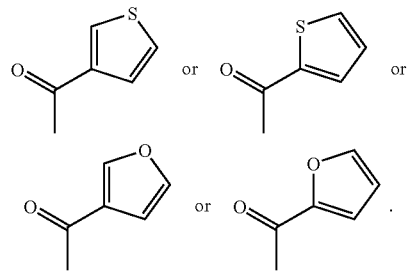

In a fourth embodiment, a compound is provided having a structure:

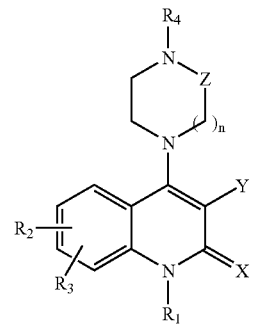

or a stereoisomer, a prodrug, or a pharmaceutically acceptable salt thereof, wherein X is oxygen or sulfur; Y is —C(=O)OCH$_2$CH$_3$; Z is —CH$_2$— or —C(=O)—; m is 0, 1, or 2; n is 0, 1, or 2, with the proviso that when n is 0, Z is —C(═O)—; $R_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; $R_2$ and $R_3$ independently include halogen, —$R_5$, —$OR_5$, —$SR_5$, and —$NR_5R_6$; $R_4$ includes —$CH_2R_7$, —C(═O)$NR_5R_6$, —C(═O)$OR_7$, —C(═O)$R_7$, and $R_8$; $R_5$ and $R_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or $R_5$ and $R_6$ taken together with a nitrogen atom to which they are attached form a heterocycle or substituted heterocycle; $R_7$ includes alkyl, substituted alkyl, aryl, substituted aryl, arylalkyl, substituted arylalkyl, heterocycle, substituted heterocycle, heterocyclealkyl, and substituted heterocyclealkyl; and $R_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the provisos that $R_4$ is not hydrogen or methyl when $R_1$ is phenyl, $R_2$ and $R_3$ are both hydrogen, and X is oxygen; $R_4$ is not —CH$_2$CH$_2$OH when $R_1$ is hydrogen or methyl, $R_2$ is 7-chloro, $R_3$ is hydrogen, and X is oxygen; and $R_4$ is not methyl when $R_1$ is methyl, $R_2$ is hydrogen or 7-chloro, $R_3$ is hydrogen, and X is oxygen.

In aspects of the fourth embodiment, X is oxygen; or Z is —CH$_2$— and n is 1; or $R_4$ is

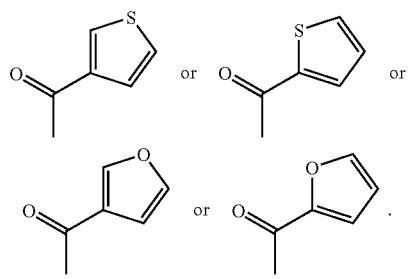

In a fifth embodiment, a compound is provided having a structure:

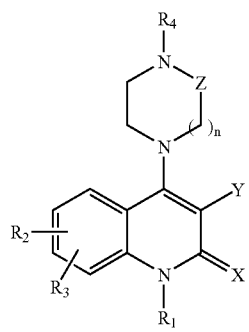

or a stereoisomer, a prodrug, or a pharmaceutically acceptable salt thereof, wherein X is oxygen or sulfur; Y includes —NO, —NO$_2$, —C(═O)$R_5$, —C(═O)$OR_5$, —C(═O)$NR_5R_6$, —$NR_5$C(═O)$R_5$, —$NR_5SO_2R_5$, and —S(O)$_mR_5$; Z is —CH$_2$— or —C(═O)—; m is 0, 1, or 2; n is 0, 1, or 2, with the proviso that when n is 0, Z is —C(═O)—; $R_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; $R_2$ and $R_3$ independently include halogen, —$R_5$, —$OR_5$, —$SR_5$, and —$NR_5R_6$; $R_4$ is

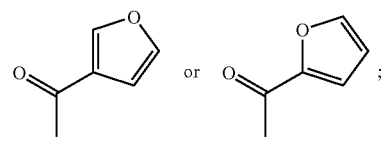

or and $R_5$ and $R_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or $R_5$ and $R_6$ taken together with a nitrogen atom to which they are attached form a heterocycle or substituted heterocycle.

In aspects of the fifth embodiment, X is oxygen; or Z is —CH$_2$— and n is 1; or Y is —C(═O)OCH$_2$CH$_3$; or Y is —NO$_2$.

In a sixth embodiment, a compound is provided having a structure:

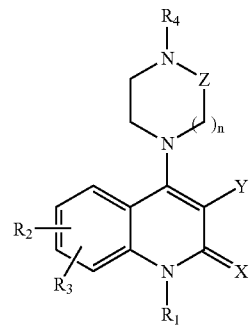

or a stereoisomer, a prodrug, or a pharmaceutically acceptable salt thereof, wherein X is oxygen or sulfur; Y includes —NO, —NO$_2$, —C(═O)$R_5$, —C(═O)$OR_5$, —C(═O)$NR_5R_6$, —$NR_5$C(═O)$R_5$, —$NR_5SO_2R_5$, and —S(O)$_mR_5$; Z is —CH$_2$— or —C(═O)—; m is 0, 1, or 2; n is 0, 1, or 2, with the proviso that when n is 0, Z is —C(═O)—; $R_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; $R_2$ and $R_3$ independently include halogen, —$R_5$, —$OR_5$, —$SR_5$, and —$NR_5R_6$; $R_4$ is

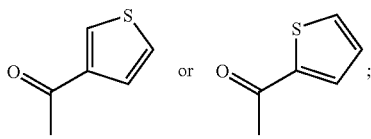

and $R_5$ and $R_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or $R_5$ and $R_6$ taken together with a nitrogen atom to which they are attached form a heterocycle or substituted heterocycle.

In aspects of the sixth embodiment, X is oxygen; or Z is —CH$_2$— and n is 1; or Y is —(=O)OCH$_2$CH$_3$; or Y is —NO$_2$.

In a seventh embodiment, a compound is provided having a structure:

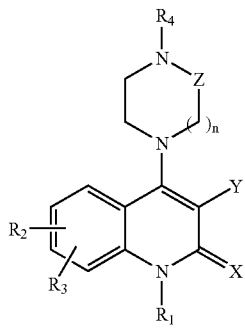

or a stereoisomer, a prodrug, or a pharmaceutically acceptable salt thereof, wherein X is oxygen; Y includes —NO, —NO$_2$, —C(=O)R$_5$, —C(=O)OR$_5$, —C(=O)NR$_5$R$_6$, —NR$_5$C(=O)R$_5$, —NR$_5$SO$_2$R$_5$, and —S(O)$_m$R$_5$; Z is —CH$_2$— or —C(=O)—; m is 0, 1, or 2; n is 0, 1, or 2, with the proviso that when n is 0, Z is —C(=O)—; R$_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R''N(CH$_2$)$_x$—, wherein x is 2 to 4, and wherein R' and R'' independently include hydrogen, alkyl, substituted alkyl, aryl, arylalkyl, substituted arylalkyl, heterocycle, substituted heterocycle, heterocyclealkyl, substituted heterocyclealkyl, and dialkyl; R$_2$ and R$_3$ independently include halogen, —R$_5$, —OR$_5$, —SR$_5$, and —NR$_5$R$_6$; R$_4$ includes —CH$_2$R$_7$, —C(=O)NR$_5$R$_6$, —C(=O)OR$_7$, —C(=O)R$_7$, and R$_8$; R$_5$ and R$_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R$_5$ and R$_6$ taken together with a nitrogen atom to which they are attached form a heterocycle or substituted heterocycle; R$_7$ includes alkyl, substituted alkyl, aryl, substituted aryl, arylalkyl, substituted arylalkyl, heterocycle, substituted heterocycle, heterocyclealkyl, and substituted heterocyclealkyl; and R$_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the provisos that R$_4$ is not hydrogen or methyl when R$_1$ is phenyl, R$_2$ and R$_3$ are both hydrogen, and Y is —C(=O)OCH$_2$CH$_3$; R$_4$ is not methyl when R$_1$ is methyl, R$_2$ and R$_3$ are both hydrogen, and Y is —NO$_2$; R$_4$ is not —CH$_2$CH$_2$OH when R$_1$ is hydrogen or methyl, R$_2$ is 7-chloro, R$_3$ is hydrogen, and Y is —C(=O)OCH$_2$CH$_3$; and R$_4$ is not methyl when R$_1$ is methyl, R$_2$ is hydrogen or 7-chloro, R$_3$ is hydrogen, and Y is —C(=O)OCH$_2$CH$_3$.

In aspects of the seventh embodiment, Z is —CH$_2$— and n is 1; or Y is —C(=O)OCH$_2$CH$_3$; or Y is —NO$_2$; or R$_4$ is

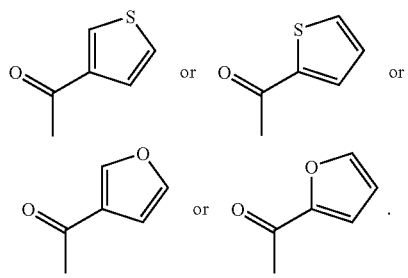

In an eighth embodiment, a composition is provided including a compound of the first embodiment in combination with a pharmaceutically acceptable carrier or diluent.

In a ninth embodiment, a method for reducing MIF activity in a patient in need thereof is provided, including administering to the patient an effective amount of a compound having the structure:

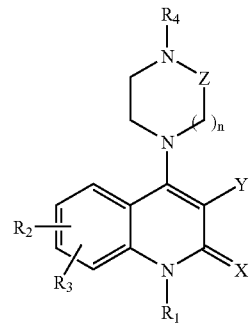

or a stereoisomer, a prodrug, or a pharmaceutically acceptable salt thereof, wherein X is oxygen or sulfur; Y includes —NO, —NO$_2$, —C(=O)R$_5$, —C(=O)OR$_5$, —C(=O)NR$_5$R$_6$, —NR$_5$C(=O)R$_5$, —NR$_5$SO$_2$R$_5$, and —S(O)$_m$R$_5$; Z is —CH$_2$— or —C(=O)—; m is 0, 1, or 2; n is 0, 1, or 2, with the proviso that when n is 0, Z is —C(=O)—; R$_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R''N(CH$_2$)$_x$—, wherein x is 2 to 4, and wherein R' and R'' independently include hydrogen, alkyl, substituted alkyl, aryl, arylalkyl, substituted arylalkyl, heterocycle, substituted heterocycle, heterocyclealkyl, substituted heterocyclealkyl, and dialkyl; R$_2$ and R$_3$ independently include halogen, —R$_5$, —OR$_5$, —SR$_5$, and —NR$_5$R$_6$; R$_4$ includes —CH$_2$R$_7$, —C(=O)NR$_5$R$_6$, —C(=O)OR$_7$, —C(=O)R$_7$, and R$_8$; R$_5$ and R$_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R$_5$ and R$_6$ taken together with a nitrogen atom to which they are attached form a heterocycle or substituted heterocycle; $R_7$ includes alkyl, substituted alkyl, aryl, substituted aryl, arylalkyl, substituted arylalkyl, heterocycle, substituted heterocycle, heterocyclealkyl, and substituted heterocyclealkyl; and $R_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the provisos that $R_4$ is not hydrogen or methyl when $R_1$ is phenyl, $R_2$ and $R_3$ are both hydrogen, X is oxygen, and Y is —C(=O)OCH$_2$CH$_3$; $R_4$ is not methyl when $R_1$ is methyl, $R_2$ and $R_3$ are both hydrogen, X is oxygen, and Y is —NO$_2$; $R_4$ is not —CH$_2$CH$_2$OH when $R_1$ is hydrogen or methyl, $R_2$ is 7-chloro, $R_3$ is hydrogen, X is oxygen and Y is —C(=O)OCH$_2$CH$_3$; and $R_4$ is not methyl when $R_1$ is methyl, $R_2$ is hydrogen or 7-chloro, $R_3$ is hydrogen, X is oxygen, and Y is —C(=O)OCH$_2$CH$_3$.

In a tenth embodiment, a method is provided for treating inflammation in a warm-blooded animal, including administering to the animal an effective amount of the compound of the first embodiment.

In an eleventh embodiment, a method is provided for treating septic shock in a warm-blooded animal, including administering to the animal an effective amount of the compound of the first embodiment.

In a twelfth embodiment, a method is provided for treating arthritis in a warm-blooded animal, including administering to the animal an effective amount of the compound of the first embodiment.

In a thirteenth embodiment, a method is provided for treating cancer in a warm-blooded animal, including administering to the animal an effective amount of the compound of the first embodiment.

In a fourteenth embodiment, a method is provided for treating acute respiratory distress syndrome in a warm-blooded animal, including administering to the animal an effective amount of the compound of the first embodiment.

In a fifteenth embodiment, a method is provided for treating an inflammatory disease in a warm-blooded animal, including administering to the animal an effective amount of the compound of the first embodiment. In aspects of the fifteenth embodiment, the inflammatory disease may include rheumatoid arthritis, osteoarthritis, inflammatory bowel disease, and asthma.

In a sixteenth embodiment, a method is provided for treating an autoimmune disorder in a warm-blooded animal, including administering to the animal an effective amount of the compound of the first embodiment. In aspects of the sixteenth embodiment, the autoimmune disorder includes diabetes, asthma, and multiple sclerosis.

In a seventeenth embodiment, a method is provided for suppressing an immune response in a warm-blooded animal, including administering to the animal an effective amount of the compound of the first embodiment.

In an eighteenth embodiment, a method is provided for decreasing angiogenesis in a warm-blooded animal, including administering to the animal an effective amount of the compound of the first embodiment.

In a nineteenth embodiment, a method is provided for treating a disease associated with excess glucocorticoid levels in a warm-blooded animal, including administering to the animal an effective amount of the compound of the first embodiment. In an aspect of the nineteenth embodiment, the disease is Cushing's disease.

In a twentieth embodiment, a method is provided for detecting an agent that modulates MIF activity, including contacting a sample containing MIF with an agent; and detecting the ability of the agent to modulate MIF by determining a differential ability of an antibody to bind MIF. In an aspect of the twentieth embodiment, the antibody is a monoclonal antibody. In an aspect of the twentieth embodiment, MIF includes fusion proteins, mutants or variants thereof.

In a twenty first embodiment, a method is provided for using antibody binding as a surrogate marker for screening for an agent that modulates the activity of a polypeptide, including contacting the polypeptide with a suspected modulating agent, contacting the polypeptide with a monoclonal antibody, and detecting a differential activity of the polypeptide relative to a control.

In a twenty second embodiment, a compound is provided having a structure:

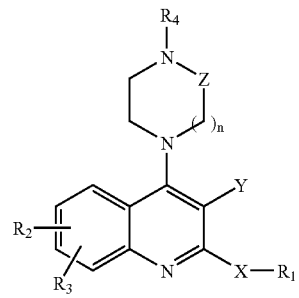

or a stereoisomer, a prodrug, or a pharmaceutically acceptable salt thereof, wherein X is oxygen or sulfur; Y includes —NO, —NO$_2$, —C(=O)R$_5$, —C(=O)OR$_5$, —C(=O)NR$_5$R$_6$, —NR$_5$C(=O)R$_5$, —NR$_5$SO$_2$R$_5$, and —S(O)$_m$R$_5$; Z is —CH$_2$— or —C(=O)—; m is 0, 1, or 2; n is 0, 1, or 2, with the proviso that when n is 0, Z is —C(=O)—; $R_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; $R_2$ and $R_3$ independently include halogen, —R$_5$, —OR$_5$, —SR$_5$, and —NR$_5$R$_6$; $R_4$ includes —CH$_2$R$_7$, —C(=O)NR$_5$R$_6$, —C(=O)OR$_7$, —C(=O)R$_7$, and $R_8$; $R_5$ and $R_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or $R_5$ and $R_6$ taken together with a nitrogen atom to which they are attached form a heterocycle or substituted heterocycle; $R_7$ includes alkyl, substituted alkyl, aryl, substituted aryl, arylalkyl, substituted arylalkyl, heterocycle, substituted heterocycle, heterocyclealkyl, and substituted heterocyclealkyl; and $R_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the provisos that: $R_4$ is not hydrogen or methyl when $R_1$ is phenyl, $R_2$ and $R_3$ are both hydrogen, X is oxygen, and Y is —C(=O)OCH$_2$CH$_3$; $R_4$ is not methyl when $R_1$ is methyl, $R_2$ and $R_3$ are both hydrogen, X is oxygen, and Y is —NO$_2$; $R_4$ is not —CH$_2$CH$_2$OH when $R_1$ is hydrogen or methyl, $R_2$ is 7-chloro, $R_3$ is hydrogen, X is oxygen and Y is —C(=O)OCH$_2$CH$_3$; and $R_4$ is not methyl when $R_1$ is methyl, $R_2$ is hydrogen or 7-chloro, $R_3$ is hydrogen, X is oxygen, and Y is —C(=O)OCH$_2$CH$_3$.

In a twenty third embodiment, a compound is provided having a structure:

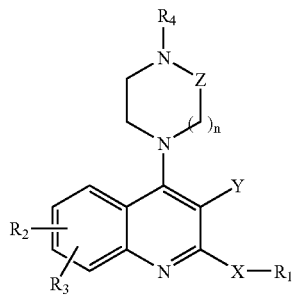

or a stereoisomer, a prodrug, or a pharmaceutically acceptable salt thereof, wherein X is oxygen or sulfur; Y includes —NO, —NO$_2$, —C(=O)R$_5$, —C(=O)OR$_5$, —C(=O)NR$_5$R$_6$, —NR$_5$C(=O)R$_5$, —NR$_5$SO$_2$R$_5$, and —S(O)$_m$R$_5$; Z is —CH$_2$—; m is 0, 1, or 2; n is 1; R$_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; R$_2$ and R$_3$ independently include halogen, —R$_5$, —OR$_5$, —SR$_5$, and —NR$_5$R$_6$; R$_4$ includes —CH$_2$R$_7$, —C(=O)NR$_5$R$_6$, —C(=O)OR$_7$, —C(=O)R$_7$, and R$_8$; R$_5$ and R$_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R$_5$ and R$_6$ taken together with a nitrogen atom to which they are attached form a heterocycle or substituted heterocycle; R$_7$ includes alkyl, substituted alkyl, aryl, substituted aryl, arylalkyl, substituted arylalkyl, heterocycle, substituted heterocycle, heterocyclealkyl, and substituted heterocyclealkyl; and R$_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the provisos that R$_4$ is not hydrogen or methyl when R$_1$ is phenyl, R$_2$ and R$_3$ are both hydrogen, X is oxygen, and Y is —C(=O)OCH$_2$CH$_3$; R$_4$ is not methyl when R is methyl, R$_2$ and R$_3$ are both hydrogen, X is oxygen, and Y is —NO$_2$; R$_4$ is not —CH$_2$CH$_2$OH when R$_1$ is hydrogen or methyl, R$_2$ is 7-chloro, R$_3$ is hydrogen, X is oxygen and Y is —C(=O)OCH$_2$CH$_3$; and R$_4$ is not methyl when R$_1$ is methyl, R$_2$ is hydrogen or 7-chloro, R$_3$ is hydrogen, X is oxygen, and Y is —C(=O)OCH$_2$CH$_3$.

In aspects of the twenty third embodiment, R$_1$ is —NCH$_2$CH$_2$N(CH$_3$)$_2$; or X is oxygen; or Y is —C(=O)OCH$_2$CH$_3$; or Y is —NO$_2$; or R$_4$ is

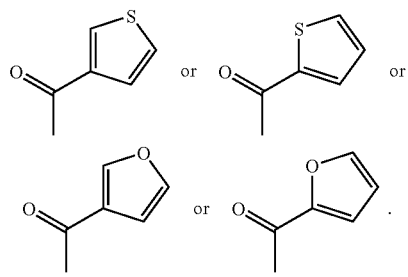

In a twenty fourth embodiment, a compound is provided having a structure:

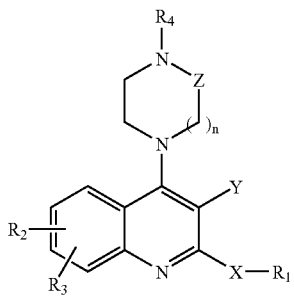

or a stereoisomer, a prodrug, or a pharmaceutically acceptable salt thereof, wherein X is oxygen or sulfur; Y is —C(=O)OCH$_2$CH$_3$; Z is —CH$_2$— or —C(=O)—; m is 0, 1, or 2; n is 0, 1, or 2, with the proviso that when n is 0, Z is —C(=O)—; R$_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; R$_2$ and R$_3$ independently include halogen, —R$_5$, —OR$_5$, —SR$_5$, and —NR$_5$R$_6$; R$_4$ includes —CH$_2$R$_7$, —C(=O)NR$_5$R$_6$, —C(=O)OR$_7$, —C(=O)R$_7$, and R$_8$; R$_5$ and R$_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R$_5$ and R$_6$ taken together with a nitrogen atom to which they are attached form a heterocycle or substituted heterocycle; R$_7$ includes alkyl, substituted alkyl, aryl, substituted aryl, arylalkyl, substituted arylalkyl, heterocycle, substituted heterocycle, heterocyclealkyl, and substituted heterocyclealkyl; and R$_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the provisos that R$_4$ is not hydrogen or methyl when R$_1$ is phenyl, R$_2$ and R$_3$ are both hydrogen, and X is oxygen; R$_4$ is not —CH$_2$CH$_2$OH when R$_1$ is hydrogen or methyl, R$_2$ is 7-chloro, R$_3$ is hydrogen, and X is oxygen; and R$_4$ is not methyl when R$_1$ is methyl, R$_2$ is hydrogen or 7-chloro, R$_3$ is hydrogen, and X is oxygen.

In aspects of the twenty forth embodiment, X is oxygen; or Z is —CH$_2$— and n is 1; or R$_4$ is

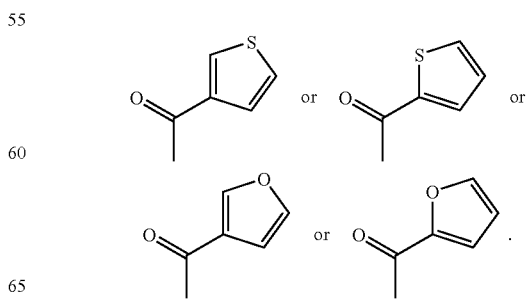

In a twenty fifth embodiment, a compound is provided having a structure:

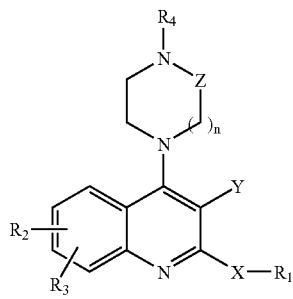

or a stereoisomer, a prodrug, or a pharmaceutically acceptable salt thereof, wherein X is oxygen or sulfur; Y includes —NO, —NO$_2$, —C(=O)R$_5$, —C(=O)OR$_5$, —C(=O)NR$_5$R$_6$, —NR$_5$C(=O)R$_5$, —NR$_5$SO$_2$R$_5$, and —S(O)$_m$R$_5$; Z is —CH$_2$— or —C(=O)—; m is 0, 1, or 2; n is 0, 1, or 2, with the proviso that when n is 0, Z is —C(=O)—; R$_1$ is —NCH$_2$CH$_2$CH$_2$N(CH$_3$)$_2$; R$_2$ and R$_3$ independently include halogen, —R$_5$, —OR$_5$, —SR$_5$, and —NR$_5$R$_6$; R$_4$ includes —CH$_2$R$_7$, —C(=O)NR$_5$R, —C(=O)OR$_7$, —C(=O)R$_7$, and R$_5$; R$_5$ and R$_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R$_5$ and R$_6$ taken together with a nitrogen atom to which they are attached form a heterocycle or substituted heterocycle; R$_7$ includes alkyl, substituted alkyl, aryl, substituted aryl, arylalkyl, substituted arylalkyl, heterocycle, substituted heterocycle, heterocyclealkyl, and substituted heterocyclealkyl; and R$_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl.

In aspects of the twenty fifth embodiment, Z is —CH$_2$— and n is 1; or Y is —C(=O)OCH$_2$CH$_3$; or Y is —NO$_2$; or R$_4$ is

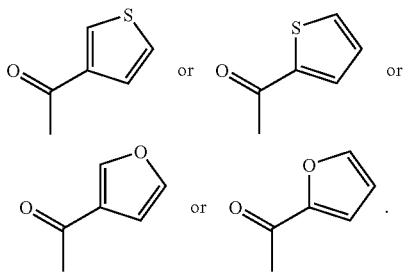

In a twenty sixth embodiment, a compound is provided having a structure:

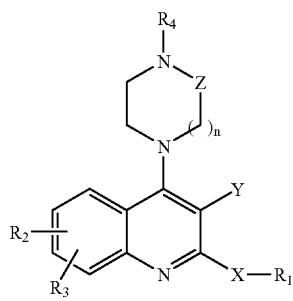

or a stereoisomer, a prodrug, or a pharmaceutically acceptable salt thereof, wherein X is oxygen or sulfur; Y is —NO$_2$; Z is —CH$_2$— or —C(=O)—; m is 0, 1, or 2; n is 0, 1, or 2, with the proviso that when n is 0, Z is —C(=O)—; R$_1$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH$_2$)$_x$—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; R$_2$ and R$_3$ independently include halogen, —R$_5$, —OR$_5$, —SR$_5$, and —NR$_5$R$_6$; R$_4$ includes —CH$_2$R$_7$, —C(=O)NR$_5$R$_6$, —C(=O)OR$_7$, —C(=O)R$_7$, and R$_8$; R$_5$ and R$_6$ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R$_5$ and R$_6$ taken together with a nitrogen atom to which they are attached form a heterocycle or substituted heterocycle; R$_7$ includes alkyl, substituted alkyl, aryl, substituted aryl, arylalkyl, substituted arylalkyl, heterocycle, substituted heterocycle, heterocyclealkyl, and substituted heterocyclealkyl; and R$_8$ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the proviso that R$_4$ is not methyl when R$_1$ is methyl, R$_2$ and R$_3$ are both hydrogen, and X is oxygen.

In aspects of the twenty sixth embodiment, R$_1$ is —NCH$_2$CH$_2$CH$_2$N(CH$_3$)$_2$; or X is oxygen; or Z is —CH$_2$— and n is 1; or R$_4$ is

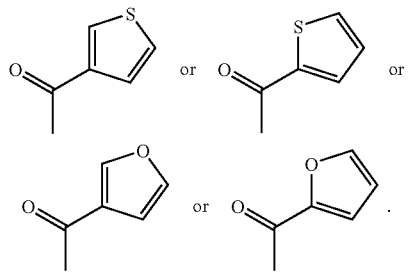

In a twenty seventh embodiment, a compound is provided having a structure:

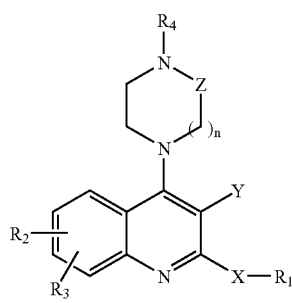

or a stereoisomer, a prodrug, or a pharmaceutically acceptable salt thereof, wherein X is oxygen or sulfur; Y includes —NO, —NO$_2$, —C(=O)R$_5$, —C(=O)OR$_5$, —C(=O)NR$_5$R$_6$, —NR$_5$C(=O)R$_5$, —NR$_5$SO$_2$R$_5$, and —S(O)$_m$R$_5$; Z is —CH₂— or —C(=O)—; m is 0, 1, or 2; n is 0, 1, or 2, with the proviso that when n is 0, Z is —C(=O)—; R₁ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH₂)ₓ—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; R₂ and R₃ independently include halogen, —R₅, —OR₅, —SR₅, and —NR₅R₆; R₄ includes

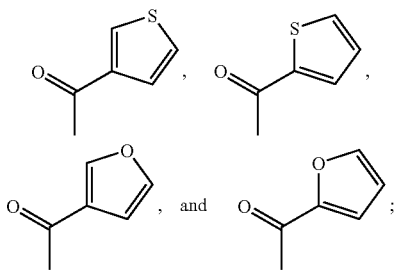

R₅ and R₆ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R₅ and R₆ taken together with a nitrogen atom to which they are attached form a heterocycle or substituted heterocycle; R₇ includes alkyl, substituted alkyl, aryl, substituted aryl, arylalkyl, substituted arylalkyl, heterocycle, substituted heterocycle, heterocyclealkyl, and substituted heterocyclealkyl; and R₈ includes hydrogen, alkyl, substituted alkyl, aryl, substituted aryl, arylalkyl, substituted arylalkyl, heterocycle, substituted heterocycle, heterocyclealkyl, and substituted heterocyclealkyl.

In aspects of the twenty seventh embodiment, R₁ is —NCH₂CH₂CH₂N(CH₃)₂; or X is oxygen; or Z is —CH₂— and n is 1; or Y is —C(=O)OCH₂CH₃; or Y is —NO₂.

In a twenty eighth embodiment, a method is provided for reducing MIF activity in a patient in need thereof, including administering to the patient an effective amount of a compound having the structure:

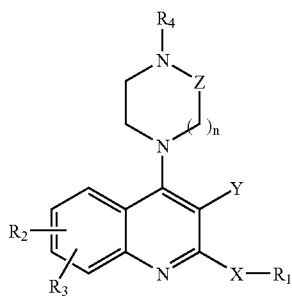

or a stereoisomer, a prodrug, or a pharmaceutically acceptable salt thereof, wherein X is oxygen or sulfur; Y includes —NO, —NO₂, —C(=O)R₅, —C(=O)OR₅, —C(=O)NR₅R₆, —NR₅C(=O)R₅, —NR₅SO₂R₅, and —S(O)ₘR₅; Z is —CH₂— or —C(=O)—; m is 0, 1, or 2; n is 0, 1, or 2, with the proviso that when n is 0, Z is —C(=O)—; R₁ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and R'R"N(CH₂)ₓ—, wherein x is 2 to 4, and wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl; R₂ and R₃ independently include halogen, —R₅, —OR₅, —SR₅, and —NR₅R₆; R₄ includes —CH₂R₇, —C(=O)NR₅R₆, —C(=O)OR₇, —C(=O)R₇, and R₈; R₅ and R₆ independently include hydrogen, alkyl, substituted alkyl, aryl, substituted aryl, arylalkyl, substituted arylalkyl, heterocycle, substituted heterocycle, heterocyclealkyl, and substituted heterocyclealkyl; or R₅ and R₆ taken together with a nitrogen atom to which they are attached form a heterocycle or substituted heterocycle; R₇ includes alkyl, substituted alkyl, aryl, substituted aryl, arylalkyl, substituted arylalkyl, heterocycle, substituted heterocycle, heterocyclealkyl, and substituted heterocyclealkyl; and R₈ includes hydrogen, alkyl, substituted alkyl, aryl, substituted aryl, arylalkyl, substituted arylalkyl, heterocycle, substituted heterocycle, heterocyclealkyl, and substituted heterocyclealkyl; with the provisos that R₄ is not hydrogen or methyl when R₁ is phenyl, R₂ and R₃ are both hydrogen, X is oxygen, and Y is —C(=O)OCH₂CH₃; R₄ is not methyl when R₁ is methyl, R₂ and R₃ are both hydrogen, X is oxygen, and Y is —NO₂; R₄ is not —CH₂CH₂OH when R₁ is hydrogen or methyl, R₂ is 7-chloro, R₃ is hydrogen, X is oxygen and Y is —C(=O)OCH₂CH₃; and R₄ is not methyl when R₁ is methyl, R₂ is hydrogen or 7-chloro, R₃ is hydrogen, X is oxygen, and Y is —C(=O)OCH₂CH₃.

In a twenty ninth embodiment, a method is provided for treating inflammation in a warm-blooded animal, including administering to the animal an effective amount of the compound of the twenty eighth embodiment.

In a thirtieth embodiment, a method is provided for treating septic shock in a warm-blooded animal, including administering to the animal an effective amount of the compound of the twenty eighth embodiment.

In a thirty first embodiment, a method is provided for treating arthritis in a warm-blooded animal, including administering to the animal an effective amount of the compound of the twenty eighth embodiment.

In a thirty second embodiment, a method is provided for treating cancer in a warm-blooded animal, including administering to the animal an effective amount of the compound of the twenty eighth embodiment.

In a thirty third embodiment, a method is provided for treating acute respiratory distress syndrome in a warm-blooded animal, including administering to the animal an effective amount of the compound of the twenty eighth embodiment.

In a thirty fourth embodiment, a method is provided for treating an inflammatory disease in a warm-blooded animal, including administering to the animal an effective amount of the compound of the twenty eighth embodiment. In aspects of the thirty fourth embodiment, the inflammatory disease includes rheumatoid arthritis, osteoarthritis, inflammatory bowel disease, and asthma.

In a thirty fifth embodiment, a method is provided for treating an autoimmune disorder in a warm-blooded animal, including administering to the animal an effective amount of the compound of the twenty eighth embodiment. In aspects of the thirty fifth embodiment, the autoimmune disorder includes diabetes, asthma, and multiple sclerosis.

In a thirty sixth embodiment, a method is provided for suppressing an immune response in a warm-blooded animal, including administering to the animal an effective amount of the compound of the twenty eighth embodiment.

In a thirty seventh embodiment, a method is provided for decreasing angiogenesis in a warm-blooded animal, including administering to the animal an effective amount of the compound of the twenty eighth embodiment.

In a thirty eighth embodiment, a method is provided for treating a disease associated with excess glucocorticoid levels in a warm-blooded animal, including administering to the animal an effective amount of the compound of the twenty eighth embodiment. In an aspect of the thirty eighth embodiment, the disease is Cushing's disease.

In a thirty ninth embodiment, a process is provided for preparing a compound including the steps of reacting a compound of Formula I:

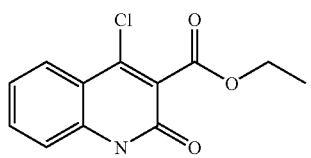

(Formula I)

with a compound of Formula II:

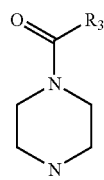

(Formula II)

thereby obtaining a compound of Formula III:

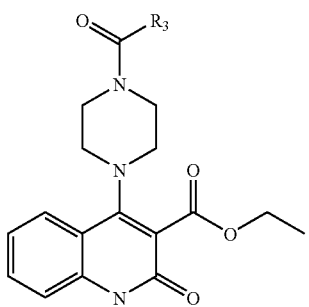

(Formula III)

wherein $R_3$ includes $R_4$ is amino, substituted amino hydrogen, alkyl, substituted alkyl, aryl, substituted aryl, arylalkyl, substituted arylalkyl, heterocycle, substituted heterocycle, heterocyclealkyl, and substituted heterocyclealkyl; and reacting the compound of Formula III with a compound including X—$R_4$, wherein X includes Cl, Br, and I, and wherein $R_4$ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and aminoalkyl R'R"N(CH$_2$)$_x$—, wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl, wherein x is 2 to 4, thereby obtaining a compound of Formula IV:

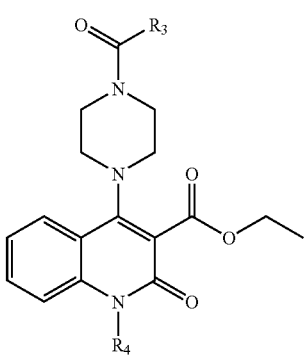

(Formula IV)

wherein the compound of Formula IV is suitable for use as a MIF inhibitor.

In aspects of the thirty ninth embodiment, $R_4$ is

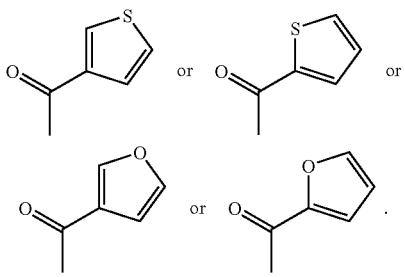

In a fortieth embodiment, a process is provided for preparing a compound including the steps of reacting a compound of Formula AI:

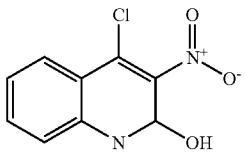

(Formula AI)

with a compound of Formula II:

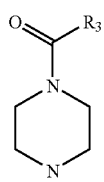

(Formula II)

thereby obtaining a compound of Formula AIII:

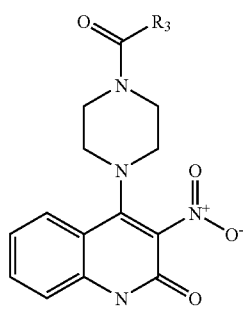

(Formula AIII)

wherein R₃ includes R₄ is amino, substituted amino hydrogen, alkyl, substituted alkyl, aryl, substituted aryl, arylalkyl, substituted arylalkyl, heterocycle, substituted heterocycle, heterocyclealkyl, and substituted heterocyclealkyl; and reacting the compound of Formula AIII with a compound including X—R₄, wherein X includes Cl, Br, and I, and wherein R₄ includes hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, and aminoalkyl R'R"N(CH₂)$_x$—, wherein R' and R" independently include hydrogen, alkyl, substituted alkyl, aryl, arylalkyl, substituted arylalkyl, heterocycle, substituted heterocycle, heterocyclealkyl, substituted heterocyclealkyl, and dialkyl, wherein x is 2 to 4, thereby obtaining a compound of Formula AIV:

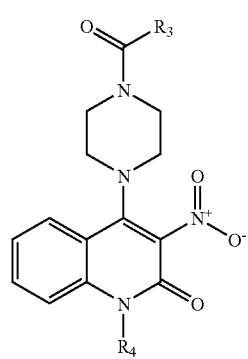

(Formula AIV)

wherein the compound of Formula IV is suitable for use as a MIF inhibitor.

In aspects of the fortieth embodiment, R₄ is

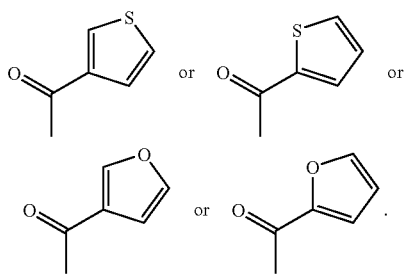

In a forty first embodiment, a pharmaceutical composition is provided for treating a disease or disorder wherein MIF is pathogenic, the pharmaceutical composition including a MIF inhibiting compound and a drug for treating the disease or disorder, wherein the drug has no measurable MIF inhibiting activity.

In a forty second embodiment, a pharmaceutical composition is provided for treating a disease or disorder wherein MIF is pathogenic, the pharmaceutical composition including a MIF inhibiting compound and a drug selected from the group consisting of nonsteroidal anti-inflammatory drugs, anti-infective drugs, beta stimulants, steroids, antihistamines, anticancer drugs, asthma drugs, sepsis drugs, arthritis drugs, and immunosuppresive drugs.

These and other embodiments and aspects thereof will be apparent upon reference to the following detailed description. To this end, various references are set forth herein which describe in more detail certain procedures, compounds and/or compositions, and are hereby incorporated by reference in their entirety.

DETAILED DESCRIPTION OF THE PREFERRED EMBODIMENT

Figure 1:
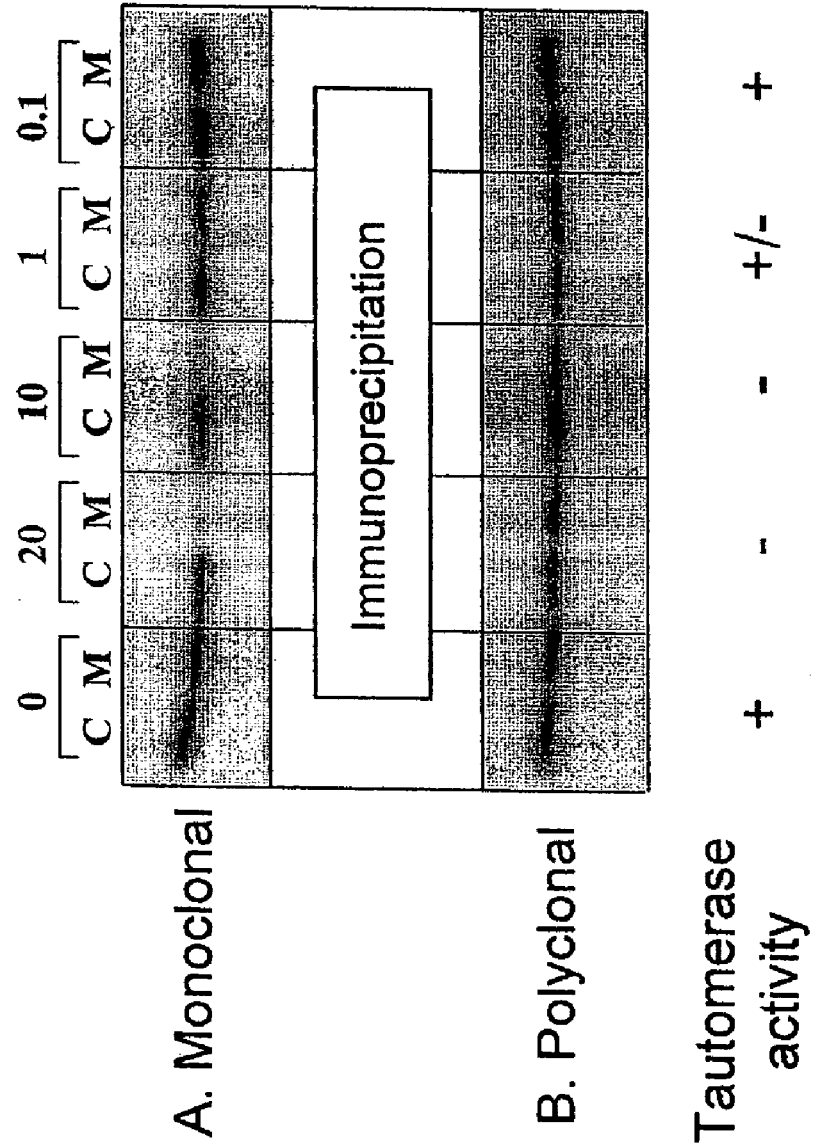
FIGS. 1A–1B are scanned images of an autoradiogram demonstrating antibody immunoprecipitation with an anti-MIF monoclonal antibody (FIG. 1A) and anti-MIF polyclonal sera (FIG. 1B) in cytosolic extracts (C) as well as conditioned media (M) of THP-1 cells following LPS stimulation and treatment with various micromolar concentrations of compound 7e. Also depicted are the results of tautomerase activity detected in the various fractions. Plus signs indicate tautomerase activity, minus signs indicate no detectable activity, and +/− signs indicating partial activity.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

As an aid to understanding the preferred embodiments, certain definitions are provided herein.

The term "MIF activity," as used herein is a broad term and is used in its ordinary sense, including, without limitation, to refer to an activity or effect mediated at least in part by macrophage migration inhibitory factor. Accordingly, MIF activity includes, but is not limited to, inhibition of macrophage migration, tautomerase activity (e.g., using phenylpyruvate or dopachrome), endotoxin induced shock, inflammation, glucocorticoid counter regulation, induction of thymidine incorporation into 3T3 fibroblasts, induction of erk phosphorylation and MAP kinase activity.

The term "export," as used herein is a broad term and is used in its ordinary sense, including, without limitation, to refer to a metabolically active process, which may or may not be energy-dependent, of transporting a translated cellular product to the cell membrane or the extracellular space by a mechanism other than standard leader sequence directed secretion via a canonical leader sequence. Further, "export," unlike secretion that is leader sequence-dependent, is resistant to brefeldin A (i.e., the exported protein is not transported via the ER/Golgi; brefeldin A is expected to have no direct effect on trafficking of an exported protein) and other similar compounds. As used herein, "export" may also be referred to as "non-classical secretion."

The term "leaderless protein," as used herein is a broad term and is used in its ordinary sense, including, without limitation, to refer to a protein or polypeptide that lacks a canonical leader sequence, and is exported from inside a cell to the extracellular environment. Leaderless proteins in the extracellular environment refer to proteins located in the extracellular space, or associated with the outer surface of the cell membrane. Within the context of preferred embodiments, leaderless proteins include naturally occurring proteins, such as macrophage migration inhibitory factor and fragments thereof as well as proteins that are engineered to lack a leader sequence and are exported, or proteins that are engineered to include a fusion of a leaderless protein, or fraction thereof, with another protein.

The term "inhibitor," as used herein is a broad term and is used in its ordinary sense, including, without limitation, to refer to a molecule (e.g., natural or synthetic compound) that can alter the conformation of MIF and/or compete with a monoclonal antibody to MIF and decrease at least one activity of MIF or its export from a cell as compared to activity or export in the absence of the inhibitor. In other words, an "inhibitor" alters conformation and/or activity and/or export if there is a statistically significant change in the amount of MIF measured, MIF activity or in MIF protein detected extracellularly and/or intracellularly in an assay performed with an inhibitor, compared to the assay performed without the inhibitor.

The term "binding agent," as used herein is a broad term and is used in its ordinary sense, including, without limitation, to refer to any molecule that binds MIF, including inhibitors.

In general, MIF inhibitors inhibit the physiological function of MIF, and thus are useful in the treatment of diseases where MIF may be pathogenic.

In certain of the preferred embodiments, inhibitors of MIF are provided that have the following structures (Ia) and (Ib):

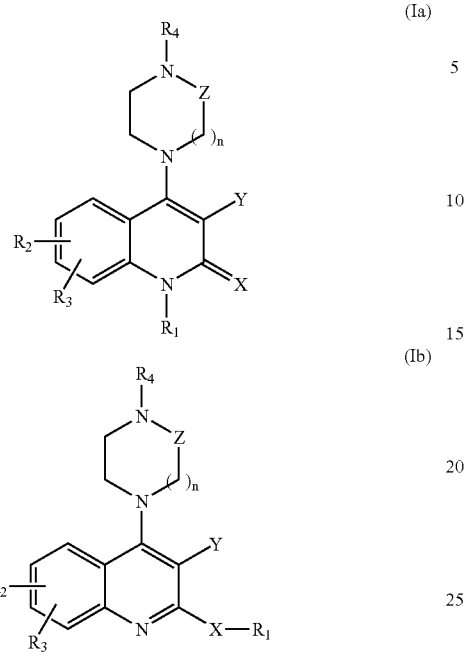

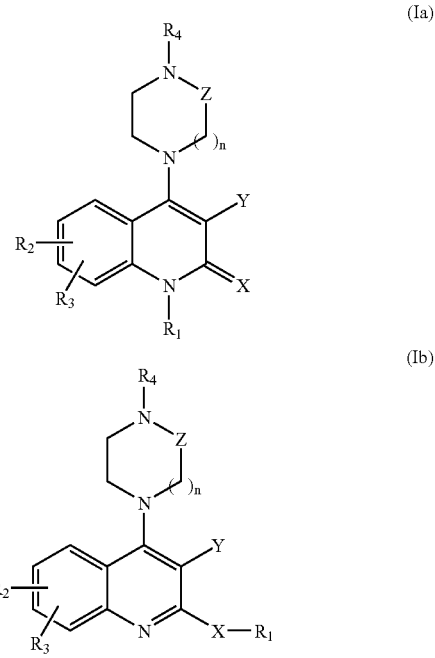

including stereoisomers, prodrugs and pharmaceutically acceptable salts thereof, wherein: X is oxygen or sulfur; Y is —NO, —NO$_2$, —C(=O)R$_5$, —C(=O)OR$_5$, —C(=O)NR$_5$R$_6$, —NR$_5$C(=O)R$_5$, —NR$_5$SO$_2$R$_5$, or —S(O)$_m$R$_5$; Z is —CH$_2$— or —C(=O)—; m is 0, 1, or 2; n is 0, 1 or 2, with the proviso that when n is 0, Z is —C(=O)—; R$_1$ is hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, or aminoalkyl R'R"N(CH$_2$)$_x$— wherein R' and R" are independently hydrogen, alkyl, substituted alkyl, aryl, arylalkyl, substituted arylalkyl, heterocycle, substituted heterocycle, heterocyclealkyl, substituted heterocyclealkyl, or dialkyl, and wherein x is 2 to 4; R$_2$ and R$_3$ are the same or different and are independently, halogen, —R$_5$, —OR$_5$, —SR$_5$ or —NR$_5$R$_6$; R$_4$ is —CH$_2$R$_7$, —C(=O)NR$_5$R$_6$, —C(=O)OR$_7$, —C(=O)R$_7$ or R$_8$; R$_5$ and R$_6$ are the same or different and are independently hydrogen, alkyl, substituted alkyl, aryl, substituted aryl, arylalkyl, substituted arylalkyl, heterocycle, substituted heterocycle, heterocyclealkyl or substituted heterocyclealkyl; or R$_5$ and R$_6$ taken together with the nitrogen atom to which they are attached form a heterocycle or substituted heterocycle; R$_7$ is alkyl, substituted alkyl, aryl, substituted aryl, arylalkyl, substituted arylalkyl, heterocycle, substituted heterocycle,

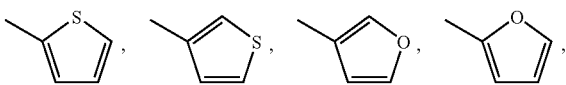

heterocyclealkyl or substituted heterocyclealkyl; and R$_8$ is hydrogen, alkyl, substituted alkyl, aryl, substituted aryl, arylalkyl, substituted arylalkyl, heterocycle, substituted heterocycle, heterocyclealkyl or substituted heterocyclealkyl; with the provisos that: R$_4$ is not hydrogen or methyl when R$_1$ is phenyl, R$_2$ and R$_3$ are both hydrogen, X is oxygen and Y is —C(=O)OCH$_2$CH$_3$; R$_4$ is not methyl when R$_1$ is methyl, R$_2$ and R$_3$ are both hydrogen, X is oxygen and Y is —NO$_2$; R$_4$ is not —CH$_2$CH$_2$OH when R$_1$ is hydrogen or methyl, R$_2$ is 7-chloro, R$_3$ is hydrogen, X is oxygen and Y is —C(=O)OCH$_2$CH$_3$; and R$_4$ is not methyl when R$_1$ is methyl, R$_2$ is hydrogen or 7-chloro, R$_3$ is hydrogen, X is oxygen and Y is —C(=O)OCH$_2$CH$_3$. In certain embodiments, one or more of the provisos may not apply.

In a preferred embodiment, methods are provided for reducing MIF activity in a patient in need thereof by administering to the patient an effective amount of a compound having the following structure (Ia) and/or (Ib):

including stereoisomers, prodrugs and pharmaceutically acceptable salts thereof, wherein: X is oxygen or sulfur; Y is —NO, —NO$_2$, —C(=O)R$_5$, —C(=O)OR$_5$, —C(=O)NR$_5$R$_6$, —NR$_5$C(=O)R$_5$, —NR$_5$SO$_2$R$_5$, or —S(O)$_m$R$_5$; Z is —CH$_2$— or —C(=O)—; m is 0, 1, or 2; n is 0, 1 or 2, with the proviso that when n is 0, Z is —C(=O)—; R$_1$ is hydrogen, alkyl, substituted alkyl, aryl, substituted aryl, arylalkyl, substituted arylalkyl, heterocycle, substituted heterocycle, heterocyclealkyl or substituted heterocyclealkyl, dialkyl, or aminoalkyl R'R"N(CH$_2$)$_x$— wherein R' and R" are independently hydrogen, alkyl, substituted alkyl, aryl, arylalkyl, substituted arylalkyl, heterocycle, substituted heterocycle, heterocyclealkyl, substituted heterocyclealkyl, or dialkyl, and wherein x is 2 to 4; R$_2$ and R$_3$ are the same or different and are independently, halogen, —R$_5$, —OR$_5$, —SR$_5$ or —NR$_5$R$_6$; R$_4$ is —CH$_2$R$_7$, —C(=O)NR$_5$R$_6$, —C(=O)OR$_7$, —C(=O)R$_7$ or R$_8$; R$_5$ and R$_6$ are the same or different and are independently hydrogen, alkyl, substituted alkyl, aryl, substituted aryl, arylalkyl, substituted arylalkyl, heterocycle, substituted heterocycle, heterocyclealkyl or substituted heterocyclealkyl; or R$_5$ and R$_6$ taken together with the nitrogen atom to which they are attached form a heterocycle or substituted heterocycle; R$_7$ is alkyl, substituted alkyl, aryl, substituted aryl, arylalkyl, substituted arylalkyl, heterocycle, substituted heterocycle, heterocyclealkyl or substituted heterocyclealkyl; and R$_8$ is hydrogen, alkyl, substituted alkyl, aryl, substituted aryl, arylalkyl, substituted arylalkyl, heterocycle, substituted heterocycle, heterocyclealkyl or substituted heterocyclealkyl; with the provisos that: $R_4$ is not hydrogen or methyl when $R_1$ is phenyl, $R_2$ and $R_3$ are both hydrogen, X is oxygen and Y is —C(=O)OCH$_2$CH$_3$; $R_4$ is not methyl when $R_1$ is methyl, $R_2$ and $R_3$ are both hydrogen, X is oxygen and Y is —NO$_2$; $R_4$ is not —CH$_2$CH$_2$OH when $R_1$ is hydrogen or methyl, $R_2$ is 7-chloro, $R_3$ is hydrogen, X is oxygen and Y is —C(=O)OCH$_2$CH$_3$; and $R_4$ is not methyl when $R_1$ is methyl, $R_2$ is hydrogen or 7-chloro, $R_3$ is hydrogen, X is oxygen and Y is —C(=O)OCH$_2$CH$_3$. In certain embodiments, one or more of the provisos may not apply.

As used herein, the above terms have the following meanings. The term "alkyl," as used herein is a broad term and is used in its ordinary sense, including, without limitation, to refer to a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantane. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

The term "aryl," as used herein is a broad term and is used in its ordinary sense, including, without limitation, to refer to an aromatic carbocyclic moiety such as phenyl or naphthyl.

The term "arylalkyl," as used herein is a broad term and is used in its ordinary sense, including, without limitation, to refer to an alkyl having at least one alkyl hydrogen atoms replaced with an aryl moiety, such as benzyl, —CH$_2$(1 or 2-naphthyl), —(CH$_2$)$_2$phenyl, —(CH$_2$)$_3$phenyl, —CH(phenyl)$_2$, and the like.

The term "heteroalkyl," as used herein is a broad term and is used in its ordinary sense, including, without limitation, to refer to an aromatic heterocycle ring of 5- to 10 members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The term "heteroarylalkyl," as used herein is a broad term and is used in its ordinary sense, including, without limitation, to refer to an alkyl having at least one alkyl hydrogen atom replaced with a heteroaryl moiety, such as —CH$_2$pyridinyl, —CH$_2$pyrimidinyl, and the like.

The terms "heterocycle" and "heterocycle ring," as used herein, are broad terms and are used in their ordinary sense, including, without limitation, to refer to a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocyclealkyl," as used herein is a broad term and is used in its ordinary sense, including, without limitation, to refer to an alkyl having at least one alkyl hydrogen atom replaced with a heterocycle, such as —CH$_2$morpholinyl, and the like.

The term "substituted," as used herein is a broad term and is used in its ordinary sense, including, without limitation, to refer to any of the above groups (e.g., alkyl, aryl, arylalkyl, heteroaryl, heteroarylalkyl, heterocycle or heterocyclealkyl) wherein at least one hydrogen atom is replaced with a substituent. In the case of a keto substituent ("—C(=O)—") two hydrogen atoms are replaced. When substituted, "substituents," within the context of preferred embodiment, include halogen, hydroxy, cyano, nitro, amino, alkylamino, dialkylamino, alkyl, alkoxy, alkylthio, haloalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$ —NR$_a$SO$_2$R$_b$, —OR$_a$, —C(=O)R$_a$ —C(=O)OR$_a$, —C(=O)NR$_a$R$_b$, —OC(=O)NR$_a$R$_b$, —SH, —SR$_a$, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

The term "halogen," as used herein is a broad term and is used in its ordinary sense, including, without limitation, to refer to fluoro, chloro, bromo and iodo.

The term "haloalkyl," as used herein is a broad term and is used in its ordinary sense, including, without limitation, to refer to an alkyl having at least one hydrogen atom replaced with halogen, such as trifluoromethyl and the like.

The term "alkoxy," as used herein is a broad term and is used in its ordinary sense, including, without limitation, to refer to an alkyl moiety attached through an oxygen bridge (i.e., —O-alkyl) such as methoxy, ethoxy, and the like.

The term "thioalkyl," as used herein is a broad term and is used in its ordinary sense, including, without limitation, to refer to an alkyl moiety attached through a sulfur bridge (i.e., —S-alkyl) such as methylthio, ethylthio, and the like.

The term "alkylsulfonyl," as used herein is a broad term and is used in its ordinary sense, including, without limitation, to refer to an alkyl moiety attached through a sulfonyl bridge (i.e., —SO$_2$-alkyl) such as methylsulfonyl, ethylsulfonyl, and the like.

The terms "alkylamino" and "dialkyl amino" as used herein, are broad terms and are used in their ordinary sense, including, without limitation, to refer to one alkyl moiety or two alkyl moieties, respectively, attached through a nitrogen bridge (i.e., —N-alkyl) such as methylamino, ethylamino, dimethylamino, diethylamino, and the like.

The term "hydroxyalkyl," as used herein is a broad term and is used in its ordinary sense, including, without limitation, to refer to an alkyl substituted with at least one hydroxyl group.

The term "mono- or di(cycloalkyl)methyl," as used herein is a broad term and is used in its ordinary sense, including, without limitation, to refer to a methyl group substituted with one or two cycloalkyl groups, such as cyclopropylmethyl, dicyclopropylmethyl, and the like.

The term "alkylcarbonylalkyl," as used herein is a broad term and is used in its ordinary sense, including, without limitation, to refer to an alkyl substituted with a —C(=O) alkyl group.

The term "alkylcarbonyloxyalkyl," as used herein is a broad term and is used in its ordinary sense, including, without limitation, to refer to an alkyl substituted with a —C(=O)Oalkyl group or a —OC(=O)alkyl group.

The term "alkyloxyalkyl," as used herein is a broad term and is used in its ordinary sense, including, without limitation, to refer to an alkyl substituted with an —O-alkyl group.

The term "alkylthioalkyl," as used herein is a broad term and is used in its ordinary sense, including, without limitation, to refer to an alkyl substituted with a —S-alkyl group.

The term "mono- or di(alkyl)amino," as used herein is a broad term and is used in its ordinary sense, including, without limitation, to refer to an amino substituted with one alkyl or with two alkyls, respectively.

The term "mono- or di(alkyl)aminoalkyl," as used herein is a broad term and is used in its ordinary sense, including, without limitation, to refer to an alkyl substituted with a mono- or di(alkyl)amino.

The following numbering schemes are used in the context of preferred embodiments:

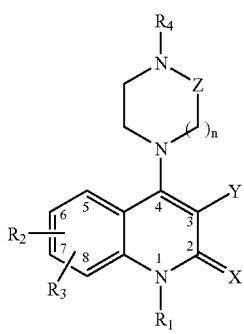

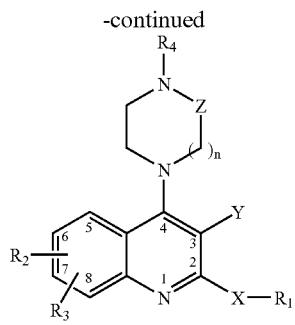

Depending upon the Z moiety, representative compounds of preferred embodiments include the following structure (II) when Z is methylene (—CH$_2$—) and structure (III) when Z is carbonyl (—C(=O)—):

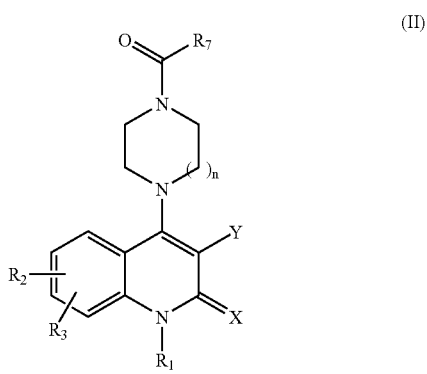

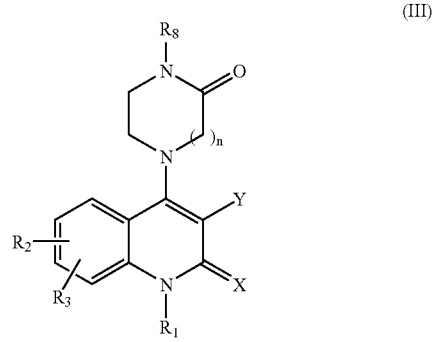

In further embodiments, n is 0, 1, or 2 as represented by structures (IV), (V) and (VI), respectively:

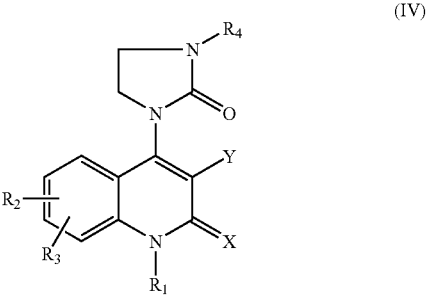

-continued
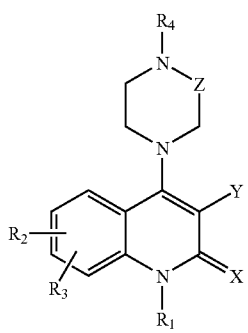
(V)
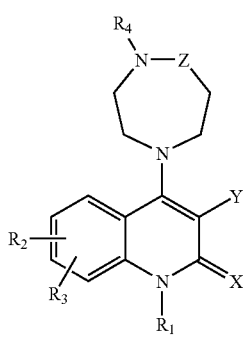
(VI)
In still further embodiments, compounds of preferred embodiments have the following structure (VII) when X is oxygen and structure (VIII) when X is sulfur:
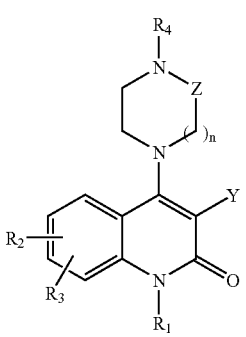
(VII)
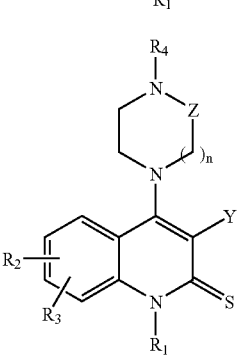
(VIII)
Depending upon the Y group, compounds of preferred embodiments have the following structures (IX) through (XIII):
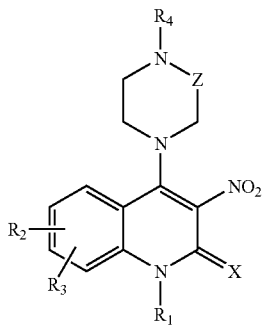
(IX)
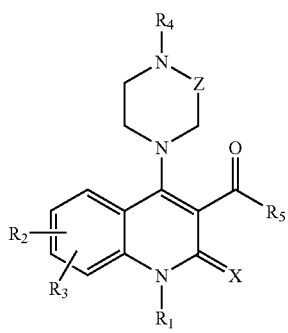
(X)
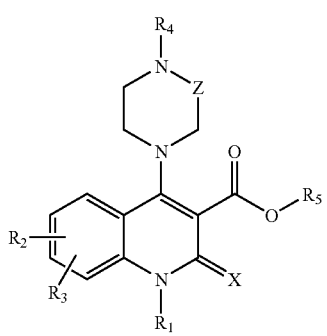
(XI)
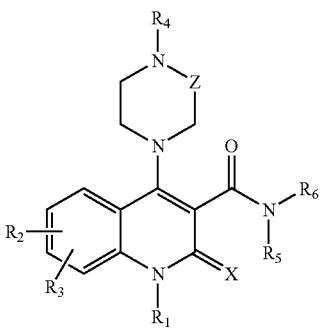
(XII)
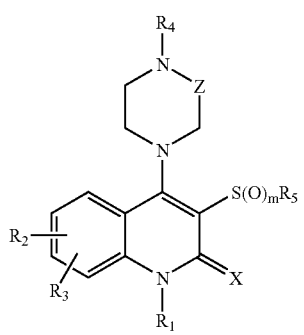
(XIII)

The compounds of preferred embodiments may generally be employed as the free acid or free base. Alternatively, the compounds of preferred embodiments may preferably be in the form of acid or base addition salts. Acid addition salts of the free base amino compounds of preferred embodiments may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts of the free acid may similarly be prepared by methods well known in the art, and may be formed from suitable bases, such as cations chosen from the alkali and alkaline earth metals (e.g., lithium, sodium, potassium, magnesium, barium or calcium) as well as the ammonium cation. The term "pharmaceutically acceptable salt" of structure (Ia) or (Ib) is intended to encompass any and all acceptable salt forms.

The compounds of structure (Ia) and (Ib) may be made according to the organic synthesis techniques known to those skilled in this field, as well as by the representative methods set forth in Example 1. In general, compounds of structure (Ia) may be made according to the following Reaction Schemes.

Reaction Scheme 1

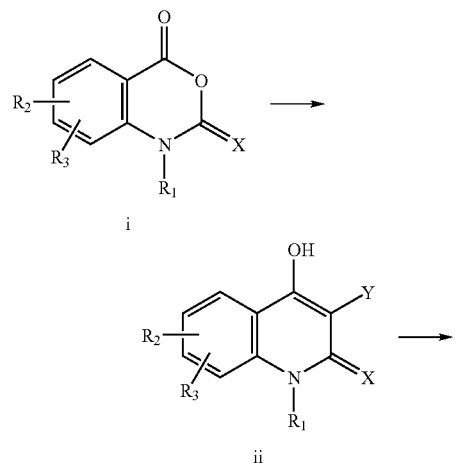

In general, chloro intermediates of structure iii may be prepared from the corresponding alcohol ii by known techniques. The alcohol intermediate may, in turn, be prepared from starting material i by reaction with appropriate agents. Representative reactants and conditions are set forth in Example 1.

Reaction Scheme 2

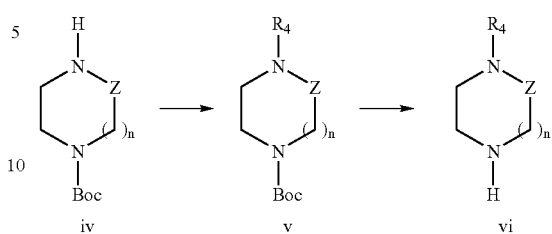

N-substituted piperazines of structure vi may be prepared by deprotection of protected intermediate v (in this case, protected with N-tert-butyloxycarbonyl or "Boc" for purpose of illustration). The protected intermediate may be made from the N-protected piperazine iv by addition of the desired $R_4$ group.

Reaction Scheme 3

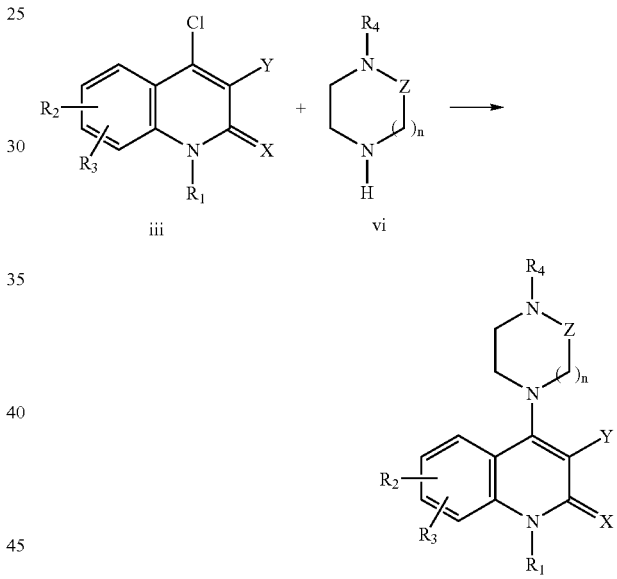

Intermediate iii from Reaction Scheme 1 may be reacted with intermediate vi from Reaction Scheme 3 to give compounds of preferred embodiments having structure (Ia).

Reaction Scheme 4

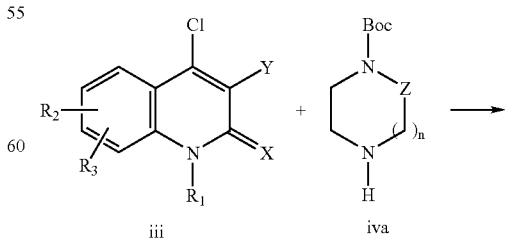

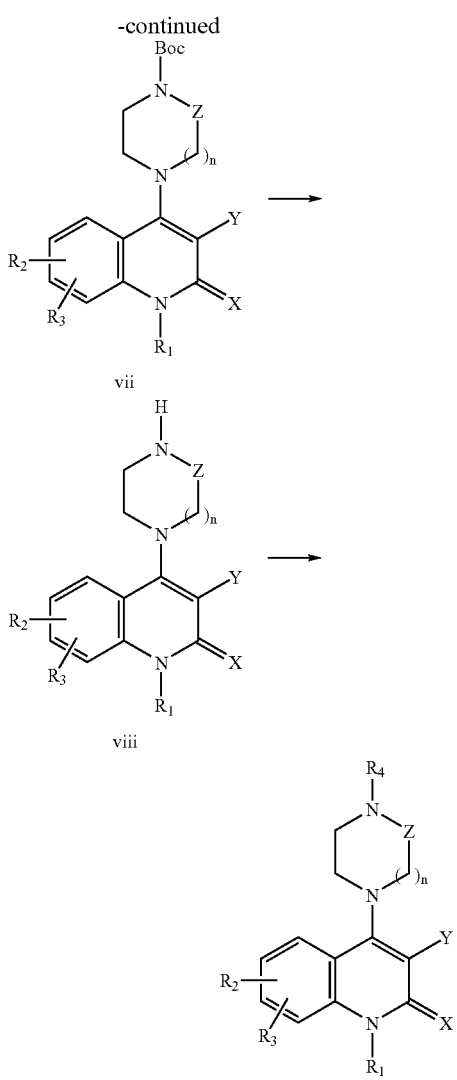

Alternatively, intermediate iii of Reaction Scheme 1 may be reacted with protected intermediate iva, to yield the protected reaction product vii. This protected reaction product may then be deprotected to yield intermediate viii, followed by addition of the desired $R_4$ group to give compounds of preferred embodiments having structure (Ia).

MIF as a Drug Target

Macrophage migration inhibitory factor (MIF) may be well suited for analysis as a drug target as its activity has been implicated in a variety of pathophysiological conditions. For instance, MIF has been shown to be a significant mediator in both inflammatory responses and cellular proliferation. In this regard, MIF has been shown to play roles as a cytokine, a pituitary hormone, as glucocorticoid-induced immunomodulator, and just recently as a neuroimmunomodulator and in neuronal function. Takahashi et al., *Mol. Med.* 4:707–714, 1998; Bucala, *Ann. N.Y. Acad. Sci.* 840:74–82, 1998; Bacher et al., *Mol. Med.* 4(4):217–230, 1998. Further, it has been recently demonstrated that anti-MIF antibodies have a variety of uses, notably decreased tumor growth, along with an observed reduction in angiogenesis. Ogawa et al., *Cytokine* 12(4):309–314, 2000; Metz and Bucala (supra). Accordingly, small molecules that can inhibit MIF have significant value in the treatment of inflammatory responses, reduction of angiogenesis, viral infection, bacterial infection, treatment of cancer (specifically tumorigenesis and apoptosis), treatment of graft versus host disease and associated tissue rejection. A MIF inhibitor may be particularly useful in a variety of immune related responses, tumor growth, glomerulonephritis, inflammation, malarial anemia, septic shock, tumor associated angiogenesis, vitreoretinopathy, psoriasis, graft versus host disease (tissue rejection), atopic dermatitis, rheumatoid arthritis, inflammatory bowel disease, inflammatory lung disorders, otitis media, Crohn's disease, acute respiratory distress syndrome, delayed-type hypersensitivity. A MIF inhibitor may also be useful in the treatment of stress and glucocorticoid function disorders, e.g., counter regulation of glucocorticoid action; or overriding of glucocorticoid mediated suppression of arachidonate release (Cys-60 based catalytic MIF oxidoreductase activity or JAB1/CSNS-MIF-interaction based mechanism).

One example of the utility of a MIF inhibitor may be evidenced by the fact that following endotoxin exposure detectable serum concentrations of MIF gradually increase during the acute phase (1–8 hours), peak at 8 hours and persist during the post-acute phase (>8 hours) for up to 20 hours. While not limited to any theory of operation, MIF may likely be produced by activated T-cells and macrophages during the proinflammatory stage of endotoxin-induced shock, e.g., as part of the localized response to infection. Once released by a pro-inflammatory stimulus, e.g., low concentrations of LPS, or by TNF-α and IFN-γ, macrophage-derived MIF may be the probable source of MIF produced during the acute phase of endotoxic shock. Both the pituitary, which releases MIF in response to LPS, and macrophages are the probable source of MIF in the post-acute phase of endotoxic shock, when the infection is no longer confined to a localized site. See, e.g., U.S. Pat. No. 6,080,407, incorporated herein by reference in its entirety and describing these results with anti-MIF antibodies.

As demonstrated herein, inhibitors of preferred embodiments inhibit lethality in mice following LPS challenge and likely attenuate IL-1β and TNF-α levels. Accordingly, a variety of inflammatory conditions may be amenable to treatment with a MIF inhibitor. In this regard, among other advantages, the inhibition of MIF activity and/or release may be employed to treat inflammatory response and shock. Beneficial effects may be achieved by intervention at both early and late stages of the shock response. In this respect, while not limited to any theory or mechanism responsible for the protective effect of MIF inhibition, anti-MIF studies have demonstrated that introduction of anti-MIF antibodies is associated with an appreciable (up to 35–40%) reduction in circulating serum TNF-α levels. This reduction is consistent with the TNF-α-inducing activity of MIF on macrophages in vitro, and suggests that MIF may be responsible, in part, for the extremely high peak in serum TNF-α level that occurs 1–2 hours after endotoxin administration despite the fact that MIF cannot be detected in the circulation at this time. Thus, MIF inhibition therapy may be beneficial at the early stages of the inflammatory response.

MIF also plays a role during the post-acute stage of the shock response, and therefore, offers an opportunity to intervene at late stages where other treatments, such as anti-TNF-α therapy, are ineffective. Inhibition of MIF can protect against lethal shock in animals challenged with high concentrations of endotoxin (i.e., concentrations that induce release of pituitary MIF into the circulation), and in animals challenged with TNF-α. Accordingly, the ability to inhibit MIF and protect animals challenged with TNF indicates that neutralization of MIF during the later, post-acute phase of septic shock may be efficacious.

As evidenced herein, TNF-α and IL-1β levels are correlated at least in some instances to MIF levels. Accordingly, an anti-MIF small molecule may be useful in a variety of TNF-α and/or IL-1β associated disease states including transplant rejection, immune-mediated and inflammatory elements of CNS disease (e.g., Alzheimer's, Parkinson's, multiple sclerosis, etc.), muscular dystrophy, diseases of hemostasis (e.g., coagulopathy, veno occlusive diseases, etc.), allergic neuritis, granuloma, diabetes, graft versus host disease, chronic renal damage, alopecia (hair loss), acute pancreatitis, joint disease, congestive heart failure, cardiovascular disease (restenosis, atherosclerosis), joint disease, and osteoarthritis.

Further, additional evidence in the art has indicated that steroids while potent inhibitors of cytokine production actually increase MIF expression. Yang et al., *Mol. Med.* 4(6): 413–424, 1998; Mitchell et al., *J. Biol. Chem.* 274(25): 18100–18106, 1999; Calandra and Bucala, *Crit. Rev. Immunol.* 17(1):77–88, 1997; Bucala, *FASEB J.* 10(14): 1607–1613, 1996. Accordingly, it may be of particular utility to utilize MIF inhibitors in combination with steroidal therapy for the treatment of cytokine mediated pathophysiological conditions, such as inflammation, shock, and other cytokine-mediated pathological states, particularly in chronic inflammatory states such as rheumatoid arthritis. Such combination therapy may be beneficial even subsequent to the onset of pathogenic or other inflammatory responses. For example, in the clinical setting, the administration of steroids subsequent to the onset of septic shock symptoms has proven of little benefit. See Bone et al., *N. Engl. J. Med.* 317: 653–658, 1987; Spring et al., *N. Engl. J. Med.* 311: 1137–1141, 1984. Combination steroids/MIF inhibition therapy may be employed to overcome this obstacle. Further, one of skill in the art may understand that such therapies may be tailored to inhibit MIF release and/or activity locally and/or systemically.

Assays

The effectiveness of a compound as an inhibitor of MIF may be determined by various assay methods. Suitable inhibitors of preferred embodiments are capable of decreasing one or more activities associated with MIF and/or MIF export. A compound of structure (Ia) or (Ib) or any other structure may be assessed for activity as an inhibitor of MIF by one or more generally accepted assays for this purpose, including (but not limited to) the assays described below.

The assays may generally be divided into three categories, those being, assays which monitor export; those which monitor effector or small molecule binding, and those that monitor MIF activity. However, it should be noted that combinations of these assays are within the scope of the present application. Surprisingly, it appears that epitope mapping of MIF acts as surrogate for biological activity. For example, in one assay, the presence of a candidate inhibitor blocks the detection of export of MIF from cells (e.g., THP-1 cells) measured using a monoclonal antibody such as that commercially available from R&D systems (Minneapolis, Minn.) whereas a polyclonal antibody demonstrates that MIF is present. Further, cellular based or in vitro assays may be employed to demonstrate that these potential inhibitors inhibit MIF activity. In an alternative, these two assays (i.e., binding and activity assays) may be combined into a singular assay which detects binding of a test compound (e.g., the ability to displace monoclonal antibodies or inhibit their binding) while also affecting MIF activity. Such assays include combining an ELISA type assay (or similar binding assay) with a MIF tautomerism assay or similar functional assay. As one of ordinary skill in the art may readily recognize, the exact assay employed is irrelevant, provided it is able to detect the ability of the compound of interest to bind MIF. In addition, the assay preferably detects the ability of the compound to inhibit a MIF activity because it selects for compounds that interact with biologically active MIF and not inactive MIF.

It should also be understood that compounds demonstrating the ability to inhibit monoclonal antibody binding to biologically active and not inactive MIF (e.g., small molecule inhibited), necessarily indicate the presence of a compound (e.g., a small molecule) that is interacting with MIF either in a fashion which changes the conformation of MIF or blocks an epitope necessary for antibody binding. In other embodiments, MIF inhibitory activity may also be recognized as a consequence of interfering with the formation of a polypeptide complex that includes MIF; disturbing such a complex may result in a conformational change inhibiting detection. Accordingly, the use of assays that monitor conformational changes in MIF, are advantageous when employed either in addition to assays measuring competition between compounds, such as small molecules with mAb or as a replacement of such an assay. A variety of such assays are known in the art and include, calorimetry, circular-dichroism, fluorescence energy transfer, light-scattering, nuclear magnetic resonance (NMR), surface plasmon resonance, scintillation proximity assays (see U.S. Pat. No. 5,246,869), and the like. See also WO02/07720-A1 and WO97/29635-A1. Accordingly, one of skill in the art may recognize that any assay that indicates binding and preferably conformational change or placement near the active site of MIF may be utilized. Descriptions of several of the more complicated proximity assays and conformational assays are set forth below, this discussion is merely exemplary and in no way should be construed as limiting to the type of techniques that may be utilized in preferred embodiments.

In one example, circular dichroism may be utilized to determine candidate inhibitor binding. Circular dichroism (CD) is based in part on the fact that most biological protein macromolecules are made up of asymmetric monomer units, L-amino acids, so that they all possess the attribute of optical activity. Additionally, rigid structures like DNA or an alpha helical polypeptide have optical properties that can be measured using the appropriate spectroscopic system. In fact, large changes in an easily measured spectroscopic parameter can provide selective means to identify conformational states and changes in conformational states under various circumstances, and sometimes to observe the perturbation of single groups in or attached to the macromolecule. Further, CD analysis has been frequently employed to probe the interactions of various macromolecules with small molecules and ligands. See Durand et al., *Eur. Biophys. J.* 27(2):147–151, 1998; Kleifeld et al., *Biochem* 39(26):7702–7711, 2000; Bianchi et al., *Biochem* 38(42): 13844–13852, 1999; Sarver et al., *Biochim Biophys Acta* 1434(2):304–316, 1999.

The Pasteur principle states that an optically active molecule must be asymmetric; that is, the molecule and its mirror image cannot be superimposed. Plane polarized light is a combination of left circularly polarized light and right circularly polarized light traveling in phase. The interaction of this light with an asymmetric molecule results in a preferential interaction of one circularly polarized component which, in an absorption region, is seen as a differential absorption (i.e., a dichroism). See Urry, D. W., Spectroscopic Approaches to Biomolecular Conformation, American Medical Association Press, Chicago, Ill., pp. 33–120 (1969); Berova and Woody, Circular Dichroism: Principles and Applications, John Wiley & Sons, N.Y., (2000).

Circular dichroism, then, is an absorptive phenomenon that results when a chromophore interacts with plane polarized light at a specific wavelength. The absorption band can be either negative or positive depending on the differential absorption of the right and left circularly polarized components for that chromophore. Unlike optical rotatory dispersion (ORD) that measures the contributions of background and the chromophore of interest many millimicrons from the region of actual light interaction, CD offers the advantage of measuring optical events at the wavelength at which the event takes place. Circular dichroism, then, is specific to the electronic transition of the chromophore. See Berova and Woody, Circular Dichroism: Principles and Applications, John Wiley & Sons, N.Y., (2000).

Application of circular dichroism to solutions of macromolecules has resulted in the ability to identify conformation states (Berova and Woody, Circular Dichroism: Principles and Applications, John Wiley & Sons, N.Y., (2000)). The technique can distinguish random coil, alpha helix, and beta chain conformation states of macromolecules. In proteins, alpha helical fibrous proteins show absorption curves closely resembling those of alpha helical polypeptides, but in globular proteins of known structure, like lysozyme and ribonuclease, the helical structures are in rather poor agreement with X-ray crystallography work. A further source of difficulty in globular proteins is the prevalence of aromatic chromophores on the molecules around 280 nm. An interesting example of helical changes has been demonstrated using myoglobin and apomyoglobin. After removing the prosthetic group heme, the apoprotein remaining has a residual circular dichroic ellipticity reduced by 25%. This loss of helix is attributable to an uncoiling of 10–15 residues in the molecule. Other non-peptide, optically active chromophores include tyrosine, tryptophan, phenylalanine, and cysteine when located in the primary amino acid sequence of a macromolecule. Examples of non-peptide ellipticities include the disulfide transition in ribonuclease and the cysteine transitions of insulin.

Accordingly, circular dichroism may be employed to screen candidate inhibitors for the ability to affect the conformation of MIF.

In certain embodiments provided herein, MIF-binding agent or inhibitor complex formation may be determined by detecting the presence of a complex including MIF and a detectably labeled binding agent. As described in greater detail below, fluorescence energy signal detection, for example by fluorescence polarization, provides determination of signal levels that represent formation of a MIF-binding agent molecular complex. Accordingly, and as provided herein, fluorescence energy signal-based comparison of MIF-binding agent complex formation in the absence and in the presence of a candidate inhibitor provides a method for identifying whether the agent alters the interaction between MIF and the binding agent. For example, the binding agent may be a MIF substrate, an anti-MIF antibody, or a known inhibitor, while the candidate inhibitor may be the compound to be tested or vice versa.

As noted above, certain preferred embodiments also pertain in part to fluorescence energy signal-based determination of MIF-binding agent complex formation. Fluorescence energy signal detection may be, for example, by fluorescence polarization or by fluorescence resonance energy transfer, or by other fluorescence methods known in the art.

As an example of certain other embodiments, the MIF polypeptide may be labeled as well as the candidate inhibitor and may comprise an energy transfer molecule donor-acceptor pair, and the level of fluorescence resonance energy transfer from energy donor to energy acceptor is determined.

In certain embodiments the candidate inhibitor and/or binding agent is detectably labeled, and in particularly preferred embodiments the candidate inhibitor and/or binding agent is capable of generating a fluorescence energy signal. The candidate inhibitor and/or binding agent can be detectably labeled by covalently or non-covalently attaching a suitable reporter molecule or moiety, for example any of various fluorescent materials (e.g., a fluorophore) selected according to the particular fluorescence energy technique to be employed, as known in the art and based upon the methods described herein. Fluorescent reporter moieties and methods for as provided herein can be found, for example in Haugland (1996 *Handbook of Fluorescent Probes and Research Chemicals-Sixth Ed.*, Molecular Probes, Eugene, Oreg.; 1999 *Handbook of Fluorescent Probes and Research Chemicals-Seventh Ed.*, Molecular Probes, Eugene, Oreg., http://www.probes.com/lit/) and in references cited therein. Particularly preferred for use as such a fluorophore in preferred embodiments are fluorescein, rhodamine, Texas Red, AlexaFluor-594, AlexaFluor-488, Oregon Green, BODIPY-FL, and Cy-5. However, any suitable fluorophore may be employed, and in certain embodiments fluorophores other than those listed may be preferred.

As provided herein, a fluorescence energy signal includes any fluorescence emission, excitation, energy transfer, quenching, or dequenching event or the like. Typically a fluorescence energy signal may be mediated by a fluorescent detectably labeled candidate inhibitor and/or binding agent in response to light of an appropriate wavelength. Briefly, and without wishing to be bound by theory, generation of a fluorescence energy signal generally involves excitation of a fluorophore by an appropriate energy source (e.g., light of a suitable wavelength for the selected fluorescent reporter moiety, or fluorophore) that transiently raises the energy state of the fluorophore from a ground state to an excited state. The excited fluorophore in turn emits energy in the form of detectable light typically having a different (e.g., usually longer) wavelength from that preferred for excitation, and in so doing returns to its energetic ground state. The methods of preferred embodiments contemplate the use of any fluorescence energy signal, depending on the particular fluorophore, substrate labeling method and detection instrumentation, which may be selected readily and without undue experimentation according to criteria with which those having ordinary skill in the art are familiar.

In certain embodiments, the fluorescence energy signal is a fluorescence polarization (FP) signal. In certain other embodiments, the fluorescence energy signal may be a fluorescence resonance energy transfer (FRET) signal. In certain other preferred embodiments the fluorescence energy signal can be a fluorescence quenching (FQ) signal or a fluorescence resonance spectroscopy (FRS) signal. (For details regarding FP, FRET, FQ and FRS, see, for example, WO97/39326; WO99/29894; Haugland, *Handbook of Fluorescent Probes and Research Chemicals*-6th Ed., 1996, Molecular Probes, Inc., Eugene, Oreg., p. 456; and references cited therein.)

FP, a measurement of the average angular displacement (due to molecular rotational diffusion) of a fluorophore that occurs between its absorption of a photon from an energy source and its subsequent emission of a photon, depends on the extent and rate of rotational diffusion during the excited state of the fluorophore, on molecular size and shape, on solution viscosity and on solution temperature (Perrin, 1926 J. Phys. Rad. 1:390). When viscosity and temperature are held constant, FP is directly related to the apparent molecular volume or size of the fluorophore. The polarization value is a ratio of fluorescence intensities measured in distinct planes (e.g., vertical and horizontal) and is therefore a dimensionless quantity that is unaffected by the intensity of the fluorophore. Low molecular weight fluorophores, such as the detectably labeled candidate inhibitor and/or binding agent provided herein, are capable of rapid molecular rotation in solution (i.e., low anisotropy) and thus give rise to low fluorescence polarization readings. When complexed to a higher molecular weight molecule such as MIF as provided herein, however, the fluorophore moiety of the substrate associates with a complex that exhibits relatively slow molecular rotation in solution (i.e., high anisotropy), resulting in higher fluorescence polarization readings.

This difference in the polarization value of free detectably labeled candidate inhibitor and/or binding agent compared to the polarization value of MIF:candidate inhibitor and/or binding agent complex may be employed to determine the ratio of complexed (e.g., bound) to free. This difference may also be employed to detect the influence of a candidate agent (i.e., candidate inhibitor) on the formation of such complexes and/or on the stability of a pre-formed complex, for example by comparing FP detected in the absence of an agent to FP detected in the presence of the agent. FP measurements can be performed without separation of reaction components.

As noted above, one aspect of a preferred embodiment utilizes the binding or displacement of a monoclonal antibody, known inhibitor, or other binding agent and/or complex formation of the candidate inhibitor with MIF to provide a method of identifying an inhibitor that alters the activity of MIF. Surprisingly, the inhibitors of preferred embodiments were identified in such a nonconventional manner. In this regard, a class of compounds demonstrated the ability to inhibit/decrease monoclonal antibody binding to a biologically active MIF that is naturally produced from cells while not affecting the antibody's ability to recognize inactive (recombinant) MIF (as is available from commercial sources) and also demonstrated pronounced modulation of MIF activity in vivo. Accordingly, antibody binding may be preferred as a surrogate for enzyme activity, thus eliminating the need to run expensive and complex enzymatic assays on each candidate compound. As those of ordinary skill in the art readily appreciate, the ability to avoid enzymatic assays leads to an assay that may be extremely well suited for high throughput use.

Further, as those of ordinary skill in the art can readily appreciate, such an assay may be employed outside of the MIF context and wherever enzyme or biological activity can be replaced by a binding assay. For example, any enzyme or other polypeptide whose biologically active form is recognized by a monoclonal antibody that does not recognize the inactive form (e.g., small molecule inhibited form) may be preferred. Within the context of an enzyme, the monoclonal antibody may bind the active site, but be displaced by a small molecule. Thus, any small molecule that displaces the antibody may be a strong lead as a potential enzyme inhibitor. As those of skill in the art appreciate, the antibody may recognize an epitope that changes conformation depending on the active state of the enzyme, and that binding of a small molecule such that it precludes antibody binding to this epitope may also act as a surrogate for enzymatic activity even though the epitope may not be at the active site. Accordingly, the type of assay utilized herein may be expanded to be employed with essentially any polypeptide wherein antibody displacement is predictive of activity loss. Thus, in its simplest form any polypeptide, e.g., enzyme and its associated neutralizing antibody may be employed to screen for small molecules that displace this antibody, thereby identifying likely inhibitors.

A MIF-binding agent/candidate inhibitor complex may be identified by any of a variety of techniques known in the art for demonstrating an intermolecular interaction between MIF and another molecule as described above, for example, co-purification, co-precipitation, co-immunoprecipitation, radiometric or fluorimetric assays, western immunoblot analyses, affinity capture including affinity techniques such as solid-phase ligand-counterligand sorbent techniques, affinity chromatography and surface affinity plasmon resonance, NMR, and the like (see, e.g., U.S. Pat. No. 5,352,660). Determination of the presence of such a complex may employ antibodies, including monoclonal, polyclonal, chimeric and single-chain antibodies, and the like, that specifically bind to MIF or the binding agent.

Labeled MIF and/or labeled binding agents/candidate inhibitors can also be employed to detect the presence of a complex. The molecule of interest can be labeled by covalently or non-covalently attaching a suitable reporter molecule or moiety, for example any of various enzymes, fluorescent materials, luminescent materials, and radioactive materials. Examples of suitable enzymes include, but are not limited to, horseradish peroxidase, alkaline phosphatase, β-galactosidase, and acetylcholinesterase. Examples of suitable fluorescent materials include, but are not limited to, umbelliferone, fluorescein, fluorescein isothiocyanate, rhodamine, dichlorotriazinylamine fluorescein, dansyl chloride, phycoerythrin, Texas Red, AlexaFluor-594, AlexaFluor-488, Oregon Green, BODIPY-FL and Cy-5. Appropriate luminescent materials include, but are not limited to, luminol and suitable radioactive materials include radioactive phosphorus [$^{32}$P], iodine [$^{125}$I or $^{131}$I] or tritium [$^{3}$H].

MIF and the binding agent and/or the candidate inhibitor are combined under conditions and for a time sufficient to permit formation of an intermolecular complex between the components. Suitable conditions for formation of such complexes are known in the art and can be readily determined based on teachings provided herein, including solution conditions and methods for detecting the presence of a complex and/or for detecting free substrate in solution.

Association of a detectably labeled binding agent(s) and/or candidate inhibitor(s) in a complex with MIF, and/or binding agent or candidate inhibitor that is not part of such a complex, may be identified according to a preferred embodiment by detection of a fluorescence energy signal generated by the substrate. Typically, an energy source for detecting a fluorescence energy signal is selected according to criteria with which those having ordinary skill in the art are familiar, depending on the fluorescent reporter moiety with which the substrate is labeled. The test solution, containing (a) MIF and (b) the detectably labeled binding agent and/or candidate inhibitor, is exposed to the energy source to generate a fluorescence energy signal, which is detected by any of a variety of well known instruments and identified according to the particular fluorescence energy signal. In preferred embodiments, the fluorescence energy signal is a fluorescence polarization signal that can be detected using a spectrofluorimeter equipped with polarizing filters. In particularly preferred embodiments the fluorescence polarization assay is performed simultaneously in each of a plurality of reaction chambers that can be read using an LJL CRI- TERION™ Analyst (LJL Biosystems, Sunnyvale, Calif.) plate reader, for example, to provide a high throughput screen (HTS) having varied reaction components or conditions among the various reaction chambers. Examples of other suitable instruments for obtaining fluorescence polarization readings include the POLARSTAR™ (BMG Lab Technologies, Offenburg, Germany), BEACON™ (Panvera, Inc., Madison, Wis.) and the POLARION™ (Tecan, Inc., Research Triangle Park, N.C.) devices.

Determination of the presence of a complex that has formed between MIF and a binding agent and/or a candidate inhibitor may be performed by a variety of methods, as noted above, including fluorescence energy signal methodology as provided herein and as known in the art. Such methodologies may include, by way of illustration and not limitation FP, FRET, FQ, other fluorimetric assays, co-purification, co-precipitation, co-immunoprecipitation, radiometric, western immunoblot analyses, affinity capture including affinity techniques such as solid-phase ligand-counterligand sorbent techniques, affinity chromatography and surface affinity plasmon resonance, circular dichroism, and the like. For these and other useful affinity techniques, see, for example, Scopes, R. K., *Protein Purification: Principles and Practice,* 1987, Springer-Verlag, NY; Weir, D. M., *Handbook of Experimental Immunology,* 1986, Blackwell Scientific, Boston; and Hermanson, G. T. et al., *Immobilized Affinity Ligand Techniques,* 1992, Academic Press, Inc., California; which are hereby incorporated by reference in their entireties, for details regarding techniques for isolating and characterizing complexes, including affinity techniques. In various embodiments, MIF may interact with a binding agent and/or candidate inhibitor via specific binding if MIF binds the binding agent and/or candidate inhibitor with a $K_a$ of greater than or equal to about $10^4$ $M^{-1}$, preferably of greater than or equal to about $10^5$ $M^{-1}$, more preferably of greater than or equal to about $10^6$ $M^{-1}$ and still more preferably of greater than or equal to about $10^7$ $M^{-1}$ to $10^{11}$ $M^{-1}$. Affinities of binding partners can be readily calculated from data generated according to the fluorescence energy signal methodologies described above and using conventional data handling techniques, for example, those described by Scatchard et al., *Ann. N.Y. Acad. Sci.* 51:660 (1949).

For example, in various embodiments where the fluorescence energy signal is a fluorescence polarization signal, fluorescence anisotropy (in polarized light) of the free detectably labeled candidate inhibitor and/or binding agent can be determined in the absence of MIF, and fluorescence anisotropy (in polarized light) of the fully bound substrate can be determined in the presence of a titrated amount of MIF. Fluorescence anisotropy in polarized light varies as a function of the amount of rotational motion that the labeled candidate inhibitor and/or binding agent undergoes during the lifetime of the excited state of the fluorophore, such that the anisotropies of free and fully bound candidate inhibitor and/or binding agent can be usefully employed to determine the fraction of candidate inhibitor and/or binding agent bound to MIF in a given set of experimental conditions, for instance, those wherein a candidate agent is present (see, e.g., Lundblad et al., 1996 *Molec. Endocrinol.* 10:607; Dandliker et al., 1971 *Immunochem.* 7:799; Collett, E., *Polarized Light: Fundamentals and Applications,* 1993 Marcel Dekker, New York).

Certain of the preferred embodiments pertain in part to the use of intermolecular energy transfer to monitor MIF-binding agent complex formation and stability and/or MIF-candidate inhibitor complex formation.

Energy transfer (ET) is generated from a resonance interaction between two molecules: an energy-contributing "donor" molecule and an energy-receiving "acceptor" molecule. Energy transfer can occur when (1) the emission spectrum of the donor overlaps the absorption spectrum of the acceptor and (2) the donor and the acceptor are within a certain distance (for example, less than about 10 nm) of one another. The efficiency of energy transfer is dictated largely by the proximity of the donor and acceptor, and decreases as a power of 6 with distance. Measurements of ET thus strongly reflect the proximity of the acceptor and donor compounds, and changes in ET sensitively reflect changes in the proximity of the compounds such as, for example, association or dissociation of the donor and acceptor.

It is therefore an aspect of a preferred embodiment to provide a method for assaying a candidate MIF inhibitor, in pertinent part, by contacting MIF or an MIF-binding agent complex including one or more ET donor and an ET acceptor molecules, exciting the ET donor to produce an excited ET donor molecule and detecting a signal generated by energy transfer from the ET donor to the ET acceptor. As also provided herein, the method can employ any suitable ET donor molecule and ET acceptor molecule that can function as a donor-acceptor pair.

In certain preferred embodiments, a detectable signal that is generated by energy transfer between ET donor and acceptor molecules results from fluorescence resonance energy transfer (FRET), as discussed above. FRET occurs within a molecule, or between two different types of molecules, when energy from an excited donor fluorophore is transferred directly to an acceptor fluorophore (for a review, see Wu et al., *Analytical Biochem.* 218:1–13, 1994).

In other aspects of preferred embodiments, the ability of a candidate inhibitor to effect MIF export is tested.

The first step of such an assay is performed to detect MIF extracellularly. For this assay, test cells expressing MIF are employed (e.g., THP-1 cells). Either the test cells may naturally produce the protein or produce it from a transfected expression vector. Test cells preferably normally express the protein, such that transfection merely increases expressed levels. Thus, for expression of MIF and IL-1, THP1 cells are preferred. When one is assaying virally-derived proteins, such as HIV tat, if the test cells do not "naturally" produce the protein, they may readily be transfected using an appropriate vector, so that the test cells express the desired protein, as those of skill in the art readily appreciate.

Following expression, MIF is detected by any one of a variety of well-known methods and procedures. Such methods include staining with antibodies in conjunction with flow cytometry, confocal microscopy, image analysis, immunoprecipitation of cell cytosol or medium, Western blot of cell medium, ELISA, 1- or 2-D gel analysis, HPLC, or bioassay. A convenient assay for initial screening is ELISA. MIF export may be confirmed by one of the other assays, preferably by immunoprecipitation of cell medium following metabolic labeling. Briefly, cells expressing MIF protein are pulse labeled for 15 minutes with $^{35}$S-methionine and/or $^{35}$S-cysteine in methionine and/or cysteine free medium and chased in medium supplemented with excess methionine and/or cysteine. Media fractions are collected and clarified by centrifugation, such as in a microfuge. Lysis buffer containing 1% NP-40, 0.5% deoxycholate (DOC), 20 mM Tris, pH 7.5, 5 mM EDTA, 2 mM EGTA, 10 nM PMSF, 10 ng/ml aprotinin, 10 ng/ml leupeptin, and 10 ng/ml pepstatin is added to the clarified medium. An antibody to MIF is added and following incubation in the cold, a precipitating second antibody or immunoglobulin binding protein, such as protein A-Sepharose® or GammaBind™-Sepharose®, is added for further incubation. In parallel, as a control, a cytosolic protein is monitored and an antibody to the cytosolic protein is preferred in immunoprecipitations. Immune complexes are pelleted and washed with ice-cold lysis buffer. Complexes are further washed with ice-cold IP buffer (0.15 M NaCl, 10 mM Na-phosphate, pH 7.2, 1% DOC, 1% NP-40, 0.1% SDS). Immune complexes are eluted directly into SDS-gel sample buffer and electrophoresed in SDS-PAGE. The gel is processed for fluorography, dried and exposed to X-ray film. Alternatively cells can be engineered to produced a MIF that is tagged with a reporter so that the presence of an active MIF can be through the surrogate activity of the reporter.

While not wishing to be bound to theory, it is believed that the present inhibitors function by interacting directly with the naturally produced MIF complex in such a fashion as to alter the protein's conformation enough to block its biological activity. This interaction can be mapped by X-ray crystallography of MIF-compound co-crystals to determine the exact site of interaction. One site localizes to the pocket that is responsible for the tautomerase activity of MIF.

Screening assays for inhibitors of MIF export varies according to the type of inhibitor and the nature of the activity that is being affected. Assays may be performed in vitro or in vivo. In general, in vitro assays are designed to evaluate MIF activity, or multimerization, and in vivo assays are designed to evaluate MIF activity, extracellular, and intracellular localization in a model cell or animal system. In any of the assays, a statistically significant increase or decrease compared to a proper control is indicative of enhancement or inhibition.

One in vitro assay can be performed by examining the effect of a candidate compound on the ability of MIF to inhibit macrophage migration. Briefly, human peripheral blood monocytes are preferred as indicator cells in an agarose-droplet assay system essentially as described by Weiser et al., *Cell. Immunol.* 90:167–178, 1985 and Harrington et al., *J. Immunol.* 110:752–759, 1973. Other assay systems of analyzing macrophage migration may also be employed. Such an assay is described by Hermanowski-Vosatka et al, Biochem. 38:12841–12849, 1999.

An alternative in vitro assay is designed to measure the ability of MIF to catalyze tautomerization of the D-isomer of dopachrome (see Rosengren et al., *Mol. Med.* 2:143–149, 1996; Winder et al., *J. Cell Sci.* 106:153–166, 1993; Aroca et al., *Biochem. J.* 277:393–397). Briefly, in this method, D-dopachrome is provided to MIF in the presence and absence of a candidate inhibitor and the ability to catalyze the tautomerization to 5,6-dihydroxyindole-2-carboxylic acid (DHICA) is monitored. However, use of methyl esters of D-dopachrome may be preferred in that a faster reaction rate is observed. Detection of the tautomerization can be performed by any one of a variety of standard methods.

In a similar assay, the ability of MIF to catalyze the tautomerization of phenylpyruvate may be tested (see Johnson et al., *Biochem.* 38(48):16024–16033, 1999). Briefly, in this method, typically ketonization of phenylpyruvate or (p-hydroxyphenyl)pyruvate is followed by spectroscopy. Further, product formation may be verified by treatment of these compounds with MIF and subsequent conversion to malate for $^1$H NMR analysis.

In vivo assays can be performed in cells transfected either transiently or stably with an expression vector containing a MIF nucleic acid molecule, such as those described herein. These cells are preferred to measure MIF activity (e.g., modulation of apoptosis, proliferation, etc.) or extracellular and intracellular localization in the presence or absence of a candidate compound. When assaying for apoptosis, a variety of cell analyses may be employed including, for example, dye staining and microscopy to examine nucleic acid fragmentation and porosity of the cells.

Other assays may be performed in model cell or animal systems, by providing to the system a recombinant or naturally occurring form of MIF or inducing endogenous MIF expression in the presence or absence of test compound, thereby determining a statistically significant increase or decrease in the pathology of that system. For example, LPS can be employed to induce a toxic shock response.

The assays briefly described herein may be employed to identify an inhibitor that is specific for MIF.

In any of the assays described herein, a test cell may express the MIF naturally (e.g., THP-1 cells) or following introduction of a recombinant DNA molecule encoding the protein. Transfection and transformation protocols are well known in the art and include $Ca_2PO_4$-mediated transfection, electroporation, infection with a viral vector, DEAE-dextran mediated transfection, and the like. As an alternative to the proteins described above, chimeric MIF proteins (i.e., fusion of MIF protein with another protein or protein fragment), or protein sequences engineered to lack a leader sequence may be employed. In a similar fashion, a fusion may be constructed to direct secretion, export, or cytosolic retention. Any and all of these sequences may be employed in a fusion construct with MIF to assist in assaying inhibitors. The host cell can also express MIF as a result of being diseased, infected with a virus, and the like. Secreted proteins that are exported by virtue of a leader sequence are well known and include, human chorionic gonadatropin (hCGα), growth hormone, hepatocyte growth factor, transferrin, nerve growth factor, vascular endothelial growth factor, ovalbumin, and insulin-like growth factor. Similarly, cytosolic proteins are well known and include, neomycin phosphotransferase, β-galactosidase, actin and other cytoskeletal proteins, and enzymes, such as protein kinase A or C. The most useful cytosolic or secreted proteins are those that are readily measured in a convenient assay, such as ELISA. The three proteins (leaderless, secreted, and cytosolic) may be co-expressed naturally, by co-transfection in the test cells, or transfected separately into separate host cells. Furthermore, for the assays described herein, cells may be stably transformed or express the protein transiently.

Immunoprecipitation is one such assay that may be employed to determine inhibition. Briefly, cells expressing MIF naturally or from an introduced vector construct are labeled with $^{35}$S-methionine and/or $^{35}$S-cysteine for a brief period of time, typically 15 minutes or longer, in methionine- and/or cysteine-free cell culture medium. Following pulse labeling, cells are washed with medium supplemented with excess unlabeled methionine and cysteine plus heparin if the leaderless protein is heparin binding. Cells are then cultured in the same chase medium for various periods of time. Candidate inhibitors or enhancers are added to cultures at various concentration. Culture supernatant is collected and clarified. Supernatants are incubated with anti-MIF immune serum or a monoclonal antibody, or with anti-tag antibody if a peptide tag is present, followed by a developing reagent such as *Staphylococcus aureus* Cowan strain I, protein A-Sepharose®, or Gamma-bind™ G-Sepharose®. Immune complexes are pelleted by centrifugation, washed in a buffer containing 1% NP-40 and 0.5% deoxycholate, EGTA, PMSF, aprotinin, leupeptin, and pepstatin. Precipitates are then washed in a buffer containing sodium phosphate pH 7.2, deoxycholate, NP-40, and SDS. Immune complexes are eluted into an SDS gel sample buffer and separated by SDS-PAGE. The gel is processed for fluorography, dried, and exposed to x-ray film.

Alternatively, ELISA may be preferred to detect and quantify the amount of MIF in cell supernatants. ELISA is preferred for detection in high throughput screening. Briefly, 96-well plates are coated with an anti-MIF antibody or anti-tag antibody, washed, and blocked with 2% BSA. Cell supernatant is then added to the wells. Following incubation and washing, a second antibody (e.g., to MIF) is added. The second antibody may be coupled to a label or detecting reagent, such as an enzyme or to biotin. Following further incubation, a developing reagent is added and the amount of MIF determined using an ELISA plate reader. The developing reagent is a substrate for the enzyme coupled to the second antibody (typically an anti-isotype antibody) or for the enzyme coupled to streptavidin. Suitable enzymes are well known in the art and include horseradish peroxidase, which acts upon a substrate (e.g., ABTS) resulting in a calorimetric reaction. It is recognized that rather than using a second antibody coupled to an enzyme, the anti-MIF antibody may be directly coupled to the horseradish peroxidase, or other equivalent detection reagent. If desired, cell supernatants may be concentrated to raise the detection level. Further, detection methods, such as ELISA and the like may be employed to monitor intracellular as well as extracellular levels of MIF. When intracellular levels are desired, a cell lysate is preferred. When extracellular levels are desired, media can be screened.

ELISA may also be readily adapted for screening multiple candidate inhibitors or enhancers with high throughput. Briefly, such an assay is conveniently cell based and performed in 96-well plates. Test cells that naturally or stably express MIF are plated at a level sufficient for expressed product detection, such as, about 20,000 cells/well. However, if the cells do not naturally express the protein, transient expression is achieved, such as by electroporation or $Ca_2PO_4$-mediated transfection. For electroporation, 100 µl of a mixture of cells (e.g., 150,000 cells/ml) and vector DNA (5 µg/ml) is dispensed into individual wells of a 96-well plate. The cells are electroporated using an apparatus with a 96-well electrode (e.g., ECM 600 Electroporation System, BTX, Genetronics, Inc.). Optimal conditions for electroporation are experimentally determined for the particular host cell type. Voltage, resistance, and pulse length are the typical parameters varied. Guidelines for optimizing electroporation may be obtained from manufacturers or found in protocol manuals, such as *Current Protocols in Molecular Biology* (Ausubel et al. (ed.), Wiley Interscience, 1987). Cells are diluted with an equal volume of medium and incubated for 48 hours. Electroporation may be performed on various cell types, including mammalian cells, yeast cells, bacteria, and the like. Following incubation, medium with or without inhibitor is added and cells are further incubated for 1–2 days. At this time, culture medium is harvested and the protein is assayed by any of the assays herein. Preferably, ELISA is employed to detect the protein. An initial concentration of 50 µM is tested. If this amount gives a statistically significant reduction of export or reduction of monoclonal Ab detection, the candidate inhibitor is further tested in a dose response.

Alternatively, concentrated supernatant may be electrophoresed on an SDS-PAGE gel and transferred to a solid support, such as nylon or nitrocellulose. MIF is then detected by an immunoblot (see Harlow, *Antibodies: A Laboratory Manual*, Cold Spring Harbor Laboratory, 1988), using an antibody to MIF containing an isotopic or non-isotopic reporter group. These reporter groups include, but are not limited to enzymes, cofactors, dyes, radioisotopes, luminescent molecules, fluorescent molecules, and biotin. Preferably, the reporter group is $^{125}I$ or horseradish peroxidase, which may be detected by incubation with 2,2'-azino-di-3-ethylbenzthiazoline sulfonic acid. These detection assays described above are readily adapted for use if MIF contains a peptide tag. In such case, the antibody binds to the peptide tag. Other assays include size or charge-based chromatography, including HPLC, and affinity chromatography.

Alternatively, a bioassay may be employed to quantify the amount of active MIF present in the cell medium. For example, the bioactivity of the MIF may be measured by a macrophage migration assay. Briefly, cells transfected with an expression vector containing MIF are cultured for approximately 30 hours, during which time a candidate inhibitor or enhancer is added. Following incubation, cells are transferred to a low serum medium for a further 16 hours of incubation. The medium is removed and clarified by centrifugation. A lysis buffer containing protease inhibitors is added to the medium or, in the alternative, cells are lysed and internal levels are determined as follows. Bioactivity of MIF is then measured by macrophage migration assay, isomerase activity, or a proliferation assay. A proliferation assay is performed by adding various amounts of the eluate to cultured quiescent 3T3 cells. Tritiated thymidine is added to the medium and TCA precipitable counts are measured approximately 24 hours later. Reduction of the vital dye MTT is an alternative way to measure proliferation. For a standard, purified recombinant human FGF-2 may be employed. Other functions may be assayed in other appropriate bioassays available in the art, such as CPS induced toxic shock, TSST-1 induced toxic shock, collagen induced arthritis, etc.

Other in vitro angiogenic assays include bioassays that measure proliferation of endothelial cells within collagen gel (Goto et al., *Lab Invest.* 69:508, 1993), co-culture of brain capillary endothelial cells on collagen gels separated by a chamber from cells exporting the MIF protein (Okamure et al., *B.B.R.C.* 186:1471, 1992; Abe et al., *J. Clin. Invest.* 92:54, 1993), or a cell migration assay (see Warren et al., *J. Clin. Invest.* 95:1789, 1995).

Production of Antibodies

The term "antibody," as used herein is a broad term and is used in its ordinary sense, including, without limitation, to refer to polyclonal, monospecific, and monoclonal antibodies, as well as antigen binding fragments of such antibodies. With regard to an anti-MIF/target antibody of preferred embodiments, the term "antigen" as used herein is a broad term and is used in its ordinary sense, including, without limitation, to refer to a macrophage migration inhibitory factor polypeptide or a target polypeptide, variant, or functional fragment thereof. An anti-MIF/target antibody, or antigen binding fragment of such an antibody, may be characterized as having specific binding activity for the target polypeptide or epitope thereof of at least about $1\times10^5$ $M^{-1}$, generally at least about $1\times10^6$ $M^{-1}$, and preferably at least about $1\times10^8$ $M^{-1}$. Fab, F(ab')$_2$, Fd and Fv fragments of an anti-MIF/target antibody, which retain specific binding activity for a MIF/target polypeptide-specific epitope, are encompassed within preferred embodiments. Of particular interest are those antibodies that bind active polypeptides and are displaced upon binding of an inhibitory small molecule. Those of skill in the art readily appreciate that such displacement can be the result of a conformational change, thus changing the nature of the epitope, competitive binding with the epitope, or steric exclusion of the antibody from its epitope. In one example, the active site of an enzyme may be the epitope for a particular antibody and upon binding of a small molecule at or near the active site, immunoreactivity of the antibody is lost, thereby allowing the use of loss of immunoreactivity with an antibody as a surrogate marker for enzyme activity In addition, the term "antibody" as used herein is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. Such non-naturally occurring antibodies may be constructed using solid phase peptide synthesis, may be produced recombinantly, or may be obtained, for example, by screening combinatorial libraries including variable heavy chains and variable light chains (Huse et al., *Science* 246:1275–1281 (1989)). These and other methods of making, for example, chimeric, humanized, CDR-grafted, single chain, and bifunctional antibodies are well known in the art (Winter and Harris, *Immunol. Today* 14:243–246 (1993); Ward et al., *Nature* 341:544–546 (1989); Harlow and Lane, *Antibodies: A Laboratory Manual*, Cold Spring Harbor Laboratory, New York (1992); Borrabeck, *Antibody Engineering*, 2d ed., Oxford Univ. Press (1995); Hilyard et al., *Protein Engineering: A practical approach*, IRL Press (1992)).

In certain preferred embodiments, an anti-MIF/target antibody may be raised using as an immunogen such as, for example, an isolated peptide including the active site region of MIF or the target polypeptide, which can be prepared from natural sources or produced recombinantly, as described above, or an immunogenic fragment of a MIF/target polypeptide (e.g., immunogenic sequences including 8–30 or more contiguous amino acid sequences), including synthetic peptides, as described above. A non-immunogenic peptide portion of a MIF/target polypeptide can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (Harlow and Lane, supra, 1992).

Methods for raising polyclonal antibodies, for example, in a rabbit, goat, mouse, or other mammal, are well known in the art. In addition, monoclonal antibodies may be obtained using methods that are well known and routine in the art (Harlow and Lane, supra, 1992). For example, spleen cells from a target polypeptide-immunized mammal can be fused to an appropriate myeloma cell line such as SP/02 myeloma cells to produce hybridoma cells. Cloned hybridoma cell lines may be screened using a labeled target polypeptide or functional fragment thereof to identify clones that secrete target polypeptide monoclonal antibodies having the desired specificity. Hybridomas expressing target polypeptide monoclonal antibodies having a desirable specificity and affinity may be isolated and utilized as a continuous source of the antibodies, which are useful, for example, for preparing standardized kits. Similarly, a recombinant phage that expresses, for example, a single chain anti-target polypeptide also provides a monoclonal antibody that may be employed for preparing standardized kits.

Applications and Methods Utilizing Inhibitors of MIF

Inhibitors of MIF have a variety of applicable uses, as noted above. Candidate inhibitors of MIF may be isolated or procured from a variety of sources, such as bacteria, fungi, plants, parasites, libraries of chemicals (small molecules), peptides or peptide derivatives and the like. Further, one of skill in the art recognize that inhibition has occurred when a statistically significant variation from control levels is observed.

Given the various roles of MIF in pathology and homeostasis, inhibition of MIF activity or MIF extracellular localization may have a therapeutic effect. For example, recent studies have demonstrated that MIF is a mediator of endotoxemia, where anti-MIF antibodies fully protected mice from LPS-induced lethality. See Bernhagen et al., *Nature* 365:756–759, 1993; Calandra et al., *J. Exp. Med.* 179: 1895–1902, 1994; Bernhagen et al., *Trends Microbiol.* 2:198–201, 1994. Further, anti-MIF antibodies have markedly increased survival in mice challenged with gram-positive bacteria that induces septic shock. Bernhagen et al., *J. Mol. Med.* 76:151–161, 1998. Other studies have demonstrated the role of MIF in tumor cell growth and that anti-sense inhibition of MIF leads to resistance to apoptotic stimuli. Takahashi et al., *Mol. Med.* 4:707–714, 1998; Takahashi et al., *Microbiol. Immunol.* 43(1):61–67, 1999. In addition, the finding that MIF is a counterregulator of glucocorticoid action indicates that methods of inhibiting MIF extracellular localization may allow for treatment of a variety of pathological conditions, including autoimmunity, inflammation, endotoxemia, and adult respiratory distress syndrome, inflammatory bowel disease, otitis media, inflammatory joint disease and Crohn's disease. Bernhagen et al., *J. Mol. Med.* 76:151–161, 1998; Calandra et al., *Nature* 377:68–71, 1995; Donnelly et al., *Nat. Med.* 3:320–323, 1997. Because MIF is also recognized to be angiogenic, the inhibition of this cytokine may have anti-angiogenic activity and particular utility in angiogenic diseases that include, but are not limited to, cancer, diabetic retinopathy, psoriasis, angiopathies, fertility, obesity and genetic diseases of glucocorticoid dysfunction like Cushings and Addisons disease.

The inhibitors of MIF activity or export may be employed therapeutically and also utilized in conjunction with a targeting moiety that binds a cell surface receptor specific to particular cells. Administration of inhibitors or enhancers generally follows established protocols. Compositions of preferred embodiments may be formulated for the manner of administration indicated, including for example, for oral, nasal, venous, intracranial, intraperitoneal, subcutaneous, or intramuscular administration. Within other embodiments, the compositions described herein may be administered as part of a sustained release implant. Within yet other embodiments, compositions of preferred embodiments may be formulized as a lyophilizate, utilizing appropriate excipients that provide stability as a lyophilizate, and subsequent to rehydration.

In another embodiment, pharmaceutical compositions containing one or more inhibitors of MIF are provided. For the purposes of administration, the compounds of preferred embodiments may be formulated as pharmaceutical compositions. Pharmaceutical compositions of preferred embodiments comprise one or more MIF inhibitors of preferred embodiments (i.e., a compound of structure (Ia) or (Ib)) and a pharmaceutically acceptable carrier and/or diluent. The inhibitor of MIF is present in the composition in an amount which is effective to treat a particular disorder, that is, in an amount sufficient to achieve decreased MIF levels or activity, symptoms, and/or preferably with acceptable toxicity to the patient. Preferably, the pharmaceutical compositions of preferred embodiments may include an inhibitor of MIF in an amount from less than about 0.01 mg to more than about 1000 mg per dosage depending upon the route of administration, preferably about 0.025, 0.05, 0.075, 0.1, 0.2, 0.3, 0.4, 0.5, 0.6, 0.7, 0.8, or 0.9 mg to about 65, 70, 75, 80, 85, 90, 95, 100, 125, 150, 175, 200, 225, 250, 300, 350, 375, 400, 425, 450, 500, 600, 700, 800, or 900 mg, and more preferably from about 1, 2, 3, 4, 5, 6, 7, 8, 9, 10, 15, 20, or 25 mg to about 30, 35, 40, 45, 50, 55, or 60 mg. In certain embodiments, however, lower or higher dosages than those mentioned above may be preferred. Appropriate concentrations and dosages can be readily determined by one skilled in the art.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats, and other common additives. The compositions can also be formulated as pills, capsules, granules, or tablets that contain, in addition to an inhibitor of MIF, diluents, dispersing and surface-active agents, binders, and lubricants. One skilled in this art may further formulate the inhibitor of MIF in an appropriate manner, and in accordance with accepted practices, such as those described in *Remington's Pharmaceutical Sciences*, Gennaro, Ed., Mack Publishing Co., Easton, Pa. 1990.

In addition, prodrugs are also included within the context of preferred embodiments. Prodrugs are any covalently bonded carriers that release a compound of structure (Ia) or (Ib) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structures (Ia) and (Ib) may have chiral centers and may occur as racemates, racemic mixtures and as individual enantiomers or diastereomers. All such isomeric forms are included within preferred embodiments, including mixtures thereof. Furthermore, some of the crystalline forms of the compounds of structures (Ia) and (Ib) may exist as polymorphs, which are included in preferred embodiments. In addition, some of the compounds of structures (Ia) and (Ib) may also form solvates with water or other organic solvents. Such solvates are similarly included within the scope of the preferred embodiments.

In another embodiment, a method is provided for treating a variety of disorders or illnesses, including inflammatory diseases, arthritis, immune-related disorders, and the like. Such methods include administering of a compound of preferred embodiments to a warm-blooded animal in an amount sufficient to treat the disorder or illness. Such methods include systemic administration of an inhibitor of MIF of preferred embodiments, preferably in the form of a pharmaceutical composition. As used herein, systemic administration includes oral and parenteral methods of administration. For oral administration, suitable pharmaceutical compositions of an inhibitor of MIF include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of preferred embodiments can be prepared in aqueous injection solutions that may contain, in addition to the inhibitor of MIF activity and/or export, buffers, antioxidants, bacteriostats, and other additives commonly employed in such solutions.

As mentioned above, administration of a compound of preferred embodiments can be employed to treat a wide variety of disorders or illnesses. In particular, the compounds of preferred embodiments may be administered to a warm-blooded animal for the treatment of inflammation, cancer, immune disorders, and the like.

MIF inhibiting compounds may be used in combination therapies with other pharmaceutical compounds. In preferred embodiments, the MIF inhibiting compound is present in combination with conventional drugs used to treat diseases or conditions wherein MIF is pathogenic or wherein MIF plays a pivotal or other role in the disease process. In particularly preferred embodiments, pharmaceutical compositions are provided comprising one or more MIF inhibiting compounds, including, but not limited to compounds of structures (Ia) or (Ib), in combination with one or more additional pharmaceutical compounds, including, but not limited to drugs for the treatment of various cancers, asthma or other respiratory diseases, sepsis, arthritis, inflammatory bowel disease (IBD), or other inflammatory diseases, immune disorders, or other diseases or disorders wherein MIF is pathogenic.

In particularly preferred embodiments, one or more MIF inhibiting compounds are present in combination with one or more nonsteroidal anti-inflammatory drugs (NSAIDs) or other pharmaceutical compounds for treating arthritis or other inflammatory diseases. Preferred compounds include, but are not limited to, celecoxib; rofecoxib; NSAIDS, for example, aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids, for example, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

In particularly preferred embodiments, one or more MIF inhibiting compounds are present in combination with one or more beta stimulants, inhalation corticosteroids, antihistamines, hormones, or other pharmaceutical compounds for treating asthma, acute respiratory distress, or other respiratory diseases. Preferred compounds include, but are not limited to, beta stimulants, for example, commonly prescribed bronchodilators; inhalation corticosteroids, for example, beclomethasone, fluticasone, triamcinolone, mometasone, and forms of prednisone such as prednisone, prednisolone, and methylprednisolone; antihistamines, for example, azatadine, carbinoxamine/pseudoephedrine, cetirizine, cyproheptadine, dexchlorpheniramine, fexofenadine, loratadine, promethazine, tripelennamine, brompheniramine, cholopheniramine, clemastine, diphenhydramine; and hormones, for example, epinephrine.

In particularly preferred embodiments, one or more MIF inhibiting compounds are present in combination with pharmaceutical compounds for treating IBD, such as azathioprine or corticosteroids, in a pharmaceutical composition.

In particularly preferred embodiments, one or more MIF inhibiting compounds are present in combination with pharmaceutical compounds for treating cancer, such as paclitaxel, in a pharmaceutical composition.

In particularly preferred embodiments, one or more MIF inhibiting compounds are present in combination with immunosuppresive compounds in a pharmaceutical composition. In particularly preferred embodiments, one or more MIF inhibiting compounds are present in combination with one or more drugs for treating an autoimmune disorder, for example, Lyme disease, Lupus (e.g., Systemic Lupus Erythematosus (SLE)), or Acquired Immune Deficiency Syndrome (AIDS). Such drugs may include protease inhibitors, for example, indinavir, amprenavir, saquinavir, lopinavir, ritonavir, and nelfinavir; nucleoside reverse transcriptase inhibitors, for example, zidovudine, abacavir, lamivudine, idanosine, zalcitabine, and stavudine; nucleotide reverse transcriptase inhibitors, for example, tenofovir disoproxil fumarate; non nucleoside reverse transcriptase inhibitors, for example, delavirdine, efavirenz, and nevirapine; biological response modifiers, for example, etanercept, infliximab, and other compounds that inhibit or interfere with tumor necrosing factor; antivirals, for example, amivudine and zidovudine.

In particularly preferred embodiments, one or more MIF inhibiting compounds are present in combination with pharmaceutical compounds for treating sepsis, such as steroids or anti-infective agents. Examples of steroids include corticosteroids, for example, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone. Examples of anti-infective agents include anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscamet, ganciclovir, indinavir, lamivudine, nelfinavir, ritonavir, saquinavir, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

In the treatment of certain diseases, it may be beneficial to treat the patient with a MIF inhibitor in combination with an anesthetic, for example, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocalne, and phenazopyridine.

EXAMPLES

The inhibitors of MIF of preferred embodiments may be prepared by the methods described in Example 1. Example 2 presents an assay for screening compounds of preferred embodiments for inhibition of activity or export.

Example 1

Synthesis of Representative Compounds

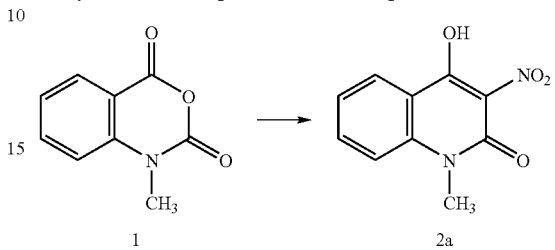

A solution of ethyl nitroacetate (6.70 ml, 60.1 mmol) in N,N-dimethylacetamide (35 ml) was treated with 95% NaH (1.52 g, 60.2 mmol) in portions. After evolution of hydrogen ceased, the reaction mixture was heated at 80° C. for 15 minutes. A solution of N-methylisatoic anhydride 1 (11.1 g, 62.5 mmol) in N,N-dimethylacetamide (65 ml) was added over a period of 15 minutes after which the reaction was heated at 120° C. for 18 hours. The solvent was removed by distillation, the residue dissolved in water, and acidified with 6 N HCl. The ensuing precipitate was collected and washed with water. Recrystallization of the remaining residue from $CH_2Cl_2$/ether gave quinolinone 2a (5.75 g, 43%) as a yellow solid.

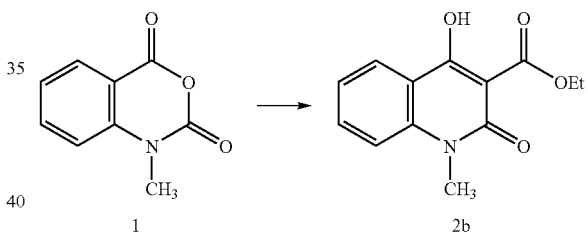

A solution of diethyl malonate (18.8 ml, 111 mmol) in N,N-dimethylacetamide (35 ml) was treated with 95% NaH (2.80 g, 111 mmol) in portions. After evolution of hydrogen ceased, the reaction mixture was heated at 80° C. for 15 minutes. A solution of N-methylisatoic anhydride 1 (22.0 g, 124 mmol) in N,N-dimethylacetamide (140 ml) was added over a period of 15 minutes after which the reaction was heated at 120° C. for 18 hours. The solvent was removed by distillation, the residue dissolved in water, and acidified with 6 N HCl. The ensuing precipitate was collected and washed with water. Recrystallization of the remaining residue from $CH_2Cl_2$/ether gave quinoline 2b (11.7 g, 40%) as a white solid.

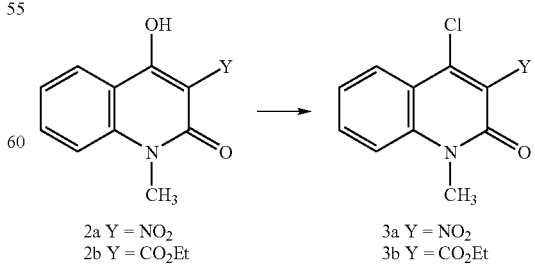

2a Y = $NO_2$
2b Y = $CO_2Et$

3a Y = $NO_2$
3b Y = $CO_2Et$

Alcohol 2 (6.2 g 2a; 11.1 g 2b) was dissolved in $POCl_3$ (70 mL for 2a; 140 mL for 2b) and the solution was heated at 95°

C. for three hours. POCl₃ was removed by distillation and the reaction mixture was poured into 500 mL of ice water. The aqueous solution was neutralized using saturated NaHCO₃, the precipitate was collected by filtration, redissolved in methylene chloride, dried over Na₂SO₄ and the solvent was removed in vacuo. The crude reaction product was purified by recrystallization from ethyl ether affording 3.5 g of 3a (52%) or 7.8 g 3b (65%).

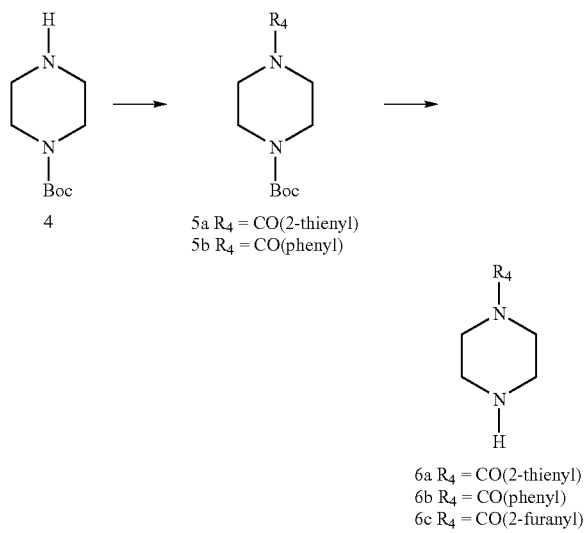

N-BOC piperazine 4 (5.0 g; 27 mmol) was dissolved in pyridine (15 mL) and 20 mg of DMAP was added. Neat acid chloride was added to the solution at 0–5° C. slowly over a period of 5 minutes. The resulting thick paste was stirred overnight (15 hours) at room temperature before it was poured on ice. The white crystalline precipitate was collected by filtration, air dried and dried in vacuo to give the corresponding N-BOC-N-Acyl piperazine 5a (6.5 g; 83%) or 5b (4.8 g; 94%). The crude reaction product was immediately employed in the next step by dissolving the compound in 100 mL methylene chloride and adding neat TFA (10 mL). After 3 hours at room temperature, the solution was evaporated, the residue dissolved in methylene chloride and washed with NaHCO₃ (saturated). The aqueous layer was extracted 10 times with methylene chloride, the combined organic layer was dried over Na₂SO₄ and the solvent was evaporated in vacuo affording compound 6a (4.5 g; 91%; 75% over two steps) or compound 6b (2.95 g; 70%; 66% over two steps), or compound 6c, as is commercially available from Lancaster Synthesis (catalogue no. 18698).

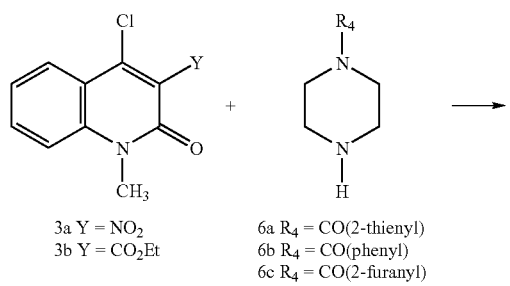

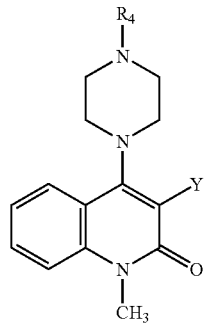

7a Y = NO₂, R₄ = CO(2-thienyl)
7b Y = NO₂, R₄ = CO(phenyl)
7c Y = CO₂Et, R₄ = CO(2-thienyl)
7d Y = CO₂Et, R₄ = CO(phenyl)
7e Y = NO₂, R₄ = CO(2-furanyl)

To a solution of chloroquinolone 3 in toluene was added piperazine 6 followed by 10 drops of pyridine before heated to 100° C. for 12 to 14 hours. The mixture was cooled to room temperature, evaporated to dryness, redissolved in methylene chloride and washed with brine. The organic solvent was dried over Na₂SO₄ and removed in vacuo. Chromatography (silica, CHCl₃:MeOH 85:15) afforded the CBX product 7, along with recovered starting material (30–40%). Product yields for the reaction are provided in Table 1.

TABLE 1

| N-Acyl Piperazine | | Chloroquinolone | | CBX Piperazine Quinolone Adduct | | |
|---|---|---|---|---|---|---|
| 6a | 1.9 g | 3a | 1.8 g | 7a | 0.9 g | 28% |
| 6a | 1.6 g | 3b | 1.5 g | 7b | 0.9 g | 34% |
| 6b | 2.6 g | 3a | 2.5 g | 7c | 1.3 g | 32% |
| 6b | 2.7 g | 3b | 2.4 g | 7d | 1.5 g | 35% |
| 6c | 2.7 g | 3a | 3.2 g | 7e | 2.8 g | 55% |

Analytical Data 7a. mp 167–159° C.; ¹H NMR (CDCl₃, 300 MHz) δ 7.95 (dd, 1H), 7.70 (dt, 1H), 7.49 (d, 1H), 7.44 (d, 1H) 7.35 (m, 2H), 7.08 (m, 1H), 3.95 (bs, 4H), 3.75 (s, 3H), 3.3 (t, 4H); HRMS (FAB) calculated for C₁₉H₁₉O₄N₄S 399.1127. found 399.1117. Anal. Calculated for C₁₉H₁₈N₄O₄S: C, 57.28; H, 4.55; N, 14.06; O, 16.06; S, 8.05. Found: C, 56.78; H, 4.50; N, 13.73.

7b. mp 215–217° C.; ¹H NMR (CDCl₃, 300 MHz) δ 7.85 (dd, 1H), 7.70 (m, 1H), 7.44 (m, 5H), 7.42 (m, 1H), 3.74 (m, 4H), 3.28 (m, 4H); HRMS (FAB) calculated for C₂₁H₂₁N₄O₄ 393.1563. found 393.1540. Anal, Calculated for C₂₁H₂₀N₄O₄; C, 64.28; H, 5.14; N, 14.28; O, 16.31. Found; C, 64.84; H, 5.16; N, 13.78.

7c. mp 183–185° C.; ¹H NMR (CDCl₃, 300 MHz) δ 7.95 (dd, 1H), 7.61 (m, 1H), 7.48 (m, 1H), 7.38 (d, 1H) 7.32(m, 1H), 7.25 (M, 1H), 7.07 (M, 1H), 4.44 (q, 2H) 3.95 (bs, 4H), 3.70 (s, 3H) 3.35 (bs, 4H), 1.44 (t, 3H); HRMS (FAB) calculated for C₂₂H₂₄N₃O₄S, 426.1488. found 426.1487. Anal, Calculated for C₂₂H₂₃N₃O₄S: C, 62.10; H, 5.45; N, 9.88; O, 15.04; S, 7.54. Found: C, 62.08; H, 5.45; N, 9.77.

7d. mp 164–166° C.; ¹H NMR (CDCl₃, 300 MHz) δ 7.92 (dd, 1H), 7.60 (m, 1H), 7.44 (m, 5H), 7.37 (m, 1H), 7.27 (m, 1H), 4.45 (q, 2H), 3.65 (bs, 7H), 3.20 (bs, 4H), 1.45 (t, 3H); HRMS (FAB) calculated for C₂₄H₂₆NO₃, 420.1923. found 420.1934. Anal. Calculated for $C_{24}H_{25}N_3O_4$; C, 69.72; H, 6.01; N, 10.02; 0, 15.26. Found: C, 66.32; H, 6.01; N, 9.66.

7e. mp 189–191° C.; $^1$H NMR (CDCl$_3$, 300 MHz) δ 7.96 (dd, 1H), 7.71 (dt, 1H), 7.51 (bd, 1H), 7.44 (bd, 1H), 7.37 (bt, 1H), 7.09 (d, 1H), 6.51 (m, 1H), 4.03 (bm, 4H), 3.74 (s, 3H), 3.33 (t, 4H); HRMS (FAB) calculated for $C_{19}H_{19}N_4O_5$ 383.1355. found 383.1358. Anal. Calculated for $C_{19}H_{18}N_4O_5$: C, 59.68; H, 4.74; N, 14.65. Found: C, 59.39; H, 4.79; N, 14.36.

Example 2

Macrophage Migration Assay

Macrophage migration is measured by using the agarose droplet assay and capillary method as described by Harrington and Stastny et al., *J. Immunol.* 110(3):752–759, 1973. Briefly, macrophage-containing samples are added to hematocrit tubes, 75 mm long with a 1.2 mm inner diameter. The tubes are heat sealed and centrifuged at 100×G for 3 minutes, cut at the cell-fluid interface and imbedded in a drop of silicone grease in Sykes-Moore culture chambers. The culture chambers contain either a control protein (BSA) or samples. Migration areas are determined after 24 and 48 hours of incubation at 37° C. by tracing a projected image of the macrophage fans and measuring the areas of the migration by planimetry.

Alternatively, each well of a 96-well plate is pre-coated with one microliter of liquid 0.8% (w/v) Sea Plaque Agarose in water dispensed onto the middle of each well. The plate is then warmed gently on a light box until the agarose drops are just dry. Two microliters of macrophage containing cell suspensions of up to 25% (v/v) in media (with or without MIF or other controls), containing 0.2% agarose (w/v) and heated to 37° C. is added to the precoated plate wells and cooled to 4° C. for 5 min. Each well is then filled with media and incubated at 37° C. under 5% CO$_2$ _95% air for 48 hr. Migration from the agarose droplets is measured at 24 and 48 hr by determining the distance from the edge of the droplet to the periphery of migration.

Migration Assay

Monocyte migration inhibitory activities of recombinant murine and human wild-type and murine mutant MIF are analyzed by use of human peripheral blood mononuclear cells or T-cell depleted mononuclear cells in a modified Boyden chamber format. Calcein AM-labeled monocytes are suspended at 2.5 to 5×10$^6$/mL in RPMI 1640 medium, with L-glutamine (without phenol red) and 0.1 mg/mL human serum albumin or bovine serum albumin. An aliquot (200 µL) of cell suspension is added to wells of a U-bottom 96-well culture plate (Costar, Cambridge, Mass.) pre-warmed to 37° C. MIF in RPMI 1640 is added to the cell suspension to yield final concentrations of 1, 10, 100, and 1000 ng/mL. The culture plate is placed into the chamber of a temperature-controlled plate reader, mixed for 30 s, and incubated at 37° C. for 10–20 min. During the incubation, 28 µL of prewarmed human monocyte chemotactic protein 1 (MCP-1; Pepro Tech., Inc., Rocky Hill, N.J.) at 10 or 25 ng/mL or RPMI 1640 with 0.1 mg/mL HSA is added to the bottom well of a ChemoTX plate (Neuro Probe Inc., Gaithersburg, Md.; 3 mm well diameter, 5 µM filter pore size). The filter plate is carefully added to the base plate. Treated cell suspensions are removed from the incubator and 30 µL is added to each well of the filter plate. The assembled plate is incubated for 90 min. at 37° C. in a humidified chamber with 5% CO$_2$. Following incubation, the cell suspension is aspirated from the surface of the filter and the filter is subsequently removed from the base plate and washed three times by adding 50 µL of 1× HBSS$^-$ to each filter segment. Between washes, a squeegee (NeuroProbe) is employed to remove residual HBSS$^-$. The filter is air-dried and then read directly in the fluorescent plate reader, with excitation at 485 nm and emission at 535 nm. Chemotactic or random migration indices are defined as average filter-bound fluorescence for a given set of wells divided by average fluorescence of filters in wells containing neither MCP-1 nor MIF. Titration of fluorescently labeled cells revealed that levels of fluorescence detected in this assay have a linear relationship to cell number (not shown).

Example 3

Tautomerase Assay

The tautomerization reaction is carried out essentially as described by Rosengren et al., *Mol. Med.* 2(1):143–149, 1996. D-dopachrome conversion to 5,6-dihydroxyindole-2-carboxylic acid is assessed. 1 ml sample cuvettes containing 0.42 mM substrate and 1.4 µg of MIF in a sample solution containing 0.1 mM EDTA and 10 mM sodium phosphate buffer, pH 6.0 are prepared and the rate of decrease in iminochrome absorbance is followed at 475 nm. L-dopachrome is employed as a control. In addition, the reaction products can be followed using an HPLC, utilizing a mobile phase including 20 mM KH$_2$PO$_4$ buffer (pH 4.0) and 15% methanol with a flow rate of 1.2 ml/min. Fluorimetric detection is followed at 295/345 nm.

Alternatively, the tautomerization reaction utilizing phenylpyruvate or (p-hydroxyphenyl)pyruvate is carried out essentially as described by Johnson et al., *Biochem.* 38:16024–16033, 1999. In this version, ketonization of phenylpyruvate is monitored at 288 nm ($\epsilon$=17300 M$^{-1}$ cm$^{-1}$) and the ketonization of (p-hydroxyphenyl)pyruvate is monitored at 300 nm ($\epsilon$=21600 M$^{-1}$ cm$^{-1}$). The assay mixture contains 50 mM Na$_2$HPO$_4$ buffer (1 mL, pH 6.5) and an aliquot of a solution of MIF sufficiently dilute (0.5–1.0 µL of a 2.3 mg/mL solution, final concentration of 93–186 nM) to yield an initial liner rate. The assay is initiated by the addition of a small quantity (1–3.3 µL) of either phenylpyruvate or (p-hydroxyphenyl)pyruvate from stock solutions made up in ethanol. The crystalline forms of phenylpyruvate and (p-hydroxyphenyl)pyruvate exist exclusively as the enol isomers (Larsen et al., *Acta Chem. Scand. B* 28:92–96, 1974). The concentration of substrate may range from 10 to 150 M, with no significant inhibition of MIF activity by ethanol observed at less than 0.5% v/v.

Example 4

Immunoprecipitation and Western Blot Analysis

Cell culture experiments were designed to characterize the activity of candidate compounds, MIF expression, trafficking, and export. Cell and conditioned medium fractions are prepared for immunoprecipitation essentially as described previously (Florkiewicz et al., *Growth Factors* 4:265–275, 1991; Florkiewicz et al., *Ann. N.Y. Acad. Sci.* 638:109–126) except that 400 µl of lysis buffer (1% NP-40, 0.5% deoxycholate, 20 mM Tris pH 7.5, 5 mM EDTA, 2 mM EGTA, 0.01 mM phenylmethylsufonyl fluoride, 10 ng/ml aprotinin, 10 ng/ml leupeptin, 10 ng/ml peptstatin) is added to the medium fraction after clarification by centrifugation in a microfuge for 15 minutes. Cell or medium fractions are incubated with monoclonal or polyclonal antibodies to MIF and GammaBind™ G Sepharose® (Pharmacia LKB Biotechnology, Uppsala, Sweden) was added for an additional 30 minutes incubation. Immune complexes are sedimented by microfuge centrifugation, washed three times with lysis buffer, and four times with ice cold immunoprecipitation wash buffer (0.15M NaCl, 0.01 M Na-phosphate pH 7.2, 1% deoxycholate, 1% NP-40, 0.1% sodium dodecyl sulfate). Immune complexes are dissociated directly in SDS gel sample buffer 125 mM Tris, pH 6.8, 4% SDS, 10% glycerol, 0.004% bromphenol blue, 2 mM EGTA, and separated by 12% SDS-PAGE. The gel is processed for fluorography, dried, and exposed to X-ray film at −70° C. When neomycin phosphotransferase is immunoprecipitated, a rabbit anti-NPT antibody (5Prime-3Prime, Boulder, Colo.) was employed.

For Western blot analysis, proteins are transferred from the 12% SDS-PAGE gel to a nitrocellulose membrane (pore size 0.45 μm in cold buffer containing 25 mM 3-[dimethyl (hydroxymethyl)methylamino]-2-hydroxypropane-sulfonic acid, pH 9.5, 20% methanol for 90 minutes at 0.4 amps. For Western blotting analysis, of cell conditioned media, the media was centrifuged (10 minutes at 800 g) and the supernatants concentrated 10-fold by membrane filtration (10 kDa cut-off, Centricon-10 Amicon). Samples were then resolved on 16% SDS Tris-glycin Gel (Novex, San Diego, Calif.) under reducing condition and transferred onto nitrocellulose membrane (Novex) at 20V for 3 hours. Membrane was incubated with rabbit polyclonal anti-rat antibodies (1:1000) (Torrey Pines Biolab, San Diego, Calif.), and then with horseradish peroxidase-conjugate (1:1000)(Pierce, Rockford, Ill.). MIF was visualized by development with chloronaphtnol/$H_2O_2$. Recombinant MIF (2 ng, purchased from R&D systems, Minneapolis) was electrophoresed and transferred as a standard. Membranes are blocked in 10 mM Tris, pH 7.5, 150 mM NaCl, 5 mM $NaN_3$, 0.35% polyoxyethylene-sorbitan monolaurate, and 5% nonfat dry milk (Carnation Co., Los Angeles, Calif.) for 1 hr at room temperature. Membranes are incubated with a monoclonal antibody (Catalog Number MAB289, purchased from R&D Systems, Minneapolis, Minn.) or polyclonal (goat polyclonal serum, R&D Systems cat#AF-289-PB). Following incubation, membranes are washed at room temperature with 10 changes of buffer containing 150 mM NaCl, 500 mM sodium phosphate pH 7.4, 5 mM $NaN_3$, and 0.05% polyoxyethylene-sorbitan monolaurate. When using monoclonal antibodies, membranes are then incubated in blocking buffer containing 1 μg/ml rabbit anti-mouse IgG (H+ L, affinipure, Jackson Immuno Research Laboratories, West Grove, Pa.) for 30 minutes at room temperature. For polyclonal probing, incubation employed rabbit anti-goat (Sigma, Catalog Number G5518). Membranes are subsequently washed in 1 L of buffer described above, and incubated for 1 hr in 100 ml of blocking buffer containing 15 μCi $^{125}$I-protein A (ICN Biochemicals, Costa Mesa, Calif.), and washed with 1 L of buffer. The radiosignal is visualized by autoradiography.

In one experiment, overnight conditioned media was collected from LPS (10 μg/ml) treated THP-1 cells also treated with varying amounts of candidate compounds, such as compound 7e and screened by immunoprecipitation with monoclonal or polyclonal antibodies to detect MIF binding. As demonstrated in FIG. 1, conditioned media showed a significant loss of detectable MIF using the monoclonal antibody in the presence of 10 μM of compound 7e that was not observed with the polyclonal antibody. This response mirrors the effects of compound 7e on MIF enzyme activity. Accordingly, this experiment demonstrates that monoclonal reactivity can act as a surrogate marker for enzymatic activity.

Figure 2:
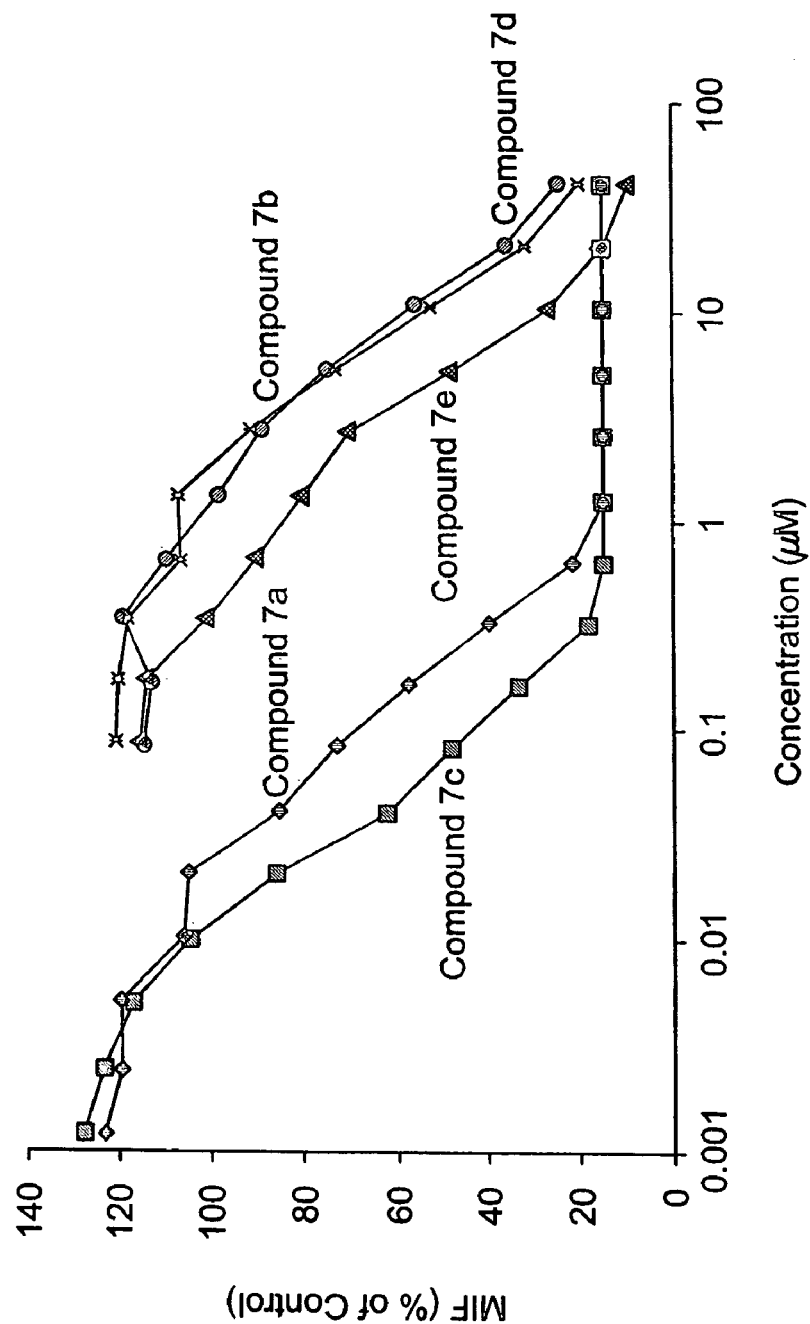
FIG. 2 is a graph depicting enzyme linked immunosorbant assay (ELISA) results following treatment of LPS stimulated THP-1 cells with five analogs of the presently claimed composition. The ability of each analog to inhibit monoclonal antibody binding is depicted and is dose dependent.

In another experiment (FIG. 2), varying concentrations of five different inhibitor analogs were added to LPS stimulated THP-1 cells and allowed to incubate overnight. The following day the amount of immunoreactive MIF detected was evaluated by ELISA. Compound 7e inhibited the ability of the antibody to recognize MIF in a dose dependent fashion with an ED50 of 2 μM, similar to the response obtained with analogs compound 7b and compound 7d. In contrast, analog compound 7a and compound 7c were almost 100 times more active.

Figure 3:
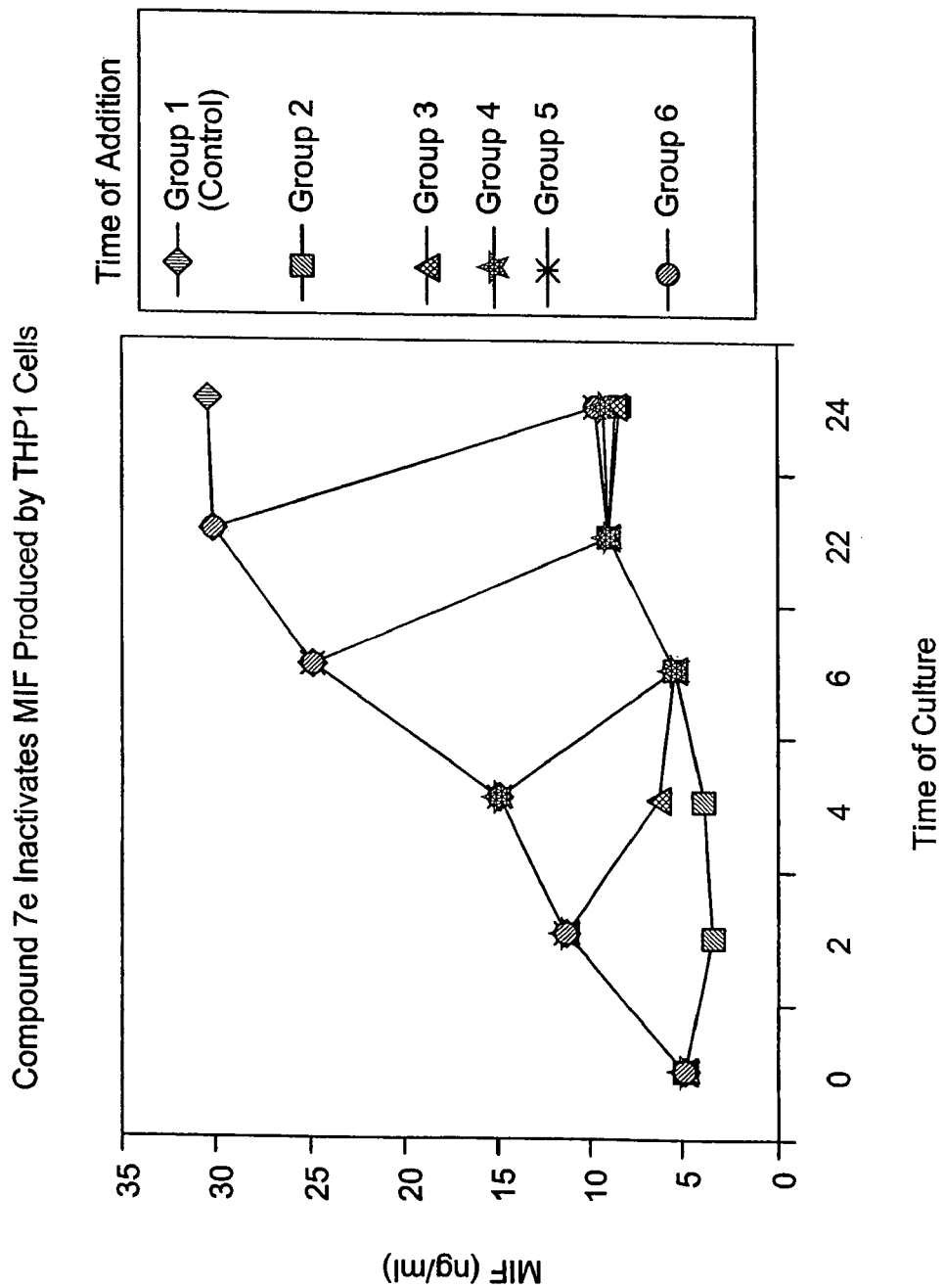
FIG. 3 is a graphical representation of the immunoreactivity of MIF in conditioned medium using ELISA following stimulation of THP-1 cells with LPS and addition of 10 μM compound 7e at various times during culture. In this Figure, LPS was added at time point zero, while compound 7e was added at 0, 2, 4, and 6 hours following LPS treatment. Six groups of THP1 cells were employed in this experiment, all cultured under standard media conditions. At the initiation of the experiment, buffer only was added to Group 1 cells and buffer containing compound 7e was added to Group 2 cells. Compound 7e in buffer was added to each other group at various times thereafter, Group 3 at 2 hrs, Group 4 at 4 hrs, Group 5 at 6 hrs and Group 6 at 22 hrs. Samples were taken from each group at the indicated times after buffer or buffer plus sample was added and assayed for detectable levels of MIF using the anti-MIF monoclonal antibody. In the absence of compound (Group 1) the level of detectable MIF increased throughout the time course of the experiment. In the presence of compound, detection of MIF is blocked.
Figure 4:
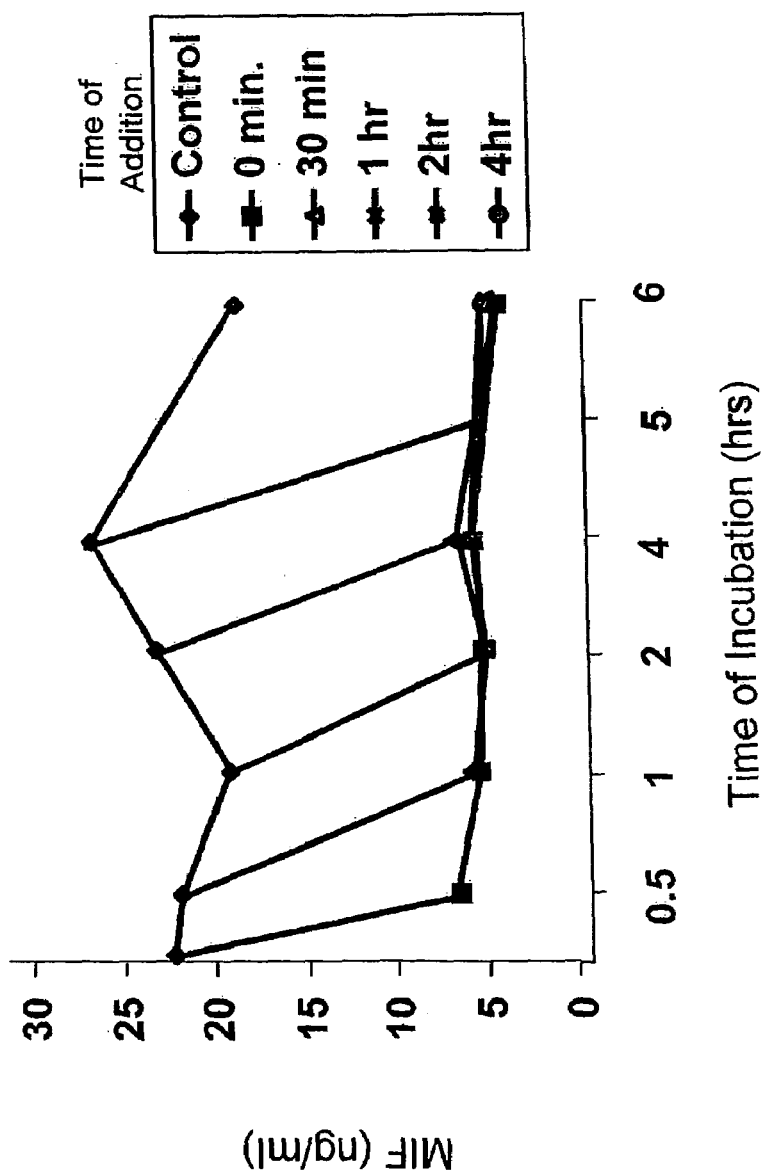
FIG. 4 is a graphical representation of an ELISA-based experiment, following the effect of compound 7e on MIF detection. In this experimental design, the test sample is pre-conditioned cell culture media, clarified of cellular debris. The starting concentration of MIF in the test sample was calculated to be approximately 22 ng/ml. Compound is added at varying times after beginning incubation at 37° C. Each sample is then incubated for an additional 30 minutes before the detectable level of MIF is again determined.

In a further experiment (FIG. 3), the ability of compound 7e to decrease the immunoreactivity of MIF produced by THP-1 cells was determined. THP-1 cells were treated with 10 μg/ml of LPS and 10 μM of compound 7e was added at various times post-LPS stimulation and immunoreactivity monitored with an anti-MIF monoclonal. As shown, following addition of compound 7e immunoreactivity is rapidly lost. Thus, this experiment measures the activity of compounds or buffer alone controls on MIF detection when the compounds are initially added at various times to cell cultures and then the corresponding conditioned media samples are processed in a time dependent fashion thereafter.

In the previous experiment (FIG. 3), the ability of compound 7e to modulate antibody binding to MIF protein was analyzed in the presence of LPS-stimulated THP1 cells. However, in the experiment shown in FIG. 4, the ability of compound 7e to modulate antibody recognition of MIF was examined using pre-conditioned media, in the absence of live cells. In this experiment, LPS was added to THP1 cells in culture as describe above. Six hours later, the conditioned media was removed, clarified of cell debris and the amount of MIF determined to be 22 ng/ml. This pre-conditioned media was then divided into two groups. Both groups were incubated at 37° C. for varying periods of time before compound 7e or buffer alone (control) was added for an additional 30 minutes of incubation at 37° C. The level of detectable MIF was then determined by ELISA using the monoclonal anti-MIF antibody for detection. The rapid loss of MIF specific ELISA signal is dependent upon the presence of compound 7e. Control levels of MIF do not change. Accordingly, this experiment demonstrates that compound 7e interacts with MIF, and blocks the antibody's ability to subsequently interact with MIF, even in the absence of cells. As this interaction takes place at the catalytic site, or constrains catalytic activity, the loss of immunoreactivity correlates with lost enzymatic activity and/or MIF associated activities.

Example 5

Extracellular Localization Assay

In order to further assess in vitro activity of compound 7e to modulate MIF export, mouse macrophage RAW 264.7 cells (American Type Culture Collection, Manassas, Va.) were selected.

Raw 264.7 macrophage ($3\times10^6$ cells per well) were plated in 12-well tissue culture plates (Costar) and cultured in RPMI/1% heat-inactivated fetal bovine serum (FBS) (Hyclone Laboratories, Logan, Utah). After three hours of incubation at 37° C. in a humidified atmosphere with 5% $CO_2$, nonadherent cells were removed and wells were washed twice with RPMI/1% FBS. Cells were then incubated for 24 hours with LPS (0111:B4) or TSST-1 (Toxin Technology, Sarasota, Fla.), which were approximately 95% pure and resuspended in pyrogen-free water, at a concentration ranging from 1 pg/ml to 1000 ng/ml (for the dose response experiment). For time-course experiments, conditioned media of parallel cultures were removed at 0.5, 1, 2, 4, 8 and 24 hours intervals after stimulation with 1 ng/ml TSST-1 or LPS. For the inhibition studies, RAW 264.7 cells ($3 \times 10^6$ cells per well) were incubated for 24 hours with 1 ng/ml of LPS (0111:B4) or 1 ng/ml of TSST-1 in the presence of 0.01 µM to 10 µM compound 7e or buffer (as control). The MIF in cell-conditioned media was concentrated on filters and the MIF remaining in the samples was analyzed by Western blotting and MIF band densities were also measured by Stratagene Eagle Eye™.

Figure 5:
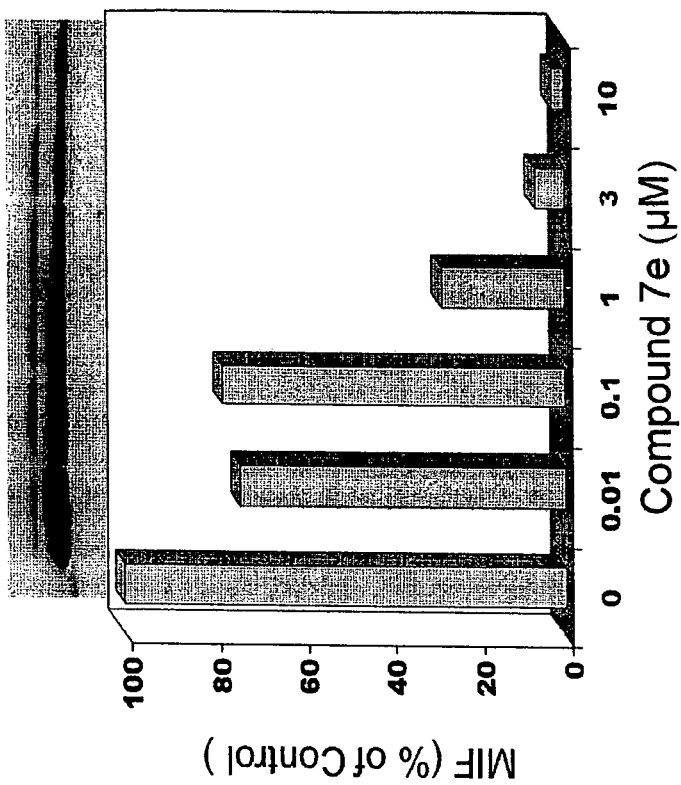
FIG. 5 is a bar graph representing the relative percent of MIF present in conditioned media from compound 7e treated and LPS induced RAW 264.7 cells compared to a control cell population that was not treated with the compound as measured by ELISA. The top panel demonstrates Western blots of the same fractions as measured by ELISA in the bottom panel.
Figure 6:
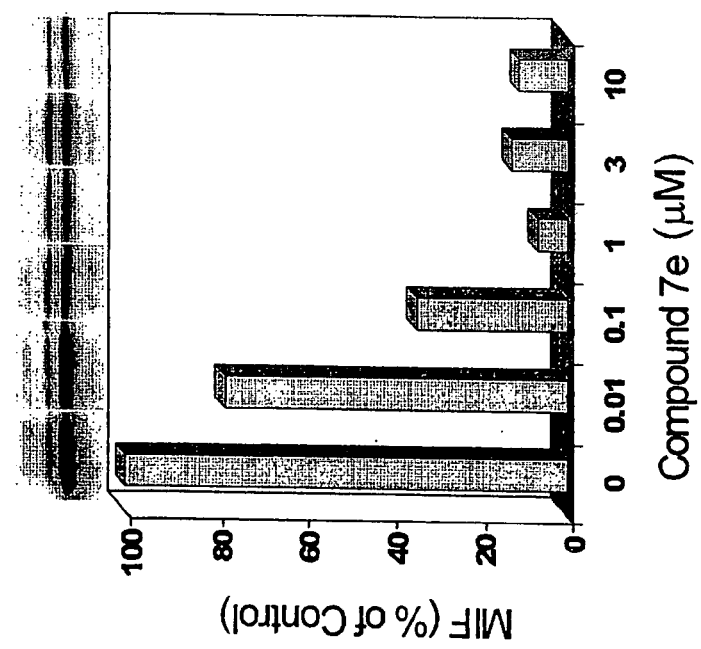
FIG. 6 is a bar graph representing the percent of MIF present in conditioned media from compound 7e treated and TSST-1 induced RAW 264.7 cells compared to a control cell population that was not treated by the compound as measured by ELISA. The top panel demonstrates Western blots of the same fractions measured by ELISA in the bottom panel.

RAW cells can be induced to express MIF by addition either 1 ng/ml TSST-1 or LPS and cultured for 24 hours. MIF in conditioned media was measured as described above. As demonstrated by FIG. 5, compound 7e reduced immunodetectable MIF levels in conditioned media in a concentration dependent manner with an $IC_{50}$ of approximately at 0.04 µM, as compared to cells incubated with buffer only. The level of MIF detected in the presence of compound 7e following TSST-1 stimulation of RAW cells is illustrated in FIG. 6, with an $IC_{50}$ of approximately 0.3 µM as compared to cells incubated with buffer only.

Example 6

Cell Culture, Transfection and Metabolic Labeling

Target cells obtained from the American Type Culture Collection (ATCC No. CRL 1650) are cultured overnight in a 48-well plate in DMEM supplemented with 10% fetal bovine serum, 2 mM L-glutamine, 1 mM sodium pyruvate, 100 nM nonessential amino acids, and 50 µg/ml gentamycin. The target cells are then transfected with 2 µg/ml of CsCl-purified plasmid DNA in transfection buffer (140 mM NaCl, 3 mM KCl, 1 mM $CaCl_2$, 0.5 mM $MgCl_2$, 0.9 mM $Na_2HPO_4$, 25 mM Tris, pH 7.4. To each well, 300 µl of the DNA in transfection buffer is added. Cells are incubated for 30 minutes at 37° C., and the buffer is aspirated. Warm medium supplemented with 100 µm chloroquine is added for 1.5 hr. This medium is removed and the cells are washed twice with complete medium. Cells are then incubated for 40–48 hr. The plasmid of interest is co-transfected with pMAMneo (Clontech, Palo Alto, Calif.), which contains the selectable marker neomycin phosphotransferase. When 2 µg of the plasmid of interest are co-transfected with 10 µg of pMAMneo, greater than 70% of transfected cells express both MIF and neo, as determined by immunofluorescence microscopy.

For immunoprecipitation assays the target cells are metabolically pulse-labeled for 15 minutes with 100 µCi of $^{35}$S-methionine and $^{35}$S-cysteine (Trans $^{35}$S-label, ICN Biomedicals, Irvine, Calif.) in 1 ml of methionine and cysteine free DMEM. Following labeling, the cell monolayers are washed once with DMEM supplemented with excess (10 mM) unlabeled methionine and cysteine for 1–2 minutes. Cells are then cultured in 2 ml of this medium for the indicated lengths of time and the cell supernatants are immunoprecipitated for the presence of leaderless protein. For the indicated cultures, chase medium is supplemented with modulator at the indicated concentrations.

Alternatively, for analysis by ELISA, the target cells are washed once with 250 µl of 0.1 M sodium carbonate, pH 11.4, for 1 to 2 minutes and immediately aspirated. A high salt solution may alternatively be preferred. The cells are washed with media containing 0.5% FBS plus 25 µg/ml heparin and then the cells are incubated in this same medium for the indicated lengths of time. For indicated cultures, chase medium is supplemented with a modulator. For cells transfected with vector encoding a protein containing a leader sequence, such as hCG-α or any other non-heparin binding protein, the carbonate wash and heparin containing medium may be omitted.

Example 7

High Throughput Screening Assay for MIF Inhibitors

The high throughput screening assay for MIF inhibitors is performed in a 96-well format using MIF produced by THP-1 cells and is performed as follows. MIF assays are performed by ELISA as indicated above. THP-1 cells are resuspended to approx. $5 \times 10^6$ cells/ml in RPMI medium containing 20 µg/ml of bacterial LPS and the cells incubated for 18–20 hours. Subsequently cell supernatant is collected and incubated with putative inhibitors. Briefly, a 96-well plate (Costar Number 3590) ELISA plate is coated with a MIF monoclonal antibody (R&D Systems Catalog Number MAB289) at a concentration of 4 µg/ml for two hours at 37° C. Undiluted culture supernate is added to the ELISA plate for a two-hour incubation at room temperature. The wells are then washed, a biotinylated MIF polyclonal antibody (R&D Systems #AF-289-PB) is added followed by Streptavidin-HRP and a chromogenic substrate. The amount of MIF is calculated by interpolation from an MIF standard curve.

Example 8

HPLC Analysis of Candidate Inhibitors in Serum

Prior to evaluating the affects of any small molecule in vivo, it is desirable to be able to detect, in a quantitative fashion, the compound in a body fluid such as blood. An analytical method was established to first reproducibly detect test compounds, such as MIF inhibitors including compound 7e, and then measure its concentration in biological fluid.

RP-HPLC was performed with a Hewlett-Packard Model HP-1100 unit using Symmetry Shield RP-8 (4.6×75 mm id, Waters, Milford, Mass.). The mobile phase was an isocratic solution of 35% Acetonitrile/water containing 0.1% trifluroacetic acid. Absorbance was monitored at 235 nm. To measure the amount of test compound in serum, the sample serum proteins were first separated using 50% Acetonitrile (4° C. overnight) followed by centrifugation at 14000 rpm for 30 minutes. The supernatant was then analyzed by the RP-HPLC and the compound concentration calculated based on a calibration curve of known standard. According to this procedure, reverse phase HPLC was employed to detect compound 7e in a linear range of 1.5–800 ng (R2=1) using spiked test samples (not shown). When the above analytical technique is applied to blood serum from animals receiving compound 7e (0.4 mg/20 gram mouse), circulating concentrations of compound 7e are quantitatively measured.

Figure 7:
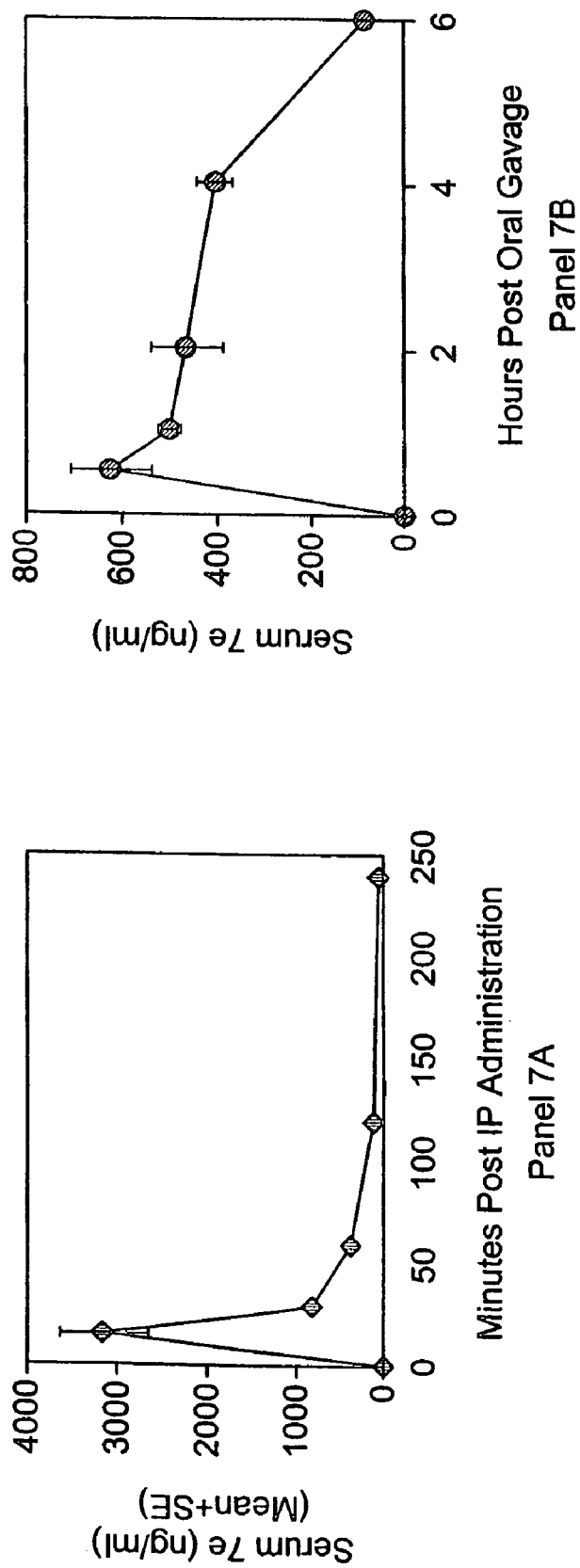
FIGS. 7A–7B are graphical representations of HPLC detection of compound 7e in mouse serum following intraperitoneal injection of compound 7e (FIG. 7A) or oral gavage administration of 20 mg of compound 7e (FIG. 7B). Results are depicted as a Mean+/−SEM (N=5 mice).

With the development of the above methods to quantify compound 7e, it is possible to evaluate the efficacy of different routes of compound administration and to characterize bioactivity. To test time dependent serum bioavailability, animals were treated with compound 7e by intraperitoneal injection (i.p.) (FIG. 7A), and orally by gavage (FIG. 7B).

Example 9

In Vivo Inhibition of MIF

The purpose for the following in vivo experiments was to confirm initial in vitro assay results using compound 7e to inhibit MIF. LPS-induced toxicity appears to be related to an overproduction of MIF as well as TNF-α and IL-1β. Since animals can be protected from endotoxin shock by neutralizing or inhibiting these inflammation mediators. The present model was chosen because it provides reproducible and rapid lethal models of sepsis and septic shock.

Doses of lipopolysacchraride (LPS) were made fresh prior to each experiment. LPS (*Escherichia Coli* 0111:B4, Sigma) was reconstituted by adding 0.5% TEA (1 ml USP water+5 ml Triethylamine (Pierce)) to a vial of 5 mg endotoxin. Once reconstituted, the solution was incubated at 37° C. for 30 minutes. Subsequently, the solution was sonicated in a 56–60° C. bath sonicator for 30 seconds 3 times. Following sonication the mixture was vortexed for 3 minutes continuously. The stock solution of LPS was then ready for use.

Detection of IL-1β and TNF-α and MIF in Blood

Ten 10-week-old (20±2 gram) female BALB/c mice (Charles River Laboratories, Kingston, N.Y.) were housed in a group of 5 per cage with free access to food and water and were acclimatized for at least one week prior to experimentation. On the day of experiment, mice were weighed and randomly distributed into group of 10 animals of equal mean body weight. Mice were injected i.p. with 200 µL of formulated compound 7e or buffer alone immediately before the i.p. injection of LPS (*Escherichia coli* 0111:B4, 10 mg/kg or 5 mg/kg body weight) and β-D-galactosamine (50 mg/kg body weight). Each dose of LPS (0.2 ml for 20 gram mouse) was administered intraperitoneally and mixed with a final concentration of β-D-galactosamine of 50 mg per ml. Following collection of blood specimens taken from cardiac puncture, the animal was sacrificed. Typical collections were performed at 4 hours post LPS treatment. The serum was separated in a serum separator (Microtainer® Becton Dickinson, Minneapolis, N.J.) according to the manufacturer's protocol. Mouse serum Il-1β and TNF-α were measured by ELISA using a "mouse IL 1β immunoassay or mouse TNF-α immunoassay" kits (R&D System Minneapolis, Minn.) following manufacturer's direction. Serum MIF concentrations in mouse serum were quantified by a sandwich ELISA (ChemiKine MIF Kit, Chemicon, San Diego, Calif.). Samples were analyzed in duplicate, and results were averaged.

Murine LPS Model

Ten 8 to 10 week-old (20±2 gram) female BALB/c mice were housed and acclimatized as described above. On the day of the experiments, the mice were weighed and randomly distributed into group of 5 animals of equal mean body weight. Mice were injected with 200 µl of formulated compound 7e or its Buffer (average 20 mg/kg compound) following i.p. injection of LPS (*E. Coli* 055B5, Sigma) (40, 10, 5, 2 or 0.5 mg/kg body weight) and 50 mg/kg of β-D-galactosamine. Mice were observed every two hours during the first 18 hours and twice a day for seven days. For these studies Kaplan-Meier estimation methods were employed to assess animal survival.

For all in vivo studies, standard statistical comparisons among treatment groups were performed using the Fisher test for categorical data and the Mantel-Cox test for continuous variables. To determine if levels of serum IL-1 correlated to serum MIF, a Fisher's test was applied. The analyses were performed using Stat View 5.0 Software (Abacus Concepts, Berkeley, Calif.). All reported p values that were two-sided and of a value less than 0.05 were considered to indicate statistical significance.

Figure 10:
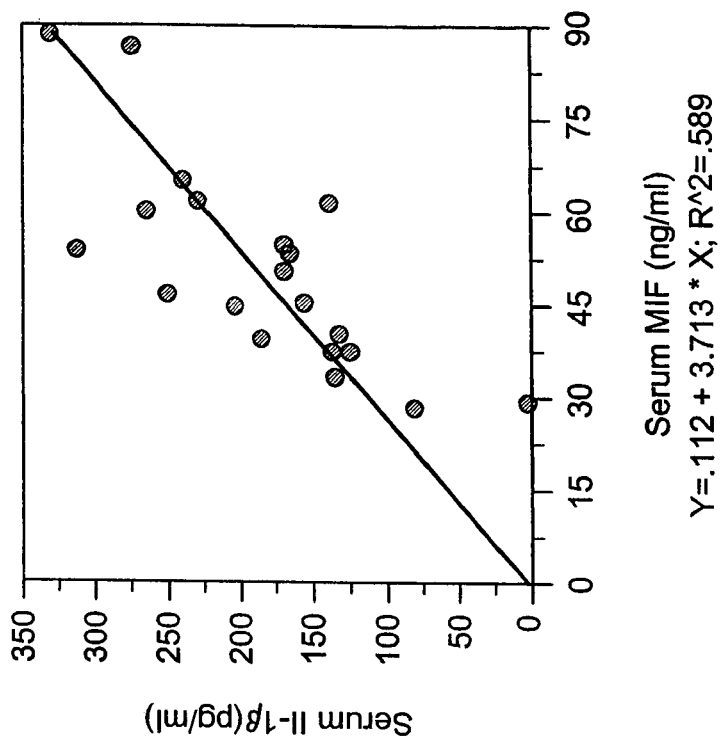
FIG. 10 is a graphical representation of ELISA measurements demonstrating the correlation between serum IL-1β levels in (pg/ml) versus serum MIF (ng/ml) five hours following LPS/Galactosamine stimulation of female Balb/c mice.
Figure 8:
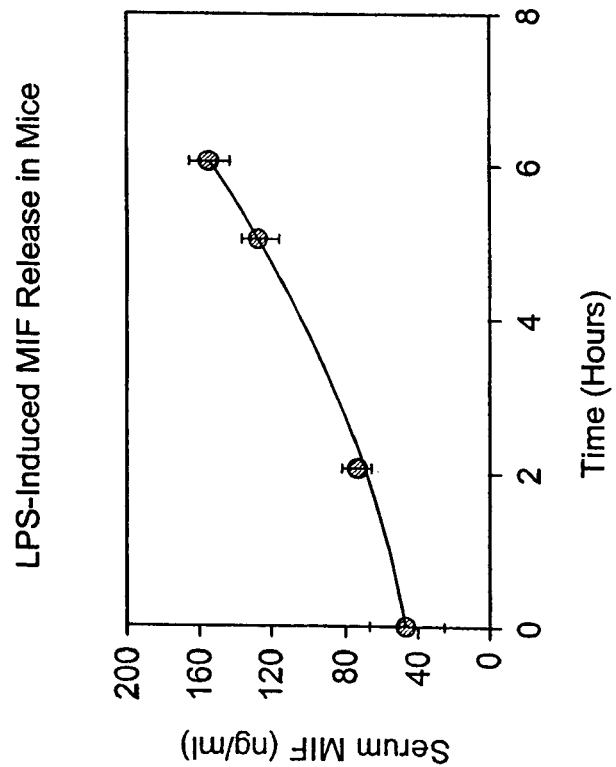
FIG. 8 is a graphical representation of ELISA detected MIF release in mouse serum at various times following LPS/galactosamine challenge. Results are presented as Mean+/−SEM (N=5).
Figure 9:
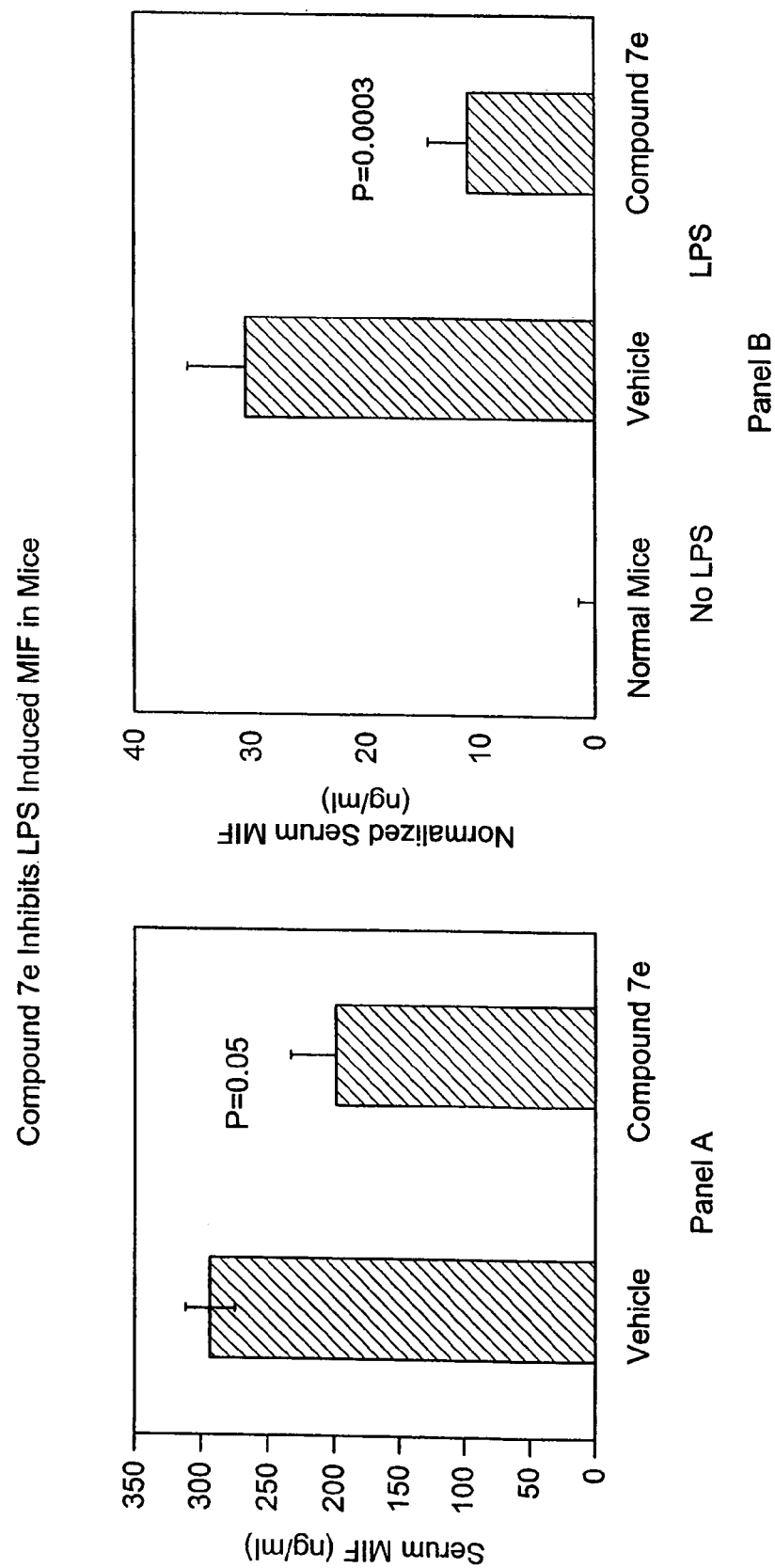
FIGS. 9A–9B graphically illustrate ELISA data of serum MIF concentrations in ng/ml five hours following a 10 mg/kg LPS challenge (FIG. 9A) or normalized serum MIF four hours following a 5 mg/kg LPS challenge (FIG. 9B) in the presence or absence of compound 7e (0.4 mg/20 gram mouse).
Figure 11:
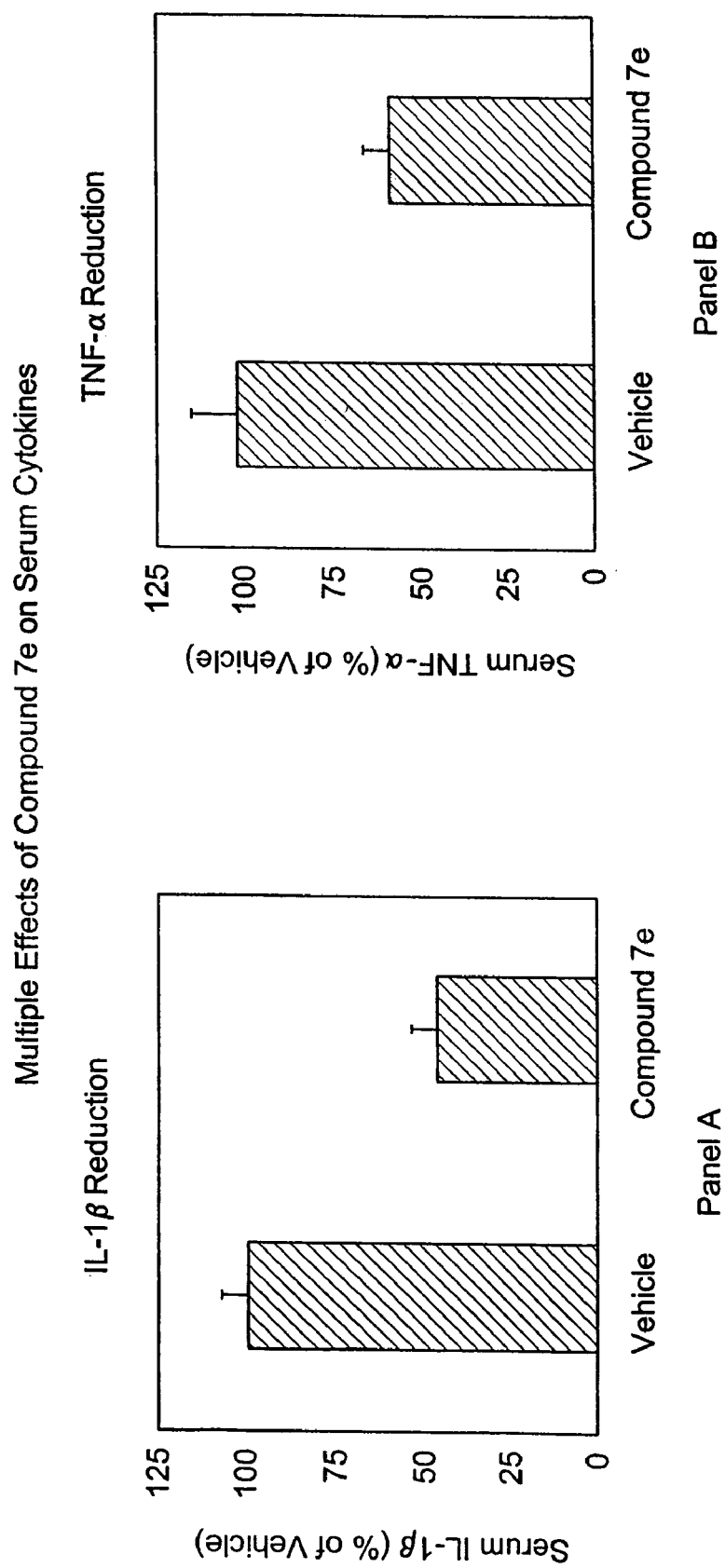
FIGS. 11A–11B are bar graphs illustrating ELISA detection of IL-1β and TNF-α four hours following LPS (5 mg/kg) stimulation and the presence or absence of 20 mg/kg body weight of compound 7e (i.p.).

An initial control experiment was conducted to determine the base line levels of endogenous MIF in the murine model system (female Balb/c mice), and further to determine the rate and extent of increase in endogenous MIF following treatment with LPS (10 mg/kg). Female Balb/c mice were treated with LPS (Sigma 0111:B1) admixed with 50 mg/kg β-D-galactosamine. The level of MIF in serum was measured by HPLC as described above at 0, 2, 5 and 6 hours following LPS/galactosamine treatment. At the initiation of this representative experiment, the baseline level of endogenous MIF was approximately 45 ng/ml. However, over the course of this six-hour experiment there was a time dependent increase in the level of MIF detected in collected serum samples. When mice were treated with compound 7e (formulated in 50% aqueous solution) and 10 mg/kg of LPS there was a significant decrease in the level of circulating MIF ($p=0.05$) that can be detected. In the experiment shown in FIG. 9A, BALB/c (n=20) mice were injected i.p. with 20 mg/kg body weight of compound 7e at time of LPS administration. Blood samples were collected 5.5 hours later. The results demonstrate that animals treated with the inhibitor have a decreased ability to respond to LPS and lowered MIF levels are detected. In a further study, in which mice were administered with half the LPS dosage (5 mg/kg), serum MIF was determined four hours following treatment. This data reveal a highly statistically significant ($p=0.0003$) 60% decrease in MIF (FIG. 9B). In a further experiment, both MIF and IL-1β were measured in mouse serum via ELISA. As shown in FIG. 10, there is a direct and highly significant correlation between the two. This correlation was also observed between MIF and TNF-α (data not shown). In a similar experiment, reductions in serum IL-1β level and serum TNF-α level were observed following administration of 20 mg/kg compound 7e (FIG. 11).

Figure 12:
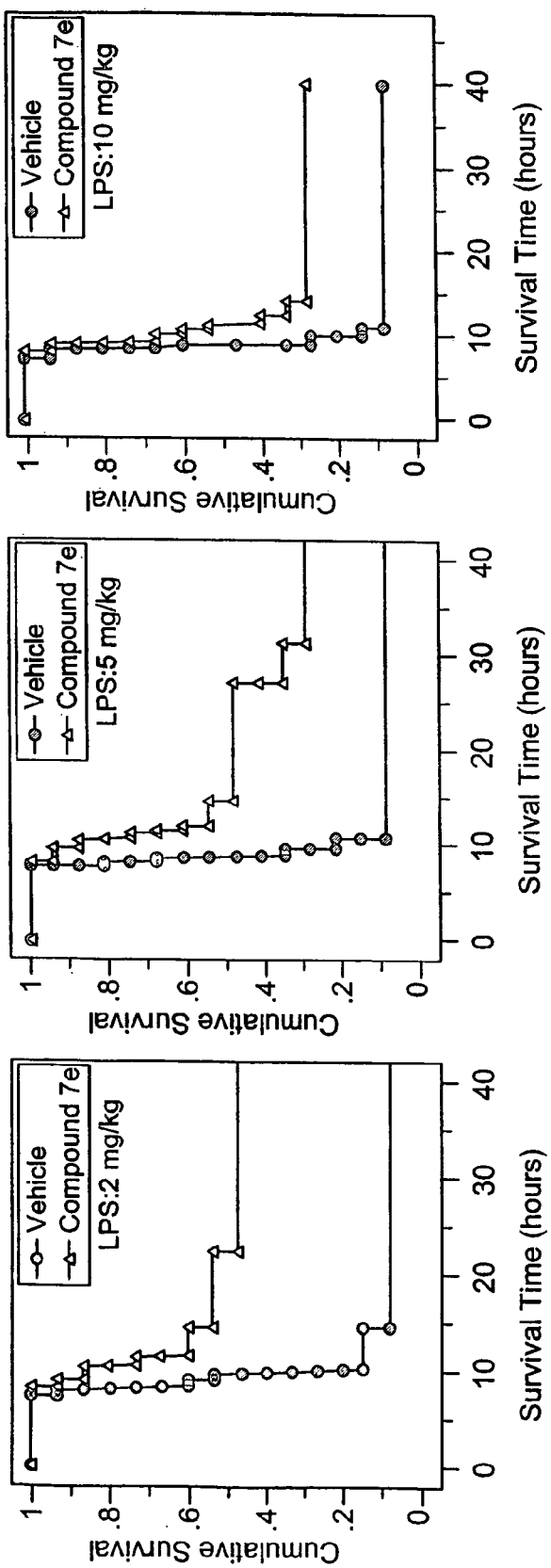
FIGS. 12A–12C depict cumulative survival versus survival time (hours) (Kaplan-Meier Assessment of Survival) for Balb/c mice following i.p. dosing with 20 mg/kg of compound 7e or control vehicle at the time of LPS (2 mg/kg (12A), 5 mg/kg (FIG. 12B), or 10 mg/kg (FIG. 12C)) and D-galactosamine (50 mg/kg) treatment. Each experiment included thirty mice with fifteen receiving the control vehicle and fifteen receiving the compound of interest.
Figure 13:
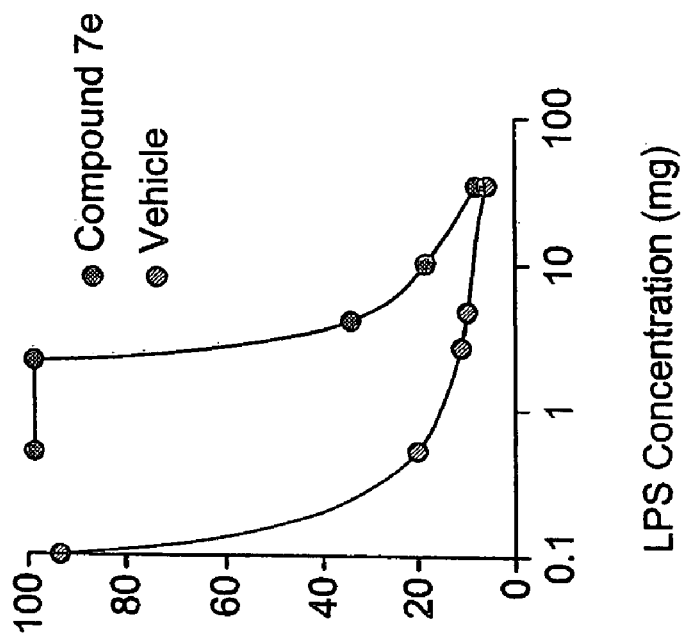
FIG. 13 is a graph illustrating survival time of 25% of mice versus LPS concentration (mg; Sigma 055:B5) and D-galactosamine (50 mg/kg) in the presence or absence of compound 7e (20 mg/kg body weight). The data represent the averaging of six experiments using thirty mice each.

Studies of experimental toxic shock induced by LPS have revealed a central role for MIF and TNF-α. The fact that LPS stimulates macrophage-like cells to produce MIF, that in turn induce TNF-α secretion by macrophage like cells suggests a potential role for MIF in the pathogenesis of LPS. To test if compound 7e can prevent LPS shock, a model of lethal LPS mediated shock in BALB/c mice sensitized with β-D-galactosamine was employed. Treatment with compound 7e at the time of injection of a lethal dose of LPS (2, 5 and 10 mg/kg) increased survival from 6% to 47% ($p=0.0004$) (FIG. 12). The effects are modulated by the concentration of LPS employed, demonstrating that when using a higher concentration of LPS, the effect compound 7e is saturable and hence specific. Table 2 is a summary of several survival experiments (total of 210 mice), indicating that compound 7e protects mice from LPS induced toxic shock in a concentration dependent fashion. FIG. 13 also depicts this data in graphical form with 25% survival time on the left axis.

TABLE 2

| LPS Dosage | 75% Animal Death (hours) | |
|---|---|---|
| (mg/kg) | Vehicle | Compound 7e |
| 40 | 10.2 | 11.6 |
| 10 | 9.9 | 18.0 |
| 5 | 10.0 | 32.0 |
| 2 | 10.2 | >100 |
| 0.5 | 22.0 | >100 |
| 0.1 | >100 | >100 |

MIF Overcomes the Effects of Compound 7e

Exogenous recombinant human MIF when administered with compound 7e, can reverse the beneficial effects of the compound, supporting the hypothesis that compound 7e acts to increase animal resistance to LPS by modulating MIF levels in mice serum. In this example, mice were treated with the standard LPS protocol except that in addition to 1 mg/kg LPS and 20 mg/kg of the inhibitor compound 7e, some animals also received 300 µg/kg human recombinant MIF. At 12 hours, significantly more ($p<0.01$) mice survive the LPS with compound 7e, but this survival is neutralized by the administration of MIF (data not shown).

Example 10

MIF Inhibitor in a Collagen Induced Arthritis Model

Figure 14:
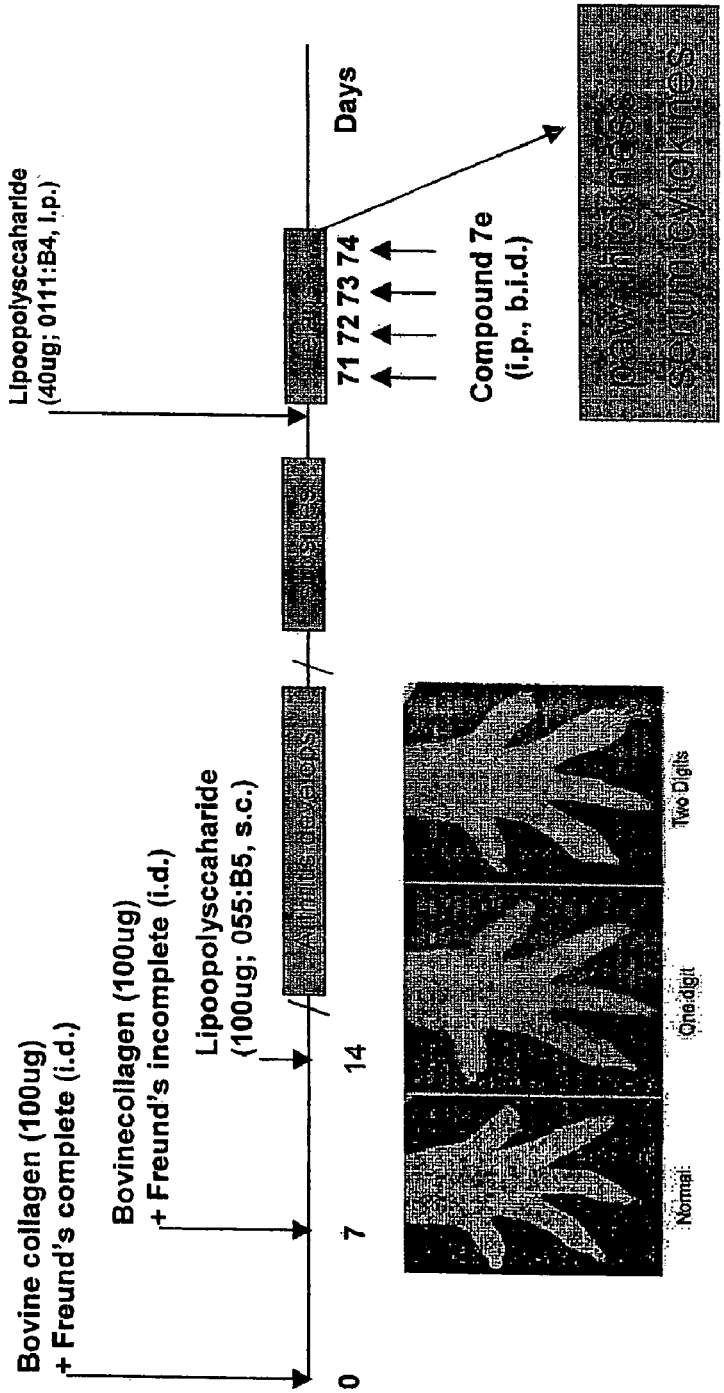
FIG. 14 represents the experimental protocol for testing MIF inhibitors for inhibiting arthritis in a collagen-induced arthritis mice model. Compound 7e was given two times a day for four days.
Figure 15:
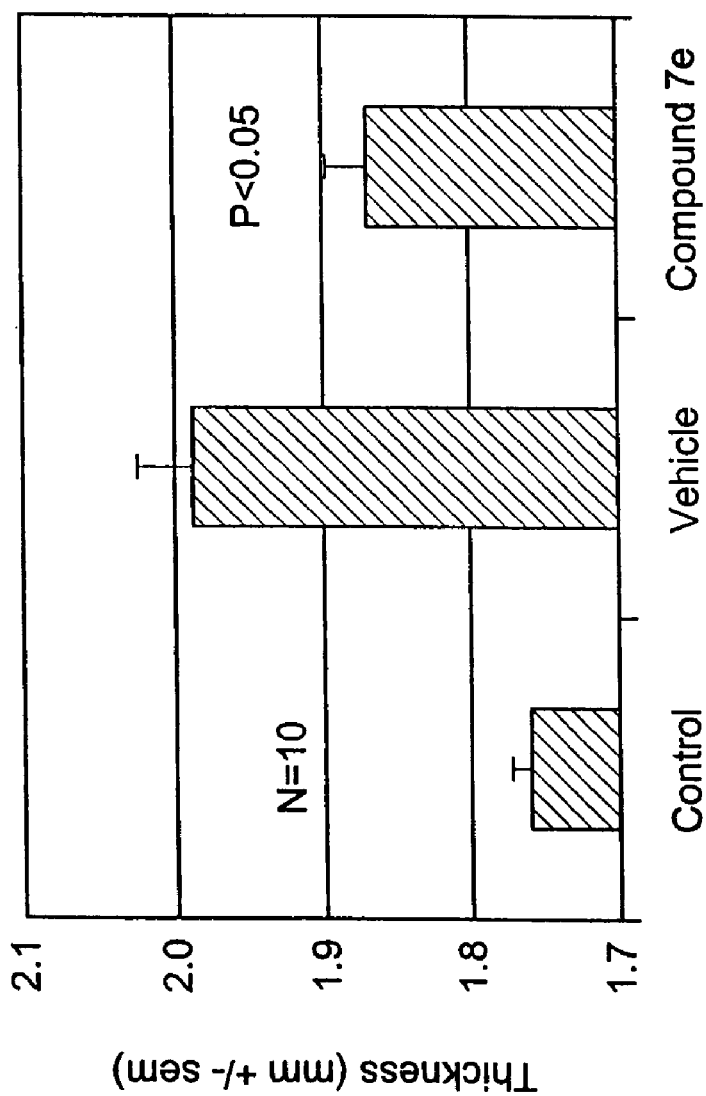
FIG. 15 is a bar graph illustrating caliper measurements of paw thickness as representative of paw edema on day 74. Values are expressed as the Mean+/−SEM for ten animals per group.

Twenty DBA/ILacJ mice, age 10–12 weeks, were immunized on day 0 at base of the tail with bovine collagen type II (CII 100 μg) emulsified in Freunds complete adjuvant (FCA; GibcoBRL). On day 7, a second dose of collagen was administrated via the same route (emulsified in Freunds incomplete adjuvant). On Day 14 mice were injected subcutaneously with 100 mg of LPS (055:B5). On day 70 mice were injected 40 μg LPS (0111:B4) intraperitoneally. Groups were divided according paw thickness, which was measured by a caliper, after randomization, to create a balanced starting group. Compound in buffer was given to mice on days 71, 72, 73, and 74 (total eight doses at 0.4 mg/dose, approximately 20 mg/kg of body weight). Mice were then examined on day 74 by two observers for paw thickness. FIG. 14 sets forth the experimental timeline. In this experiment, subsided mice (decline of full-blown arthritis) were treated with a final i.p. injection of LPS on day 70 to stimulate cytokine production as well as acute inflammation. FIG. 15 demonstrates that compound 7e treated mice develop mildly reduced edema of the paw (1.87 mm) compared with vehicle only treated controls (1.99 mm), p<0.05. In the late time point, the animals in the treated group did not reach a full-blown expression of collagen induced arthritis as compared to its control (data not shown).

Figure 16:
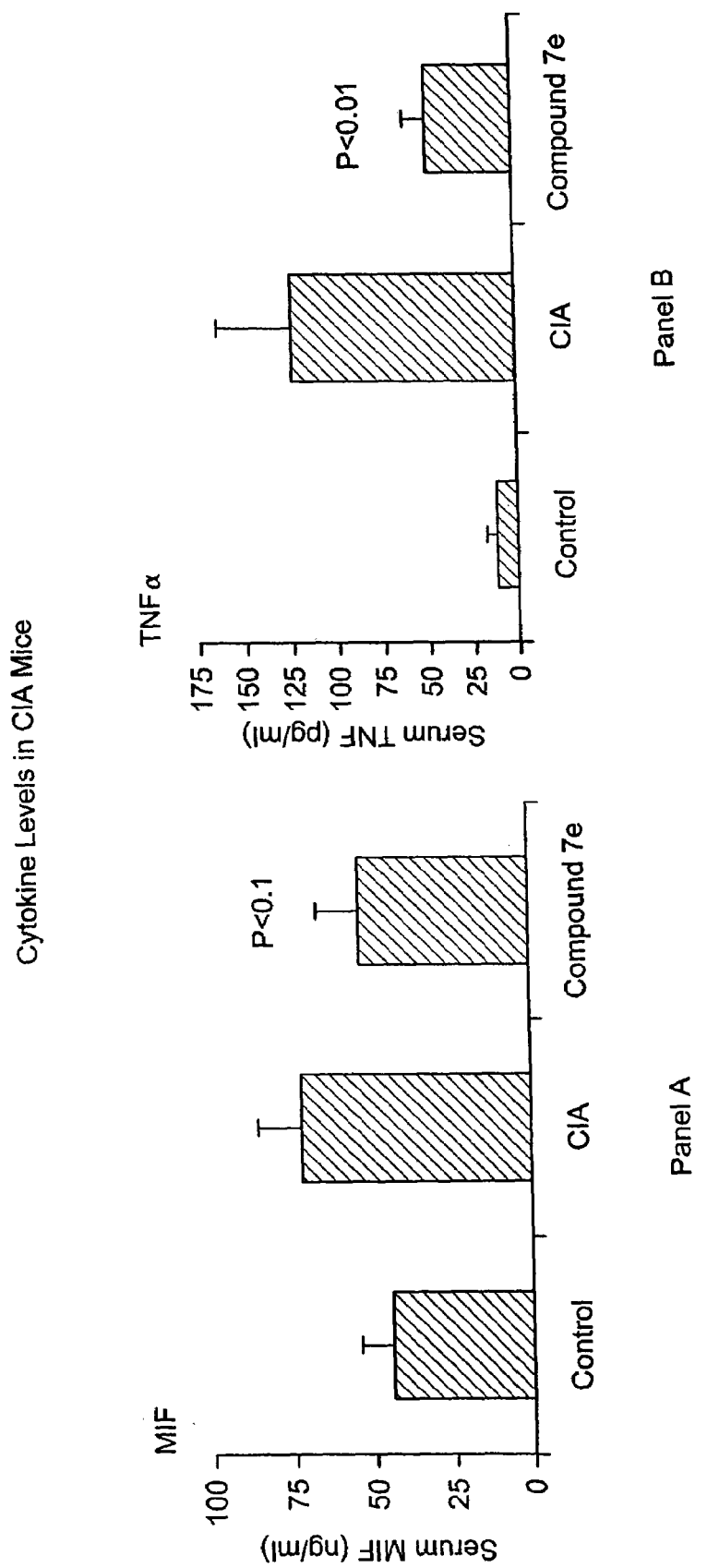
FIGS. 16A–16B are bar graphs depicting MIF (FIG. 16A) and TNF (FIG. 16B) levels in mouse sera of collagen induced-arthritic mice as measured by ELISA. Values are expressed as the Mean+/−SEM of seven animals. Controls are mice not treated with collagen or compound, CIA represents collagen induced arthritic mice, and compound 7e represents treated CIA mice.

In another experiment, fifteen DBA/1J mice, age 10–12 weeks were immunized on day 0 at the base of the tail with bovine collagen type II (CII 100 μg), emulsified in Freunds complete adjuvant (FCA; GibcoBRL). On day 21, a second dose of collagen was administered via the same route, emulsified in Freunds incomplete adjuvant. On day 28 the mice were injected subcutaneously with 100 μg of LPS (055:B5). On day 71 the mice were injected i.p. with 40 μg LPS (0111:B4). Groups and treatment protocol were the same as described as above. On day 74 blood samples were collected and cytokines were measured. FIG. 16 indicates that compound 7e reduced serum MIF levels as compared to untreated CIA samples. An even more significant inhibition of serum TNF-α levels was detected.

Example 11

The following inhibitors of MIF were prepared by the methods described in Example 1. Each of these MIF inhibitors belongs to the class of compounds of structure (1a) described above, and incorporates the following moiety:

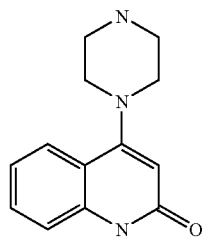

Results of tautomerase assays indicated that each of the MIF inhibitor compounds exhibited significant inhibition of MIF activity.

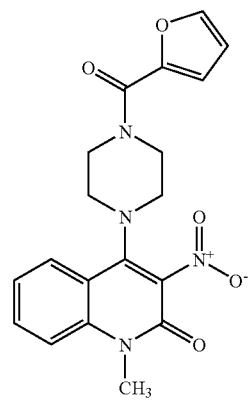

Compound 8

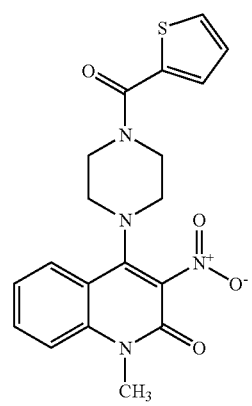

Compound 9

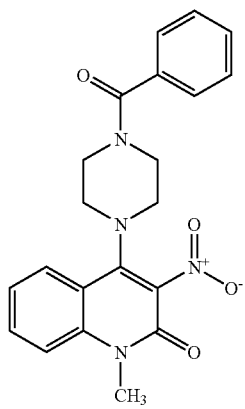

Compound 10

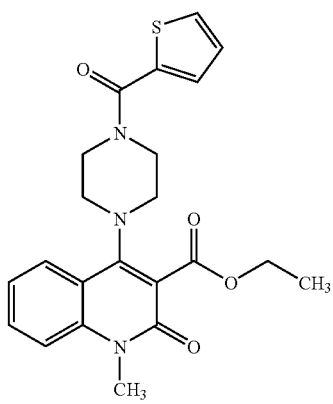

Compound 11

-continued
Compound 12
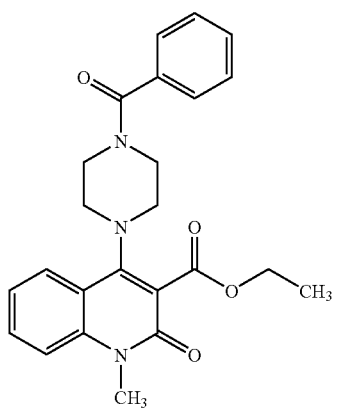
Compound 13
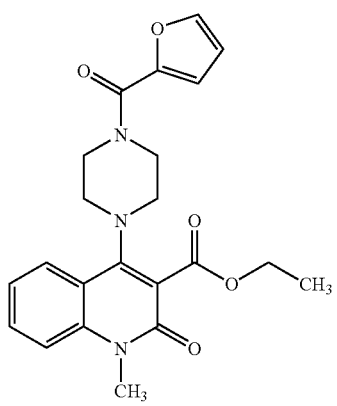
Compound 14
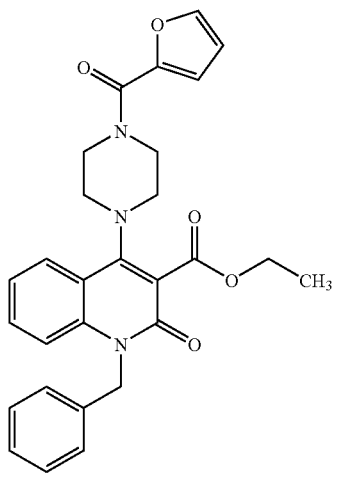
-continued
Compound 15
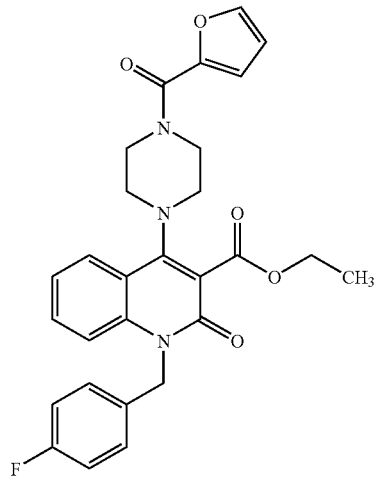
Compound 16
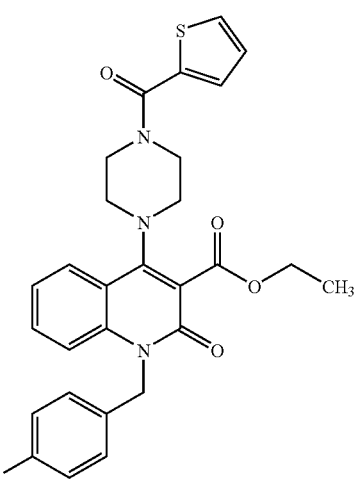
Compound 17
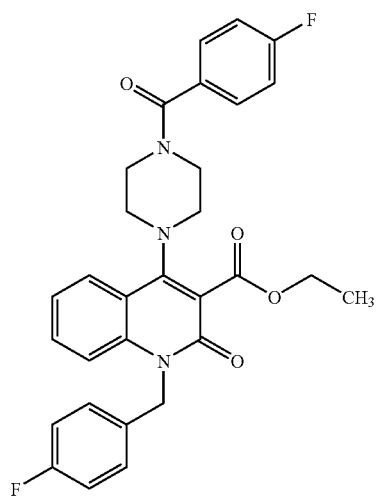

-continued
Compound 18
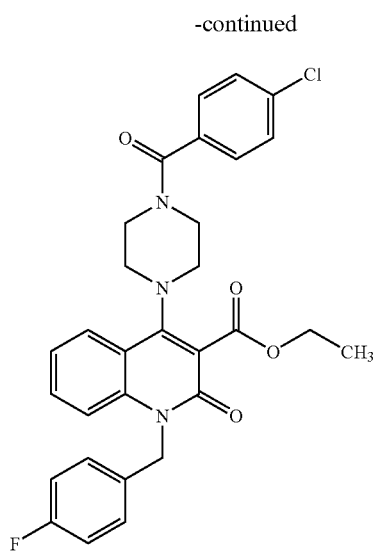
Compound 19
Compound 20
Compound 21
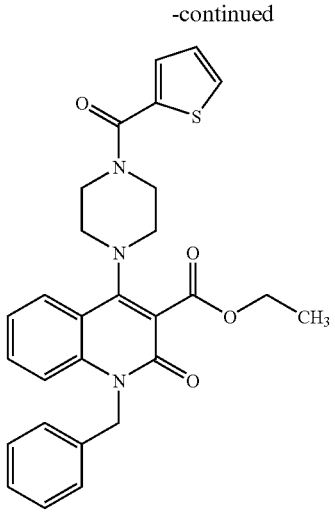
Compound 22
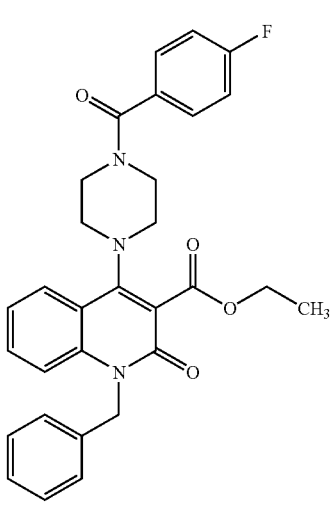
Compound 23
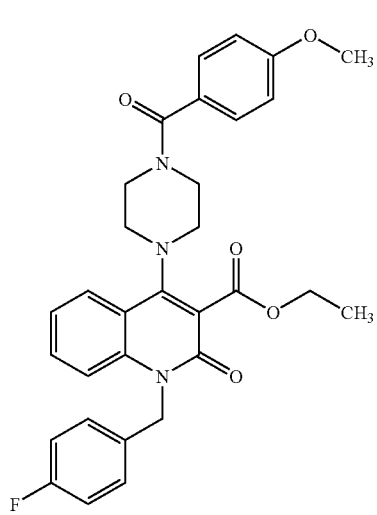
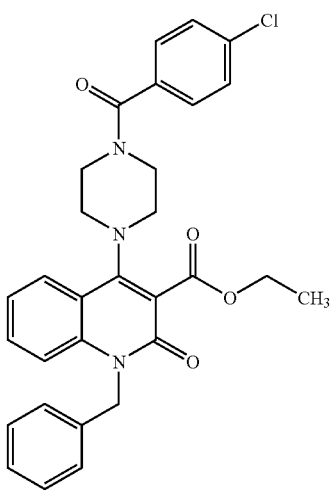

-continued
Compound 24
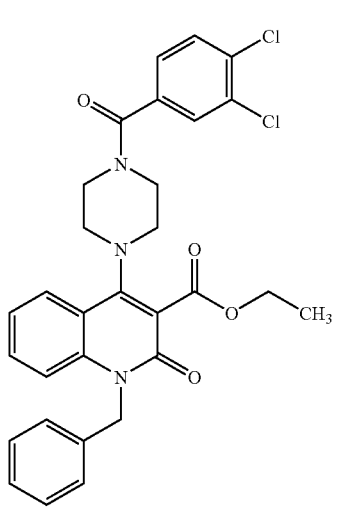
Compound 25
Compound 26
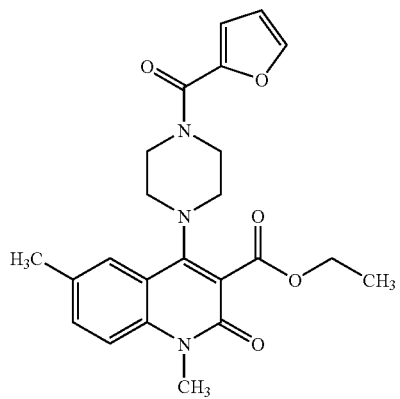
-continued
Compound 27
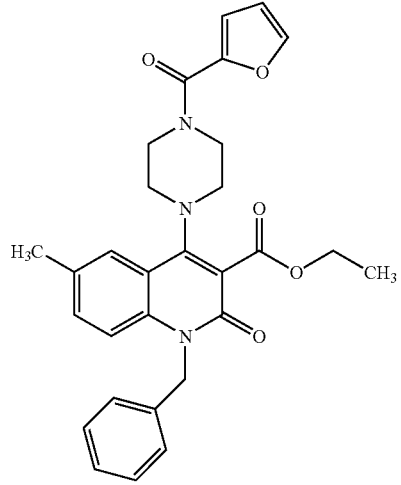
Compound 28
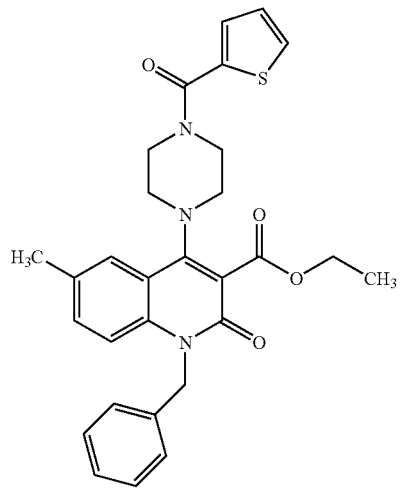
Compound 29
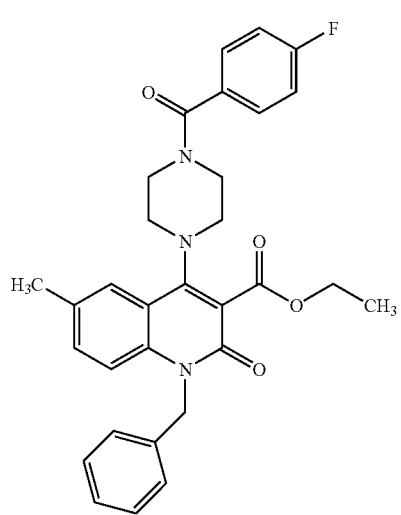

-continued
Compound 30
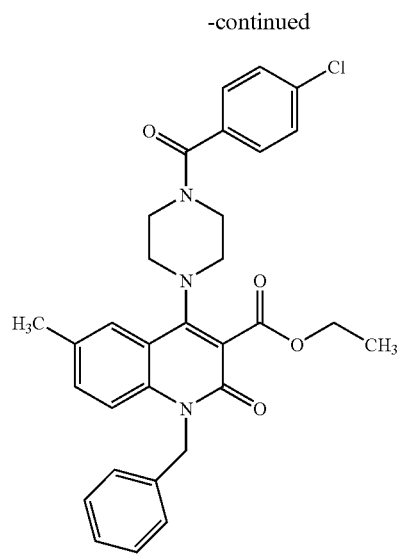
Compound 31
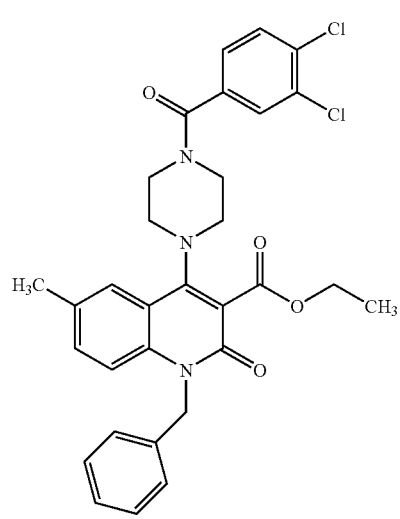
Compound 32
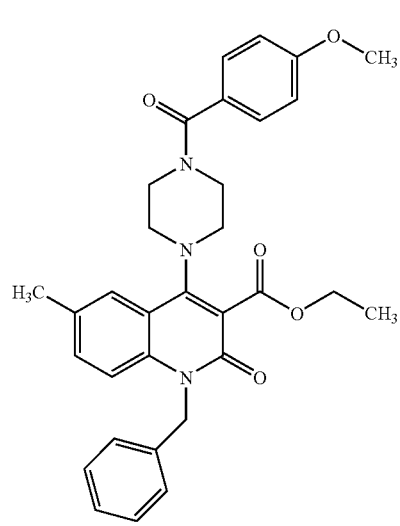
-continued
Compound 33
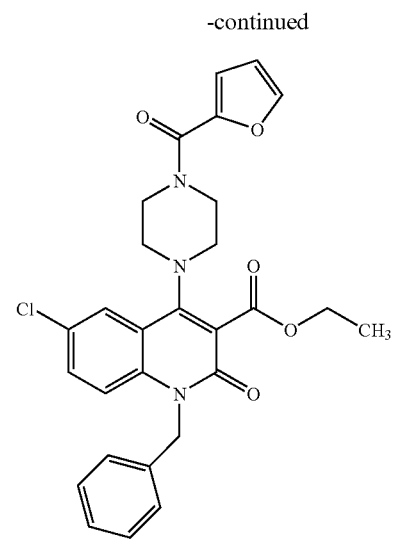
Compound 34
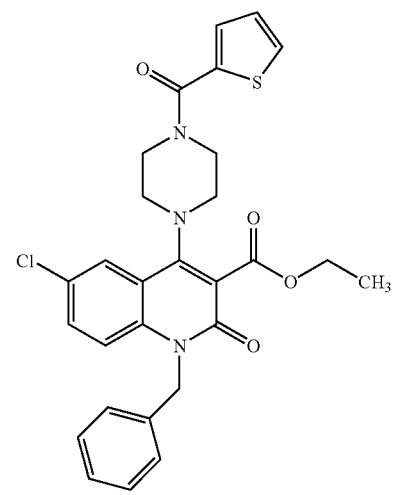
Compound 35
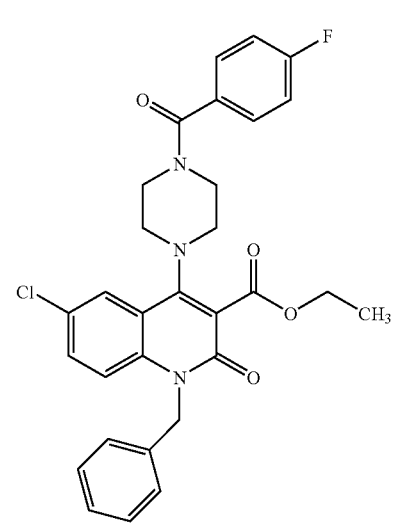

-continued
Compound 36
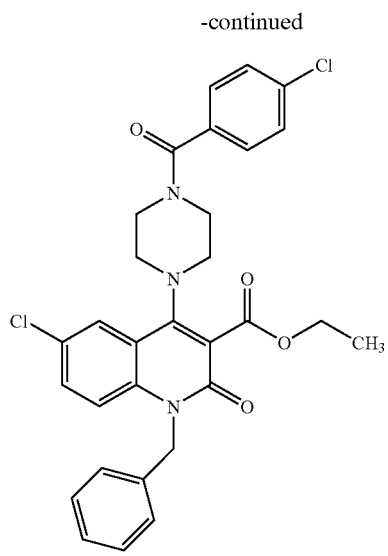
Compound 37
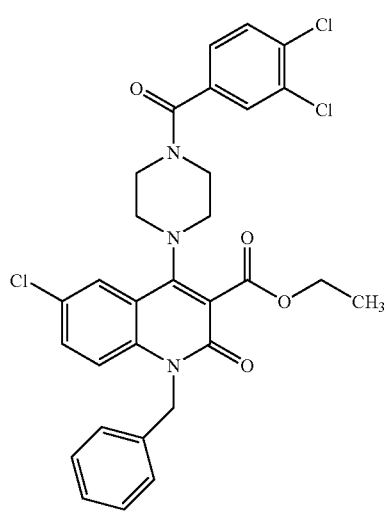
Compound 38
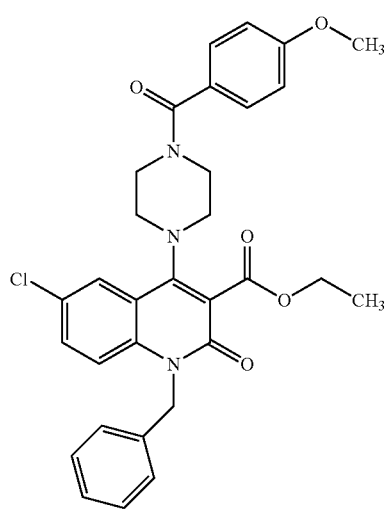
-continued
Compound 39
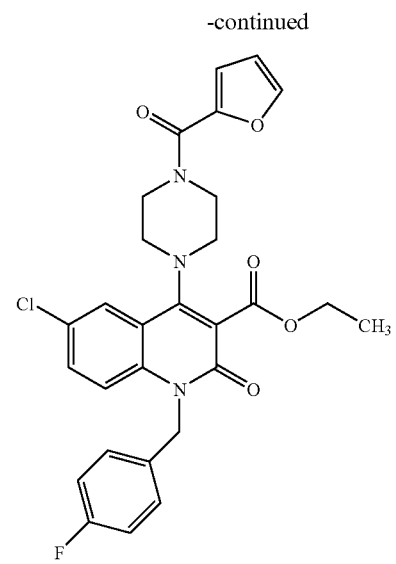
Compound 40
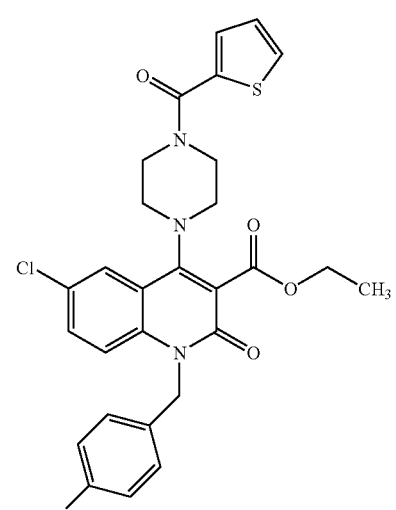
Compound 41
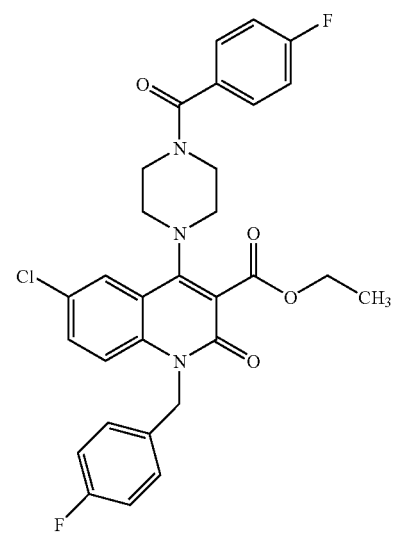

-continued
Compound 42
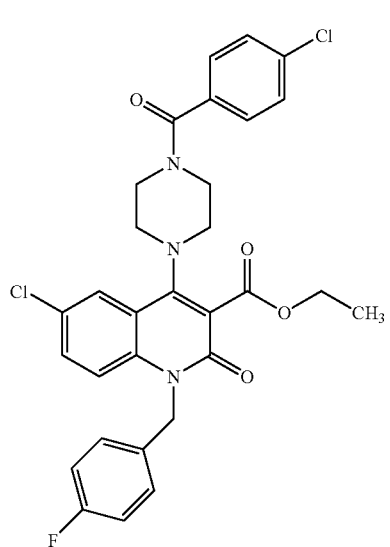
Compound 43
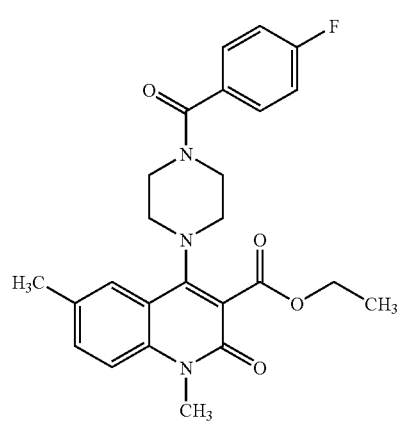
Compound 44
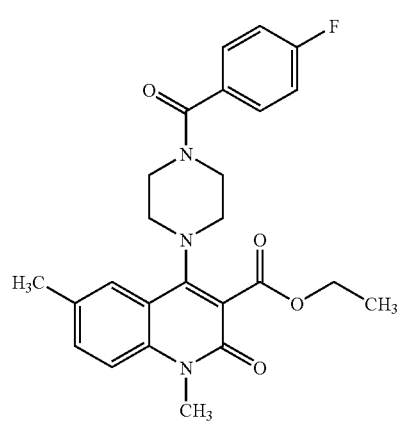
-continued
Compound 45
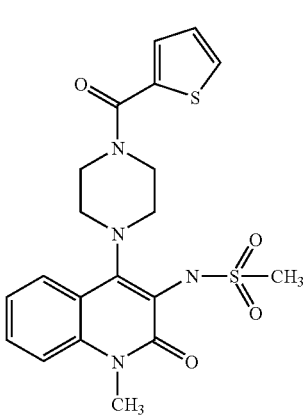
Compound 46
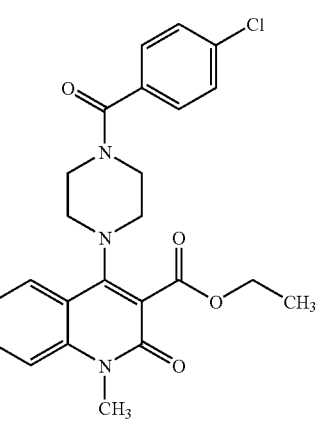
Compound 47
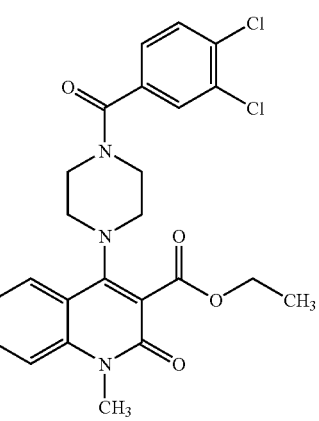
Compound 48
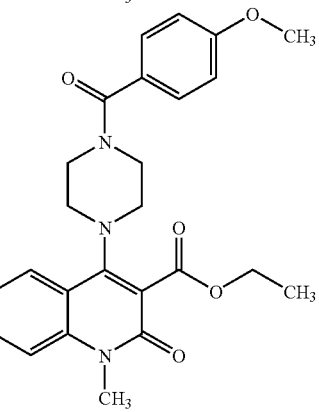

-continued
Compound 49
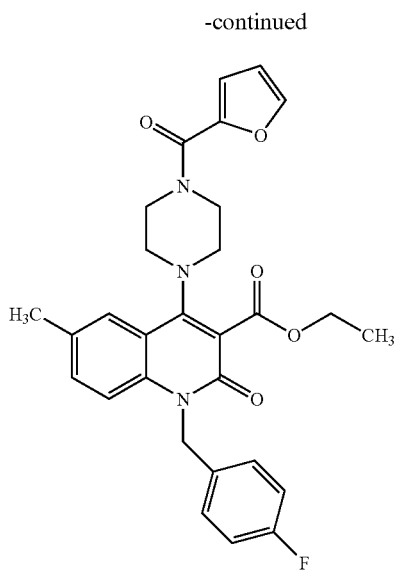
Compound 50
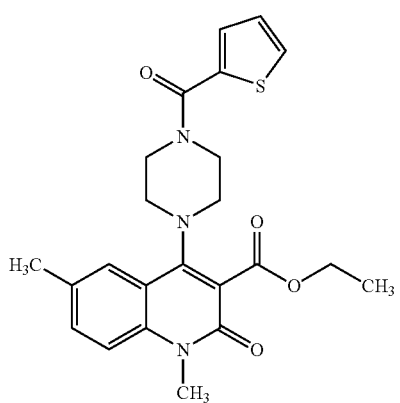
Compound 51
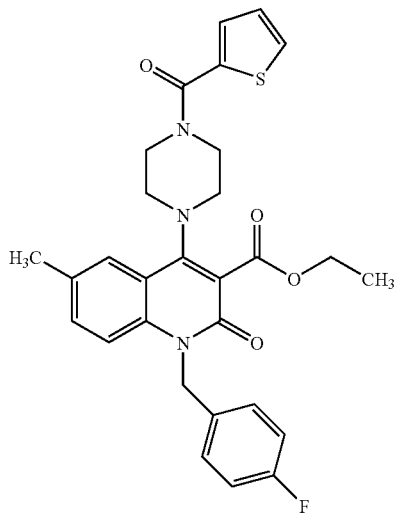
-continued
Compound 52
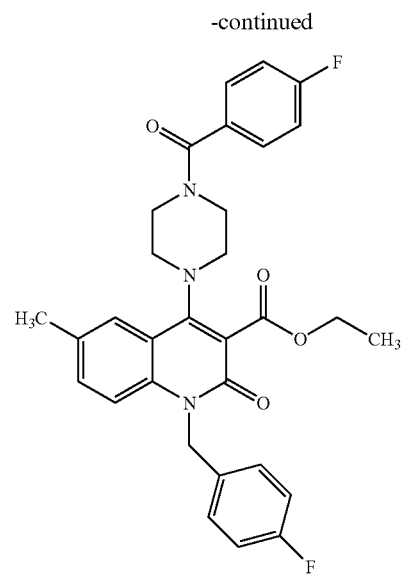
Compound 53
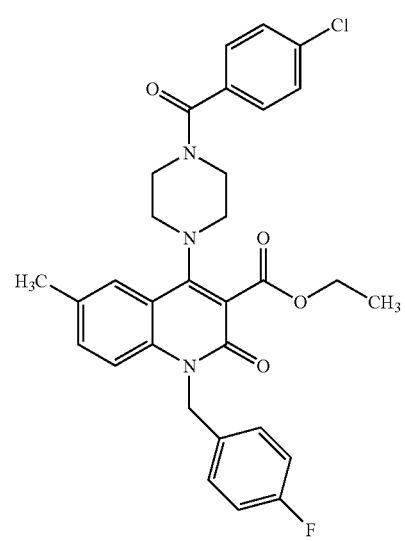
Compound 54
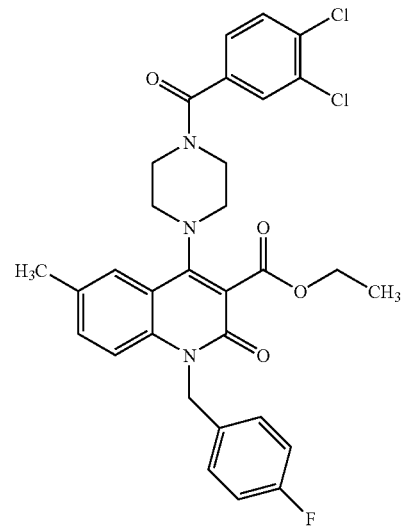

-continued
Compound 55
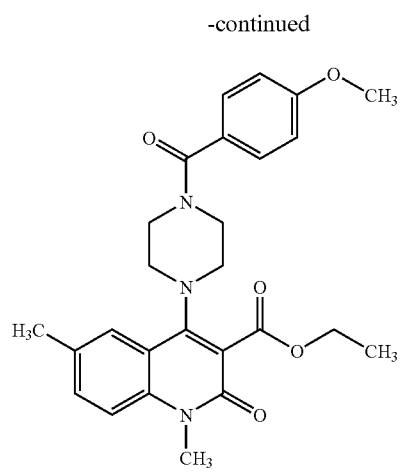
Compound 56
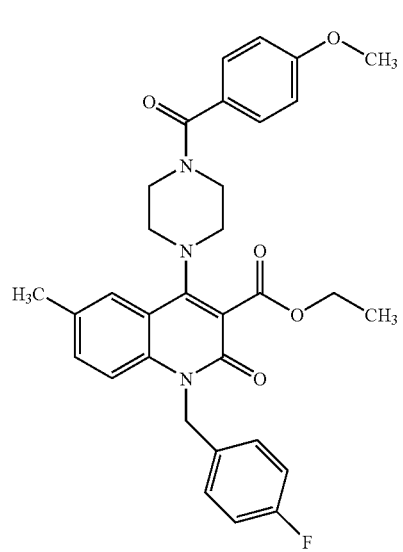
Compound 57
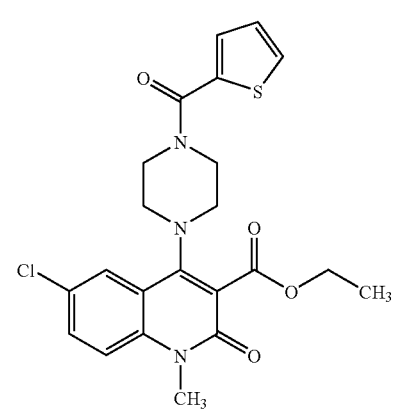
-continued
Compound 58
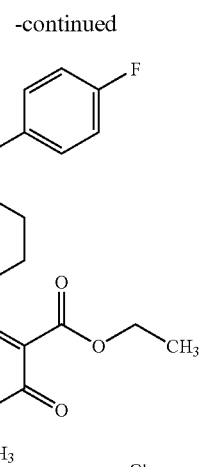
Compound 59
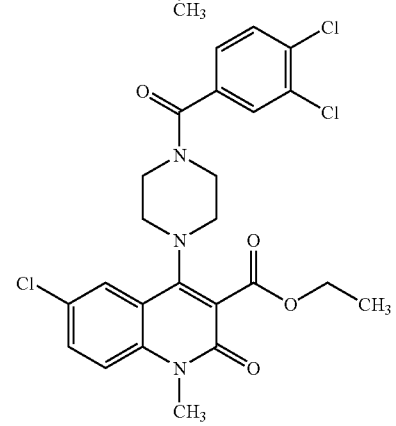
Compound 60
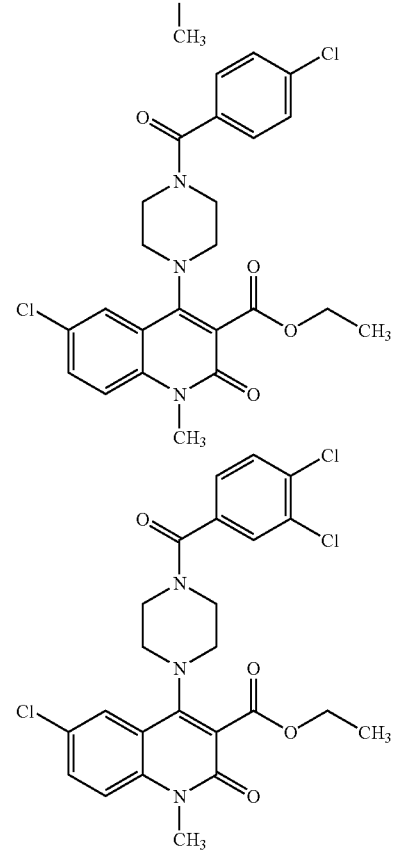
Compound 61
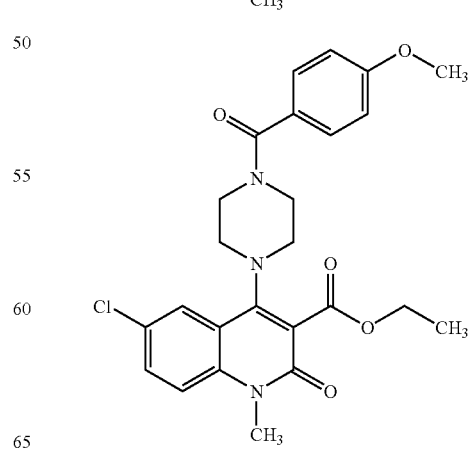

Compound 62
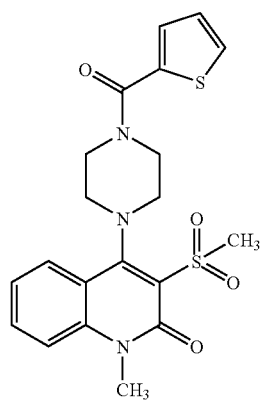
Compound 65
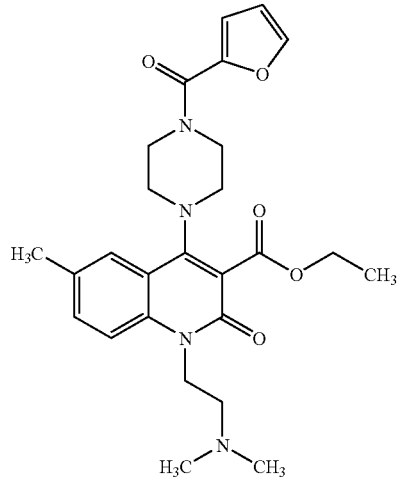
Compound 63
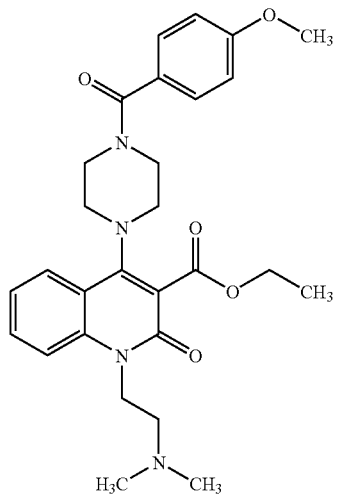
Compound 66
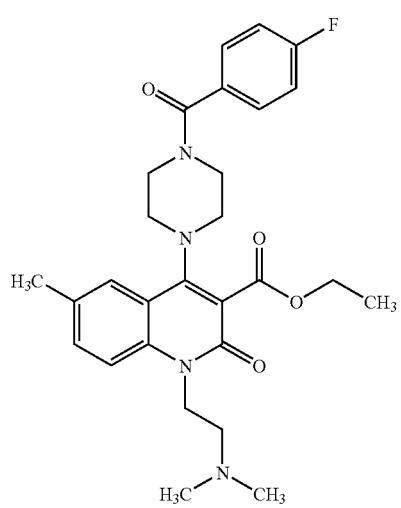
Compound 64
Compound 67
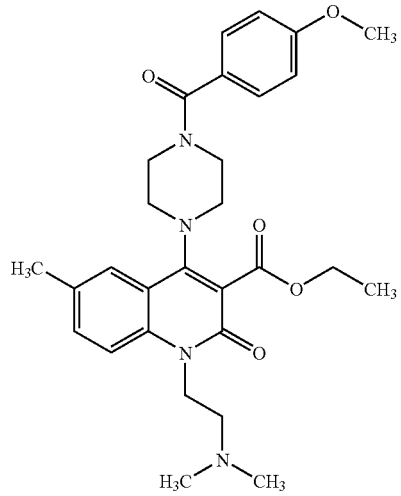

Compound 68
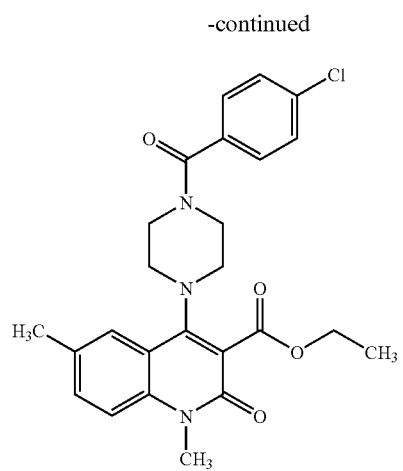
Compound 69
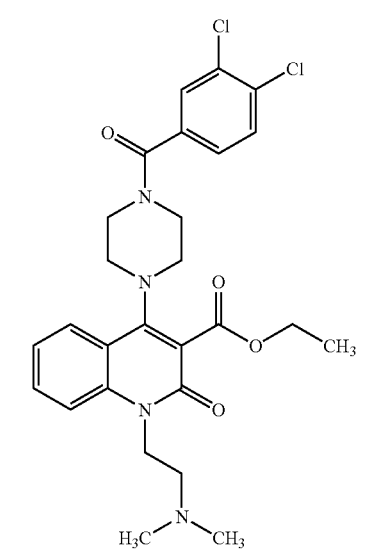
Compound 70
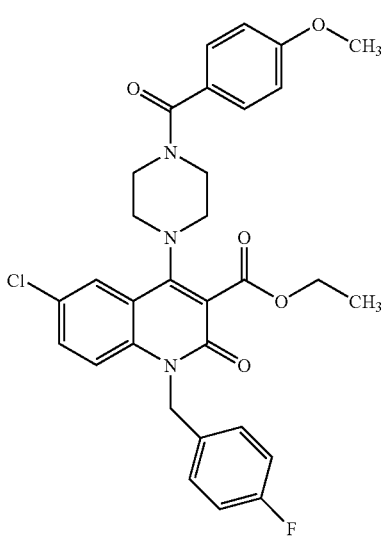
Compound 71
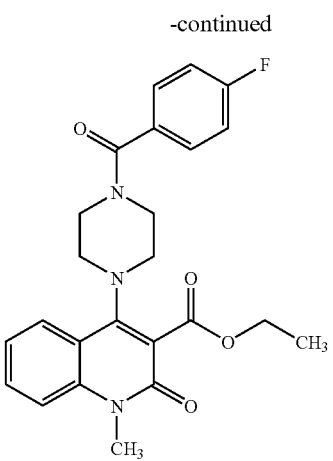
Compound 72
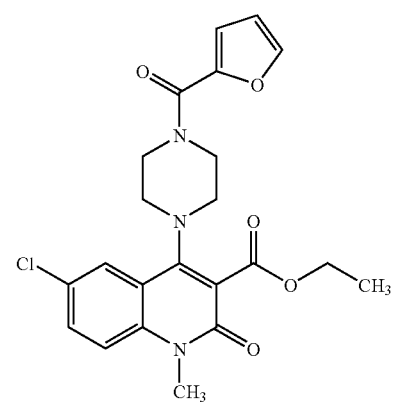
Compound 73
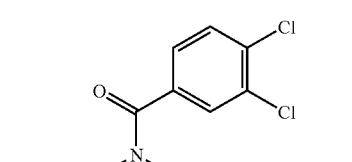
Compound 74
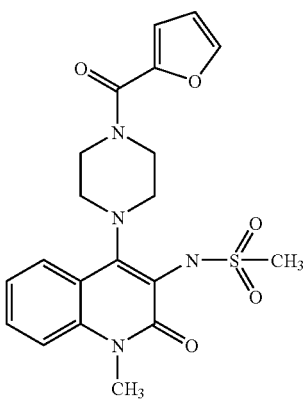

Compound 75
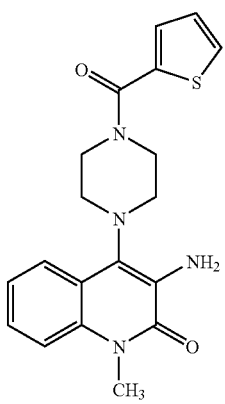
Compound 76
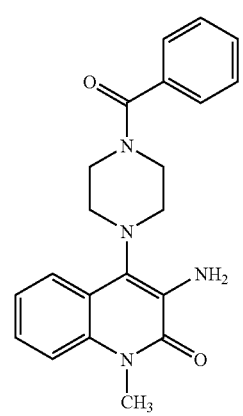
Compound 77
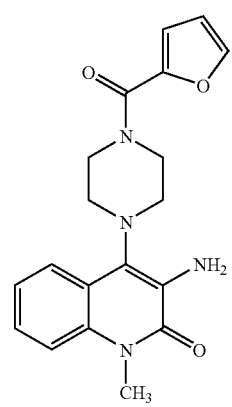
Compound 78
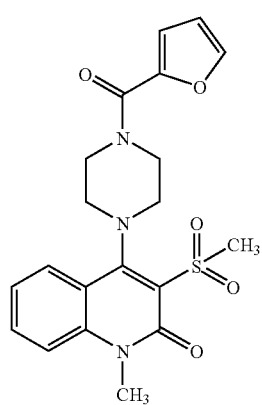
Compound 79
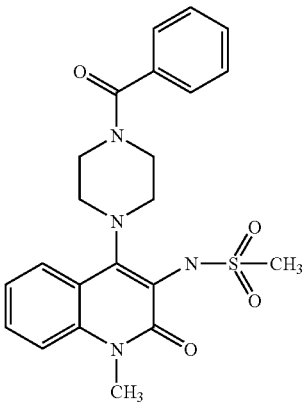
Compound 80
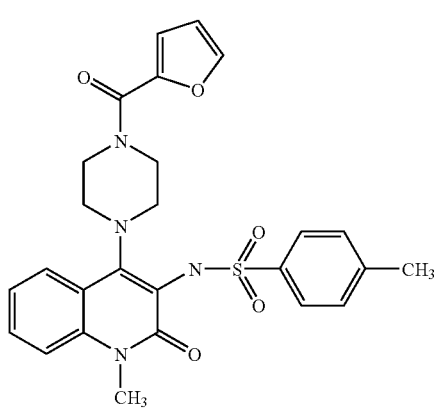
Compound 81
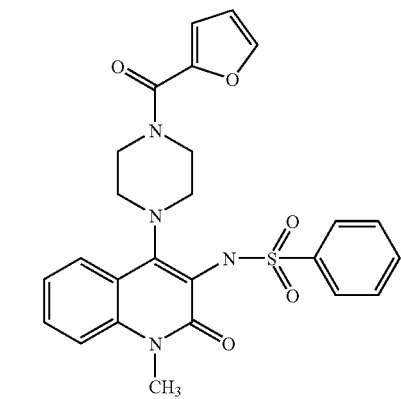
Compound 82
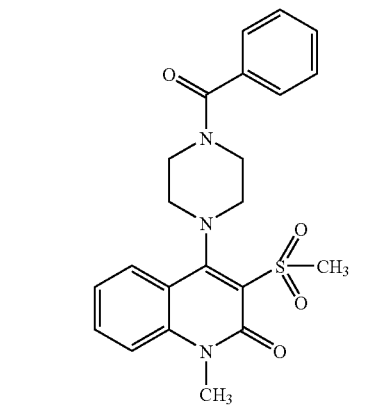

-continued
Compound 83
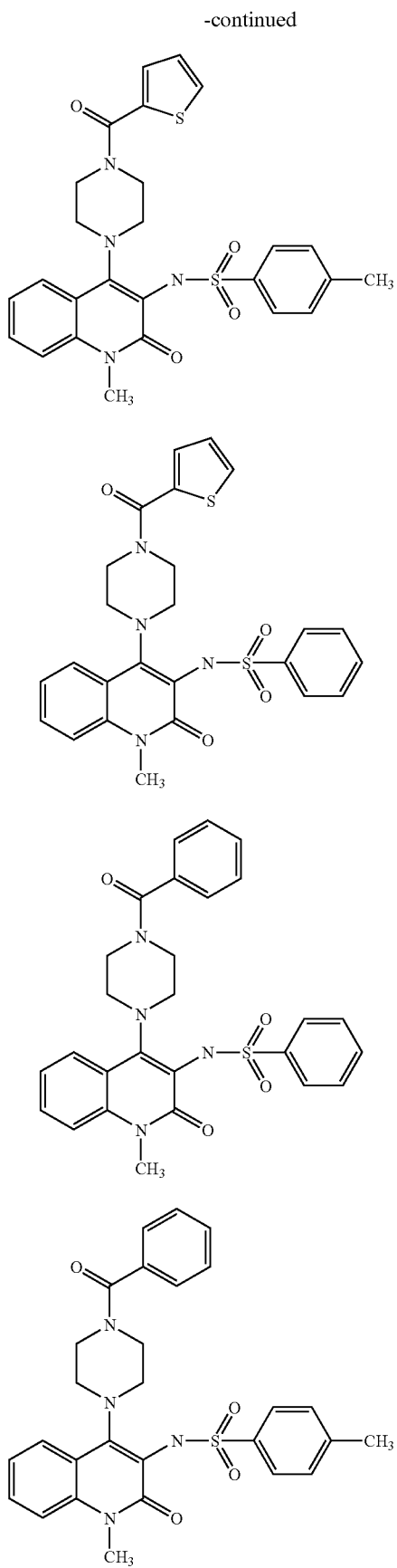
Compound 84
Compound 85
Compound 86
-continued
Compound 87
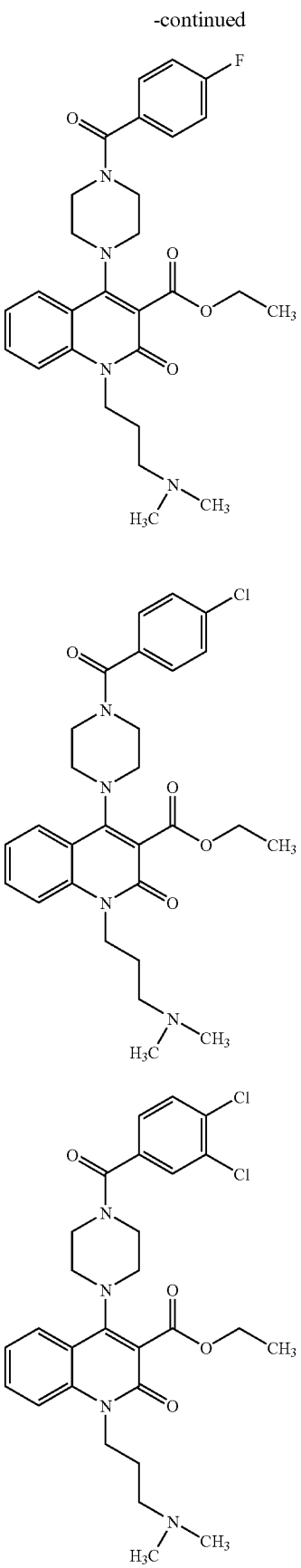
Compound 88
Compound 89

Compound 90
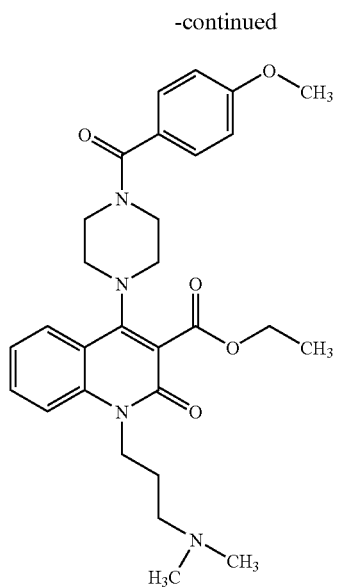
Compound 91
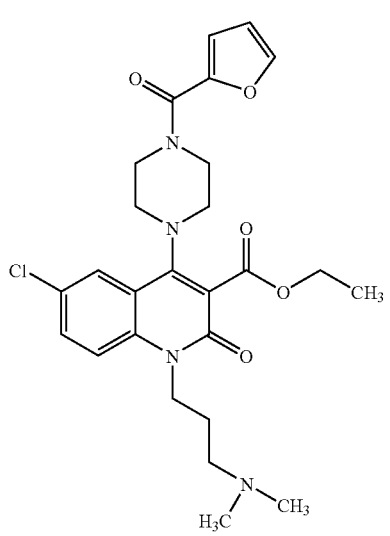
Compound 93
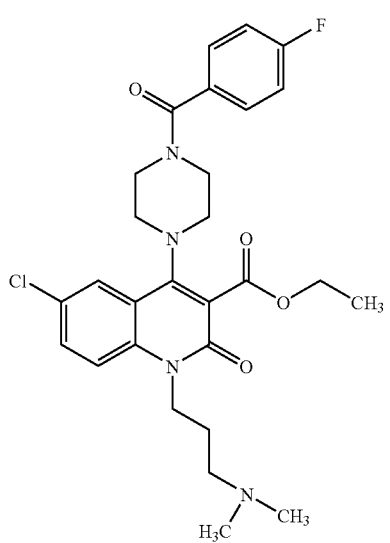
Compound 94
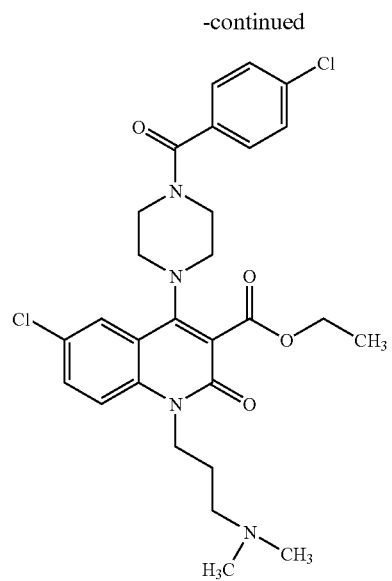
Compound 95
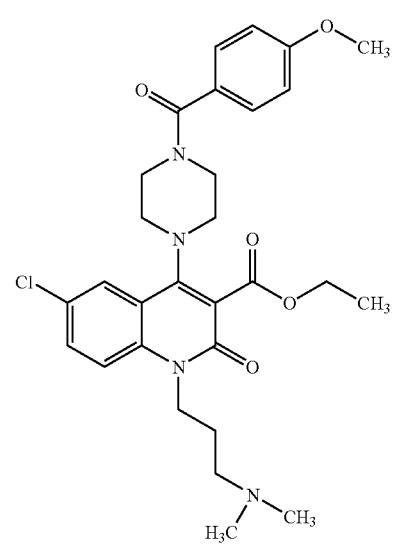
Compound 96
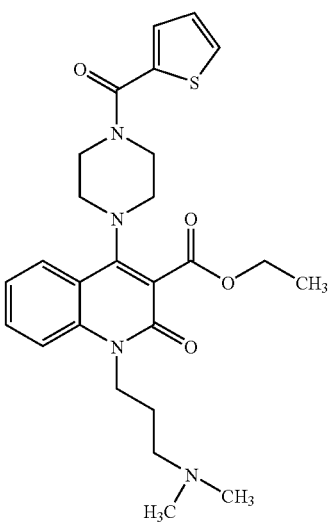

-continued
Compound 97
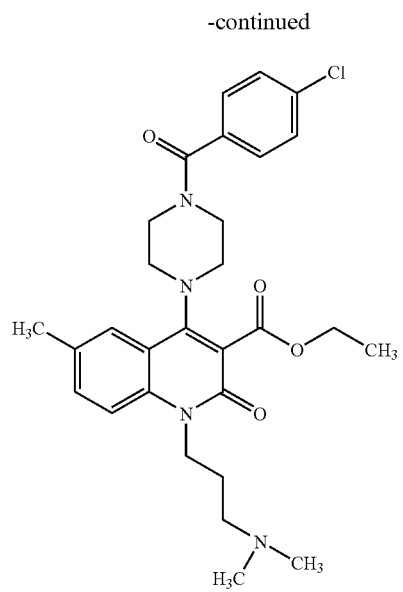
Compound 98
Compound 99
Compound 100
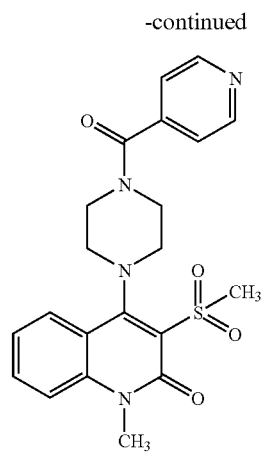
Compound 101
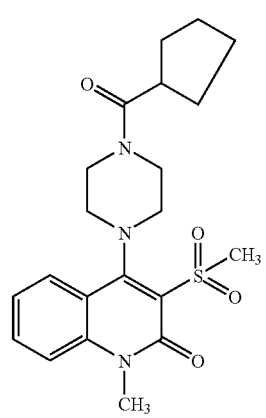
Compound 102
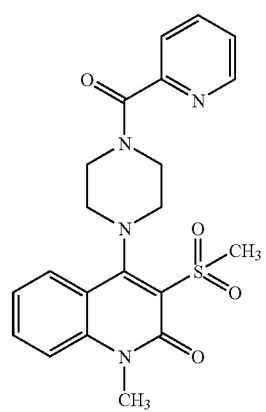
Compound 103
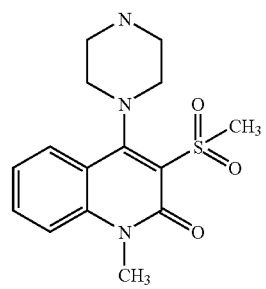

Compound 104
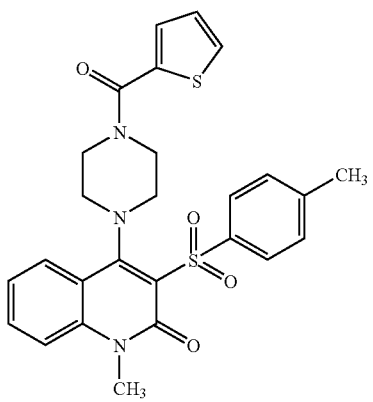
Compound 105
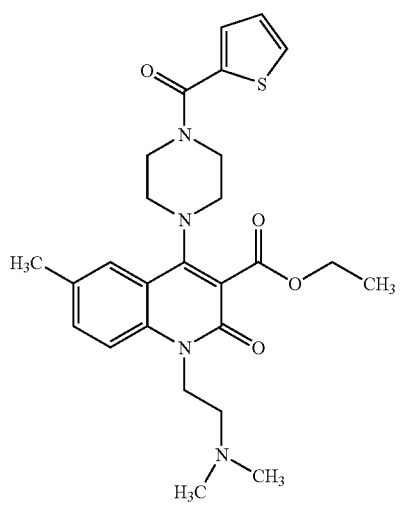
Compound 106
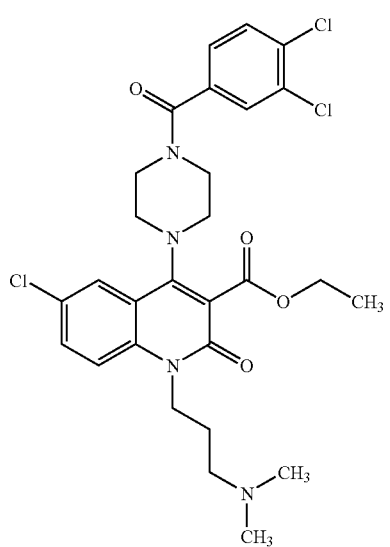
Compound 107
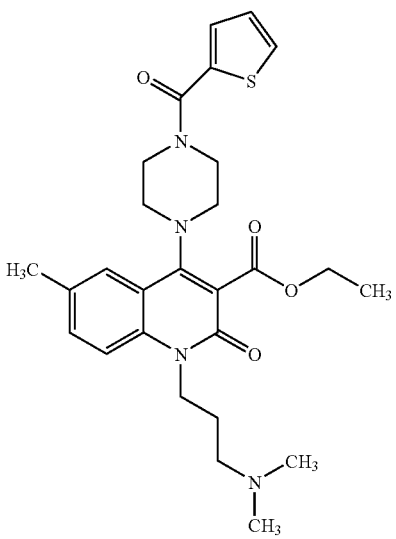
Compound 108
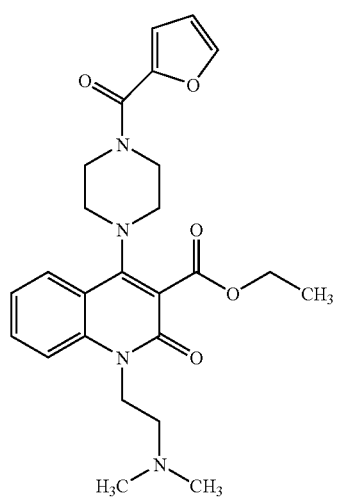
Compound 109
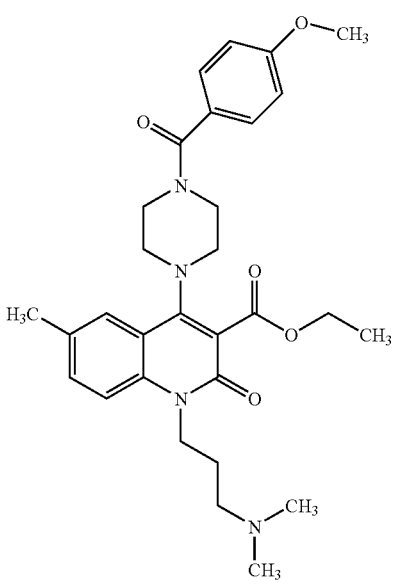

-continued
Compound 110
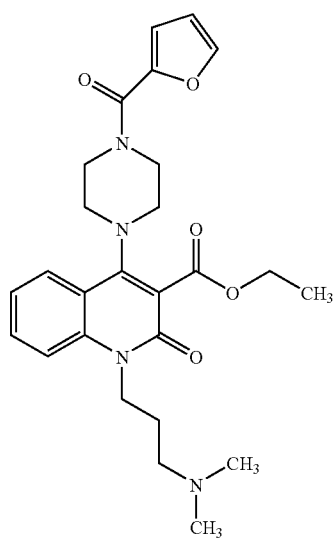
Compound 111
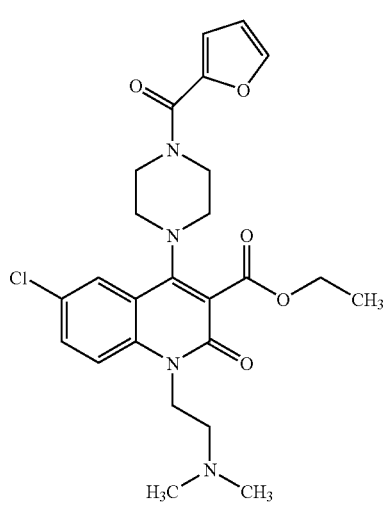
Compound 112
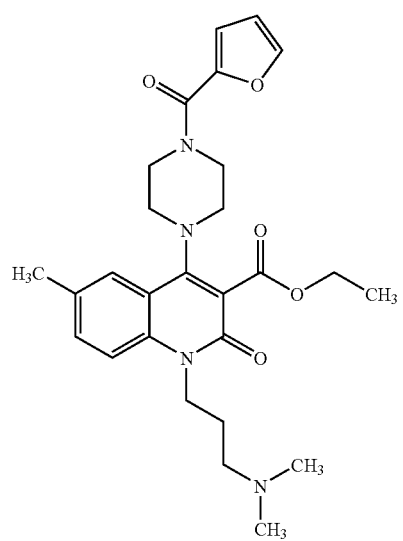
-continued
Compound 113
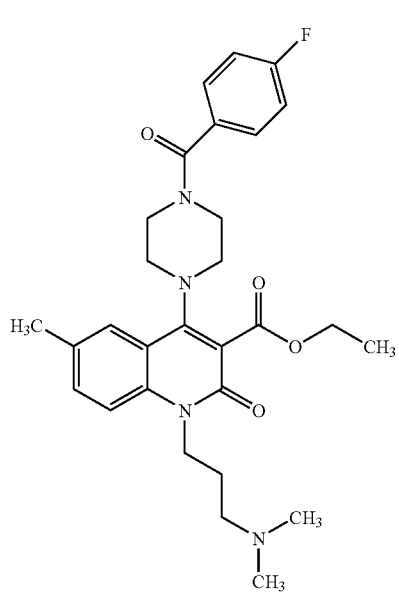
Compound 114
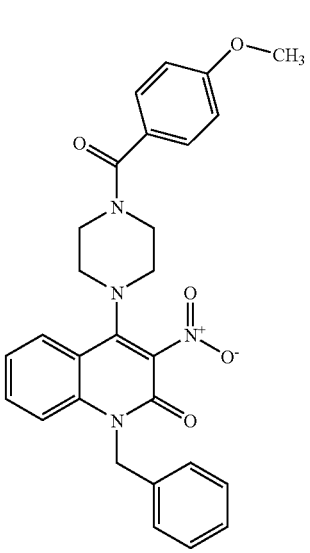
Compound 115
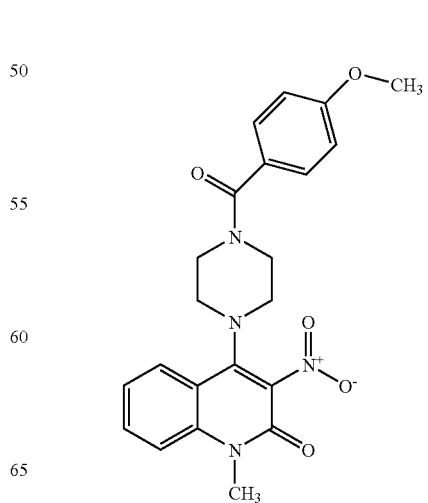

Compound 116
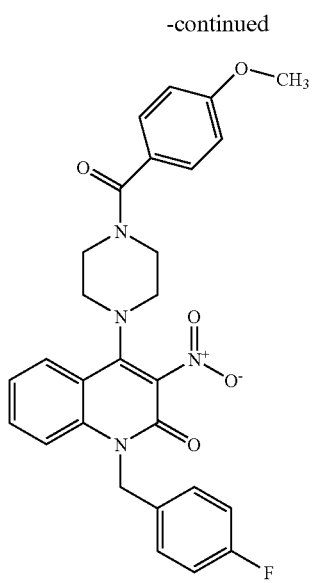
Compound 117
Compound 118
Compound 119
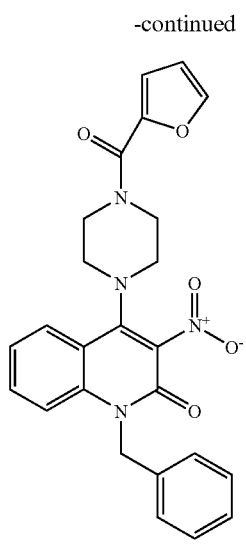
Compound 120
Compound 121

-continued

Compound 122

Compound 123

Compound 124

-continued

Compound 125

Compound 126

Compound 127

Compound 128

Compound 129
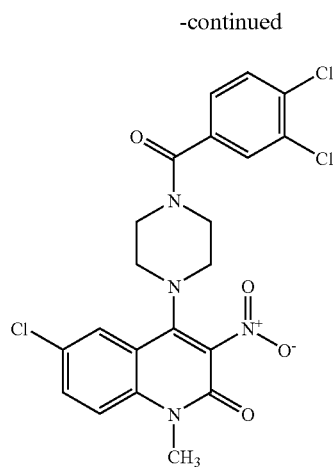
Compound 130
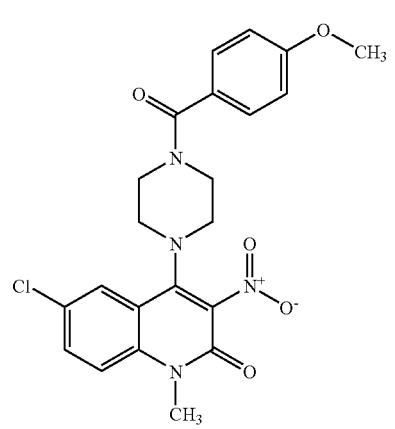
Compound 131
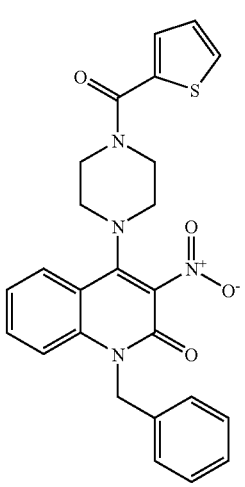
Compound 132
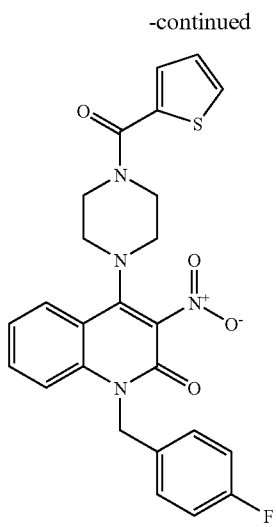
Compound 133
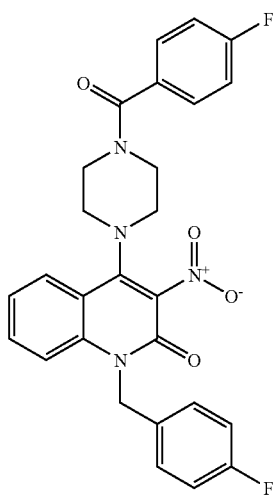
Compound 134
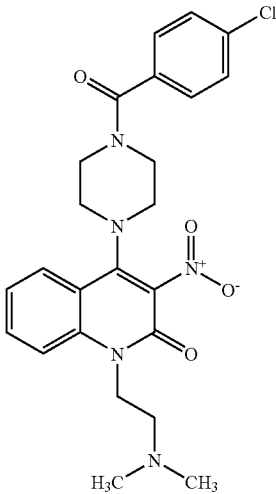

-continued

Compound 135

Compound 136

Compound 137

-continued

Compound 138

Compound 139

Compound 140

Compound 141
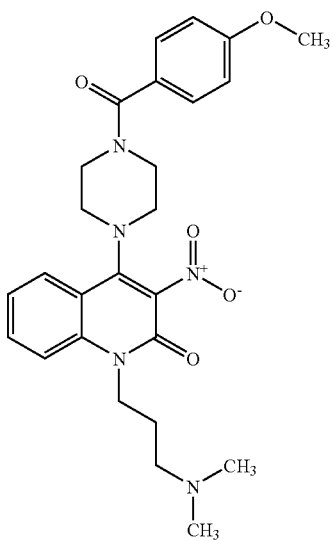
Compound 142
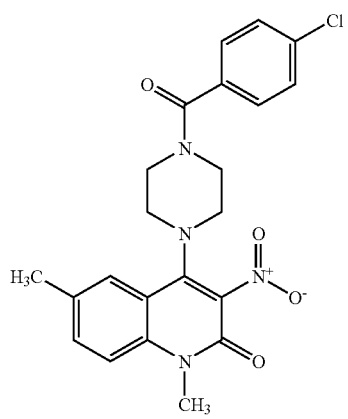
Compound 143
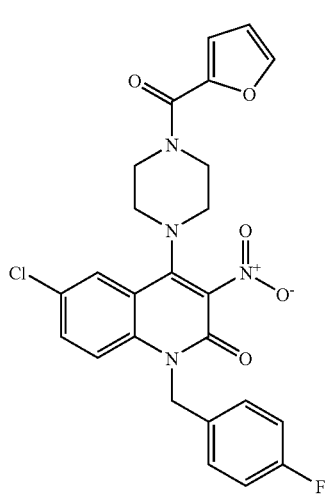
Compound 144
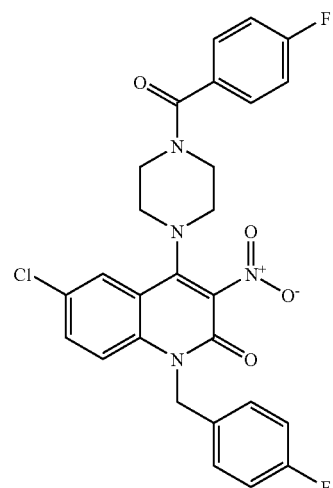
Compound 145
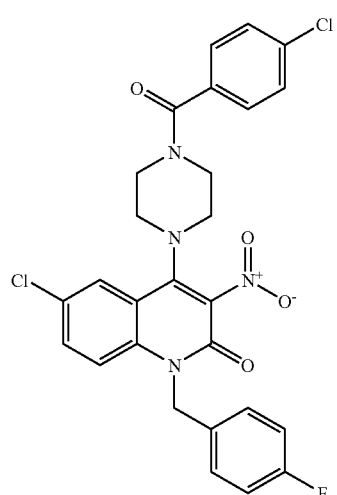
Compound 146
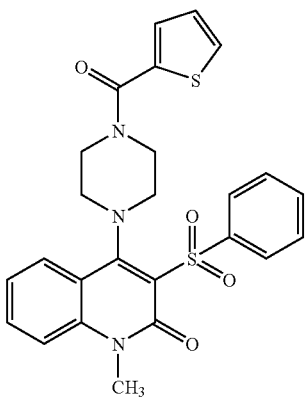

Compound 147

Compound 148

Compound 149

Compound 150

Compound 151

Compound 152

-continued
Compound 153
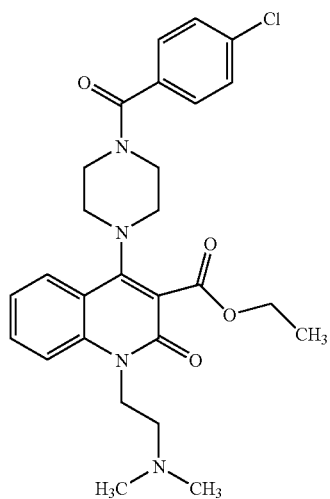
Compound 154
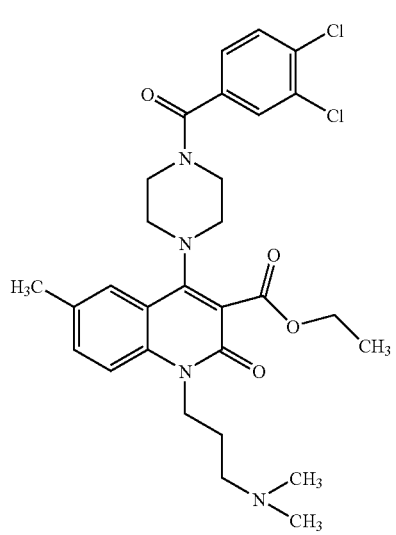
Compound 155
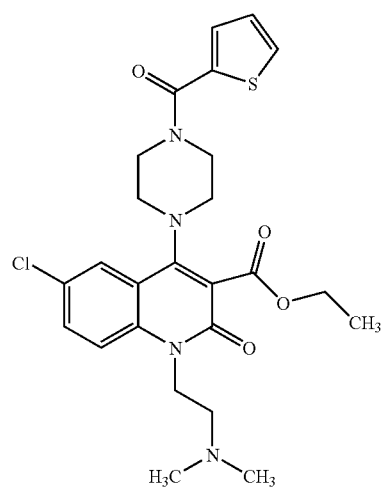
-continued
Compound 156
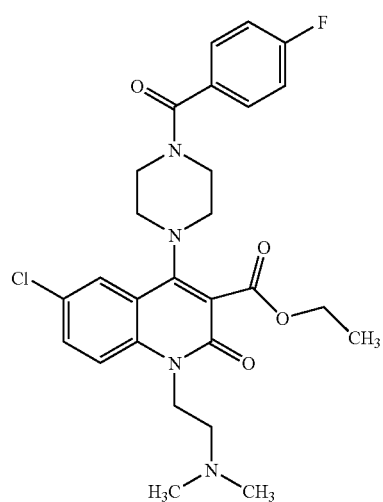
Compound 157
Compound 158
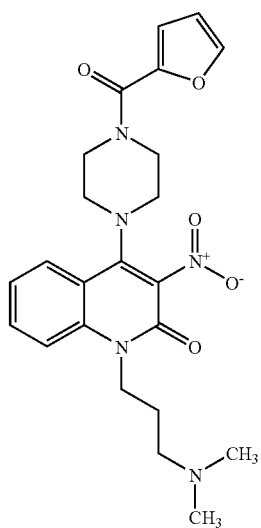

Compound 159
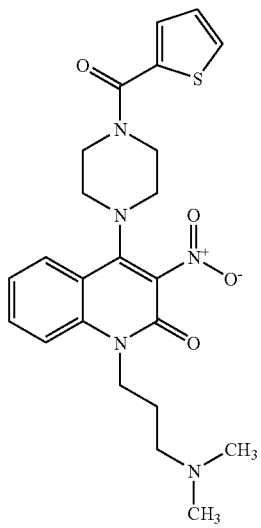
Compound 160
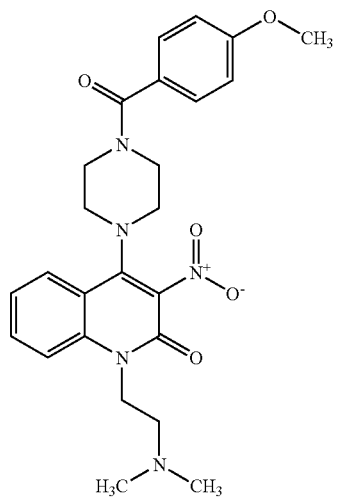
Compound 161
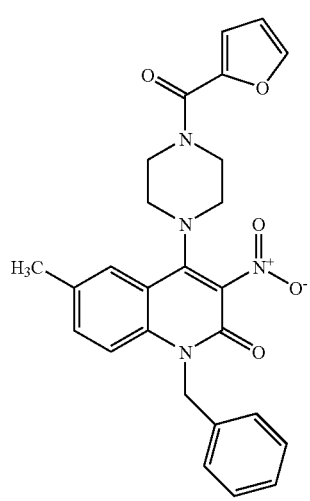
Compound 162
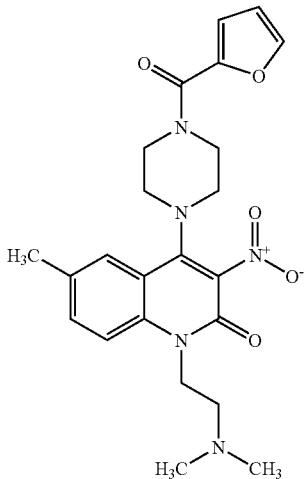
Compound 163
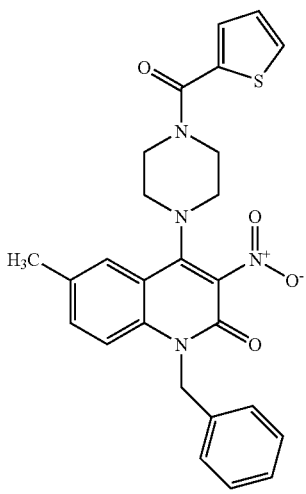
Compound 164

Compound 165
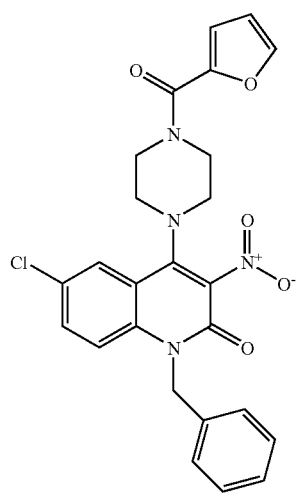
Compound 168
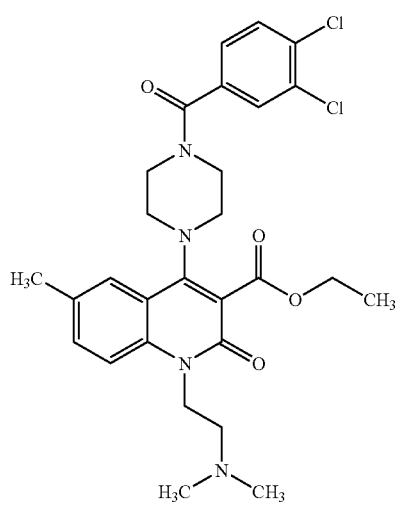
Compound 166
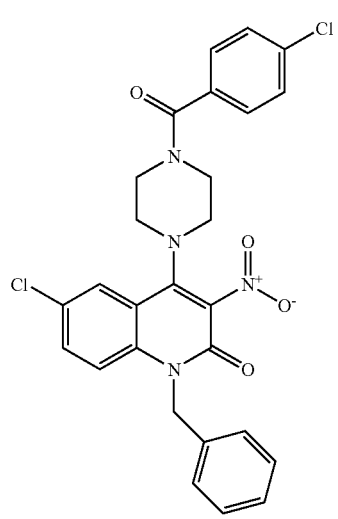
Compound 169
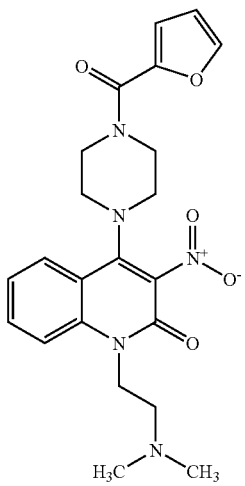
Compound 167
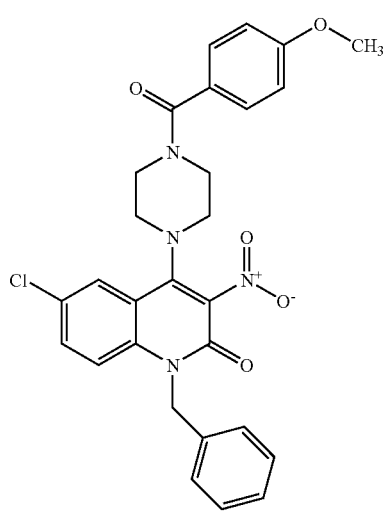
Compound 170

Compound 171
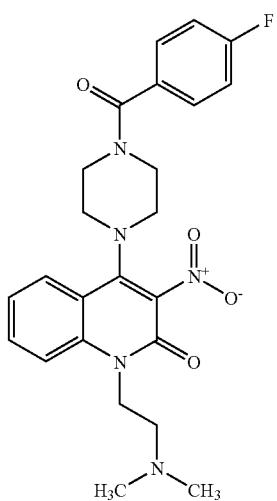
Compound 172
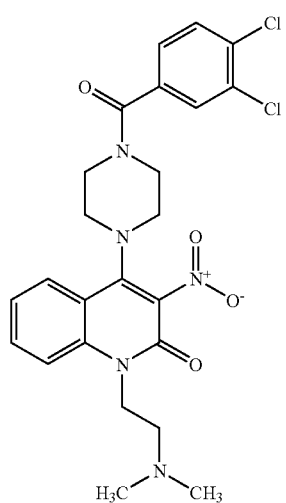
Compound 173
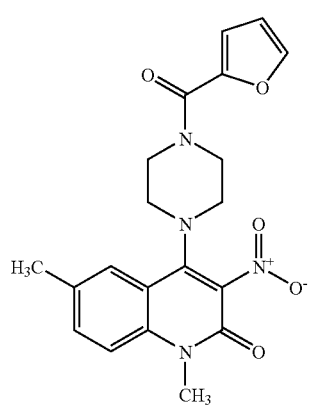
Compound 174
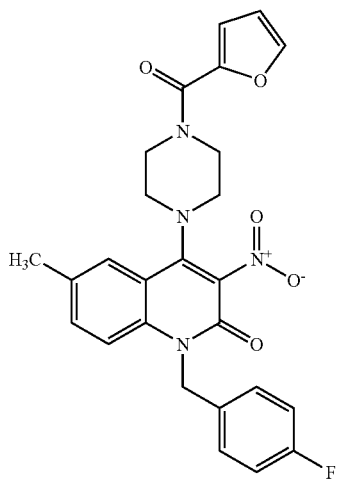
Compound 175
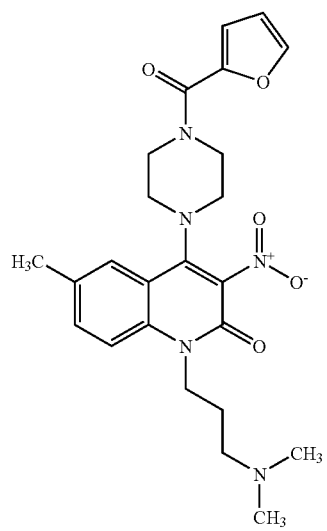
Compound 176
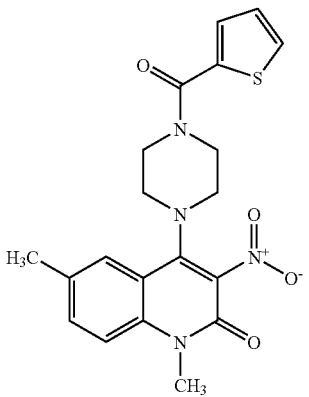

-continued
Compound 177
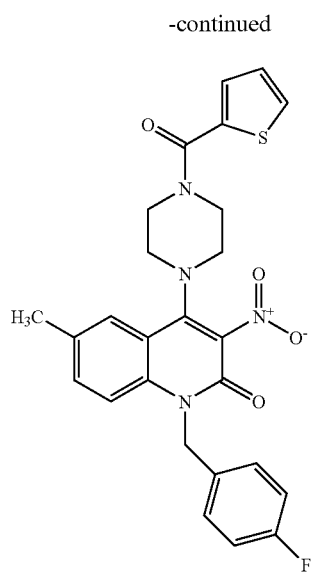
Compound 178
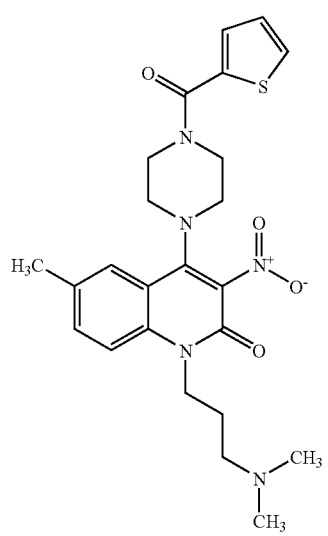
Compound 179
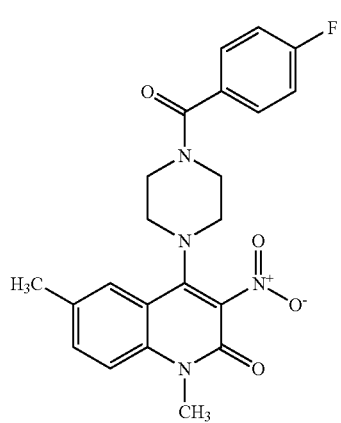
-continued
Compound 180
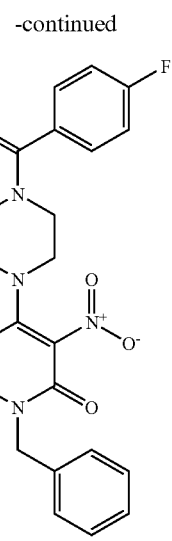
Compound 181
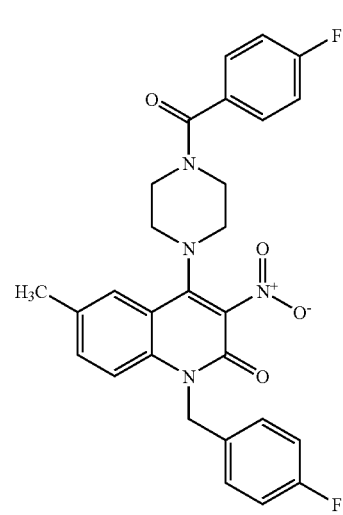
Compound 182
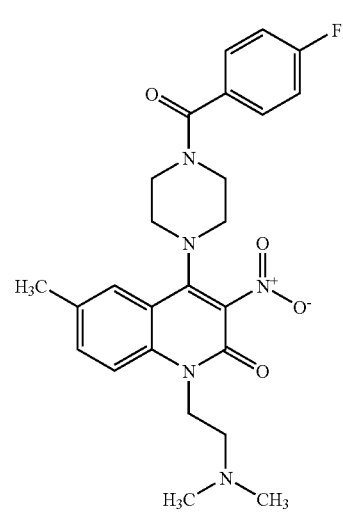

-continued
Compound 183
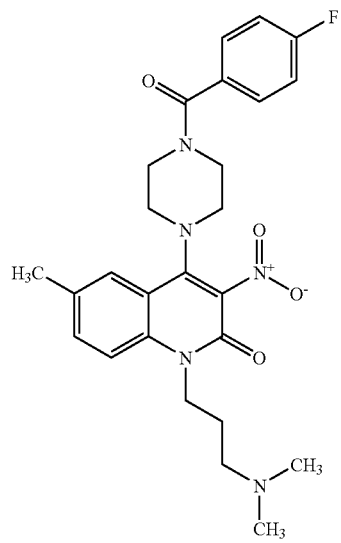
Compound 184
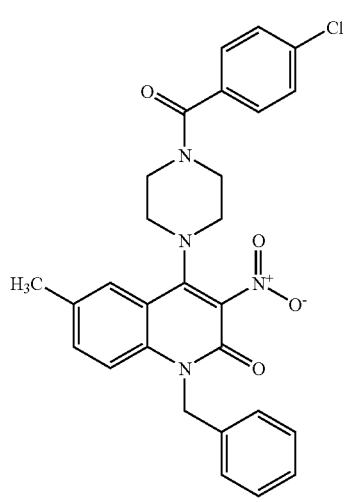
Compound 185
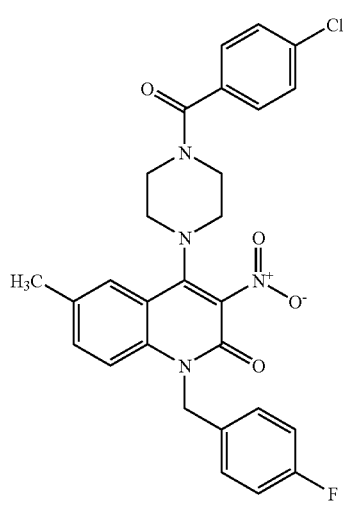
-continued
Compound 186
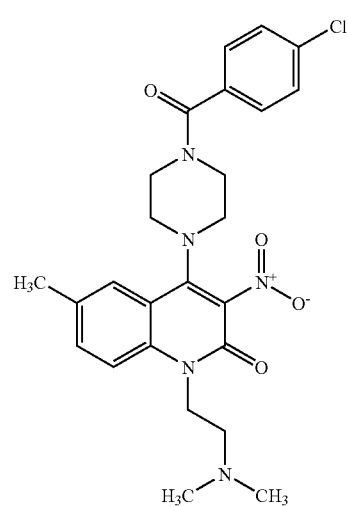
Compound 187
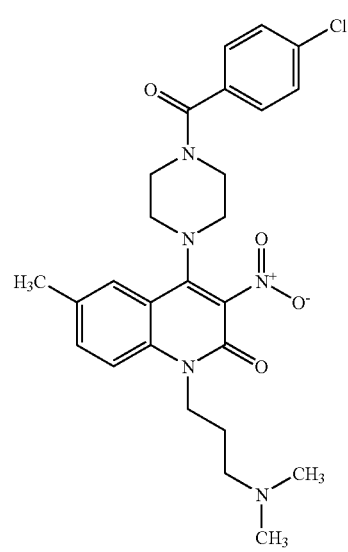
Compound 188
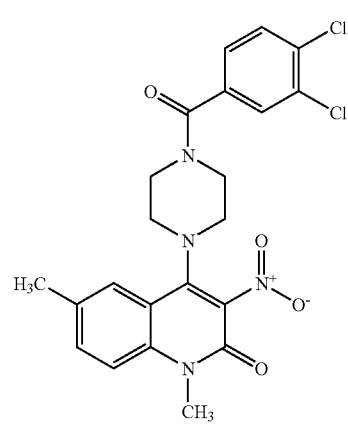

Compound 189
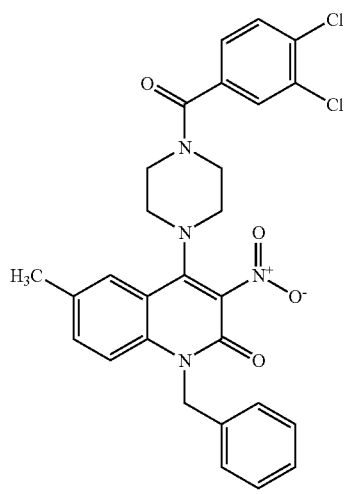
Compound 190
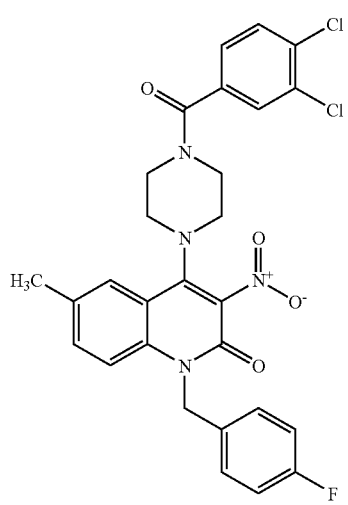
Compound 191
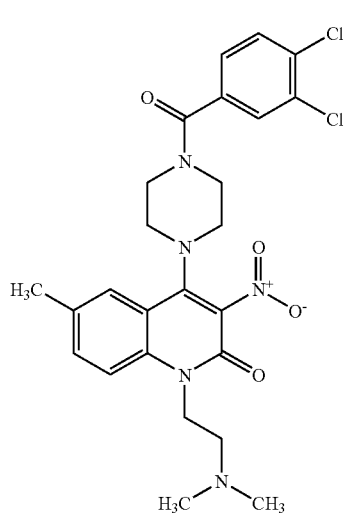
Compound 192
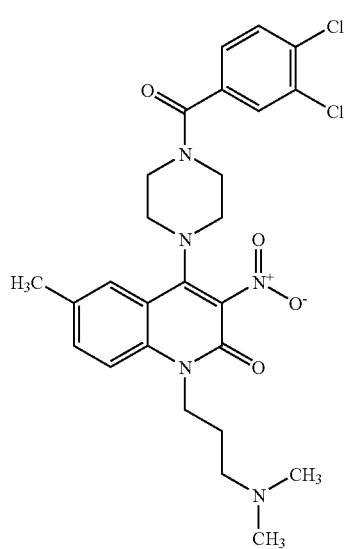
Compound 193
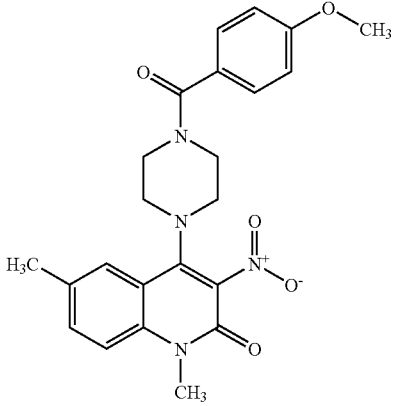
Compound 194
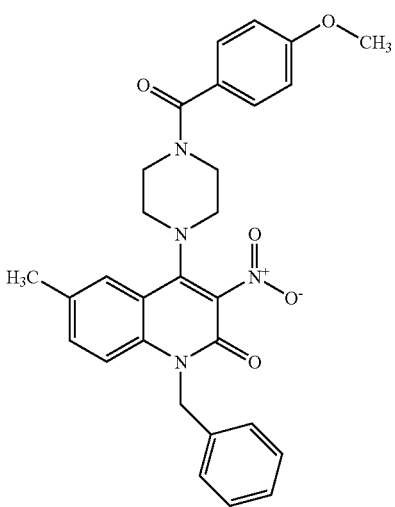

-continued
Compound 195
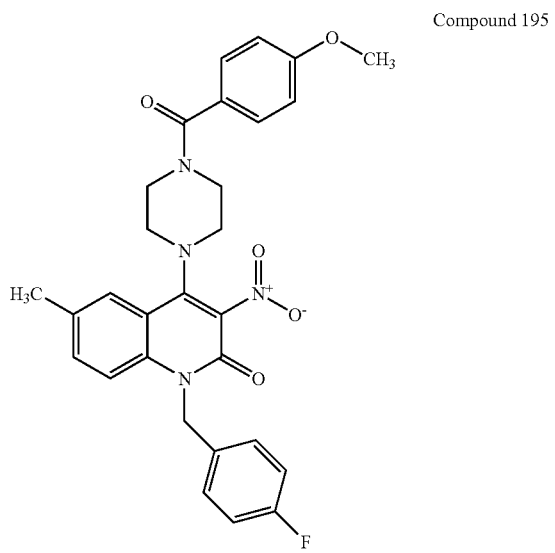
Compound 196
Compound 197
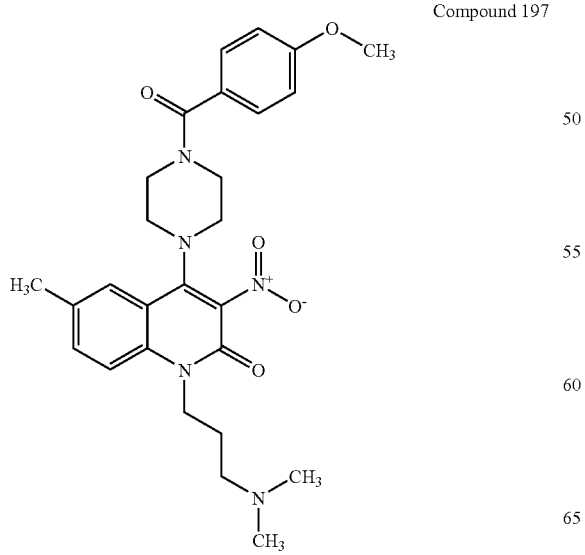
-continued
Compound 198
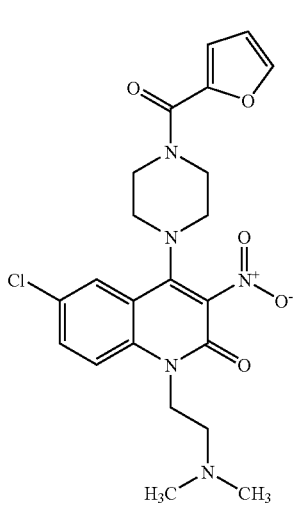
Compound 199
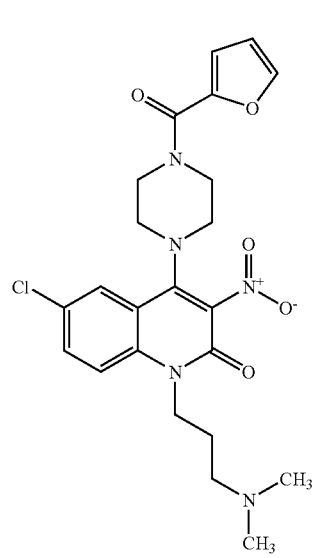
Compound 200
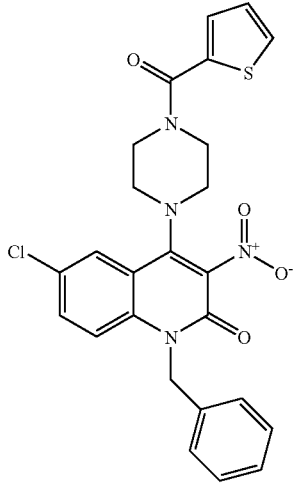

-continued
Compound 201
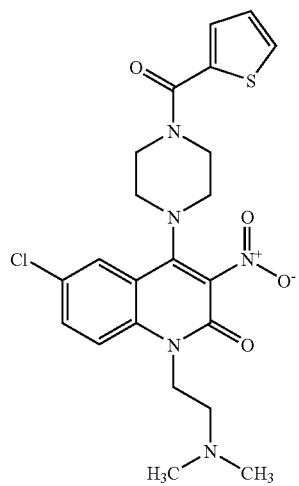
Compound 202
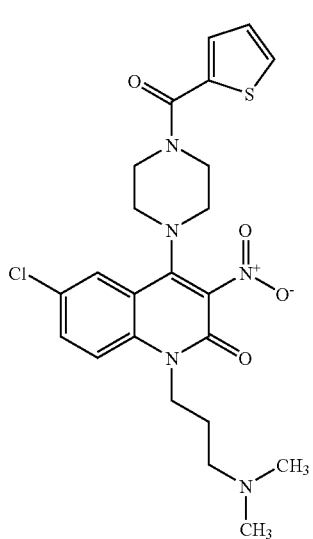
Compound 203
-continued
Compound 204
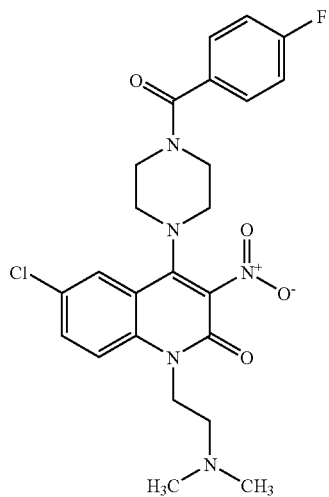
Compound 205
Compound 206
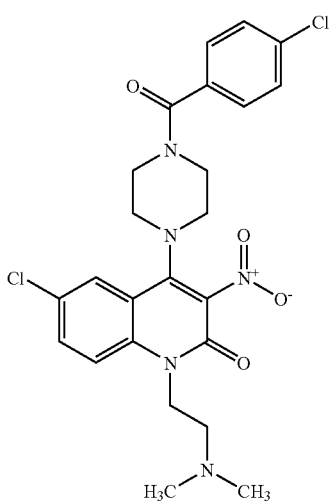

Compound 207
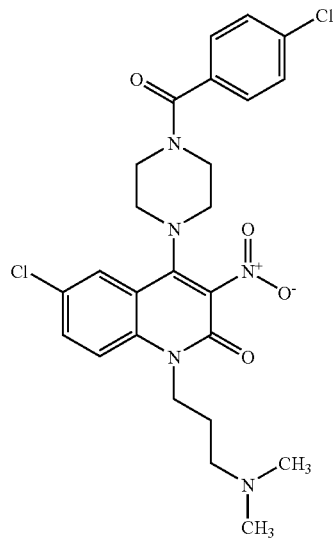
Compound 208
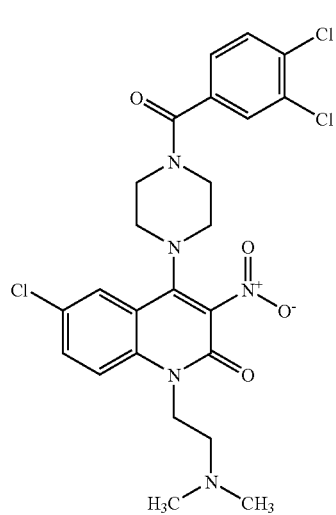
Compound 209
Compound 210
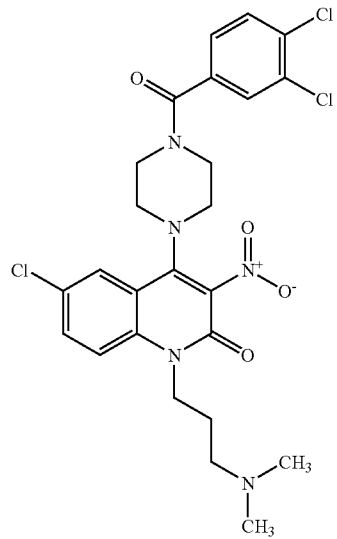
Compound 211
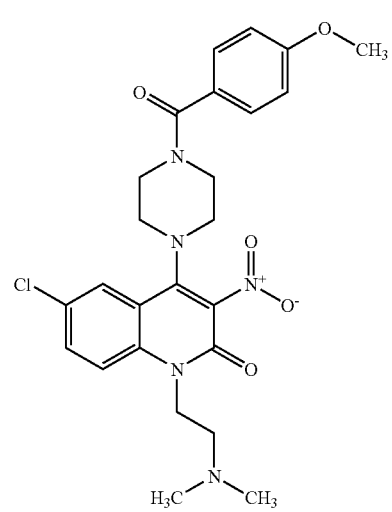
Compound 212
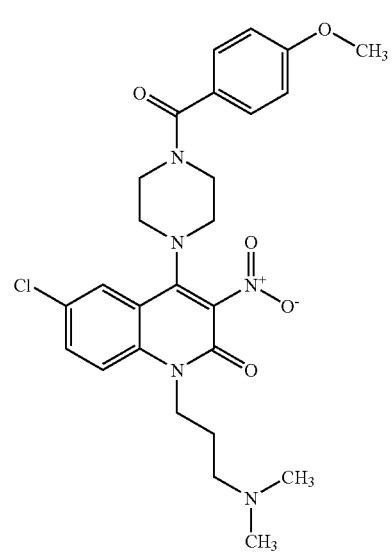

-continued
Compound 213
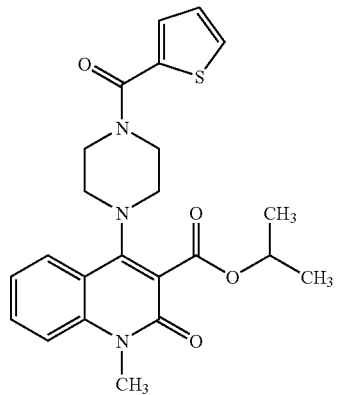
Compound 214
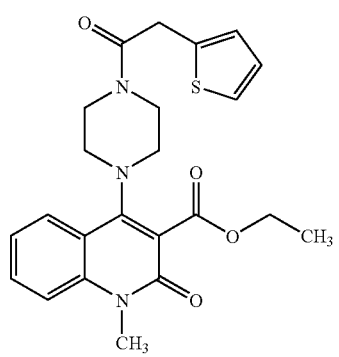
Compound 215
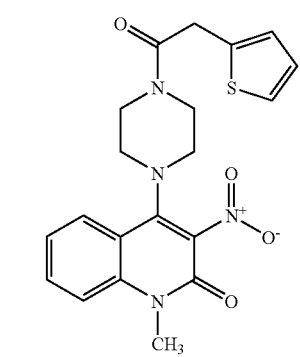
Compound 216
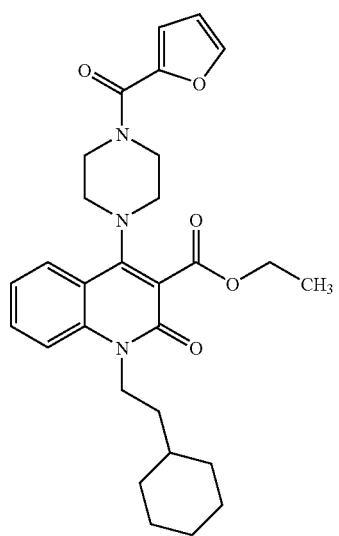
-continued
Compound 217
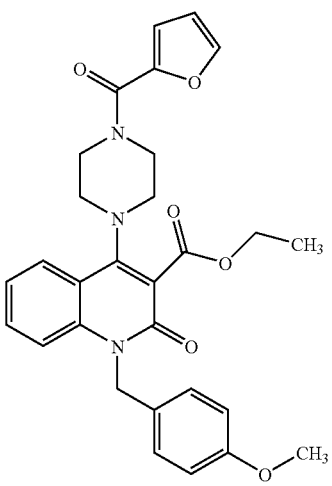
Compound 218
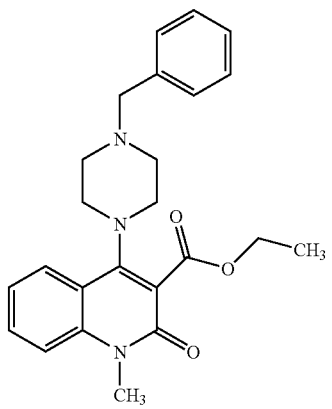
Compound 219
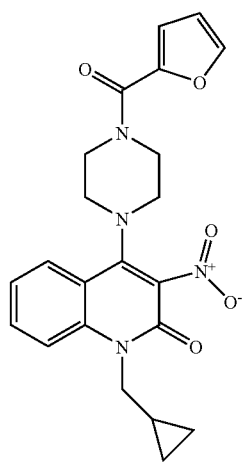

-continued
Compound 220
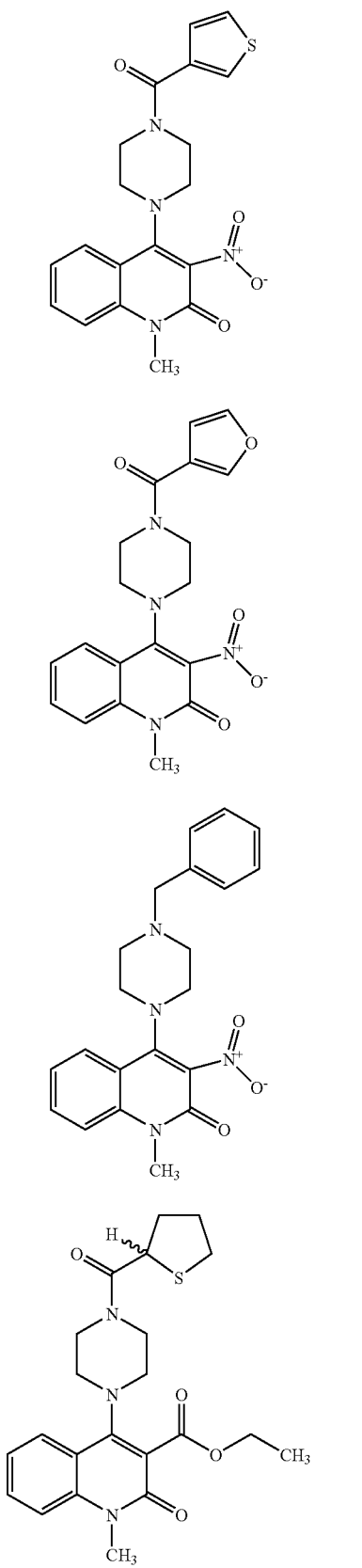
Compound 221
Compound 222
Compound 223
-continued
Compound 224
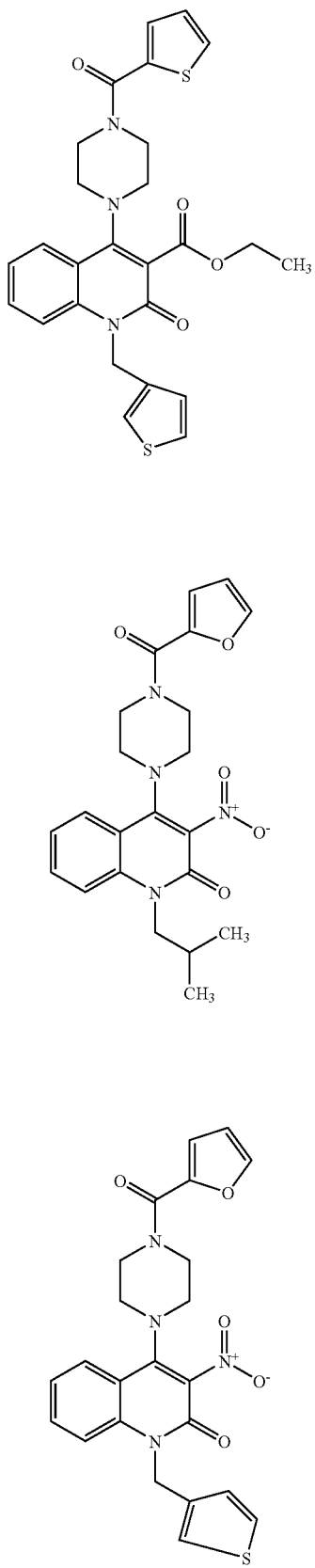
Compound 225
Compound 226

Compound 227
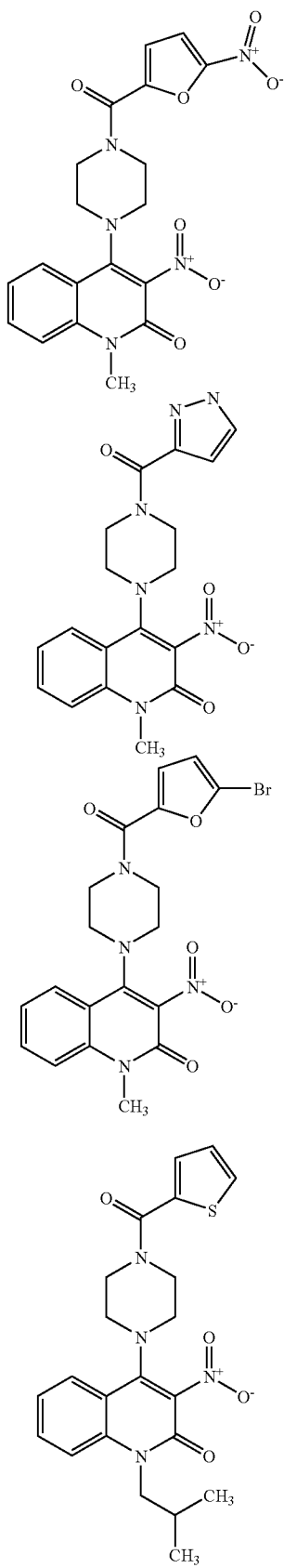
Compound 228
Compound 229
Compound 230
Compound 231
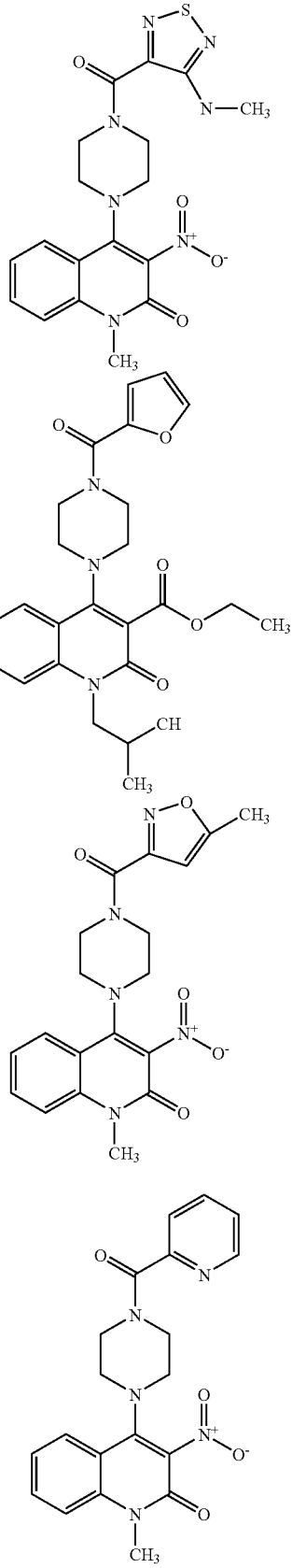
Compound 232
Compound 233
Compound 234

-continued
Compound 235
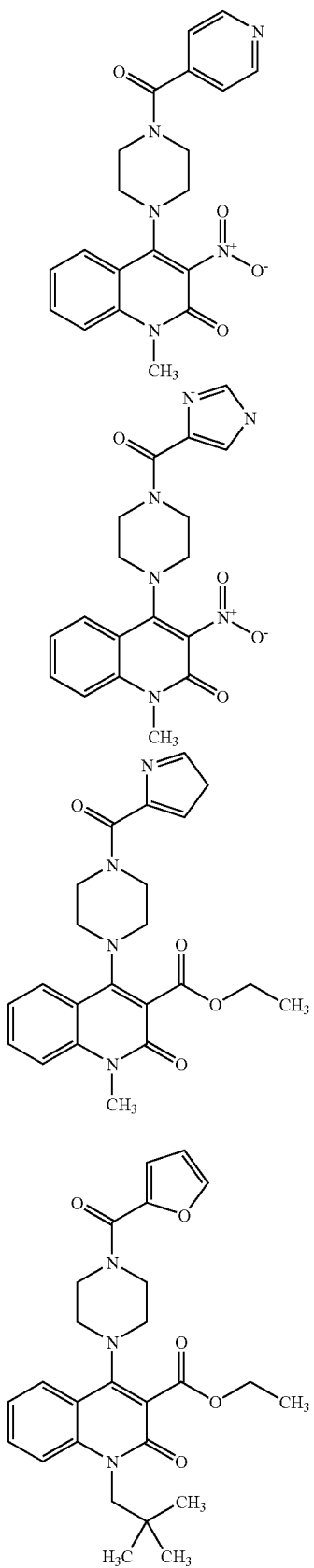
Compound 236
Compound 237
Compound 238
-continued
Compound 239
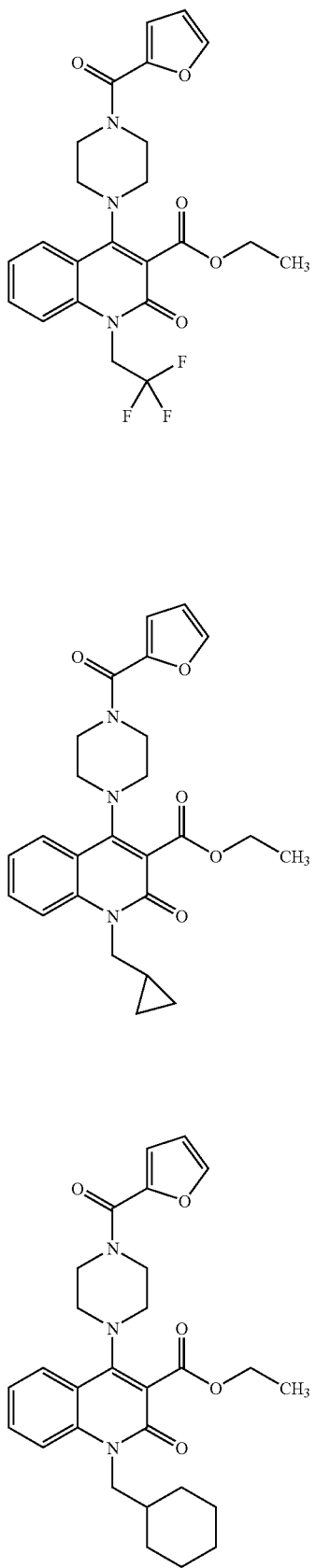
Compound 240
Compound 241

-continued
Compound 242
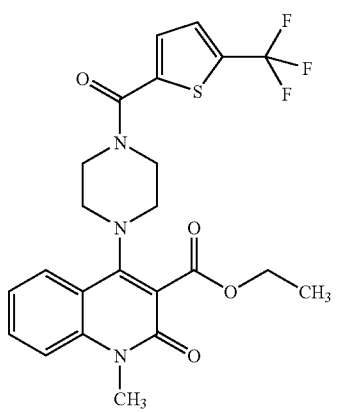
Compound 243
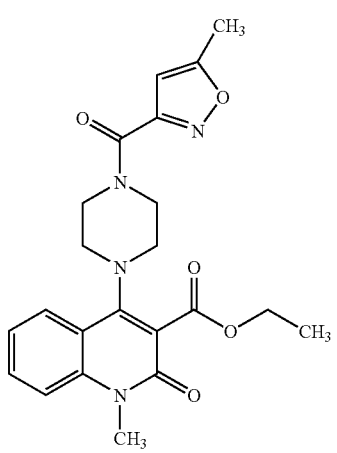
Compound 244
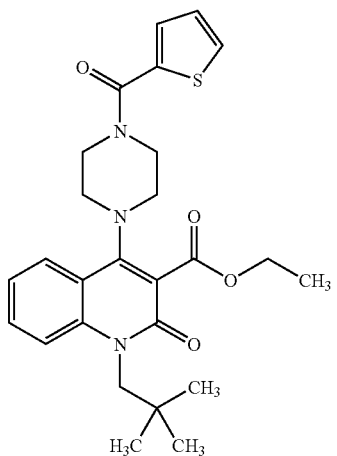
-continued
Compound 245
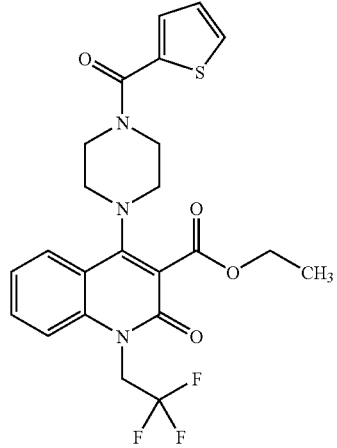
Compound 246
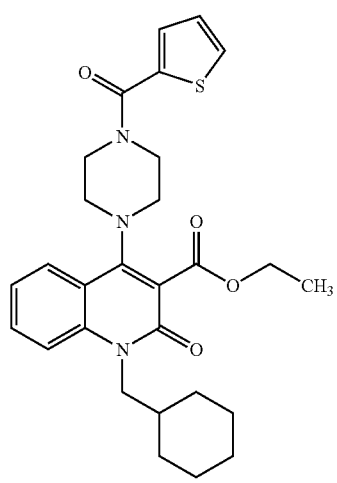
Compound 247
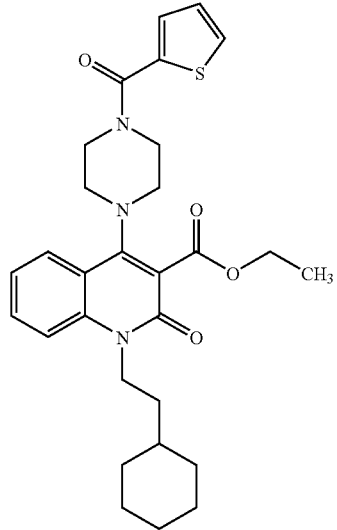

Compound 248
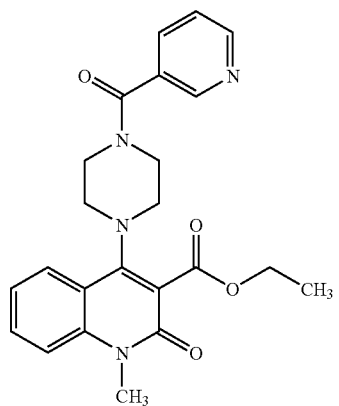
Compound 249
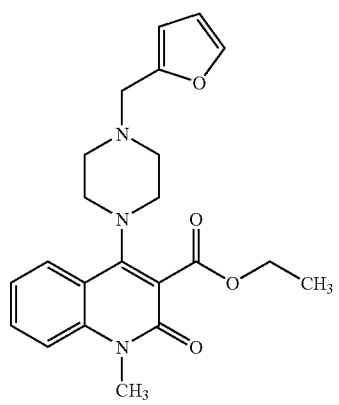
Compound 250
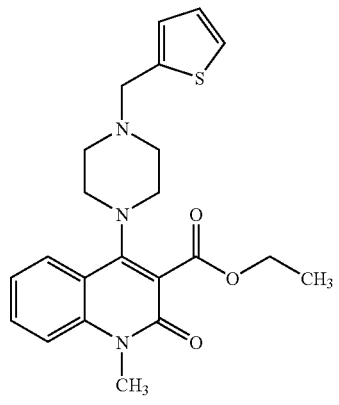
Compound 251
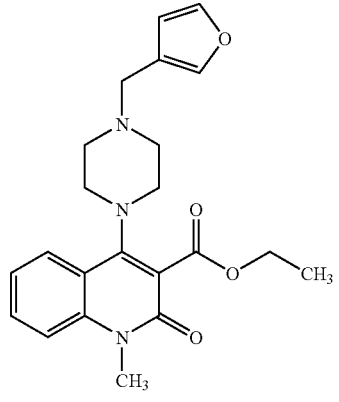
Compound 252
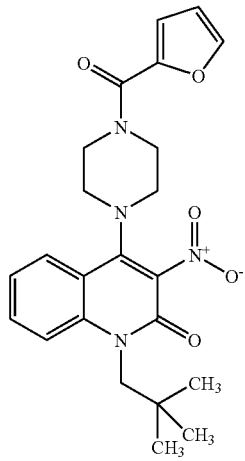
Compound 253
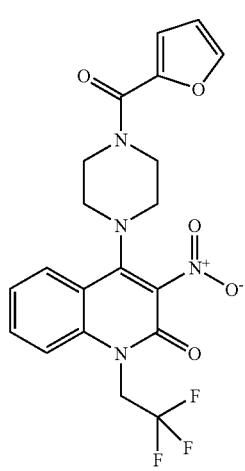
Compound 254
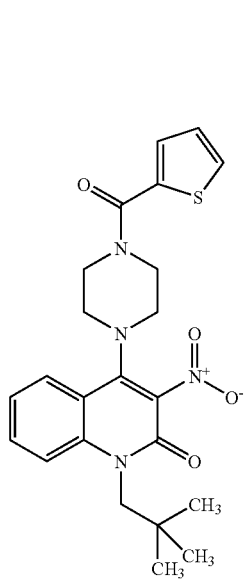

-continued
Compound 255
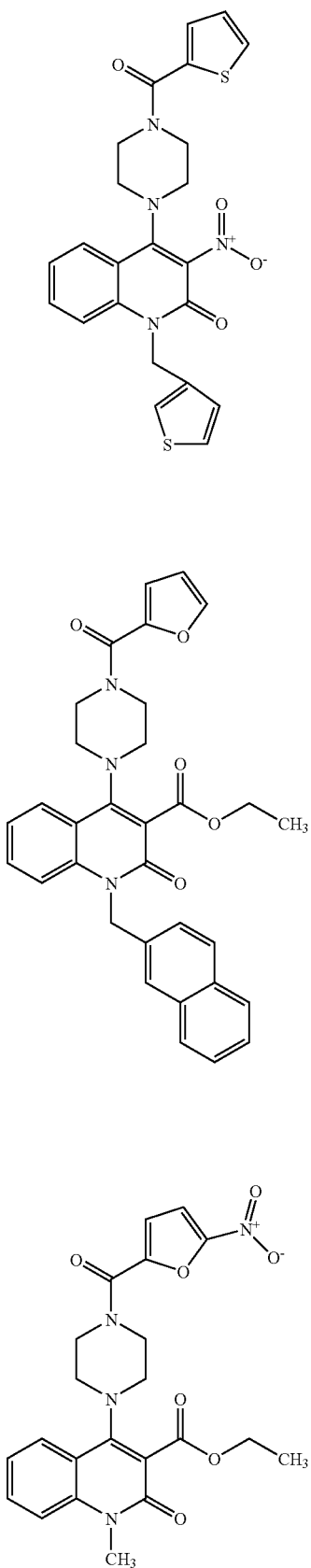
Compound 256
Compound 257
-continued
Compound 258
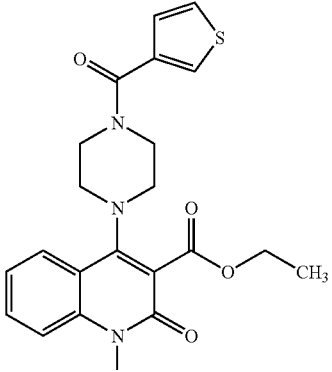
Compound 259
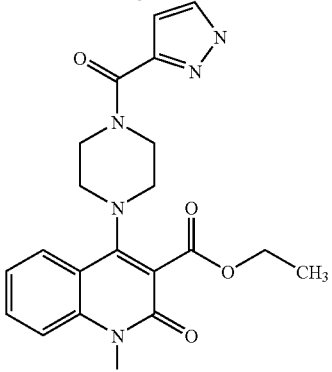
Compound 260
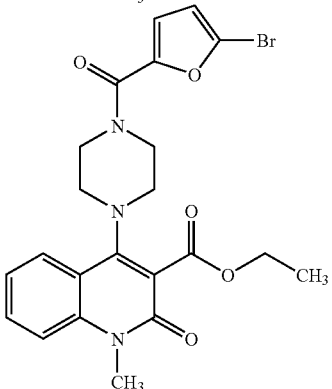
Compound 261
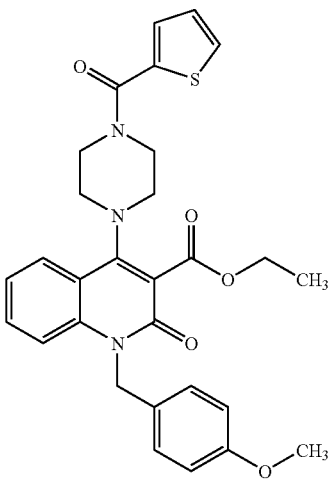

-continued
Compound 262
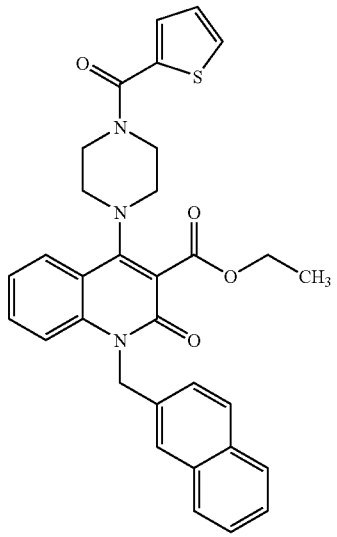
Compound 263
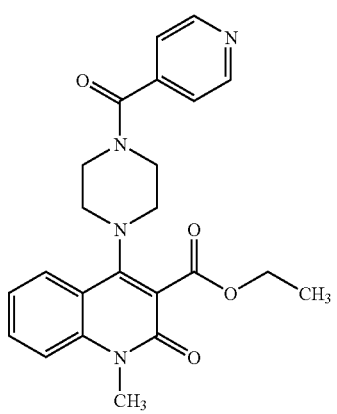
Compound 264
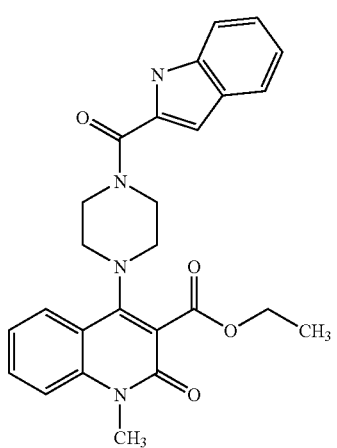
-continued
Compound 265
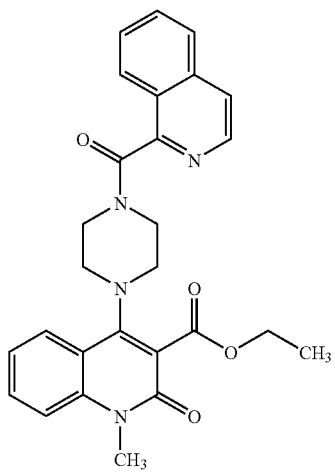
Compound 266
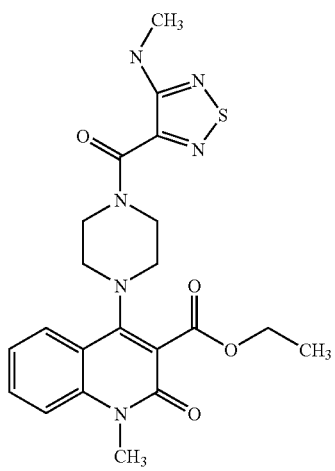
Compound 267
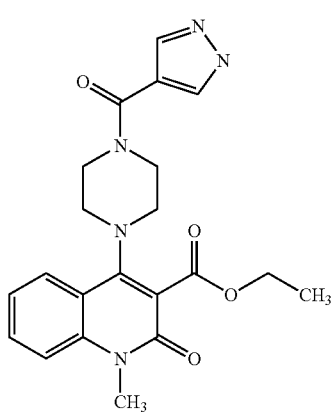

-continued
Compound 268
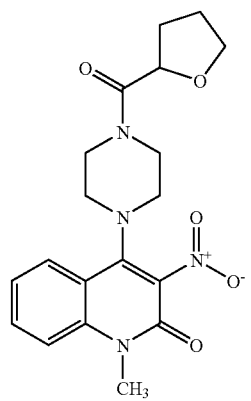
Compound 269
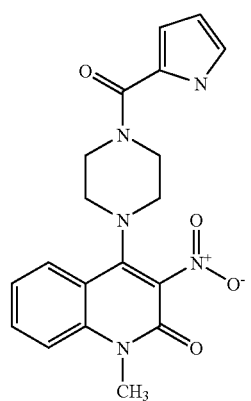
Compound 270
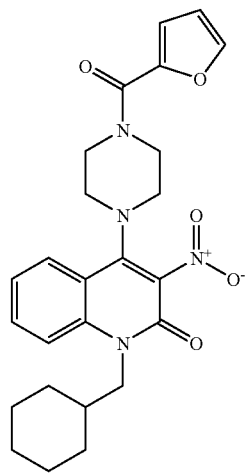
-continued
Compound 271
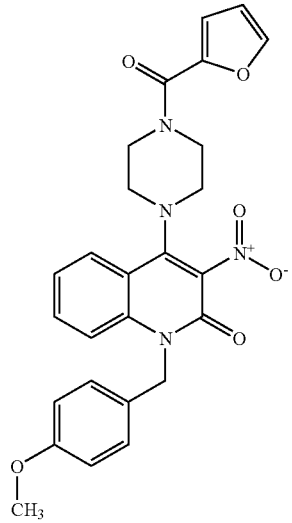
Compound 272
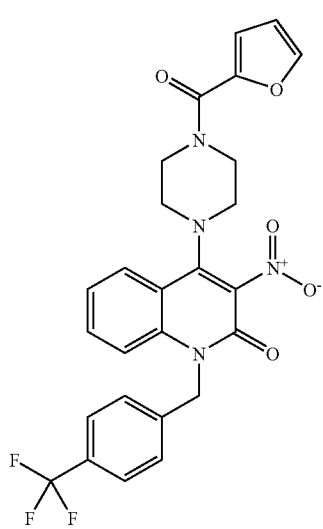
Compound 273
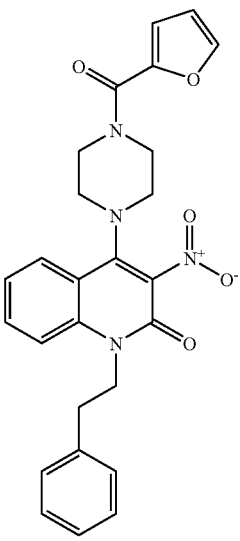

-continued
Compound 274
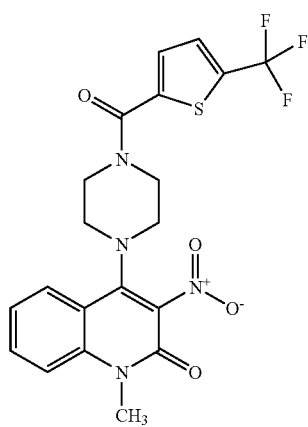
Compound 275
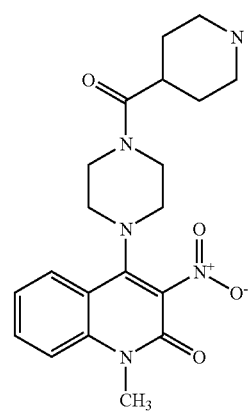
Compound 276
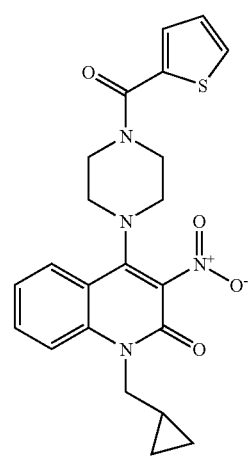
-continued
Compound 277
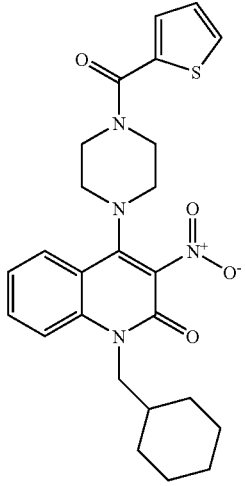
Compound 278
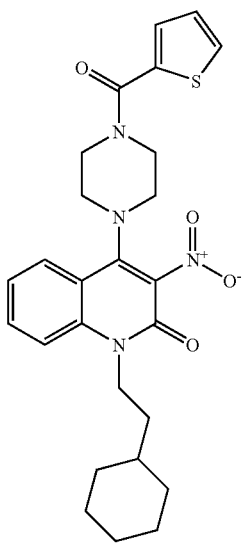
Compound 279
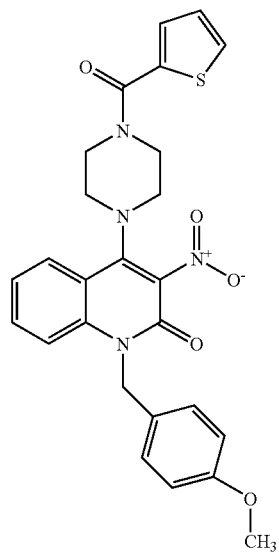

-continued
Compound 280
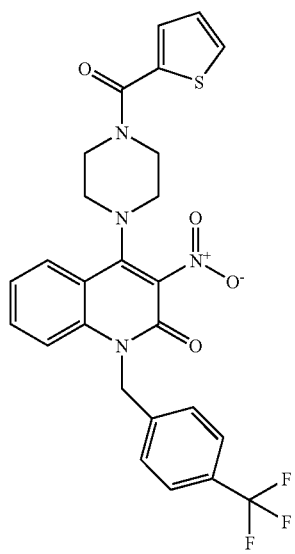
Compound 281
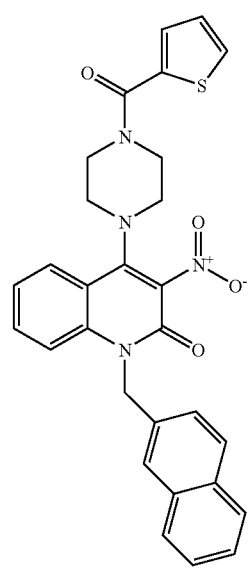
Compound 282
-continued
Compound 283
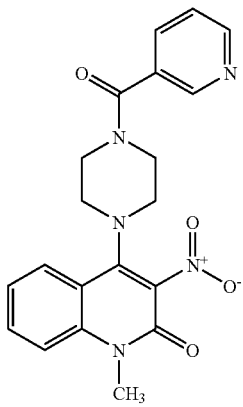
Compound 284
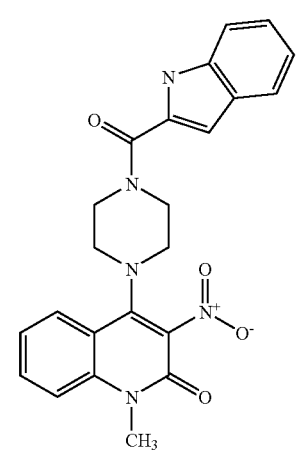
Compound 285
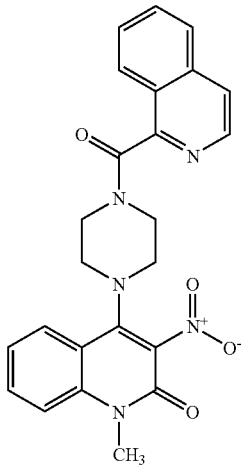

-continued
Compound 286
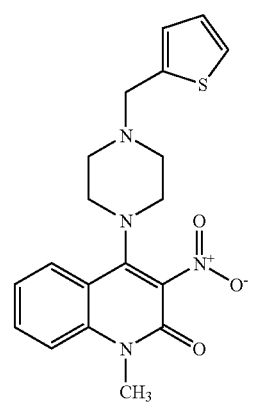
Compound 287
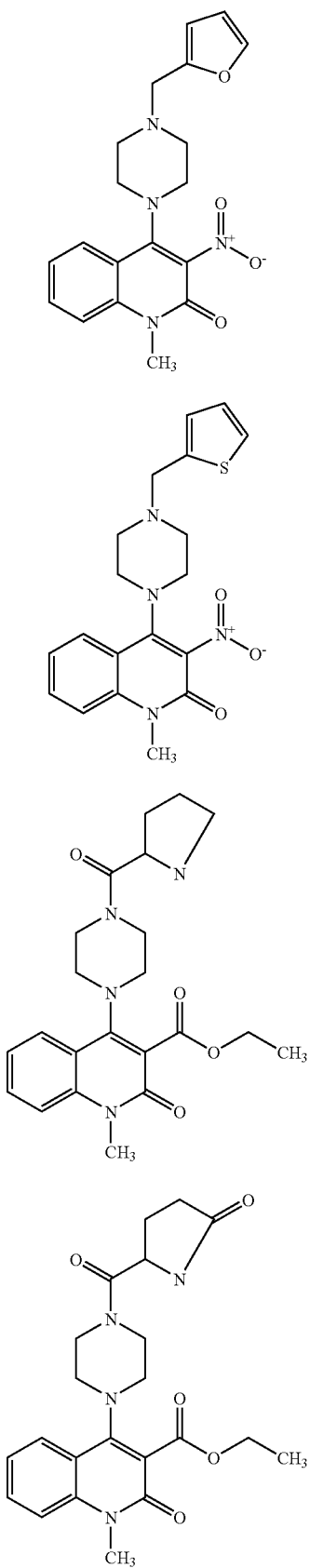
Compound 288
Compound 289
-continued
Compound 290
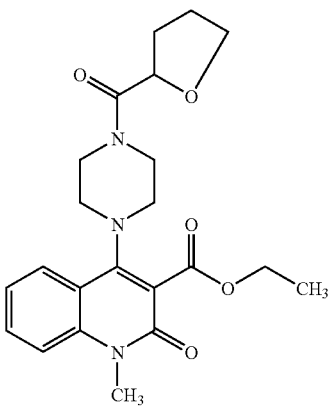
Compound 291
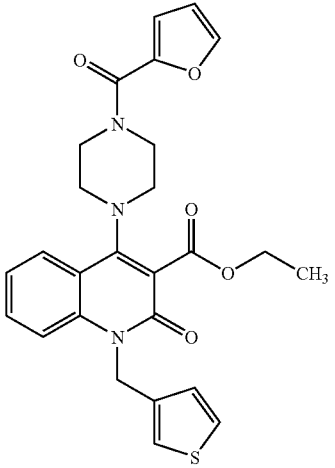
Compound 292
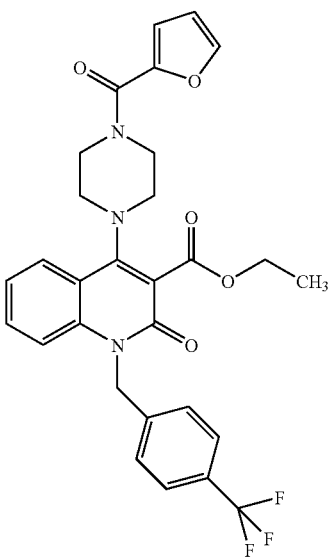

Compound 293
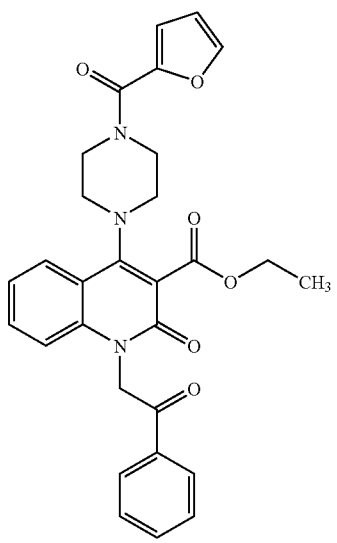
Compound 294
Compound 295
Compound 296
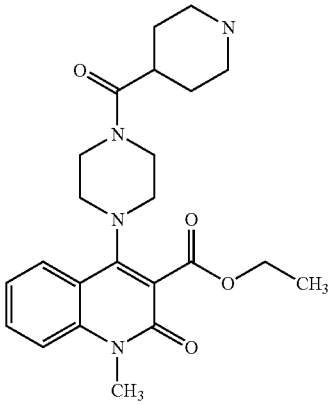
Compound 297
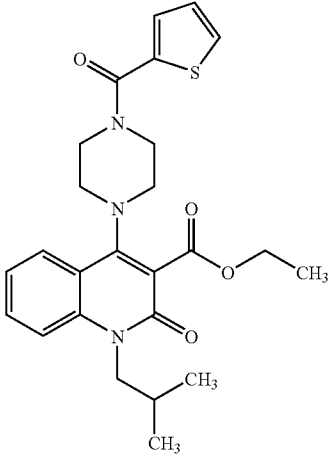
Compound 298
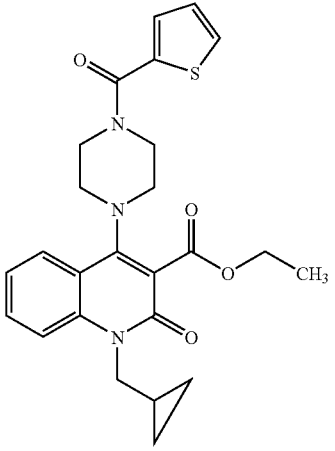

Compound 299
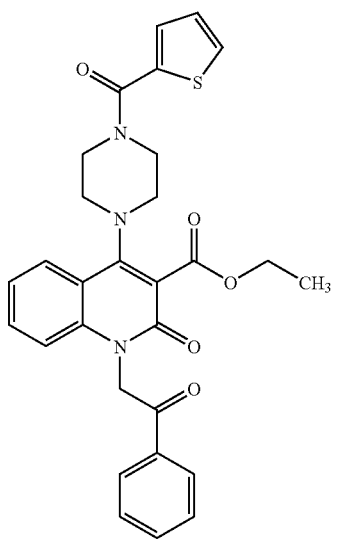
Compound 300
Compound 301
Compound 302
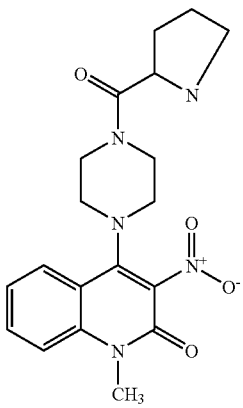
Compound 303
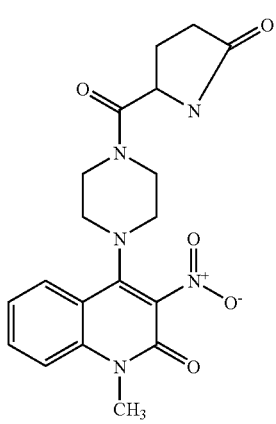
Compound 304
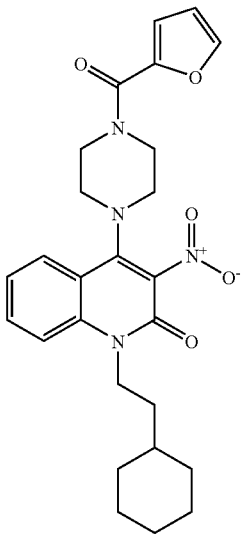

-continued
Compound 305
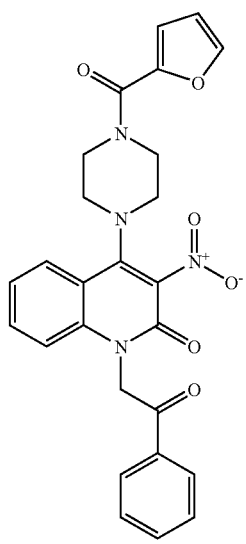
Example 12
Results of tautomerase assays indicated that the following compounds of Example 11 exhibited particularly high levels of inhibition of MIF activity.
TABLE 3
| Rank | Compound | EC50 Tautomerase (mM) | THP-1/MIF | Structure |
|---|---|---|---|---|
| 1 | 34 | 0.01 | <0.008 | 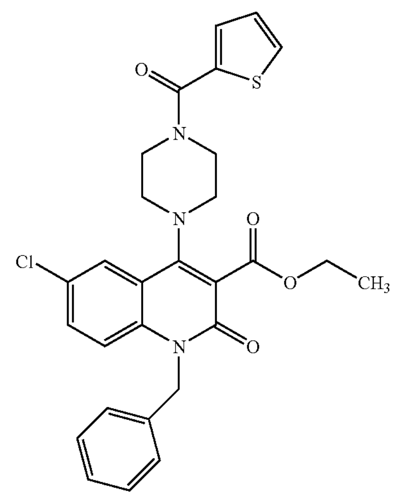 |
| 2 | 126 | 0.01 | <0.008 | 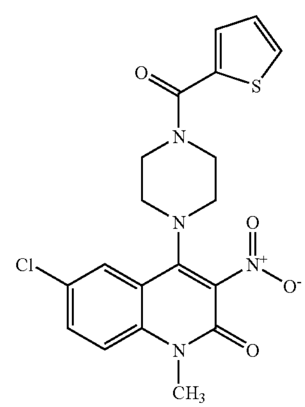 |

TABLE 3-continued

| Rank | Compound | EC50 Tautomerase (mM) | THP-1/MIF | Structure |
|---|---|---|---|---|
| 3 | 164 | 0.01 | | 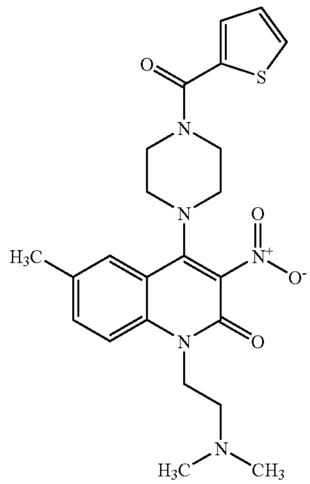 |
| 4 | 178 | 0.013 | — | 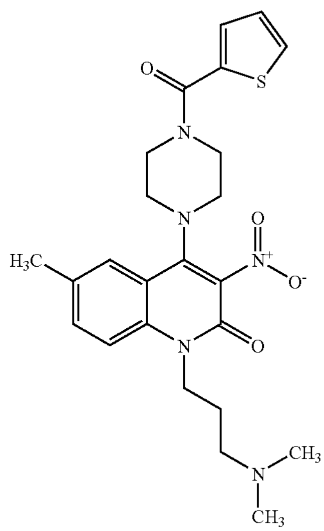 |
| 5 | 51 | 0.016 | <0.008 | 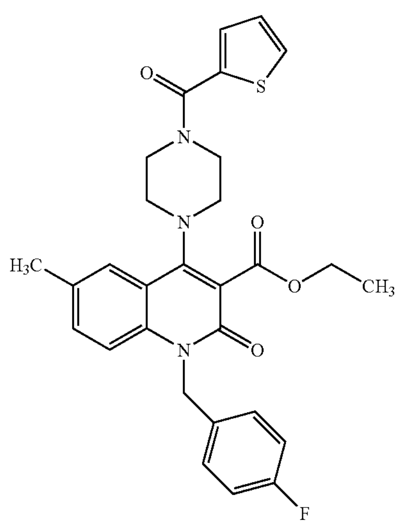 |

TABLE 3-continued

| Rank | Compound | EC50 Tautomerase (mM) | THP-1/MIF | Structure |
|---|---|---|---|---|
| 6 | 50 | 0.018 | <0.008 | 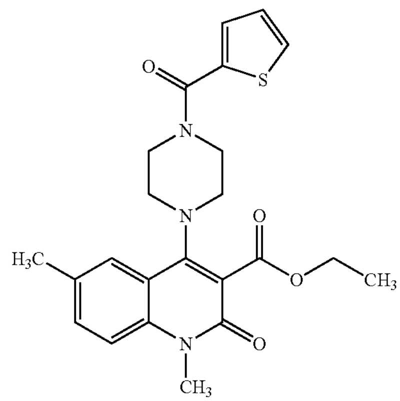 |
| 7 | 177 | 0.019 | — | 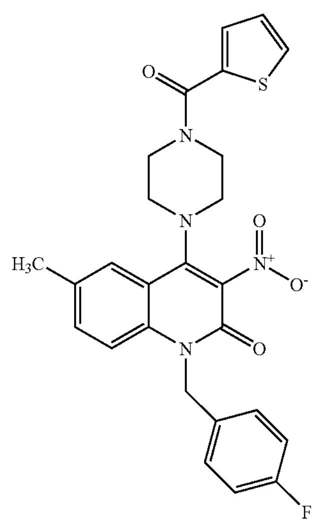 |
| 8 | 40 | 0.02 | <0.008 | 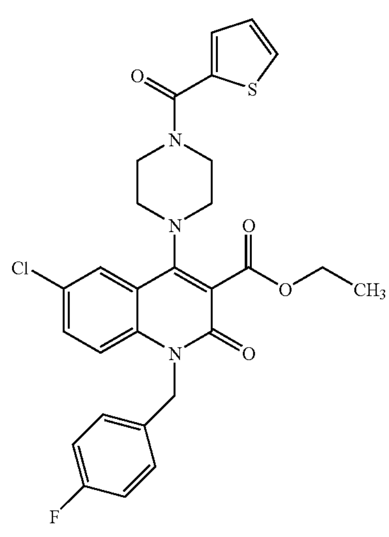 |

TABLE 3-continued

| Rank | Compound | EC50 Tautomerase (mM) | THP-1/MIF | Structure |
|------|----------|----------------------|-----------|-----------|
| 9 | 202 | 0.023 | — | 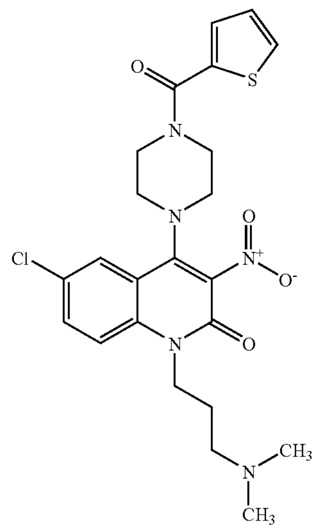 |
| 10 | 28 | 0.029 | — | 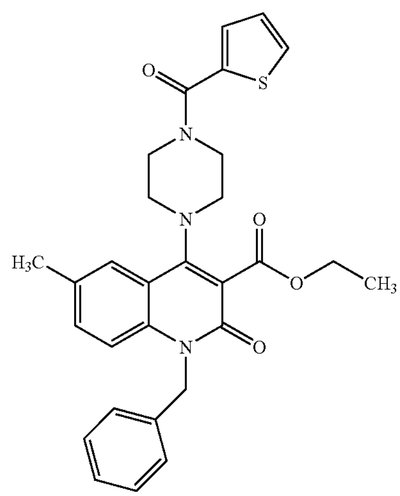 |
| 11 | 57 | 0.034 | 0.015 (0.011–0.019) | 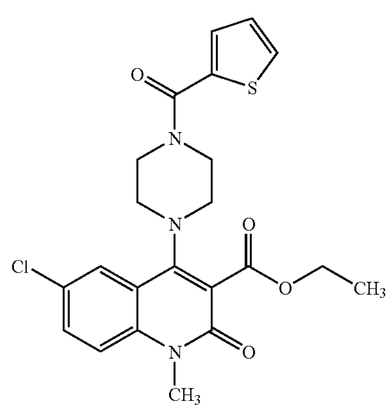 |

TABLE 3-continued
| Rank | Compound | EC50 Tautomerase (mM) | THP-1/MIF | Structure |
|---|---|---|---|---|
| 12 | 49 | 0.04 | 0.084 (0.015–0.47) | 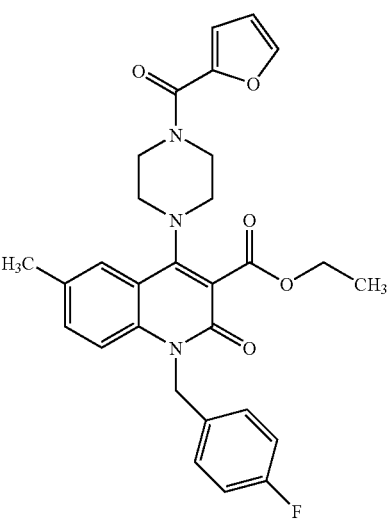 |
| 13 | 147 | 0.04 | — | 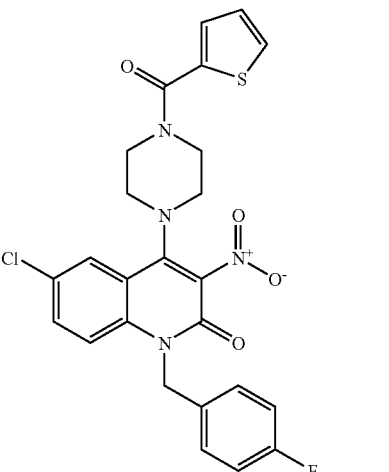 |
| 14 | 163 | 0.04 | — | 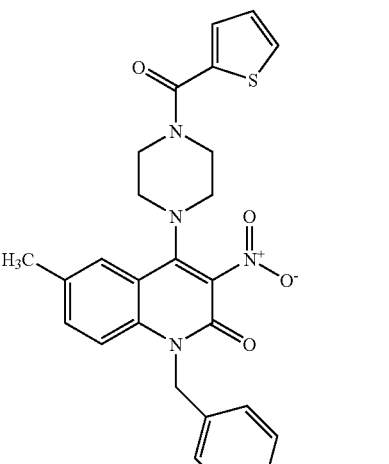 |

TABLE 3-continued

| Rank | Compound | EC50 Tautomerase (mM) | THP-1/MIF | Structure |
|---|---|---|---|---|
| 15 | 176 | 0.045 | — | 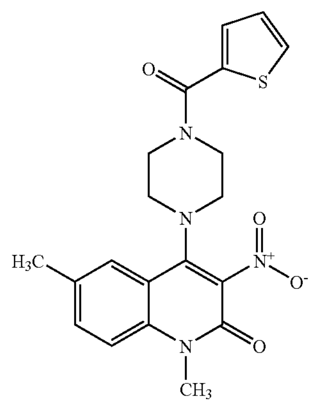 |
| 16 | 92 | 0.049 | — | 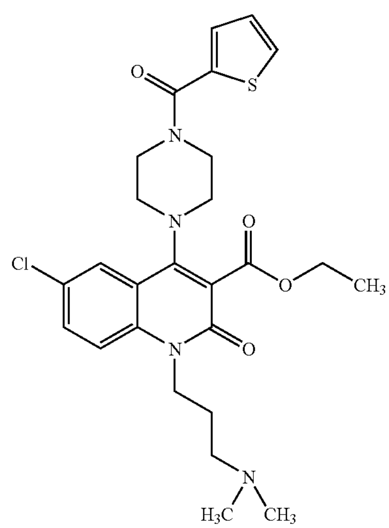 |
| 17 | 200 | 0.054 | — | 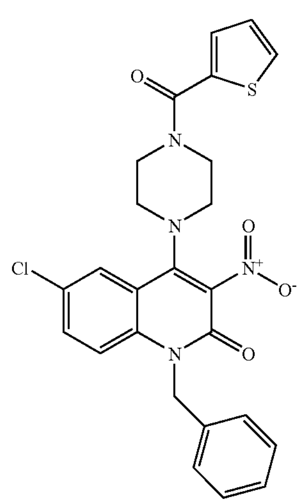 |

TABLE 3-continued

| Rank | Compound | EC50 Tautomerase (mM) | THP-1/MIF | Structure |
|------|----------|----------------------|-----------|-----------|
| 18 | 107 | 0.063 | <0.008 | 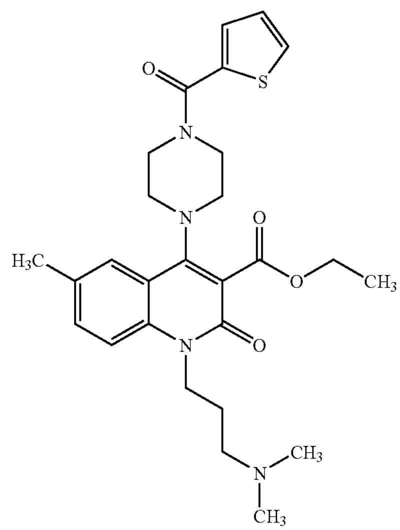 |
| 19 | 26 | 0.07 | — | 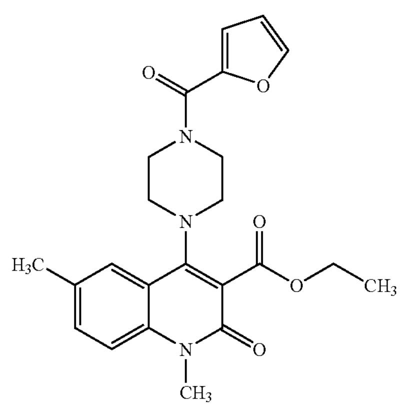 |
| 20 | 105 | 0.075 | — | 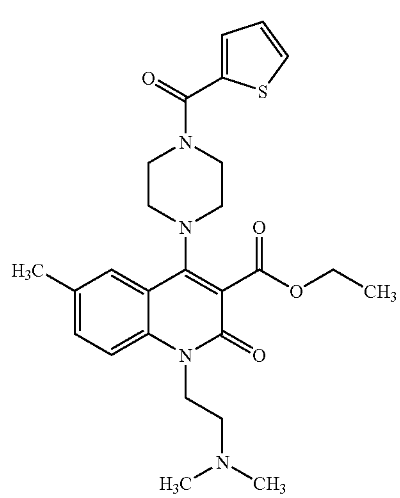 |

TABLE 3-continued

| Rank | Compound | EC50 Tautomerase (mM) | THP-1/MIF | Structure |
|---|---|---|---|---|
| 21 | 16 | 0.08 | 0.03 (0.02–0.04) | 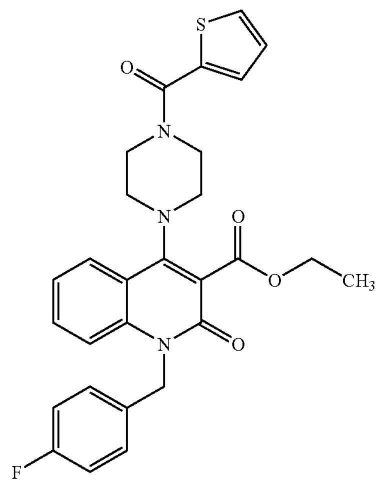 |
| 22 | 27 | 0.08 | — | 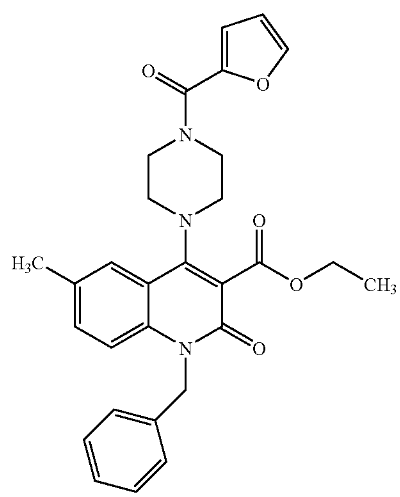 |
| 23 | 29 | 0.08 | — | 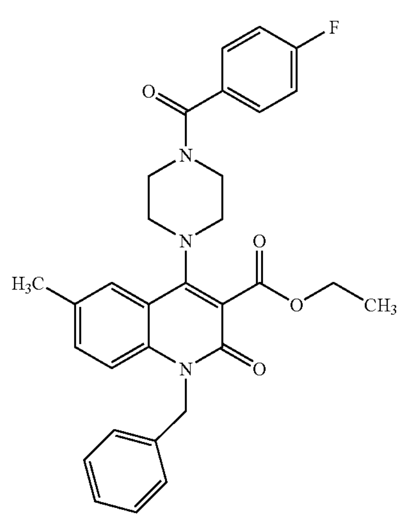 |

Example 13

The following inhibitors of MIF were prepared. Each of these MIF inhibitors belongs to the class of compounds having structure (Ib) described above:

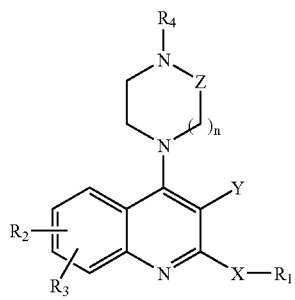

wherein $R_1$, $R_2$, $R_3$, $R_4$, X, Y, Z and n are as defined for structure (Ib) above. Results of tautomerase assays indicated that each of the MIF inhibitor compounds exhibited significant inhibition of MIF activity.

Compound 327

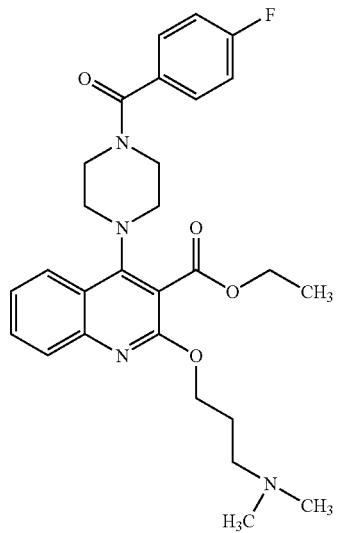

Compound 328

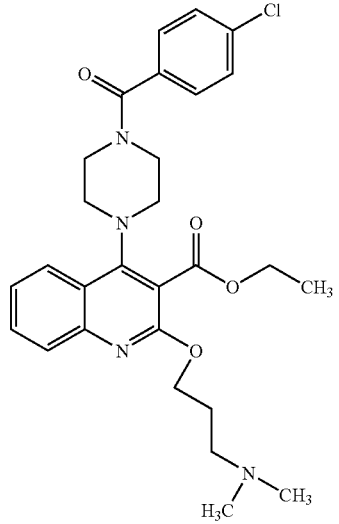

Compound 329

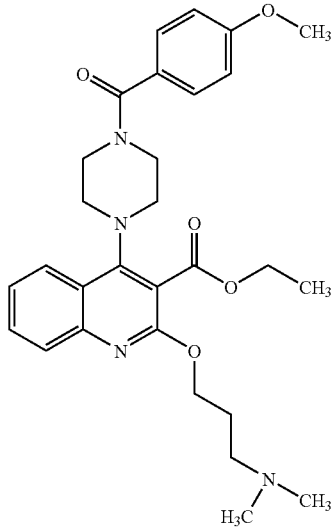

Compound 329

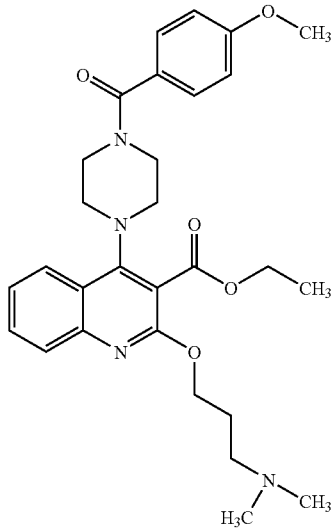

Compound 330

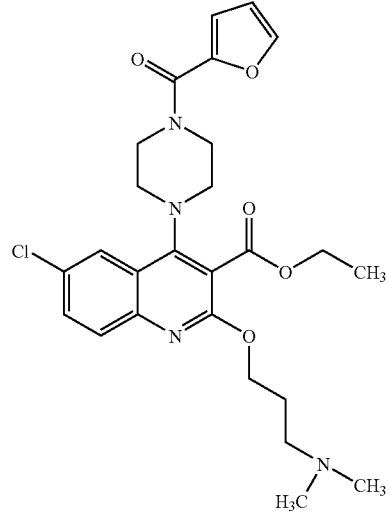

-continued
Compound 331
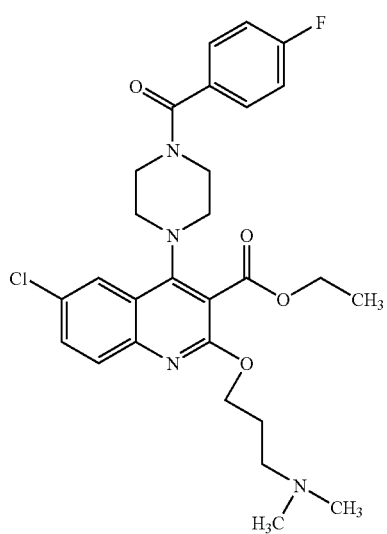
Compound 332
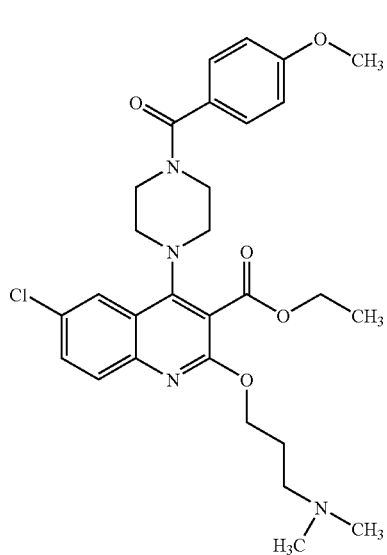
Compound 333
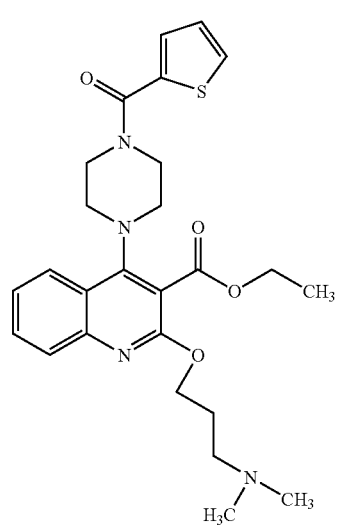
-continued
Compound 334
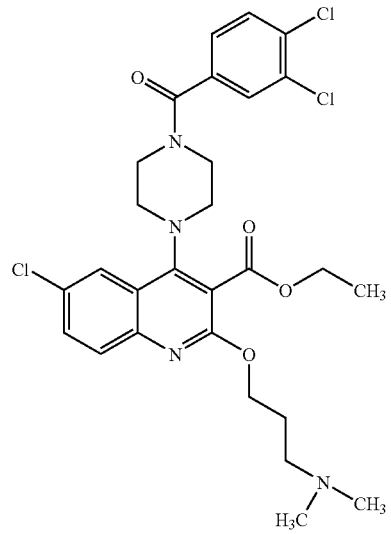
Compound 335
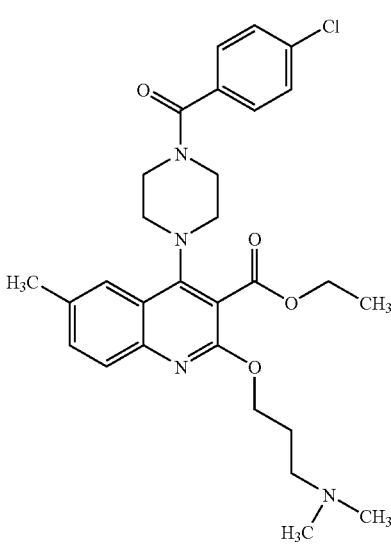
Compound 336
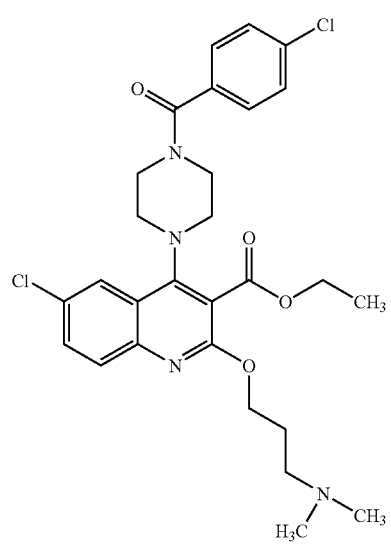

-continued
Compound 337
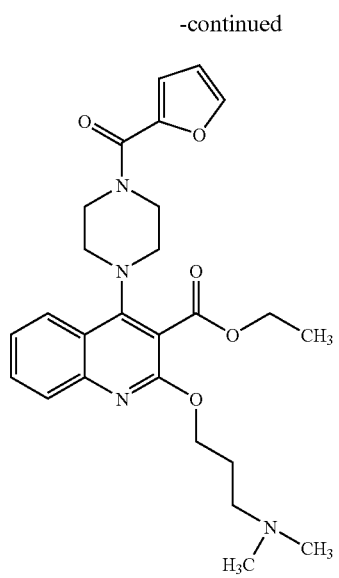
Compound 338
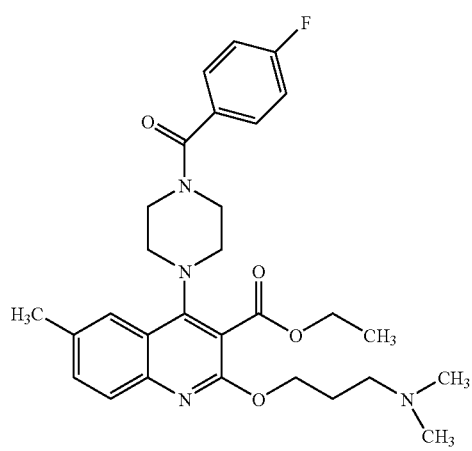
Compound 339
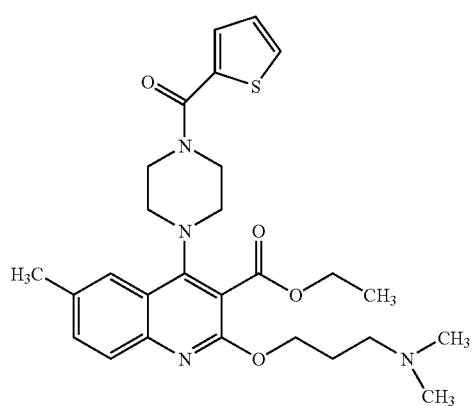
-continued
Compound 340
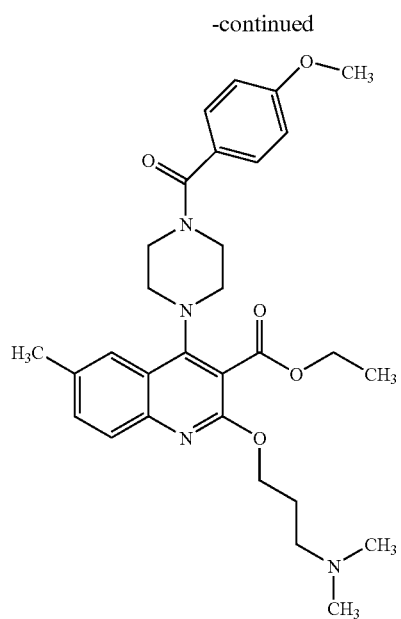
Compound 341
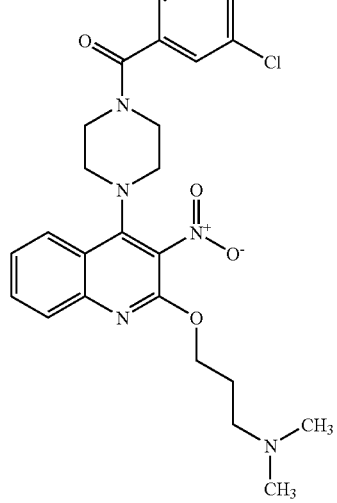
Compound 342
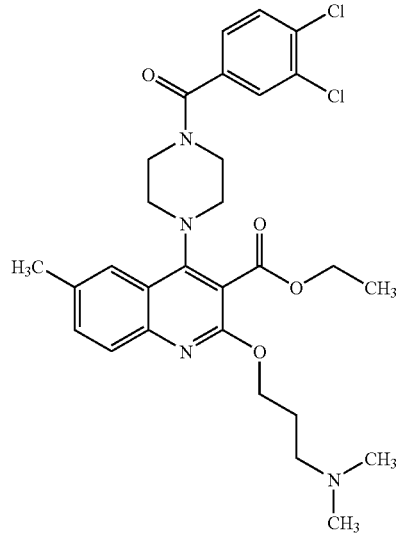

-continued

Compound 343

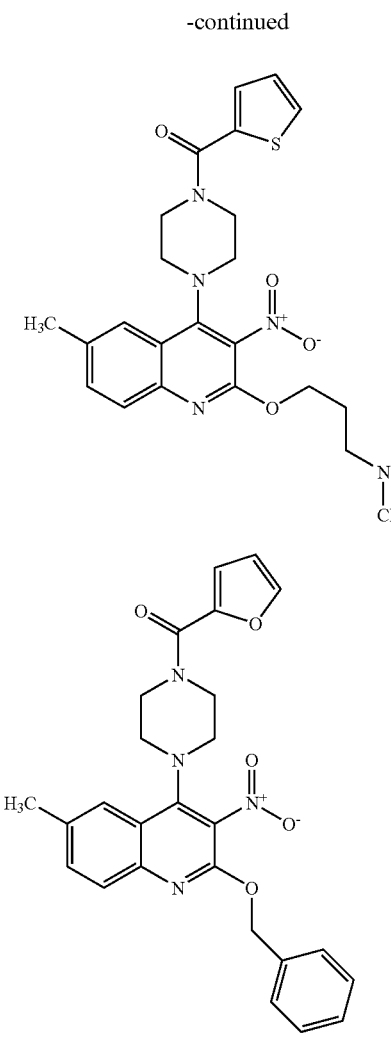

Compound 344

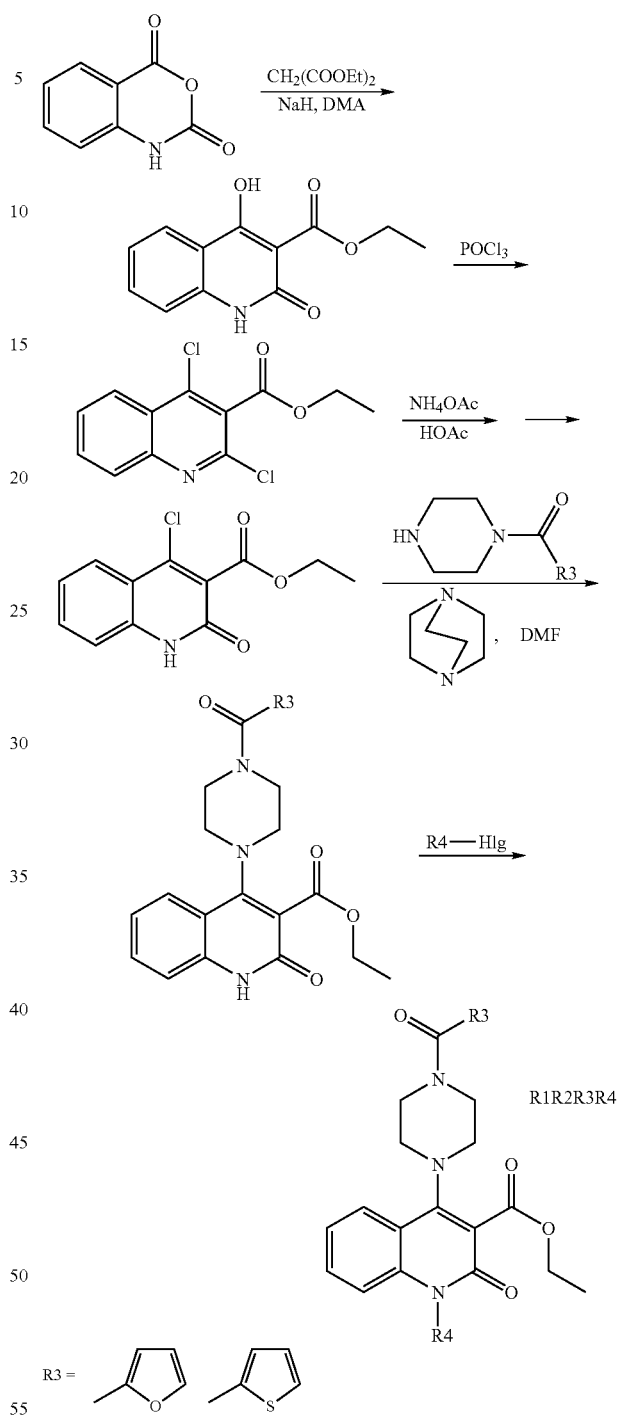

$R3 =$ [furanyl], [thienyl]

Example 14

Inhibitors of MIF of certain embodiments may be prepared according to the following reaction schemes, Scheme 5 and Scheme 6. Each of these MIF inhibitors belongs to the class of compounds of structure (1a) described above.

Reaction Scheme 5

In this scheme, isatoic anhydride is reacted with diethyl malonate in a solution of NaH in N,N-dimethylacetamide. The resulting intermediate (referred to as "1M00") is then chlorinated by reaction with POCl$_3$ to yield an intermediate (referred to as "1M00(Cl2)"). 1M00(Cl2) is then reacted with NH$_4$OAC in acetic acid to yield an intermediate (referred to as "1M00(Cl)"). IM00(Cl) is then reacted with an N-acyl piperazine in DMF. The acyl group of the piperazine compound includes as a substituent (referred to as "R3") either a furanyl group or a thienyl group, as depicted in Scheme 5, or other groups, as enumerated in subsequent examples. The resulting intermediate is then reacted with a halogen compound. The subsituent bound to the halogen atom (referred to as "R4"), may include various groups, as enumerated in subsequent examples. The resulting compound is of the structure (1a) described above. The steps in this reaction scheme are described in detail below. Compounds prepared according to Scheme 5 are referred to below by reference numbers containing an "M" and incorporate a —COOEt moiety.

Reaction Scheme 6

In this scheme, 4-Hydroxy-2(1H)-quinolone is reacted with a mixture of nitric and acetic acids. The resulting intermediate is then chlorinated by reaction with POCl$_3$ to yield another intermediate. That intermediate is then reacted with an N-acyl piperazine in DMF. The acyl group of the piperazine compound includes as a substituent an R3 group as referred to in the description of Scheme 5. The resulting intermediate is then reacted with a halogen compound including as a substituent an R4 group as referred to in the description of Scheme 5. The resulting compound is of the structure (1a) described above. The steps in this reaction scheme are described in detail below. Compounds prepared according to Scheme 6 are referred to below by reference numbers containing an "N" and incorporate a —NO$_2$ moiety.

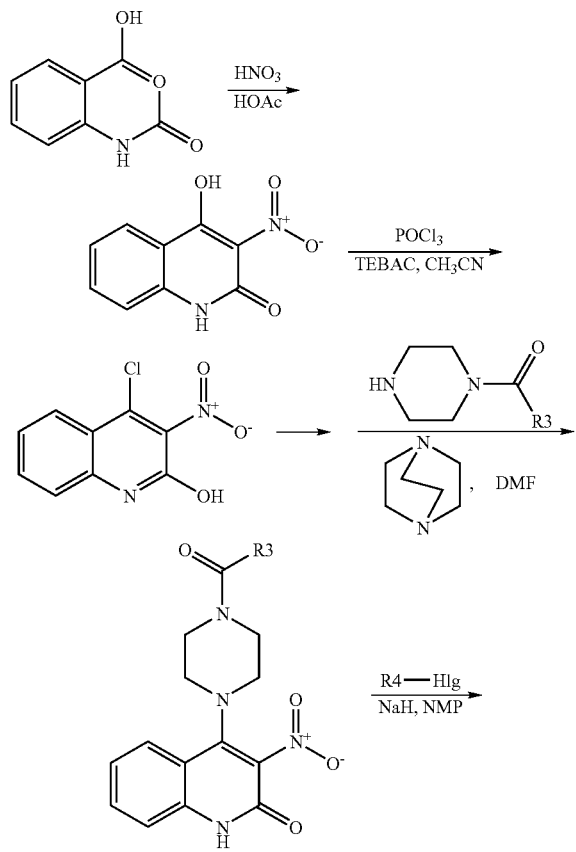

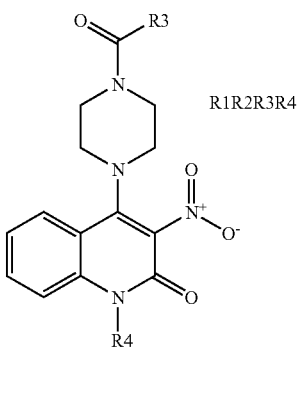

Various inhibitors of MIF belonging to the class of compounds having the structure I(a) were prepared according to Scheme 5 or Scheme 6. Table 4 provides a list of reference numbers for the compounds prepared. The designation "1M1##" indicates that the compound was prepared by Scheme 5, and incorporates a —COOEt moiety and a furan moiety as R3. The designation "1M2##" indicates that the compound was prepared by Scheme 5, and incorporates a —COOEt moiety and a thiophen moiety as R3. The designation "1N1##" indicates that the compound was prepared by Scheme 6, and incorporates a —NO$_2$ moiety and a furanyl moiety as R3. The designation "1N2##" indicates that the compound was prepared by Scheme 6, and incorporates a —NO$_2$ moiety and a thiophen moiety as R3. The two digits at the end of the designation identify the compound's R4 group.

TABLE 4

| | | M (COOEt) | | N (NO$_2$) | |
|---|---|---|---|---|---|
| | Halogen-R4 | 1M1 (Furan) | 1M2 (Thiophen) | 1N1 (Furan) | 1N2 (Thiophen) |
| 06 | 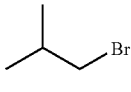 | 1M106 | 1M206 | 1N106 | 1N206 |
| 07 | 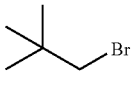 | 1M107 | 1M207 | 1N107 | 1N207 |
| 08 | 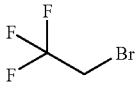 | 1M108 | 1M208 | 1N108 | 1N208 |
| 09 | 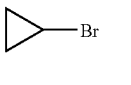 | — | — | — | — |
| 10 | 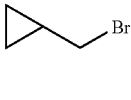 | 1M110 | 1M210 | 1N110 | 1N210 |

TABLE 4-continued
| | | M (COOEt) | | N (NO₂) | |
|---|---|---|---|---|---|
| | Halogen-R4 | 1M1 (Furan) | 1M2 (Thiophen) | 1N1 (Furan) | 1N2 (Thiophen) |
| 11 | 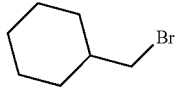 | 1M111(1) | 1M211(1) | 1N111(1) | 1N211(1) |
| 12 | 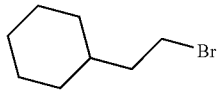 | 1M112 | 1M212 | 1N112 | 1N212 |
| 13 | 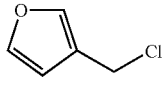 | 1M113 | 1M213 | 1N113 | 1N213 |
| 14 | 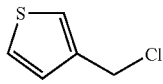 | 1M114 | 1M214 | 1N114 | 1N214 |
| 15 |  | 1M115 | 1M215 | 1N115 | 1N215 |
| 16 | 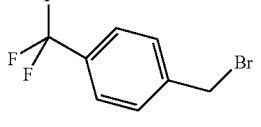 | 1M116 | 1M216 | 1N116 | 1N216 |
| 17 | 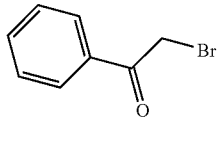 | 1M117 | 1M217 | 1N117 | 1N217 |
| 18 | 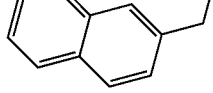 | 1M118 | 1M218 | 1N118 | 1N218 |
| 19 | 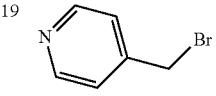 | 1M119 | 1M219 | 1N119*HCl | 1N219 |
| 20 | 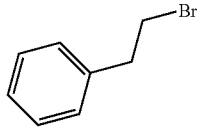 | 1M120 | 1M220 | 1N120 | 1N220 |

TABLE 4-continued

| | | M (COOEt) | | N (NO$_2$) | |
|---|---|---|---|---|---|
| | Halogen-R4 | 1M1 (Furan) | 1M2 (Thiophen) | 1N1 (Furan) | 1N2 (Thiophen) |
| 22 | 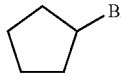 | 1M122 | 1M222 | 1N122 | 1N222 |

The halogenated R4 group "09" is disclosed in MARCH'S ADVANCED ORGANIC CHEMISTRY, Reactions, Mechanisms, and Structure, 5$^{th}$ Ed., Michael B. Smith and Jerry March, Eds., A Wiley-Interscience Publication, John Wiley & Sons, Inc., p. 437 (2001). Slighly different reaction schemes, Schemes 7 and 8, are used to prepare inhibitors of MIF incorporating this moiety.

Reaction Scheme 7

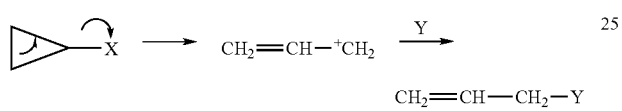

Reaction Scheme 8

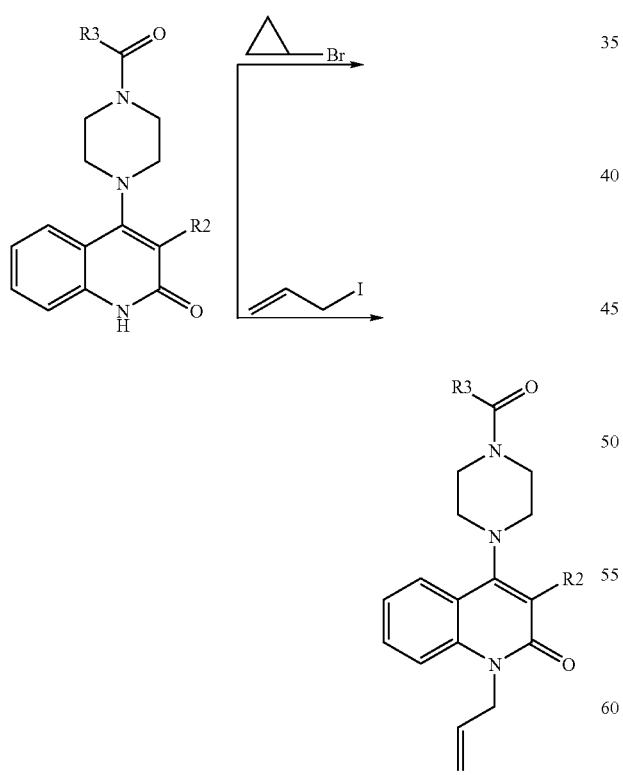

Reaction Scheme 9

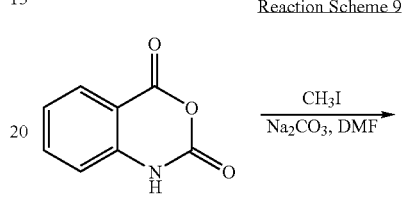

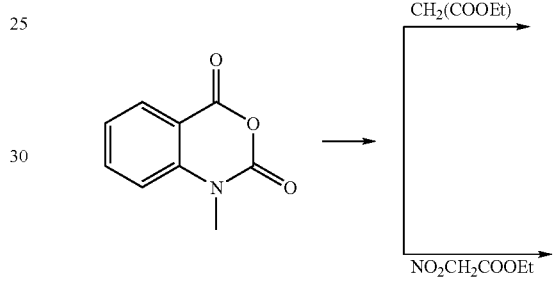

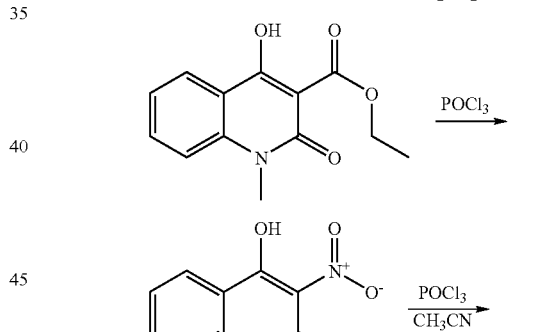

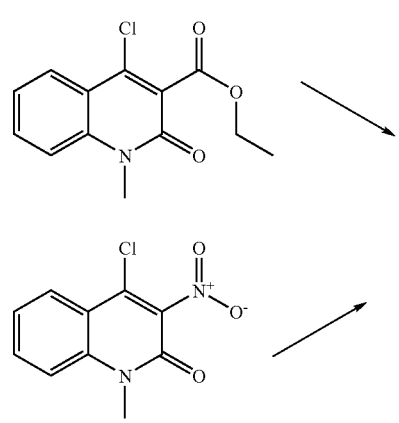

Various inhibitors of MIF belonging to the class of compounds having the structure I(a) were prepared according to Scheme 9 or Scheme 10.

-continued

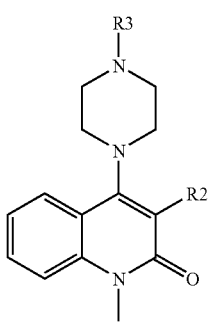

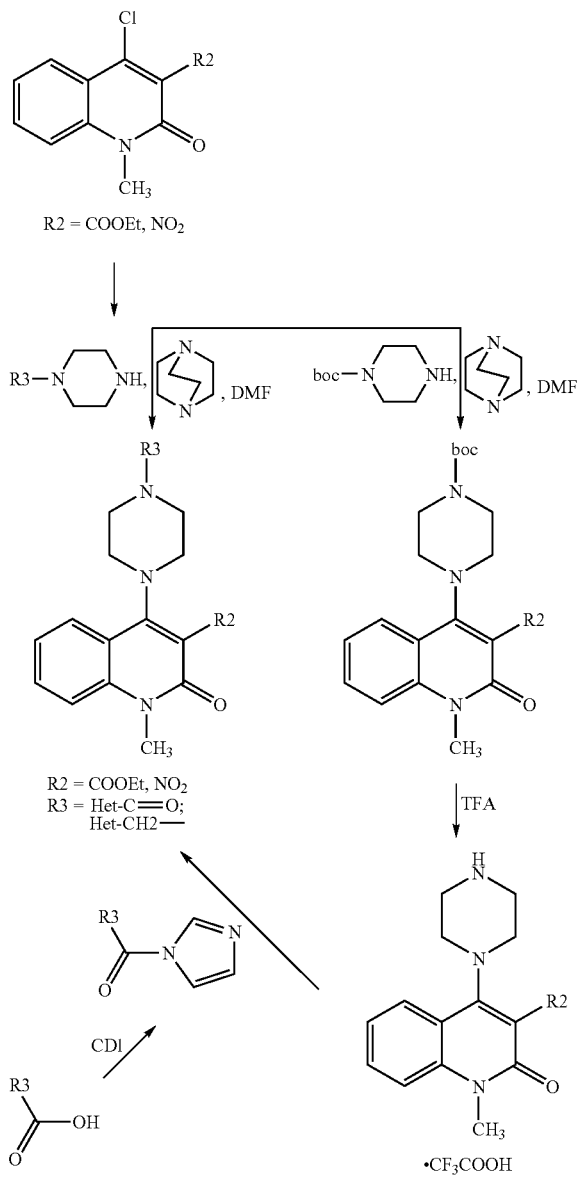

Reaction Scheme 10

Table 5 provides a list of reference numbers for the compounds prepared. The designation "1M##1" indicates that the compound was prepared by Scheme 9, and incorporates a —COOEt moiety. The designation "1M##2" indicates that the compound was prepared by Scheme 9, and incorporates a —NO$_2$ moiety. The designation "1N##1" indicates that the compound was prepared by Scheme 10, and incorporates a —COOEt moiety. The designation "1N##2" indicates that the compound was prepared by Scheme 10, and incorporates a —NO$_2$ moiety. The two digits following the letter M or N correspond to the number identifying the R3 moiety.

TABLE 5

| # | R3 | R3 | 1M##1 (COOEt) | 1N##1 (NO2) |
|---|----|----|---------------|-------------|
| 1 | 07 | | 1M071*HCl | 1N071*HCl |
| 2 | 08 | | 1M081 | 1N081 |
| 3 | 09 | | 1M091 | 1N091 |
| 4 | 10 | | 1M101 | 1N101 |
| 5 | 11 | | 1M111(2) | 1N111(2) |
| 6 | 12 | | 1M121 | 1N121 |
| 7 | 13 | | 1M131 | 1N131 |
| 8 | 14 | | 1M141 | 1N141 |
| 9 | 15 | | 1M151*HCl | 1N151*HCl |
| 10 | 16 | | 1M161 | 1N161 |

TABLE 5-continued

| # | R3 | R3 | 1M##1 (COOEt) | 1N##1 (NO2) |
|---|---|---|---|---|
| 11 | 17 | (3-acetyl-5-methylisoxazole) | 1M171 | 1N171 |
| 12 | 18 | (5-acetylisoxazole) | 1M181 | 1N181 |
| 13 | 19 | (4-acetylpiperidine) | 1M191*HCl | 1N191 |
| 14 | 20 | (5-bromo-2-acetylfuran) | 1M201 | 1N201 |
| 15 | 21 | (2-acetylpiperidine) | 1M211(2)*HCl | 1N211(2)*HCl |
| 16 | 22 | (2-acetylpyridine) | 1M221 | 1N221 |
| 17 | 23 | (3-acetylpyridine) | 1M231 | 1N231 |
| 18 | 24 | (4-acetylpyridine) | 1M241 | 1N241 |
| 19 | 27 | (acetylpyrazine) | 1M271 | 1N271 |
| 20 | 28 | (2-acetylindole) | 1M281 | 1N281 |

TABLE 5-continued

| # | R3 | R3 | 1M##1 (COOEt) | 1N##1 (NO2) |
|---|---|---|---|---|
| 21 | 29 | (1-acetylisoquinoline) | 1M291 | 1N291 |
| 22 | 30 | (methylamino-thiadiazolyl ketone) | 1M301 | 1N301 |
| 23 | 31 | (phenethyl) | 1M311 | 1N311 |
| 24 | 32 | (furfuryl ethyl) | 1M321 | 1N321 |
| 25 | 33 | (thienyl ethyl) | 1M331 | 1N331 |
| 26 | 34 | (thienyl acetone) | 1M341 | 1N341 |
| 27 | 35 | (4-acetylimidazole) | 1M351 | 1N351 |

Various inhibitors of MIF belonging to the class of compounds having the structure I(a) were prepared according to the following schemes.

Reaction Scheme 11

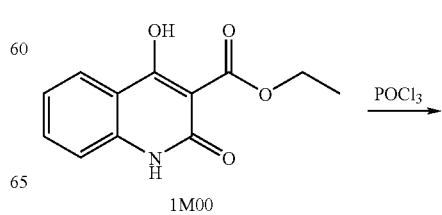

1M00 → POCl₃

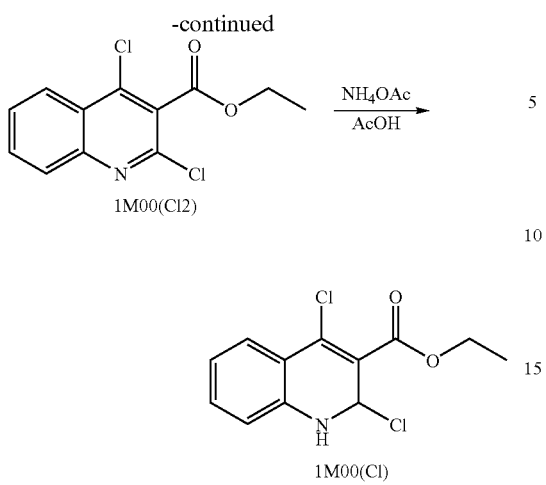

1M00(Cl2)

1M00(Cl)

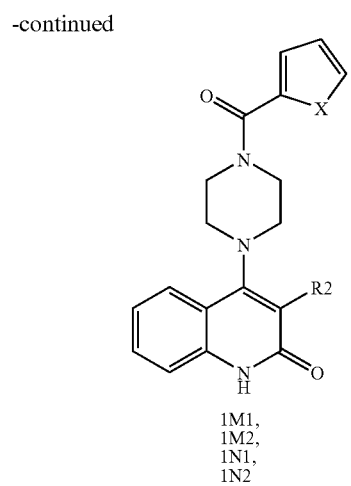

1M1,
1M2,
1N1,
1N2

To the suspension of 1M00 (33.0 g; 0.14 mole) in toluene (40 ml) was added 108 g of POCl$_3$ (0.7 mole). The resulting solution was heated under reflux for 1.5 hours. The solvent was distilled under reduced pressure and the residual oil was successively extracted with heptane (control by TLC). Combined heptane fractions were evaporated and the residue was heated with 200 ml of water and filtered off. The yield was 27 g (70%).

After drying at room temperature for 18 hours, the obtained dichloro compound was transferred to a 250 ml round bottom flask and 150 ml of acetic acid and 24.0 g of ammonium acetate was added to it. The reaction mixture was heated under reflux for approx. 6 h (control by LCMS and TLC). When no starting material could be detected in the reaction mixture, the hot solution was poured in water and the resulting precipitate was filtered off. Table 6 provides data on yield (g and %); melting point; mass to charge ratio (M/Z), wherein M/Z=754.1 [3×M]$^+$, 503.3 [2×M]$^+$; τ (8 min. run), and purity as determined by LCMS.

To the solution of 1M00(Cl) (3.27 g; 13.0 mmol) in 20 ml NMP was added sequentially acylpiperazine (2.34 g; 13.0 mmol) and DABCO (1.46 g; 13.0 mmol). The reaction mixture was stirred at 100–120° C. for 15 hours. The reaction was quenched with 20% NH$_4$Cl solution and the resulted precipitate was filtered off and washed with water. The product was dried in a desiccator over P$_2$O$_5$ at room temperature under reduced pressure. The product was used in the next reaction without any further purification.

A mixture of chloroquinolone 1N00(Cl) (2.9 g; 13.0 mmol), acylpiperazine trifluoroacetate AV-0020 (4.0 g; 13.0 mmol), and DABCO (2.91 g; 26.0 mmol) in 25 ml NMP was stirred at 100° C. overnight. The mixture was poured into 50 ml of brine, the solid obtained was filtered off, washed with water and dried in a desiccator over P$_2$O$_5$ at room temperature under reduced pressure. The product was used in the next reaction without any further purification.

The yields and additional information for the obtained compounds are provided in Table 7. For the compound designated 1M1, X is O and R2 is COOEt. For the compound designated 1M2, X is S and R2 is COOEt. For the compound designated 1N1, X is O and R2 is NO$_2$. For the compound designated 1N2, X is S and R2 is NO$_2$.

TABLE 6

| Compound | Yield, g | Yield, % | m.p., ° C. | M/Z | τ, min (8 min. run) | Purity, % (LCMS) |
|---|---|---|---|---|---|---|
| 1M00(Cl) | 23.0 | 92 | 198–200 | 754.1; 503.3; 252.2; 206.0 | 2.97 | >96 |

Reaction Scheme 12

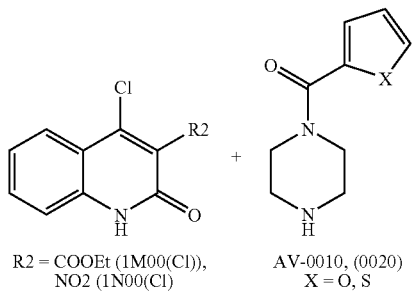

R2 = COOEt (1M00(Cl)),
NO2 (1N00(Cl))

AV-0010, (0020)
X = O, S

TABLE 7

| | Yield, g | Yield, % | m.p. ° C. | M/Z | τ, min | Purity, % (LCMS) |
|---|---|---|---|---|---|---|
| 1M1 | 4.7 | 92 | 223–226 dec. | 396.2; 350.2 | 2.67 | >94 |
| 1M2 | 4.9 | 92 | 220–222 | 366.2; 412.3 | 2.84 | >94 |
| 1N1 | 4.5 | 95 | 266–267 dec. | 369.0 | 2.73 | >92 |
| 1N2 | 4.7 | 95 | 265 dec. | 385.2 | 2.89 | >92 |

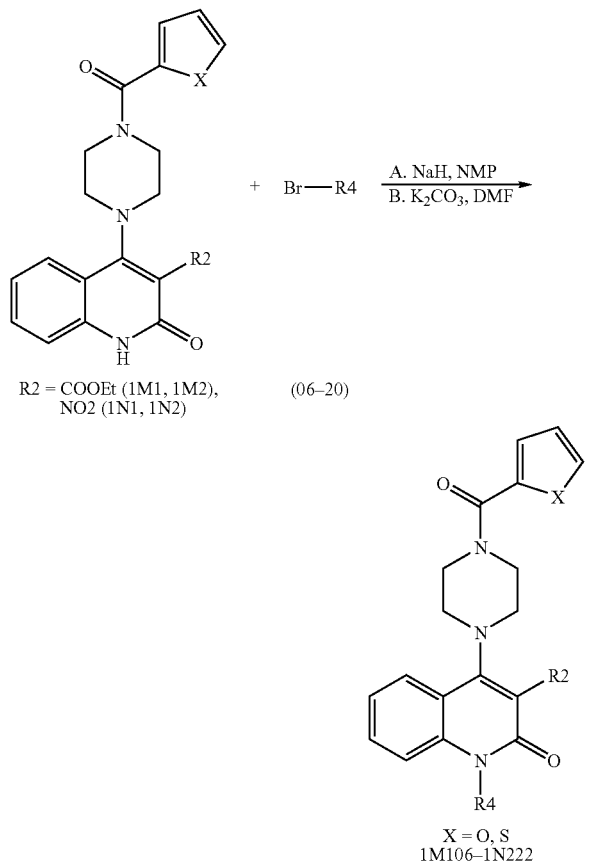

Reaction Scheme 13

R2 = COOEt (1M1, 1M2), NO2 (1N1, 1N2)

(06-20)

X = O, S
1M106–1N222

To the suspension of NaH (0.04 g; 1.0 mmol) in dry NMP (3 ml) was added compound 1M1 (or 1M2) or 1N1 (or 1N2) (0.8 mmol). After evolution of the gas ceased, the bromide (06–20) (1.0 mmol) was added. The reaction mixture was stirred until no traces of starting material could be detected (control by LCMS). A 10% solution of $NH_4Cl$ (20 ml) was added to the reaction and the resulting mixture was extracted with DCM. Compounds 1M1 and 1M2 were isolated and purified by preparative HPLC (C-18 silica column, 150 mm×41 mm, 40 ml/min, gradient:water-acetonitrile=from 60:40 to 5:95, 20 min). Compounds prepared according to this route are designated by the superscript "A" following the compound designation in Table 5.

To the solution of compound 1M1 (or 1M2) or 1N1 (or 1N2) (1.0 mmol) in dry DMF (5 ml) was added the bromide (06–20) (2.0 mmol) and $K_2CO_3$ (200 mg). Compounds 1M122; 1M222; 1N122; 1N222 were obtained in 1,4-dioxane with 4.0 mmol cyclopentyl bromide. The reaction mixture was stirred at 80–100° C. for 20–40 hours (control by LCMS). The 10% solution of $NH_4Cl$ (20 ml) was added to the reaction and resulted mixture was extracted with DCM. Compounds 1M106-1N220 were isolated and purified by preparative HPLC (C-18 silica column, 150 mm×41 mm, 40 ml/min, gradient:water-acetonitrile=from 80:20 to 5:95, 40 min). Table 5 provides purity data and other data for the resulting compounds. The compound 1N119*HCl was purified by preparative HPLC (C-18 silica column, 150 mm×41 mm, 40 ml/min, gradient:water-acetonitrile-HCl (0.001%)=from 80:20 to 5:95, 40 min). Compounds prepared according to this route are designated by the superscript "B" following the compound designation in Table 8. Physical properties of the compounds are provided in Table 8. Designations including "(1)" indicate that the compound is a regio isomer.

TABLE 8

| Compounds | Yield, mg | Yield, % | m.p. ° C. | M/Z | τ, min UV (Wave 254 nm, run 10 min.) | Purity, % (LCMS) |
|---|---|---|---|---|---|---|
| 1M112[A] | 78 | 19 | 151–152.5 | 506.2; 460.4 | 6.46 | >97 |
| 1M115[A] | 96 | 23 | 177.5–179 | 516.4; 470.5 | 5.09 | >97 |
| 1N110[A] | 99 | 29 | 163–166 | 423.2 | 4.96 | >99 |
| 1M214[A] | 116 | 29 | 180.5–182.5 | 508.3; 462.1 | 5.26 | >99 |
| 1M106[A] | 98 | 27 | 141–143 | 452.3; 406.3 | 5.13 | >97 |
| 1N106[A] | 152 | 45 | 114–116 | 425.1 | 5.13 | >99 |
| 1N114[A] | 97 | 26 | 216–217 | 465.4 | 5.08 | >96 |
| 1N206[A] | 148 | 42 | 72–74 | 441.6 | 5.41 | >97 |
| 1N111(1)[B] | 137 | 29 | 99–100 | 465.4; 447.4 | 5.91 | >99 |
| 1N115[B] | 157 | 32 | 105–110 | 489.4 | 5.14 | >92[1] |
| 1N116[A] | 143 | 34 | 205–208 | 527.3 | 5.69 | >99 |
| 1N211(1)[A] | 107 | 22 | 83–85 | 481.3 | 6.21 | >98 |
| 1N212[A] | 96 | 24 | 73–75 | 495.5 | 6.78 | >97 |
| 1N215[A] | 87 | 22 | 220–221 | 505.3 | 5.38 | >93[2] |
| 1N216[B] | 207 | 38 | 228–230 | 543.2 | 5.90 | >94[3] |
| 1N217[B] | 107 | 21 | 251–252 | 503.3 | 5.23 | >94[4] |
| 1N218[B] | 207 | 39 | 95–97 | 525.5 | 5.92 | >96 |
| 1M118[B] | 104 | 19 | 159–161 | 536.4; 490.3 | 5.64 | >97 |
| 1M215[B] | 107 | 20 | 87–88 | 532.3; 486.3 | 5.34 | >99 |
| 1M218[B] | 147 | 27 | 110–112 | 552.4; 506.3 | 5.89 | >99 |
| 1N120[B] | 92 | 19 | 179–181 | 473.4; 455.3 | 5.49 | >98 |
| 1N210[B] | 99 | 23 | 187–190 | 439.4 | 5.22 | >96 |
| 1M107[B] | 138 | 30 | 70–72 | 465.5; 420.3 | 5.31 | >95 |
| 1M108[B] | 213 | 45 | 71–73 | 478.3; 432.2 | 4.79 | >96 |
| 1M110[B] | 142 | 32 | 161–162 | 450.3; 404.3; 350.1 | 4.84 | >97 |
| 1M111(1)[B] | 185 | 38 | 174–175 | 492.4; 446.2 | 5.84 | >93 |

TABLE 8-continued

| Compounds | Yield, mg | Yield, % | m.p. °C. | M/Z | τ, min UV (Wave 254 nm, run 10 min.) | Purity, % (LCMS) |
|---|---|---|---|---|---|---|
| 1M207[B] | 131 | 27 | 65–67 | 482.4; 436.4 | 3.88 | >99 |
| 1M208[B] | 189 | 38 | 71–72 | 494.5; 448.2 | 5.05 | >97 |
| 1M211(1)[B] | 148 | 29 | 161–163 | 462.3; 508.5 | 6.19 | >99 |
| 1M212[B] | 105 | 20 | 163–165 | 522.7; 476.3 | 6.74 | >98 |
| 1N107[B] | 114 | 35 | 103–107 | 439.5 | 5.40 | >99 |
| 1N108[B] | 301 | 59 | 200–203 | 451.2 | 4.83 | >97 |
| 1N207[B] | 187 | 27 | 70–72 | 455.2 | 5.69 | >98 |
| 1N214[B] | 146 | 38 | 172–175 | 481.1 | 5.31 | >97 |
| 1M113[B] | 152 | 32 | 147–150 | 476.3; 430.2 | 4.71 | >99 |
| 1M114[B] | 202 | 41 | 170–172 | 492.4; 446.2 | 4.97 | >99 |
| 1M116[B] | 227 | 41 | 185–187 | 554.6; 508.4 | 5.67 | >98 |
| 1M117[B] | 147 | 29 | 96–98 | 514.5; 468.6 | 4.92 | >98 |
| 1M119[A] | 107 | 27 | 65–67 | 487.4; 441.6; 413.3 | 2.95 | >96 |
| 1M120[B] | 137 | 27 | 165.5–167 | 500.5; 454.2 | 5.46 | >99 |
| 1M206[B] | 167 | 36 | 157–158 | 468.6; 422.3 | 5.31 | >98 |
| 1M210[B] | 107 | 23 | 157–158 | 466.3; 420.2 | 5.13 | >99 |
| 1M213[B] | 107 | 42 | 60–63 | 492.4; 446.3 | 5.01 | >98 |
| 1M216[B] | 157 | 28 | 177–179 | 570.3; 524.5 | 5.87 | >96 |
| 1M217[B] | 102 | 19 | 134–135 | 530.4; 484.3 | 5.18 | >97 |
| 1M219[A] | 192 | 48 | 74–76 | 503.4; 457.3 | 3.14 | >97 |
| 1M220[B] | 92 | 18 | 143–145 | 516.4; 470.5 | 5.69 | >98 |
| 1N112[A] | 182 | 48 | 65–68 | 479.2 | 6.52 | >94[5] |
| 1N113 | 82 | 18 | 95–97 | 449.1 | 4.83 | >97 |
| 1N117[B] | 124 | 25 | 233.5–235 | 487.2 | 4.99 | >98 |
| 1N118[B] | 107 | 21 | 163–163.5 | 509.5 | 5.73 | >99 |
| 1N119 * HCl[A] | 27 | 5 | 251–252 | 460.3 | 3.10 | >98 |
| 1N208[B] | 179 | 38 | 204–205 | 467.5 | 5.11 | >96 |
| 1N219[A] | 107 | 28 | 258.5–260.5 | 476.3 | 3.14 | >94 |
| 1N220[B] | 202 | 41 | 231.5–232.5 | 489.3; 471.5 | 5.75 | >98 |
| 1M122 | 107 | 23 | 157–158 | 464.4; 418.4; 350.2 | 5.28 | >98[6] |
| 1N122 | 207 | 47 | 210–211 | 437.4; | 5.38 | >98[7] |
| 1M222 | 129 | 27 | 166–167 | 480.3; 434.4; 366.2 | 5.56 | >99[8] |
| 1N222 | 103 | 23 | 110–112 | 453.2 | 5.67 | >96[9] |

[1]HPLC >96%
[2]HPLC UV-254 >94%
[3]HPLC >97%
[4]HPLC >96%
[5]HPLC (UV254) pure >95%
[6]HPLC = 100%
[7]HPLC >94%
[8]HPLC = 100%
[9]HPLC >96

Reaction Scheme 14

1M01
1N01

POCl₃
TEBAC, CH₃CN
→

1M01(Cl)
1N01(Cl)

R₂ = COOEt (M-Series), NO₂ (N-Series)

To a solution of the quinolone 1N01 (or 1M01) (14.08 g; 63.94 mmol) and triethylbenzylammonium chloride (58.4 g; 256.5 mmol) in MeCN (235 ml) was added 26 ml of POCl₃ (282.4 mmol). The mixture was stirred overnight at room temperature The solvent was removed under reduced pressure and the residue was stirred in water (335 ml) for 2 hours. The precipitate was filtered off, washed with water, dried, washed with hot cyclohexane, and dried. Physical properties of the compounds prepared are provided in Table 9.

TABLE 9

| | Yield, g | Yield, % | m.p. °C. | M/Z | τ, min | Purity, % (LCMS) |
|---|---|---|---|---|---|---|
| 1N01(Cl) | 5.59 | 89 | 258–259 | 239; 193 | 3.34 | >95 |
| 1M01(Cl) | 8.63 | 51 | 95.5–98 | 266.1; 220.1 | 3.34 | >98 |

Reaction Scheme 15

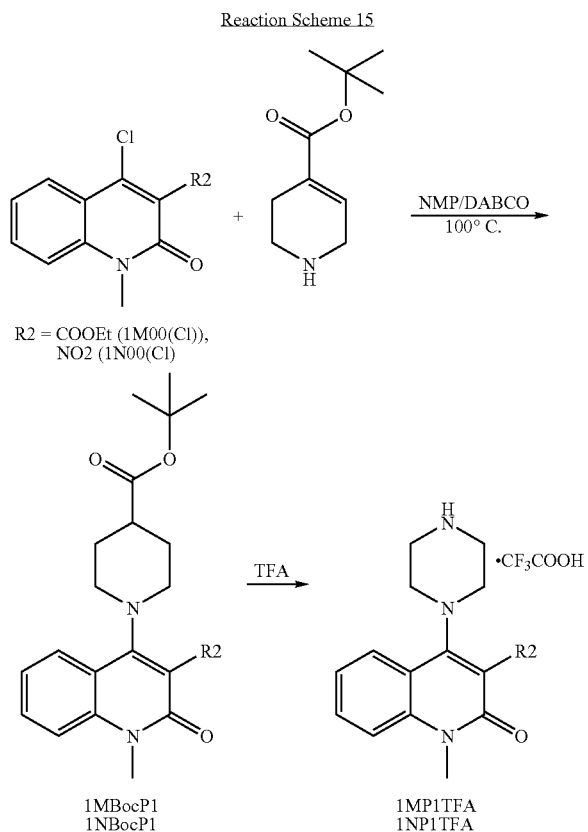

R2 = COOEt (1M00(Cl)),
NO2 (1N00(Cl))

1MBocP1
1NBocP1

1MP1TFA
1NP1TFA

TABLE 10

| | Yield, G | Yield, % | m.p. °C. | M/Z | τ, min | Purity, % (LCMS) |
|---|---|---|---|---|---|---|
| 1MP1TFA | 0.84 | 59 | 214–215 dec. | 316.1; 270.1 | 1.98 | >97 |
| 1NP1TFA | 1.01 | 75 | 234–234 dec. | 589.2; 241.2 | 1.98 | >98 |

Reaction Scheme 16

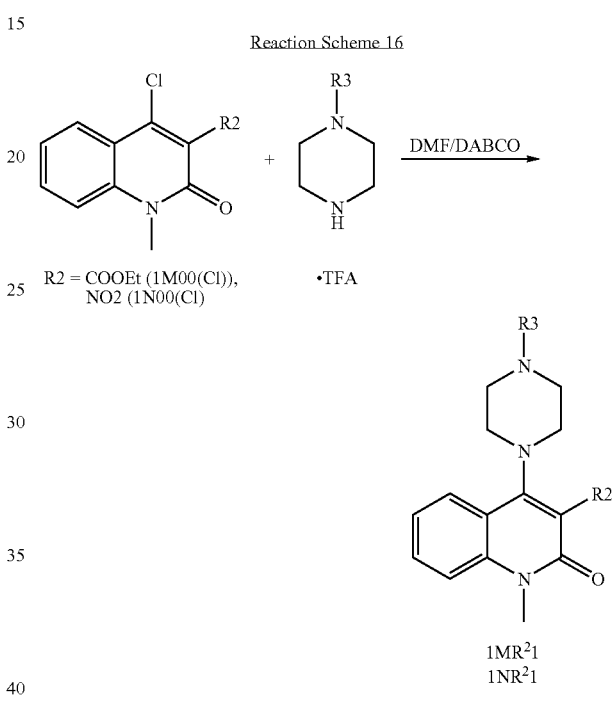

R2 = COOEt (1M00(Cl)),
NO2 (1N00(Cl))

1MR²1
1NR²1

To a solution of 1N01(Cl) (640 mg; 2.68 mmol) in 3 ml DMF was added sequentially t-butyloxycarbonylpiperazine (500 mg; 2.68 mmol) and DABCO (300 mg; 2.68 mmol). The reaction mixture was stirred at room temperature overnight. (For 1M01(Cl), the reaction was stirred at 60° C. overnight). The reaction was quenched with water (15 ml) and the resulted precipitate was filtered off and washed with water. (For 1M01 (Cl), the reaction was quenched with 20% $NH_4Cl$ solution (15 ml), extracted with DCM (3×3 ml), dried over $Na_2SO_4$, the solvent removed under reduced pressure, and the residue was triturated with hexane. The precipitate obtained was filtered off and washed with hexane). The product was dried in a desiccator over $P_2O_5$ at room temperature under reduced pressure. It was dissolved in 1 ml TFA and kept for 1 hour. The solution was triturated with 20 ml of ether, the precipitate was filtered off, washed with ether and dried in the air. Physical properties of the compounds prepared are provided in Table 10.

To a solution of 1N01(Cl) (50 mg; 0.419 mmol) in 3 ml DMF was added sequentially 3-thienoylpiperazine trifluoroacetate (69 mg; 0.440 mmol) and DABCO (47 mg; 0.419 mmol). The reaction mixture was stirred at room temperature overnight. The reaction was quenched with water (15 ml) and the resulted precipitate was filtered off and washed with water. The product was dried in a desiccator over $P_2O_5$ at room temperature under reduced pressure. Products prepared according to this scheme are designated in Table 11 by the superscript "A" following the compound designation.

Reaction Scheme 17

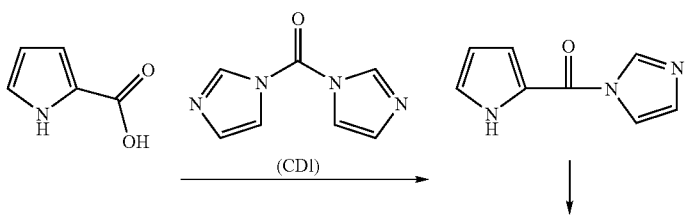

-continued

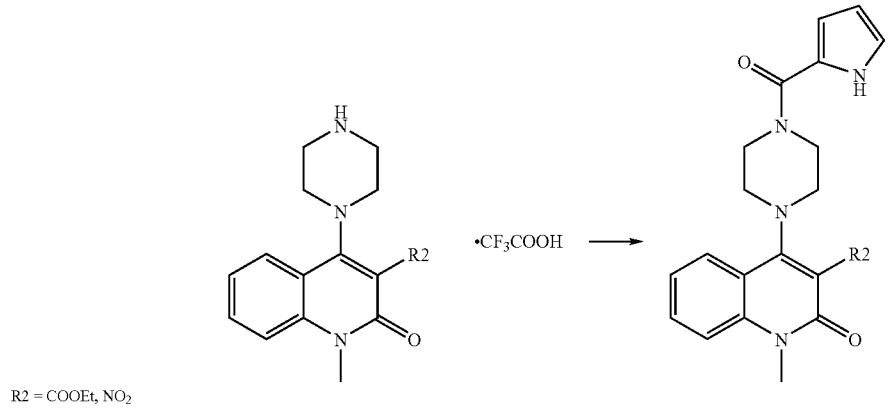

R2 = COOEt, NO₂

A mixture of pyrrole-2-carboxylic acid (91 mg; 0.82 mmol) and CDI (133 mg; 0.82 mmol) in 2 ml DMF was stirred overnight at room temperature. (In the case of 1M081, 1M091, 1M221, 1M271, 1N081, 1N211—in NMP (1 ml); 1M071, 1M151, 1M181, 1M191, 1M211, 1N071, 1N151, 1N181, 1N271—in DMSO (1 ml)). Then 1NP1TFA was added and the mixture was stirred at 60° C. for 6 hours. (In case of 1M181, 1N181—at room temperature). The mixture was diluted with brine 5 ml and extracted with CH₂Cl₂ (3×2 ml). The combined extracts were washed with water (1 ml), dried over Na₂SO₄ and evaporated under reduced pressure. (In the case of 1M071, 1M151, 1M191, 1M211, 1N071, 1N151, 1N191, 1N211, the mixture was diluted with water, the powder precipitated was filtered off, washed with water, dried on the air and dissolved in 5–6N solution of HCl in i-PrOH. The solution was heated under reflux for 10 min. The solvent was evaporated under reduced pressure, the residue was triturated with ether or acetone. The precipitate obtained was filtered off to give hydrochloride of the target compound). The residues obtained were target products. Products prepared according to this scheme are designated in Table 11 by the superscript "B" following the compound designation. Yield data and properties of compounds prepared according to Schemes 16 and 17 are provided in Table 11. Designations including "(2)" indicate that the compound is a regio isomer.

TABLE 11

| Compound | Yield, g | Yield, % | m.p. ° C. | M/Z | τ, min (run 10 min.) | Purity, % (LCMS) |
|---|---|---|---|---|---|---|
| 1M311[A] | 82 | 53 | 113–115 | 406.3; 361.4 | 2.38[1] | >97 |
| 1N111[A] | 62 | 77 | 182 | 383.1 | 3.01[1] | >99 |
| 1N131[A] | 68 | 81 | 252–254 | 399.0 | 3.01[1] | 100 |
| 1N311[A] | 138 | 87 | 212–214 | 379.1 | 2.38[1] | >97 |
| 1M101[B] | 146 | 77 | 225.5–227 | 409.2; 270.3 | 4.11 | >97 |
| 1N121[A] | 87 | 82 | 227–230 | 428.2 | 4.57 | >94 |
| 1N161[B] | 88 | 93 | 157.5–160 | 383.2 | 3.46 | >99 |
| 1N201[B] | 162 | 84 | 215–217 | 461.2 | 4.81 | >97 |
| 1N301[B] | 121 | 100 | 227–230 | 430.3 | 5.08 | >97 |
| 1N341[B] | 87 | 85 | 225–227 | 413.0 | 4.56 | >93[2] |
| 1N171[B] | 122 | 41 | 175–177 | 398.0 | 4.36 | >95 |
| 1N221[B] | 238 | 81 | 187–188 | 394.1; 348.2 | 3.69 | >98 |
| 1N241[B] | 175 | 60 | 258–260 | 394.1 | 2.89 | >96 |
| 1N351[B] | 210 | 74 | 229–231 | 383.0; 337.3 | 2.72 | >97 |
| 1M111(2)[B] | 174 | 91 | 155.5–158 | 410.2; 364.2 | 4.01 | >97 |
| 1M131[B] | 186 | 94 | 137.5–140 | 426.1; 380.1 | 4.22 | >97 |
| 1M161[B] | 170 | 89 | 189–190 | 410.1; 364.2; 346.1 | 3.43 | >96 |
| 1M201[B] | 221 | 97 | 176–178 | 490.1; 442.4; 416.0 | 4.67 | >95 |
| 1M291[B] | 212 | 97 | 210–211 | 471.3; 425.2 | 4.22 | >98 |
| 1N091[B] | 227 | 79 | 84–87 | 387.3; 369.2 | 3.70 | >98 |
| 1N141[B] | 124 | 36 | 223–224.5 | 467.3 | 5.41 | >98 |
| 1M121[B] | 146 | 69 | 52–54 | 455.3; 409.1; 381.2 | 4.45 | >94[3] |
| 1M241[B] | 116 | 59 | 209–210 | 421.3; 375.1 | 3.01 | >95 |
| 1M281 × 1.5 H₂O[B] | 222 | 98 | 164–166 | 459.4; 413.1 | 4.86 | >97 |
| 1M301[B] | 168 | 79 | 67–70 | 457.3; 411.0; 383.1 | 4.94 | >94[4] |
| 1M351[B] | 119 | 62 | 206–208 | 409.9; 364.3; 336.4 | 2.76 | >98 |

TABLE 11-continued

| Compound | Yield, g | Yield, % | m.p. ° C. | M/Z | τ, min (run 10 min.) | Purity, % (LCMS) |
|---|---|---|---|---|---|---|
| 1N101[B] | 228 | 80 | 218–221 | 382.2; 289.2 | 4.19 | >98 |
| 1N191 * HCl[B] | 250 | 77 | 270–273 | 400.1 | 2.74 | >96 |
| 1N231[B] | 256 | 87 | 217–219 | 394.1 | 2.99 | >95 |
| 1N281[B] | 249 | 77 | 283–285 | 432.2 | 4.99 | >99 |
| 1N291[B] | 254 | 77 | 293.5–294 | 444.4 | 4.30 | >97 |
| 1N321[A] | 392 | 84 | 146.5–149 | 369.0 | 2.85 | >99 |
| 1N331[A] | 455 | 94 | 189–190 | 385.1 | 2.99 | >99 |
| 1M141[B] | 103 | 45 | 130–131 | 494.5; 448.2 | 5.31 | >97 |
| 1M171[B] | 129 | 65 | 125–127 | 425.0; 379.2; 351.4 | 4.22 | >96 |
| 1M231[B] | 149 | 76 | 49–52 | 375.1; 421.1 | 3.01 | >96 |
| 1M321[A] | 247 | 55 | 130.5–131.5 | 396.3; 350.2; 269.3 | 3.04 | >98 |
| 1M331[A] | 276 | 59 | 113–114.5 | 412.3; 366.2 | 2.91 | >99 |
| 1M341[B] | 114 | 56 | 225–227 | 440.5; 394.1; 270.3 | 4.39 | >99 |
| 1M071 * HCl | 233 | 56 | 43–45 | 413.4; 367.1; 270.1 | 2.76 | >97 |
| 1M081 | 65 | 15 | 143–145 | 427.2; 270.2 | 3.09 | >99 |
| 1M091 | 171 | 39 | 60–62 | 414.4; 270.0 | 3.59 | >99 |
| 1M151 * HCl | 147 | 27 | 108–111 | 431.3; 385.1; 270.3 | 2.18 | >99 |
| 1M181 | 124 | 43 | 67–69 | 411.5; 365.3; 337.4 | 3.97 | .99 |
| 1M191 * HCl | 327 | 76 | 105–107 | 427.3; 270.3 | 2.13 | >98 |
| 1M211(2) | 70 | 14 |  | 427.3; 381.4; 270.0 | 2.79 | >96 |
| 1M221 | 247 | 56 | 160–160.5 | 421.4; 375.1; 357.1; 347.3 | 3.60 | >93 |
| 1M271 | 135 | 31 | 65–67 | 422.3; 376.2; 348.0 | 3.56 | >94 |
| 1N071 * HCl | 141 | 34 | 83–86 | 386.2 | 3.14 | >96 |
| 1N081 | 85 | 14 | 263–265 | 400.2 | 3.12 | >97 |
| 1N151 * HCl | 227 | 69 | 198–200 | 404.2 | 2.82 | >95 |
| 1N181 | 246 | 86 | 200–201 | 384.1 | 4.00 | >97 |
| 1N211(2) * HCl | 71 | 11 | 78–80 | 400.2 | 2.36 | >95 |
| 1N271 | 247 | 84 | 214–215 | 395.1; 349.2; 242.3 | 3.65 | >99 |

[1]Run 8 min.
[2]HPLC > 98%
[3]HPLC > 96%
[4]HPLC > 97%

The yield of MIF inhibitors prepared as described in selected schemes above is provided in Table 12. Designations including "(1)" or "(2)" indicate that the compound is a regio isomer.

TABLE 12

| No. | Compound | Weight, mg | m.p., (° C.) |
|---|---|---|---|
| 1 | 1M071 * HCl | 226 | 43–45 |
| 2 | 1M081 | 58 | 143–145 |
| 3 | 1M091 | 164 | 60–62 |
| 4 | 1M101 | 139 | 225.5–227 |
| 5 | 1M106 | 84 | 141–143 |
| 6 | 1M107 | 131 | 70–72 |
| 7 | 1M108 | 196 | 71–73 |
| 8 | 1M110 | 135 | 161–162 |
| 9 | 1M111(1) | 178 | 174–175 |
| 10 | 1M111(2) | 167 | 155.5–158 |
| 11 | 1M112 | 72 | 151–152.5 |
| 12 | 1M113 | 145 | 147–150 |
| 13 | 1M114 | 195 | 170–172 |
| 14 | 1M115 | 91 | 177.5–179 |
| 15 | 1M116 | 220 | 185–187 |
| 16 | 1M117 | 140 | 96–98 |
| 17 | 1M118 | 97 | 159–161 |
| 18 | 1M119 | 100 | 65–67 |
| 19 | 1M120 | 130 | 165.5–167 |
| 20 | 1M121 | 139 | 52–54 |
| 21 | 1M122 | 100 | 157–158 |
| 22 | 1M131 | 179 | 137.5–140 |
| 23 | 1M141 | 96 | 130–131 |
| 24 | 1M151 * HCl | 140 | 108–111 |
| 25 | 1M161 | 163 | 189–190 |
| 26 | 1M171 | 122 | 125–127 |
| 27 | 1M181 | 117 | 67–69 |
| 28 | 1M191 * HCl | 320 | 105–107 |
| 29 | 1M201 | 214 | 176–178 |
| 30 | 1M206 | 160 | 157–158 |
| 31 | 1M207 | 124 | 65–67 |
| 32 | 1M208 | 182 | 71–72 |
| 33 | 1M210 | 100 | 157–158 |
| 34 | 1M211(1) | 141 | 161–163 |
| 35 | 1M211(2) * HCl | 112 | 80–81 |
| 36 | 1M212 | 98 | 163–165 |
| 37 | 1M213 | 200 | 60–63 |
| 38 | 1M214 | 109 | 180.5–182.5 |
| 39 | 1M215 | 100 | 87–88 |
| 40 | 1M216 | 150 | 177–179 |
| 41 | 1M217 | 95 | 134–135 |

TABLE 12-continued

| No. | Compound | Weight, mg | m.p., (° C.) |
|---|---|---|---|
| 42 | 1M218 | 140 | 110–112 |
| 43 | 1M219 | 185 | 258.5–260.5 |
| 44 | 1M220 | 85 | 143–145 |
| 45 | 1M221 | 240 | 160–160.5 |
| 46 | 1M222 | 122 | 166–167 |
| 47 | 1M231 | 142 | 49–52 |
| 48 | 1M241 | 109 | 209–210 |
| 49 | 1M271 | 128 | 65–67 |
| 50 | 1M281 | 215 | 164–166 |
| 51 | 1M291 | 205 | 210–211 |
| 52 | 1M301 | 161 | 67–70 |
| 53 | 1M311 | 75 | 113–115 |
| 54 | 1M321 | 230 | 130.5–131.5 |
| 55 | 1M331 | 258 | 113–114.5 |
| 56 | 1M341 | 107 | 225–227 |
| 57 | 1M351 | 112 | 206–208 |
| 58 | 1N071 * HCl | 134 | 83–86 |
| 59 | 1N081 | 78 | 263–265 |
| 60 | 1N091 | 220 | 84–87 |
| 61 | 1N101 | 221 | 218–221 |
| 62 | 1N106 | 145 | 114–116 |
| 63 | 1N107 | 107 | 103–107 |
| 64 | 1N108 | 294 | 200–203 |
| 65 | 1N110 | 90 | 163–166 |
| 66 | 1N111(1) | 130 | 99–100 |
| 67 | 1N111(2) | 56 | 182 |
| 68 | 1N112 | 175 | 65–68 |
| 69 | 1N113 | 75 | 95–97 |
| 70 | 1N114 | 90 | 216–217 |
| 71 | 1N115 | 150 | 105–110 |
| 72 | 1N116 | 133 | 205–208 |
| 73 | 1N117 | 117 | 233.5–235 |
| 74 | 1N118 | 100 | 163–163.5 |
| 75 | 1N119 * HCl | 42 | 251–252 |
| 76 | 1N120 | 85 | 179–181 |
| 77 | 1N121 | 80 | 227–230 |
| 78 | 1N122 | 200 | 210–211 |
| 79 | 1N131 | 60 | 252–254 |
| 80 | 1N141 | 117 | 223–224.5 |
| 81 | 1N151 * HCl | 220 | 198–200 |
| 82 | 1N161 | 81 | 157.5–160 |
| 83 | 1N171 | 115 | 175–177 |
| 84 | 1N181 | 239 | 200–201 |
| 85 | 1N191 * HCl | 243 | 270–273 |
| 86 | 1N201 | 155 | 215–217 |
| 87 | 1N206 | 141 | 72–74 |
| 88 | 1N207 | 180 | 70–72 |
| 89 | 1N208 | 172 | 204–205 |
| 90 | 1N210 | 92 | 187–190 |
| 91 | 1N211(1) | 100 | 83–85 |
| 92 | 1N211(2) * HCl | 64 | 78–80 |
| 93 | 1N212 | 89 | 73–75 |
| 94 | — | — | — |
| 95 | 1N214 | 139 | 172–175 |
| 96 | 1N215 | 80 | 220–221 |
| 97 | 1N216 | 200 | 228–230 |
| 98 | 1N217 | 100 | 251–252 |
| 99 | 1N218 | 200 | 95–97 |
| 100 | 1N219 | 100 | 258.5–260.5 |
| 101 | 1N220 | 195 | 231.5–232.5 |
| 102 | 1N221 | 231 | 187–188 |
| 103 | 1N222 | 96 | 110–112 |
| 104 | 1N231 | 246 | 217–219 |
| 105 | 1N241 | 168 | 258–260 |
| 106 | 1N271 | 240 | 214–215 |
| 107 | 1N281 | 242 | 283–285 |
| 108 | 1N291 | 247 | 293.5–294 |
| 109 | 1N301 | 114 | 227–230 |
| 110 | 1N311 | 131 | 212–214 |
| 111 | 1N321 | 385 | 146.5–149 |
| 112 | 1N331 | 448 | 189–190 |
| 113 | 1N341 | 80 | 225–227 |
| 114 | 1N351 | 202 | 229–231 |

Example 15

The following schemes provide a general procedure for synthesizing Boc-derivatives of acids.

Reaction Scheme 20

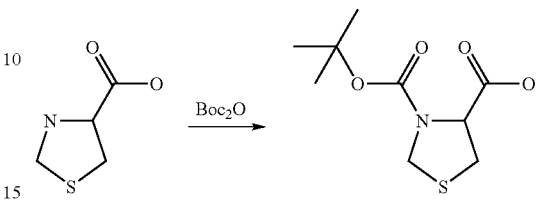

A mixture of L-thiazolidine-4-carboxylic acid (1 g; 7.51 mmol, 98% purity, AVOCADO, # 15033), $Na_2CO_3$ (1.75 g; 16.5 mmol) in $H_2O$ (9 ml) and i-PrOH (1 ml) was stirred until dissolved. Then $Boc_2O$ (1.967 g; 9.01 mmol) was added and the mixture was stirred at room temperature overnight. The suspension obtained was diluted with water (10 ml) and extracted with hexane (5 ml). Lower phase was separated, EtOAc (20 ml) was added and the stirring mixture was acidified to adjust pH 2–3. The EtOAc phase was separated, water phase was extracted with EtOAc (3×10 ml). The combined extracts were washed with water (10 ml), dried over $Na_2SO_4$ and evaporated under reduced pressure. The residue was crystallized from ether and the precipitate obtained was filtered off to give after vacuum drying, N-Boc-thiazolidine-4-carboxylic acid (1.03 g; 59%).

Example 16

Alkylpiperazines may be synthesized according to the following schemes.

Reaction Scheme 21

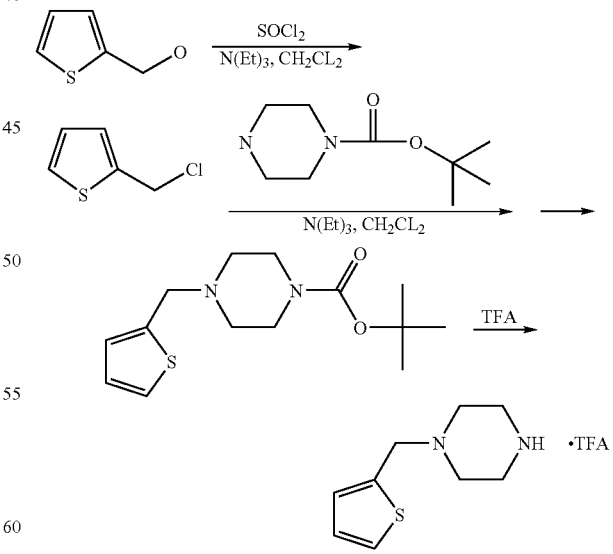

A solution of freshly distilled thionyl chloride (3.9 ml; 0.053 mol) in methylene dichloride (5 ml) was added dropwise to a stirreed solution of 2-thiophenemethanol (4.2 ml; 0.044 mol) and triethylamine (7.4 ml; 0.05 mol) in methylene dichloride (25 ml); the temperature being kept below 20° C. It was then raised to 40° C. during 1 h, poured onto crushed ice, the CH$_2$Cl$_2$-phase was separated and dried over MgSO$_4$. Then it was added dropwise to a stirred solution of N-Boc-piperazine (2 g; 0.011 mol) and triethylamine (1.5 ml; 0.011 mol) in CH$_2$Cl$_2$ (45 ml). See Nicholas A. Meanwell, Piyasena Hewawasam, Jeanine A. Thomas, J. J. Kim Wright, John W. Russel, Marianne Gamberdella, Harold J. Goldenberg, Steven M. Seiler, and George B. Zavoico, Inhibitors of Blood Platelet cAMP Phosphodiesterase. 4. Structural Variation of the Side-Chain Terminus of Water-Soluble 1,3-Dihydro-2H-imidazo[4,5-b]quinolin-2-one Derivatives, *J. Med. Chem.* (1993) Vol. 36., pp. 3251–3264; Elena Carceller, Manuel Merlos, Marta Giral, Carmen Almansa, Javier Bartroli, Julian Garcia-Rafanell, and Javier Form, Synthesis and Structure-Activity Relationships of 1-Acyl-4-((2-methyl-3-pyridyl)cyanomethyl)piperazines as PAF Antagonists, *J. Med. Chem.* (1993) No. 36, pp. 2984–2997. The mixture was stirred overnight at room temperature, the solvent was removed under reduced pressure, and the residue was extracted with ether. The ether solution was evaporated under reduced pressure, the residue was dissolved in TFA (3.3 ml; 0.043 mol) and kept during 30 min. TFA was removed under reduced pressure, the residue was triturated with ether, the precipitate was filtered off and dried on the air to give 1-(2-thienylmethyl)piperazine ditrifluoroacetate (3.16 g; 72%). See William J. Archer, Robert Cook, and Roger Taylor, Electrophilic Aromatic Substitution. Part 34. Partial Rate Factors for Detritiation of Dithieno[1,2-b:4,3-b']benzene, Dithieno[1,2-b:3,4-b']benzene, and Dithieno[2,1-b:3,4-b']benzene, *J. Chem. Soc. Perkin Trans. II.* (1983) pp. 813–819.

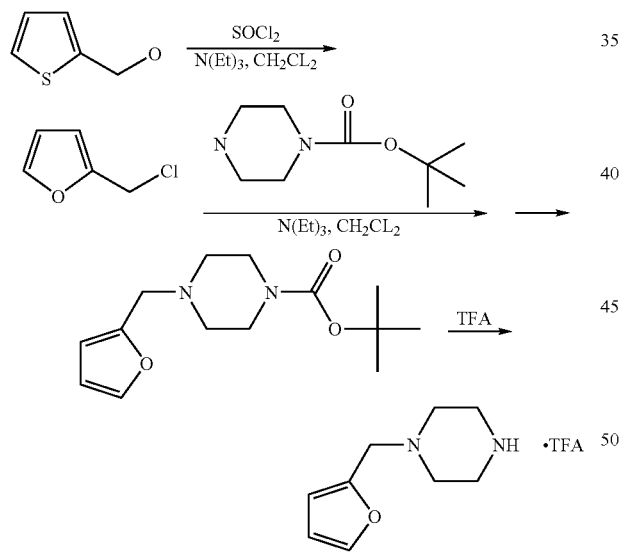

A solution of freshly distilled thionyl chloride (3.9 ml; 0.053 mol) in methylene dichloride (5 ml) was added dropwise to a stirred solution of furfuryl alcohol (3.8 ml; 0.044 mol) and triethylamine (7.4 ml; 0.05 mol) in methylene dichloride (25 ml); the temperature being kept below 20° C. The mixture was stirred for 1 h. Then the solvent was evaporated, the residue was dissolved in CH$_2$Cl$_2$ (150 ml). The solution obtained was added dropwise to a stirred solution of N-Boc-piperazine (2 g; 0.011 mol) and triethylamine (4 ml; 0.029 mol) in CH$_2$Cl$_2$ (45 ml). The mixture was stirred overnight at room temperature, the solvent was removed under reduced pressure, and the residue was extracted with ether. The ether solution was evaporated under reduced pressure, the residue was dissolved in TFA (3.3 ml; 0.043 mol) and maintained for 30 min. TFA was removed under reduced pressure, the residue was titrated with ether, and the black precipitate obtained was filtered off. Then, the precipitate was dissolved in 200 ml of MeOH, activated charcoal was added, and the mixture was heated under reflux for 30 min. Charcoal was filtered off, the solvent was evaporated, the residue was triturated with ether. The white precipitate obtained was filtered off and dried on the air to give 1-(2-furylmethyl)piperazine ditrifluoroacetate (1.64 g; 40%). See R. Lukes and V. Dienstbierova, Synthese von α-methylfural, *Collection Czechoslov. Chem. Commun.* (1954) Vol. 19, pp. 609–610.

Example 17

Sulfonamides may be Synthesized According to the Following Schemes.

4-Hydroxy-1-methyl-3-nitro-1H-quinolin-2-one (referred to as 595-01)

A solution of ethylnitroacetate (15.96 g, 120 mmol) was added slowly in a suspension of sodium hydride (60% in mineral oil, 5.28 g, 132 mmol) in dimethylacetamide under N$_2$ atmosphere. The mixture was allowed to stir at room temperature until the evolution of hydrogen gas ceased, then heated to 90° C. for 30 min. and cooled to room temperature. A solution of N-methylisatoic anhydride (23.38 g, 132 mmol) in dimethylacetamide was added slowly and heated overnight at 120° C. The mixture was cooled to room temperature, poured into ice water, and acidified by cold 10% HCl. The solids formed were filtered and washed several times by water to yield 7.1 g (27%) of yellow solids. Mp 193° C. $^1$H NMR (DMSO-d$_6$): δ 3.60 (s, 3H), 7.37 (t, J=7.6 Hz, 1H), 7.58 (d, J=8.5 Hz, 1H), 7.77 (t, J=7.5 Hz, 1H), 8.12 (d, J=7.9 Hz, 1H). EIMS m/z 221 (M+1), 243 (M+23). Anal. (C$_{10}$H$_8$N$_2$O$_4$) C, H, N.

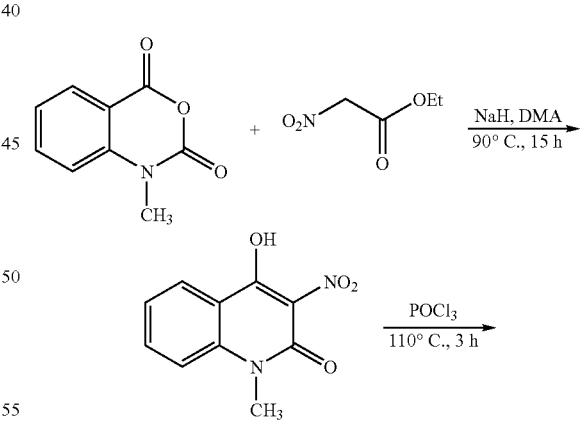

595-01

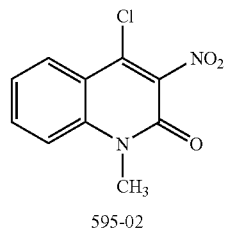

595-02

4-Chloro-1-methyl-3-nitro-1H-quinolin-2-one (Referred to as 595-02)

A suspension of 595-01 (6.2 g, 28.18 mmol) in 70 ml phosphorus oxychloride was heated at 90° C. for 3 h. The solvent was evaporated under reduced pressure. The residue was suspended in ice water and neutralized by sodium bicarbonte. The solids formed were filtered and dried to get 4.91 g (73%) of brown solids. Mp 235° C. $^1$H NMR (DMSO-d$_6$): δ 3.72 (s, 3H), 7.56 (t, J=7.5 Hz, 1H), 7.78 (d, J=8.6 Hz, 1H), 7.92 (t, J=8.6 Hz, 1H), 8.12 (d, J=7.9 Hz, 1H). EIMS m/z 239 (M+1), 261 (M+23). Anal. (C$_{10}$H$_7$N$_2$O$_3$Cl) C, H, N.

4-(Thiophene-2-carbonyl)-piperazine-1-carboxylic acid tert-butyl ester (Referred to as 595-03)

2-Thiophenecarbonylchloride (2.04 g, 1.49 mL) was added to a solution of tert-butyl-1-piperazinecarboxylate (2.5 g, 13.4 mmol) and DMAP (20 mg) in pyridine (15 mL) at 0° C. under N$_2$ atmosphere and stirred at room temperature for overnight. The mixture was poured into ice water, the precipitate was filtered, washed several times with water, and dried to yield white solids (3.5 g, 88%). Mp 76° C. $^1$H NMR (DMSO-d$_6$): δ 1.42 (s, 12H), 3.40 (m, 4H), 3.61 (m, 4H), 7.12 (m, 1H), 7.43 (d, J=4.1 Hz, 1H), 7.77 (d, J=4.8 Hz, 1H). EIMS m/z 297 (M+1), 319 (M+23). Anal. (C$_{14}$H$_{20}$N$_2$O$_3$S)C, H, N.

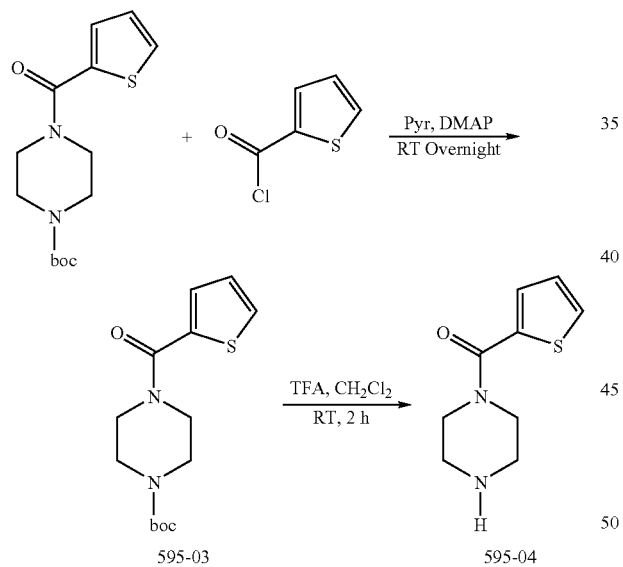

Piperazine-1-yl-thiophen-2-yl-methanone (Referred to as 595-04)

To a solution of 595-03 (3.5 g, 11.8 mmol) in dichloromethane (50 mL) was added trifluoroacetic acid (10 mL). The solution was stirred at room temperature for 3 h. The solvent was evaporated under vacuum and the residue was dissolved in chloroform. The organic phase was washed by saturated solution of sodium bicarbonate, dried over Na$_2$SO$_4$ and evaporated to get 2.20 g (94%) of brown viscous oil. $^1$H NMR (DMSO-d$_6$): δ 2.78 (m, 4H), 3.59 (m, 4H), 7.12 (t, J=4.1, 1H), 7.38 (d, J=4.1 Hz, 1H), 7.74 (d, J=4.8 Hz, 1H). EIMS m/z 197 (M+1).

1-Methyl-3-nitro-4-[4-(thiophene-2-carbonyl)-piperazine-1-yl]-1H-quinolin-2-one (Referred to as 595-06)

595-04 (1 g, 5.5 mmol) and diisopropylethylamine (1.74 mL, 10 mmol) was added to a solution of 595-02 (1.2 g, 5 mmol) in toluene (100 mL) and heated at 100° C. for 15 h. The solvent was removed under vacuum. The purification of residue by flash chromatography (CH$_2$Cl$_2$/MeOH, 49:1) afforded 1.05 g (53%) yellow solids. Mp 105° C. $^1$H NMR (DMSO-d$_6$): δ 3.19 (m, 4H), 3.65 (s, 3H), 3.90 (m, 4H), 7.14 (t, J=4.5 Hz, 1H), 7.43 (t, J=7.5 Hz, 1H), 7.48 (d, J=4.1 Hz, 1H), 7.67 (d, J=8.5 Hz, 1H), 7.80 (m, 2H), 8.05 (d, J=8.5 Hz, 1H). EIMS m/z 399 (M+1), 421 (M+23). Anal. (C$_{19}$H$_{18}$N$_4$O$_4$S) C, H, N.

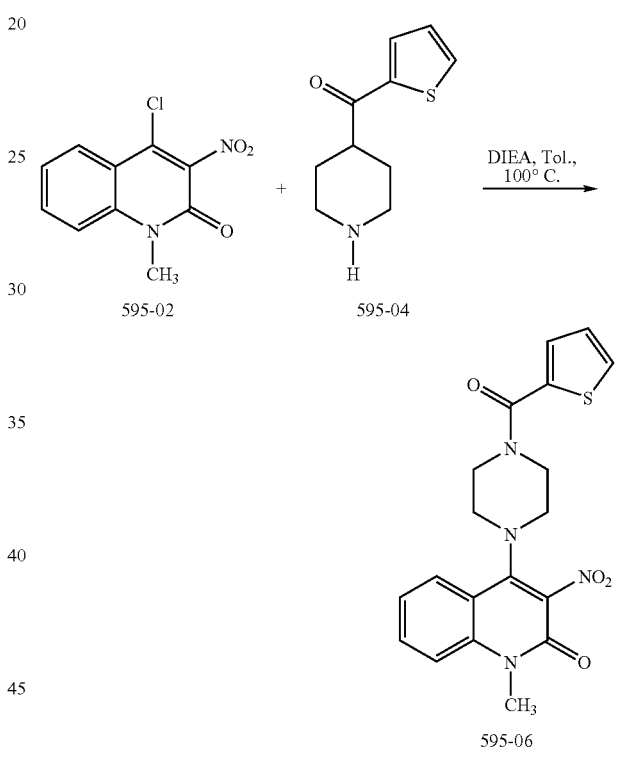

3-Amino-1-methyl-4-[4-thiophene-2-carbonyl)-piperazine-1-yl]-1H-quinolon-2-one (Referred to as 595-09)

To a suspension of 595-06 (600 mg, 1.5 mmol) in ethanol was added Pd/C (10%, 75 mg). The suspension was stirred under H$_2$ atmoshphere at 60° C. for 4 h. The hot mixture was filtered through Celite and the filtrate was evaporated to dryness. The residue was recrystallised by ethanol to yield 490 mg (88%) of white solids. Mp 202° C. $^1$H NMR (CDCl$_3$): δ 3.20 (br, 2H), 3.49 (br, 2H), 3.65 (br, 2H), 3.79 (s, 3H), 4.13 (br, 2H), 4.71 (br, 2H), 7.08 (t, J=4.3 Hz, 1H), 7.22–7.26 (m, 3H), 7.34–7.37 (m, 3H), 7.48 (d, J=4.9 Hz, 1H), 7.79 (d, J=8.0 Hz, 1H). EIMS m/z 369 (M+1), 391 (M+23). Anal. (C$_{19}$H$_{20}$N$_4$O$_2$S) C, H, N.

N-{1-Methyl-2-oxo-4-[4-(thiophene-2-carbonyl)-piperazin-1-yl]-1,2-dihydro-quinolin-3-yl}-methane-sulfonamide (Referred to as 595-15)

Methanesulfonyl chloride (0.1 mL, 1.3 mmol) was added dropwise to a solution of 595-09 (120 mg, 0.32 mmol) in pyridine (2 mL) under $N_2$ atmosphere and further stirred at room temperature overnight. The solvent was evaporated under vacuum and the residue was dissolved in ethylacetate. The organic phase was washed successively by saturated $NaHCO_3$ solution, water and brine. The organic phase was dried over $Na_2SO_4$ and evaporated to a residue which was washed by ether to yield 103 mg (73%) of white solids. Mp 223° C. $^1$H NMR (DMSO-$d_6$): δ 3.08 (s, 3H), 3.31 (m, 4H), 3.64 (s, 3H), 3.95 (m, 4H), 7.15 (t, J=4.0 Hz, 1H), 7.33 (t, J=7.6 Hz, 1H), 7.44 (d, J=4.0 Hz, 1H), 7.56 (d, J=8.5 Hz, 1H), 7.66 (t, J=7.4 Hz, 1H), 7.79 (d, J=4.9 Hz, 1H), 7.98 (d, J=8.2 Hz, 1H), 8.84 (s, 1H). EIMS m/z 447 (M+1), 469 (M+23). Anal. ($C_{20}H_{22}N_4O_4S_2$) C, H, N.

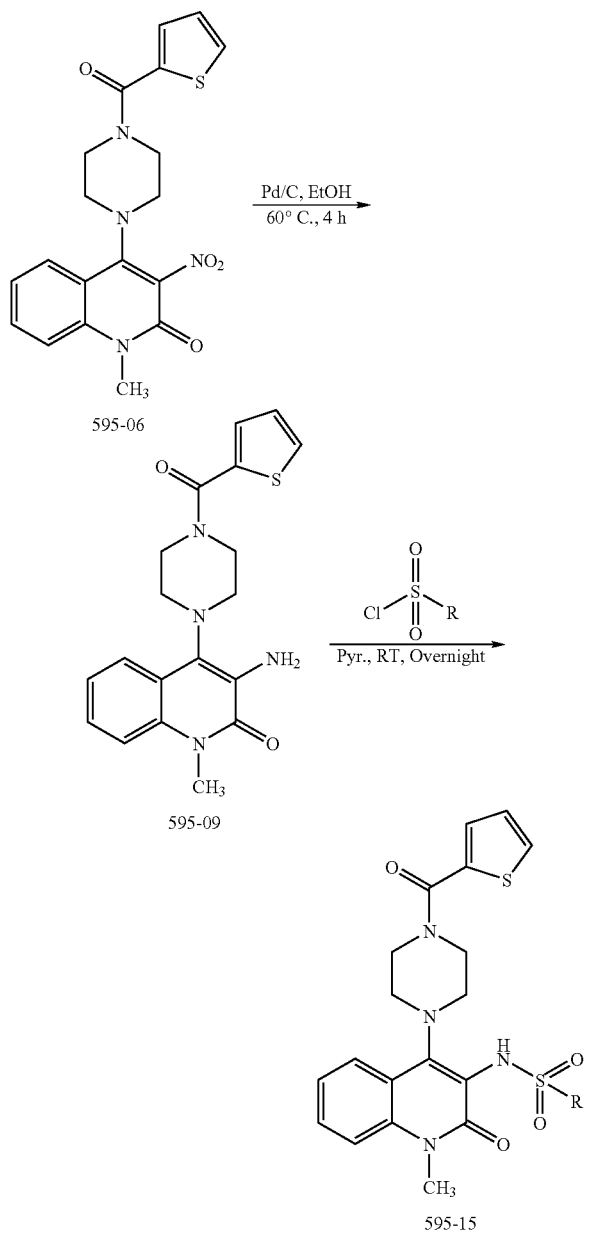

Other sulfonamides may be prepared according to similar synthetic routes.

Example 18

Sulfonyls may be synthesized according to the following schemes.

p-Tolylsulfanyl-acetic acid ethyl ester (Referred to as 595-29)

A solution of 4-methylbenzenethiol (5 g, 40.25) in dry THF was added dropwise to a suspension of NaH (60% in mineral oil, 1.98 g, 48.30) in THF at room temperature and stirred for 30 min. under $N_2$ atmosphere. Ethylbromoacetate (4.9 mL, 44.27) was added slowly to this solution and further stirred at room temperature for 3 h. The solvent was removed under vacuum. The residue was dissolved in dil. HCl and extracted by ethylacetate. The combined organic phase was washed successively with saturated $NaHCO_3$ solution, water and brine then dried over $Na_2SO_4$. Evaporation of organic phase yielded 8.46 g (99%) colorless oil. $^1$H NMR ($CDCl_3$): δ 1.22 (t, J=7.2 Hz, 3H), 2.32 (s, 3H), 3.57 (s, 2H), 4.14 (q, J=7.2 Hz, 2H), 7.11 (d, J=8.0 Hz, 2H), 7.33 (d, J=8.0 Hz, 2H). EIMS m/z 210 (M+1), 233 (M+23).

(Toluene-4-sulfonyl)-acetic acid ethyl ester (Referred to as 595-35)

To a solution of 595-29 (10 g, 47.55 mmol) in dichloromethane was added m-chloroperbenzoic acid (21.31 g, 95.10 mmol) in portion at 0° C. The mixture was warmed to room temperature and stirred overnight. The solids formed were filtered and the filtrate was washed successively by 1N NaOH, water and brine. The organic phase was dried over $Na_2SO_4$ and evaporated to yield 9.8 g (85%) of colorless oil. $^1$H NMR ($CDCl_3$): δ 1.22 (t, J=7.2 Hz, 3H), 2.45 (s, 3H), 4.08 (s, 2H), 4.17 (q, J=7.2 Hz, 2H), 7.37 (d, J=8.0 Hz, 2H), 7.83 (d, J=8.0 Hz, 2H). EIMS m/z 243 (M+1), 265 (M+23).

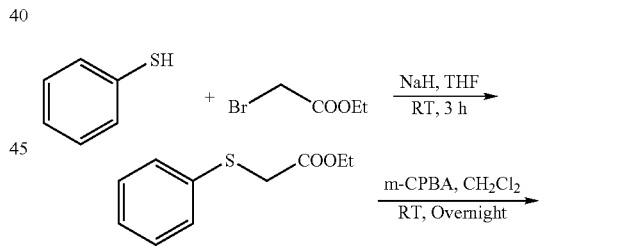

4-Hydroxy-1-methyl-3-(toluene-4-sulfonyl)-1H-quinolin-2-one (Referred to as 595-36)

A solution of 595-35 (9.8 g, 40.49 mmol) was added slowly in a suspension of sodium hydride (60% in mineral oil, 1.78 g, 44.52 mmol) in dimethylacetamide under $N_2$ atmosphere. The mixture was stirred at room temperature until the evolution of hydrogen gas ceased, then heated to 90° C. for 30 min. and cooled to room temperature. A solution of N-methylisatoic anhydride (7.88 g, 44.52 mmol) in dimethylacetamide was added slowly and heated overnight at 120° C. The mixture was cooled to room temperature, poured into ice water and acedified by cold 10% HCl. The solids formed were filtered and washed several times by water to yield 5.7 g (43%) of white solids. Mp 191° C. $^1$H NMR (DMSO-d$_6$): δ 2.39 (s, 3H), 3.44 (s, 3H), 7.36 (t, J=7.5 Hz, 1H), 7.42 (d, J=8.2 Hz, 2H), 7.55 (d, J=8.5 Hz, 1H), 7.81 (t, J=7.1 Hz, 1H), 7.95 (d, J=8.2 Hz, 2H), 8.11 (d, J=8.0 Hz, 1H). EIMS m/z 330 (M+1), 352 (M+23). Anal. (C$_{17}$H$_{15}$NO$_4$S) C, H, N.

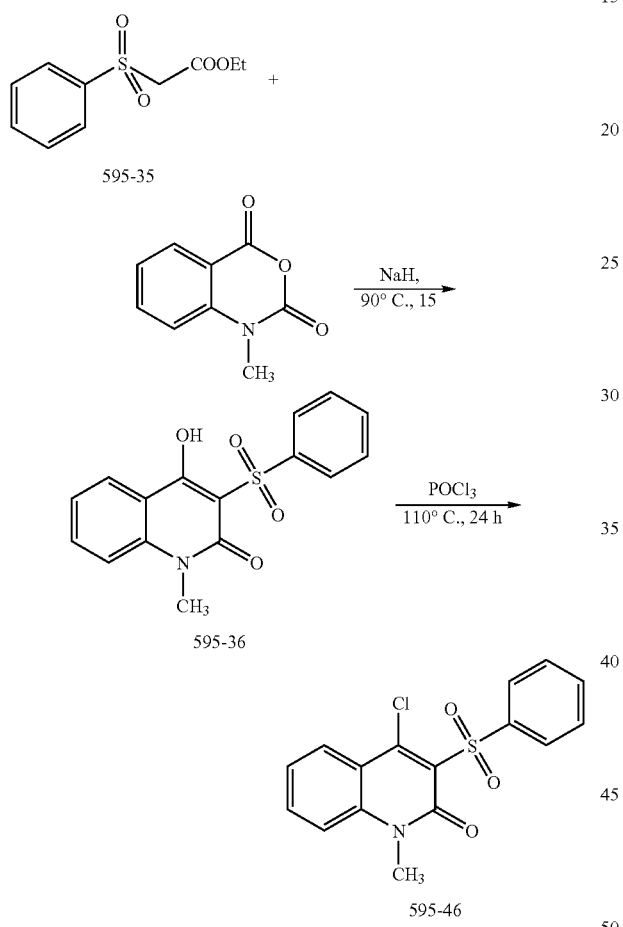

4-Chloro-1-methyl-3-(tolune-4-sulfonyl)-1H-quinolin-2-one (Referred to as 595-46)

A suspension of 595-36 (5.2 g, 5.9 mmol) in 30 mL phosphorus oxychloride was heated at 130° C. for 30 h. The solvent was evaporated under reduced pressure. The residue was suspended in ice water and neutralized by sodium bicarbonte. The solids formed were filtered and dried to yield 2.3 g (43%) of white solids. Mp 193° C. $^1$H NMR (DMSO-d$_6$): δ 2.38 (s, 3H), 3.52 (s, 3H), 7.39 (d, J=8.0 Hz, 2H), 7.48 (t, J=7.5 Hz, 1H), 7.64 (d, J=8.4 Hz, 1H), 7.84 (t, J=7.1 Hz, 1H), 7.94 (d, J=8.2 Hz, 2H), 8.32 (d, J=8.0 Hz, 1H). EIMS m/z 348 (M+1), 370 (M+23). Anal. (C$_{17}$H$_{14}$NO$_3$SCl) C, H, N.

1-Methyl-4-[4-(thiophene-2-carbonyl)-piperazin-1-yl]-3-(tolune-4-sulfonyl)-1H-quinolin-2-one (Referred to as 595-48)

Diisopropylethylamine (0.38 mL, 2.22 mmol) was added to a solution of 595-46 (289 mg, 0.83 mmol) and 595-04 (195 mg, 0.99 mmol) in toluene and heated overnight at 105° C. The solution was cooled and the solvent was evaporated under vacuum. Water was added to the oily residue and sonicated. The solids formed were filtered and washed with water and ether to yield yellow solids, 360 mg (86%), mp 213° C. $^1$H NMR (DMSO-d$_6$): δ 2.37 (s, 3H), 3.37 (s, 3H), 3.65 (m, 4H), 3.94 (m, 4H), 7.16 (t, J=4.3 Hz, 1H), 7.32 (d, J=8.0 Hz, 2H), 7.39 (t, J=7.6 Hz, 1H), 7.49 (d, J=4.0 Hz, 1H), 7.54 (d, J=8.5 Hz, 1H), 7.74 (d, J=8.0 Hz, 2H), 7.80 (d, J=4.5 Hz, 1H), 8.15 (d, J=8.2 Hz, 1H). EIMS m/z 508 (M+1), 530 (M+23). Anal. (C$_{26}$H$_{25}$N$_3$O$_4$S$_2$) C, H, N.

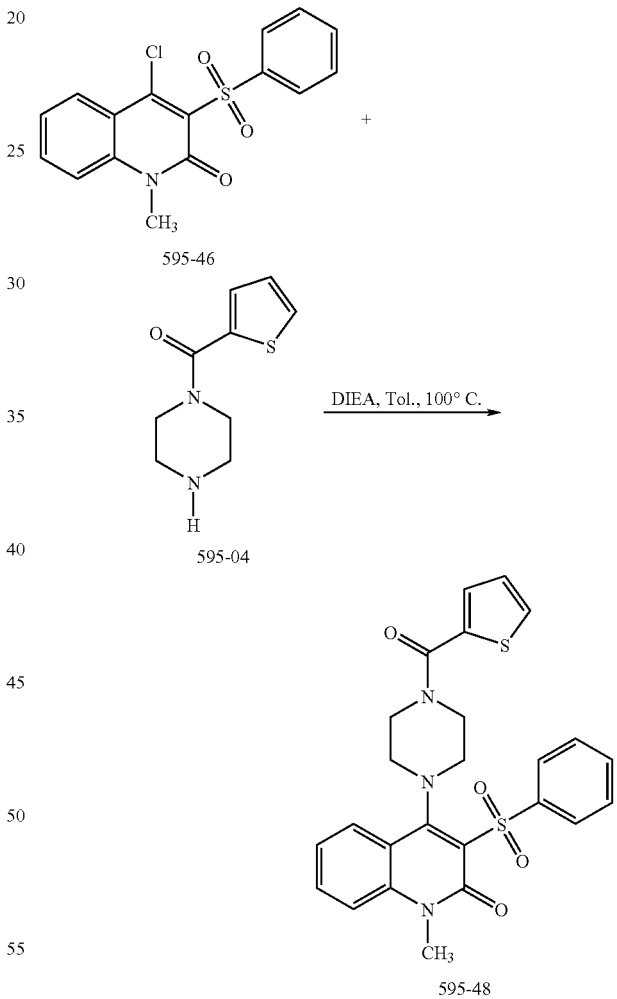

4-Hydroxy-3-methanesulfonyl-1-methyl-1H-quinolin-2-one (Referred to as 595-05)

A solution of ethylmethanesulfonylacetate (3.78 g, 22.74 mmol) was added slowly in a suspension of sodium hydride (60% in mineral oil, 1.07 g, 25 mmol) in dimethylacetamide under N$_2$ atmosphere. The mixture was allowed to stir at room temperature until the evolution of hydrogen gas ceased, then heated to 90° C. for 30 min and cooled to room temperature. A solution of N-methylisatoic anhydride (4.43 g, 25 mmol) in dimethylacetamide was added slowly and heated overnight at 120° C. The mixture was cooled to room temperature, poured into ice water and acidified by cold 10% HCl. The solids formed were filtered and washed several times by water to yield 2.76 g (48%) of white solids. Mp 170° C. $^1$H NMR (DMSO-d$_6$): δ 3.51 (s, 3H), 3.59 (s, 3H), 7.39 (t, J=7.4 Hz, 1H), 7.62 (d, J=8.5 Hz, 1H), 7.84 (t, J=7.0 Hz, 1H), 8.09 (d, J=8.0 Hz, 1H). EIMS m/z 254 (M+1), 276 (M+23). Anal. (C$_{11}$H$_{11}$NO$_4$S) C, H, N.

4-Chloro-3-methanesulfonyl-1-methyl-1H-quinolin-2-one (Referred to as 595-14)

A suspension of 595-05 (1.5 g, 5.9 mmol) in 30 mL phosphorus oxychloride was heated at 130° C. for 30 h. The solvent was evaporated under reduced pressure. The residue was suspended in ice water and neutralized by sodium bicarbonate. The solids formed were filtered and dried to yield 773 mg (48%) of white solids solids. Mp 221° C.; $^1$H NMR (DMSO-d$_6$): δ 3.48 (s, 3H), 3.68 (s, 3H), 7.49 (t, J=7.8 Hz, 1H), 7.72 (d, J=8.5 Hz, 1H), 7.89 (t, J=8.6 Hz, 1H), 8.29 (d, J=8.5 Hz, 1H). EIMS m/z 272 (M+1), 294 (M+23). Anal. (C$_{11}$H$_{10}$ClNO$_3$S) C, H, N.

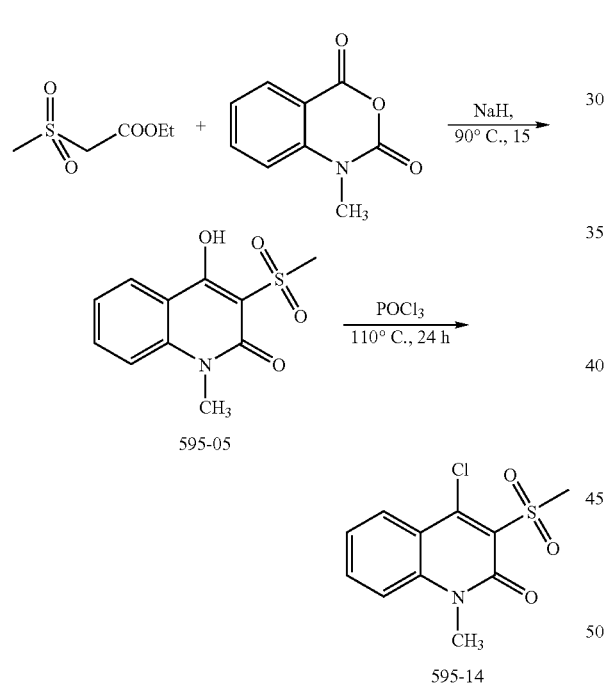

595-05

595-14

3-Methanesulfonyl-1-methyl-4-[4-(thiophene-2-carbonyl)-piperazin-1-yl]-1H-quinolin-2-one (Referred to as 595-16)

Diisopropylethylamine (0.38 mL, 2.22 mmol) was added to a solution of 595-14 (300 mg, 1.11 mmol) and 595-04 (239 mg, 1.21 mmol) in toluene and heated overnight at 105° C. The solution was cooled and the solvent was evaporated under vacuum. Water was added to the oily residue and sonicated. The solids formed were filtered and washed with water and ether to yield yellow solids, 384 mg (81%), mp 224° C. $^1$H NMR (DMSO-d$_6$): δ 3.36 (s, 3H), 3.52 (m, 4H), 3.60 (s, 3H), 3.91 (m, 4H), 7.16 (t, J=3.5 Hz, 1H), 7.37 (t, J=7.5 Hz, 1H), 7.47 (d, J=3.5 Hz, 1H), 7.61 (d, J=8.5 Hz, 1H), 7.57 (t, J=8.1 Hz, 1H), 7.79 (d, J=4.8 Hz, 1H), 8.10 (d, J=8.5 Hz, 1H). EIMS m/z 432 (M+1), 454 (M+23). Anal. (C$_{20}$H$_{21}$N$_3$O$_4$S$_2$) C, H, N.

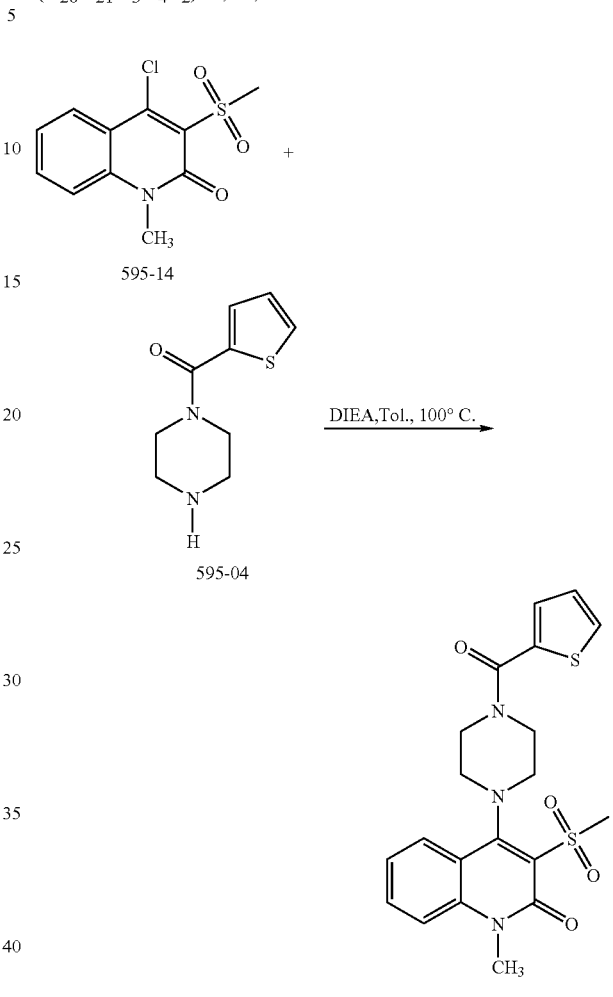

595-14

595-04

595-16

Example 19

4-Hydroxy-2-oxo-1,2-dihydro-quinoline-3-carboxylic acid ethyl ester (Referred to as 595-68)

A solution of diethylmalonate (80 g, 0.50 mol) was added slowly to a suspension of sodium hydride (60% in mineral oil, 22 g, 0.55 mol) in dimethylacetamide under N$_2$ atmosphere. The mixture was allowed to stir at room temperature until the evolution of hydrogen gas ceased, then heated to 90° C. for 30 min. and cooled to room temperature. A solution of isatoic anhydride (89.72 g, 0.55 mmol) in dimethylacetamide was added slowly and heated at 120° C. for 15 h. The mixture was cooled to room temperature, poured into ice water and acidified by cold 10% HCl. The solids formed were filtered and washed several times by water to yield 55 g (47%) of white solids. Mp 173° C. $^1$H NMR (DMSO-d$_6$): δ 1.30 (t, J=6.9 Hz, 3H), 4.33 (q, J=6.9 Hz, 2H), 7.18 (t, J=7.5 Hz, 1H), 7.26 (d, J=8.2 Hz, 1H), 7.62 (t, J=7.2 Hz, 1H), 7.93 (d, J=8.0 Hz, 1H) 11.50 (s, 1H), 13.5 (s, 1H). EIMS m/z 234 (M+1), 256 (M+23). Anal. (C$_{12}$H$_{11}$NO$_4$) C, H, N.

2,4-Dichloro-quinoline-3-carboxylic acid ethylester (Referred to as 595-72)

A suspension of 595-68 (35 g, 150 mmol) in 200 mL phosphorus oxychloride was heated at reflux for 30 min. The solvent was evaporated under reduced pressure. The residue was suspended in ice water and neutralized by sodium bicarbonte. The solid formed were filtered and dried to yield 39 g (97%) of white solids. Mp 93° C. $^1$H NMR (DMSO-d$_6$): δ 1.37 (t, J=6.9 Hz, 3H), 4.49 (q, J=6.9 Hz, 2H), 7.89 (t, J=8.5 Hz, 1H), 8.02 (t, J=7.2 Hz, 1H), 8.10 (d, J=8.3 Hz, 1H), 8.28 (d, J=8.0 Hz, 1H); EIMS m/z 270 (M+1), 292 (M+23). Anal. ($C_{12}H_9Cl_2NO_2$) C, H, N.

4-Chloro-2-oxo-1,2-dihydro-quinoline-3-carboxylic acid ethyl ester (Referred to as 595-76)

Ammonium acetate (12.6 g, 164 mmol) was added to a solution of 595-72 (40.17 g, 149 mmol) in acetic acid (150 mL). The mixture was heated at 140° C. for 4 h. The solution was cooled and poured into ice water. The solids formed were filtered, washed by water and dried to yield white solids (34 g, 91%), Mp 186° C. $^1$H NMR (DMSO-d$_6$): δ 1.37 (t, J=6.9 Hz, 3H), 4.50 (q, J=6.9 Hz, 2H), 7.87 (t, J=7.2 Hz, 1H), 8.01 (t, J=7.0 Hz, 1H), 8.08 (d, J=8.4 Hz, 1H), 8.26 (d, J=8.2 Hz, 1H). EIMS m/z 252 (M+1). Anal. ($C_{12}H_{10}ClNO_3$) C, H, N.

2-Oxo-4-[4-(thiophene-2-carbonyl)-piperazine-1-yl]-1,2-dihydro-quinoline-3-carboxylic acid ethyl ester (Referred to as 595-77)

To a solution of 595-76 (7 g, 27.8 mmol) in dimethylacetamide was added 1,4-diazabicyclo[2.2.2]octane (6.23 g, 55.6 mmol) and 595-04 (6 g, 30.6 mmol). The solution was heated at 115° C. for 15 h. The reaction mixture was cooled and poured into the ice water. The solids formed were filtered, washed with water and dried to yield white solids (7 g, 62%), mp 198° C. $^1$H NMR (DMSO-d$_6$): δ 1.28 (t, J=6.9 Hz, 3H), 3.12 (m, 4H), 3.87 (m, 4H), 4.28 (q, J=6.9 Hz, 2H), 7.15 (t, J=4.3 Hz, 1H), 7.23 (t, J=7.5 Hz, 1H), 7.31 (d, J=8.1 Hz, 1H), 7.45 (d, J=3.1 Hz, 1H), 7.54 (t, J=7.4 Hz, 1H), 7.79 (d, J=4.9 Hz, 1H), 7.87 (d, J=8.0 Hz, 1H). EIMS m/z 412 (M+1), 434 (M+23). Anal. ($C_{21}H_{21}N_3O_4S \cdot 0.5H_2O$) C, H, N.

1-(4-Fluorobenzyl)-2-oxo-4-[4-(thiophene-2-carbonyl)-piperazine-1-yl]-1,2-dihydro-quinoline-3-carboxylic acid ethyl ester (Referred to as 595-78)

To a suspension of sodium hydride (60% in mineral oil, 0.78 g, 19.46 mmol) in DMF was added slowly a solution of 595-77 (7 g, 17.03 mmol) in DMF. The suspension was stirred at room temperature for 30 min. 4-Flurobenzylbromide was added to this solution slowly and further stirred for 2 h. The mixture was poured into ice water and acidified by cold 10% HCl. The solid formed were separated, washed with water and purified by flash chromatography ($CH_2Cl_2$/MeOH, 49:1) to yield 5.9 g (67%) of white solids. Mp 52° C.; $^1$H NMR (DMSO-d$_6$): δ 1.30 (t, J=6.9 Hz, 3H), 3.16 (m, 4H), 3.89 (m, 4H), 4.32 (q, J=6.9 Hz, 2H), 7.14–7.17 (m, 3H), 7.24–7.27 (m, 2H), 7.31 (t, J=7.6 Hz, 1H), 7.44–7.47 (m, 2H), 7.58 (t, J=8.5 Hz, 1H), 7.79 (d, J=4.9 Hz, 1H), 8.02 (d, J=8.5 Hz, 1H). EIMS m/z 520 (M+1), 542 (M+23). Anal. ($C_{28}H_{26}FN_3O_4S \cdot H_2O$) C, H, N.

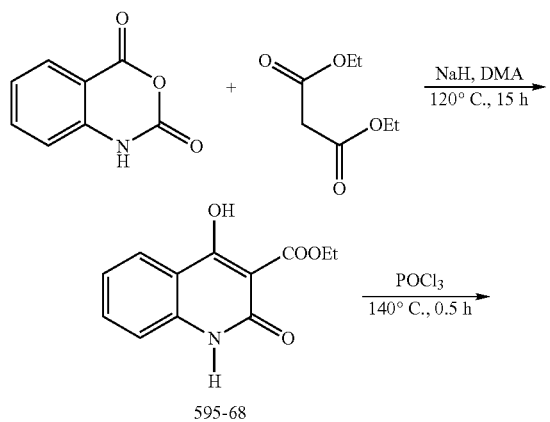

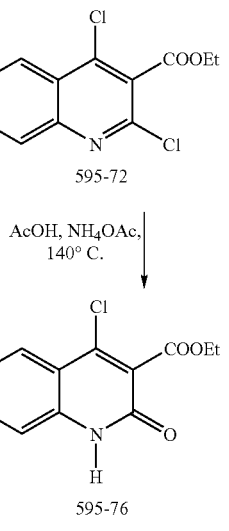

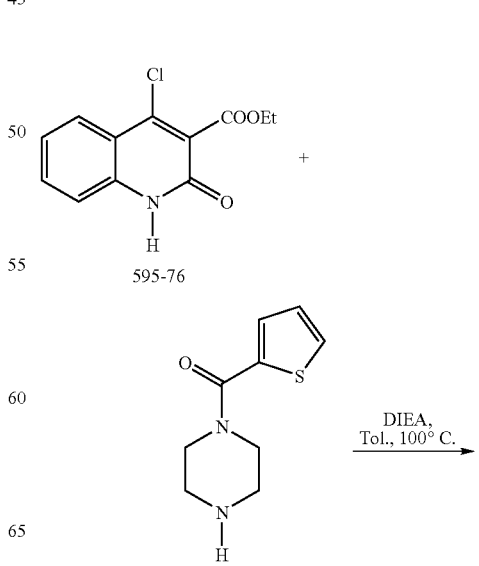

-continued

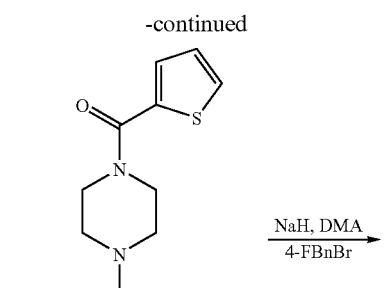

595-77

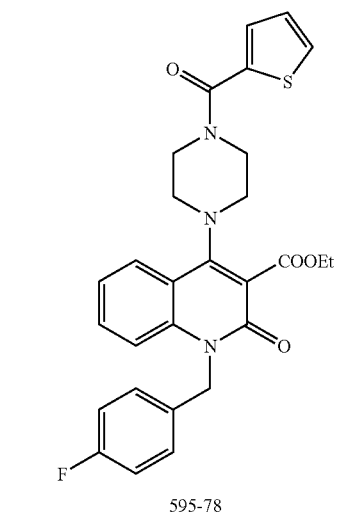

595-78

Example 20

The following describes the synthesis of a library of compounds of general structure 1(a) and 1(b) as depicted above. Compounds including an "M" in the designation incorporate a —COOEt moiety. Compounds incorporating an "N" in the designation incorporate a —NO$_2$ moiety. The two digits following "M" or "N" correspond to the numerical designation for the functional group R2 and R3 respectively, provided below. The digit preceeding "M" or "N" corresponds to the numerical designation for the functional group R1. The compounds have the following structures, except for those with designations including "+i".

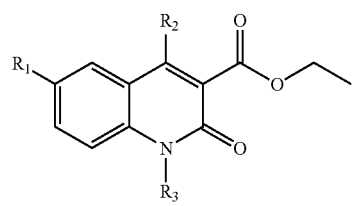

-continued

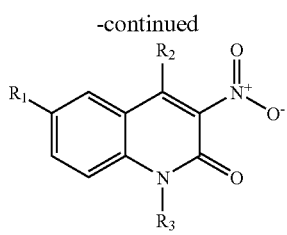

In compounds that have designations including "+i", R$_3$ is a substituent on the oxygen atom of the quinolone group rather than the nitrogen atom, i.e., a compound of structure 1(b), as depicted below. The designation "i" appears elsewhere in the preferred embodiments, and refers to a substituent on the oxygen atom of the quinolone group rather than the nitrogen atom.

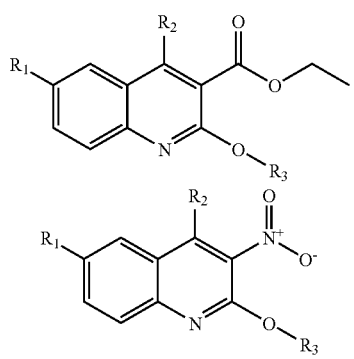

Numerical Designations for R1 Functional Groups

| Hydrogen | Methyl | Chlorine |
|----------|--------|----------|
| 1        | 2      | 3        |

Numerical Designations for R2 Functional Groups

1

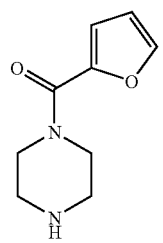

2

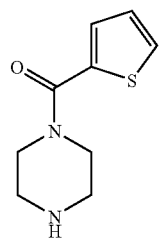

-continued

3 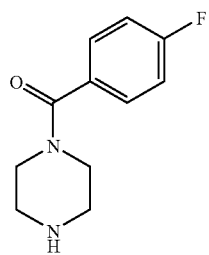

4 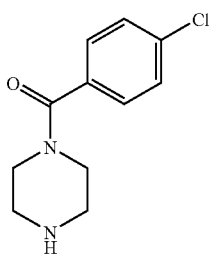

5 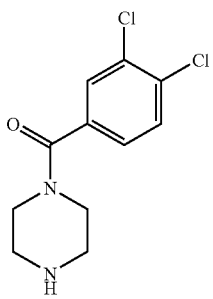

6 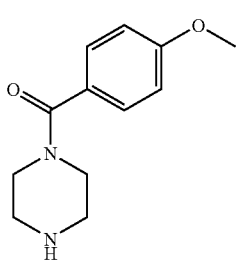

Numerical Designations for R3 Functional Groups

1 Me 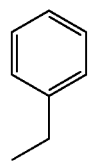

2

3 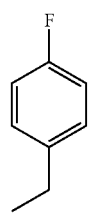

-continued

4 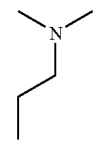

5 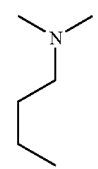

The numerical designations of the MIF inhibitors prepared are provided in Table 13.

TABLE 13

| R3 = 1 | R3 = 2 | R3 = 4 | R3 = 5 | R3 = 6 |
|---|---|---|---|---|
| Methyl | phenyl | 4-F-phenyl | N,N-dimethylpropyl | N,N-dimethylbutyl |
| 1N11 | 1N12 | 1N13 | 1N14 | 1N15 |
| 1N21 | 1N22 | 1N23 | 1N24 | 1N25 |
| 1N31 | 1N32 | 1N33 | 1N34 | 1N35 |
| 1N41 | 1N42 | 1N43 | 1N44 | 1N45 |
| 1N51 | 1N52 | 1N53 | 1N54 | 1N55 + i |
| 1N61 | 1N62 | 1N63 | 1N64 | 1N65 |
| 2N11 | 2N12 + i | 2N13 | 2N14 | 2N15 |
| 2N21 | 2N22 | 2N23 | 2N24 | 2N25 |
| 2N31 | 2N32 | 2N33 | 2N34 | 2N35 |
| 2N41 | 2N42 | 2N43 | 2N44 | 2N45 |
| 2N51 | 2N52 | 2N53 | 2N54 | 2N55 + i |
| 2N61 | 2N62 | 2N63 | 2N64 | 2N65 |
| 1M11 | 1M12 | 1M13 | 1M14 | 1M15 + i |
| 1M21 | 1M22 | 1M23 | 1M24 | 1M25 + i |
| 1M31 | 1M32 | 1M33 | 1M34 | 1M35 + i |
| 1M41 | 1M42 | 1M43 | 1M44 | 1M45 + i |
| 1M51 | 1M52 | 1M53 | 1M54 | 1M55 |
| 1M61 | 1M62 | 1M63 | 1M64 | 1M65 |
| 2M11 | 2M12 | 2M13 | 2M14 | 2M15 |
| 2M21 | 2M22 | 2M23 | 2M24 | 2M25 + i |
| 2M31 | 2M32 | 2M33 | 2M34 | 2M35 + i |
| 2M41 | 2M42 | 2M43 | 2M44 | 2M45 + i |
| 2M51 | 2M52 | 2M53 | 2M54 | 2M55 |
| 2M61 | 2M62 | 2M63 | 2M64 | 2M65 + i |
| 3M11 | 3M12 | 3M13 | 3M14 | 3M15 + i |
| 3M21 | 3M22 | 3M23 | 3M24 | 3M25 |
| 3M31 | 3M32 | 3M33 | 3M34 | 3M35 + i |
| 3M41 | 3M42 | 3M43 | 3M44 | 3M45 + i |
| 3M51 | 3M52 | 3M53 | 3M54 | 3M55 + i |
| 3M61 | 3M62 | 3M63 | 3M64 | 3M65 + i |

Details of reaction schemes for preparing intermediates or MIF inhibitors are provided below.

Reaction Scheme 21

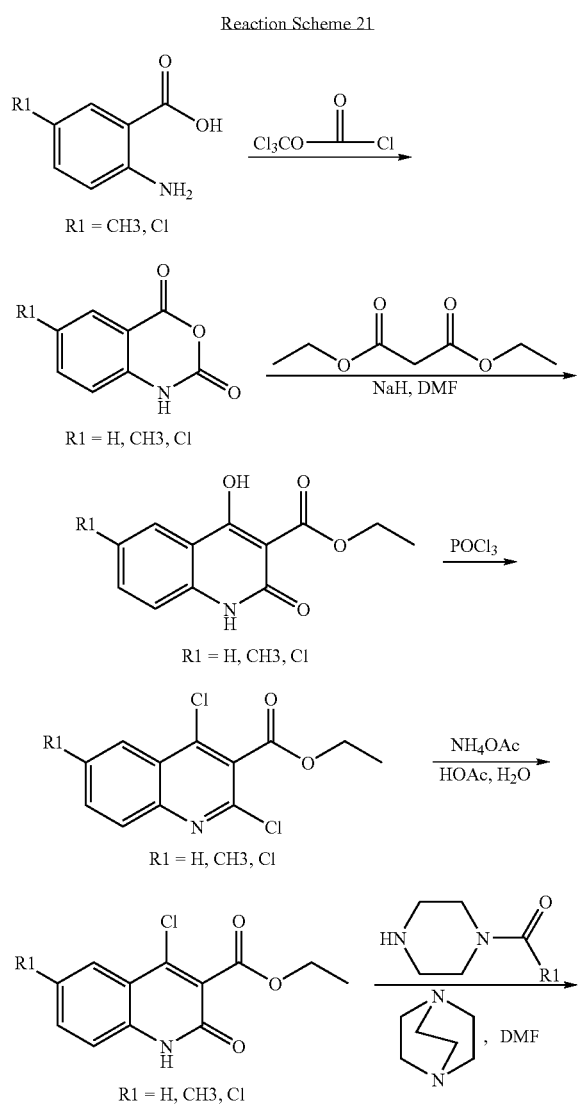

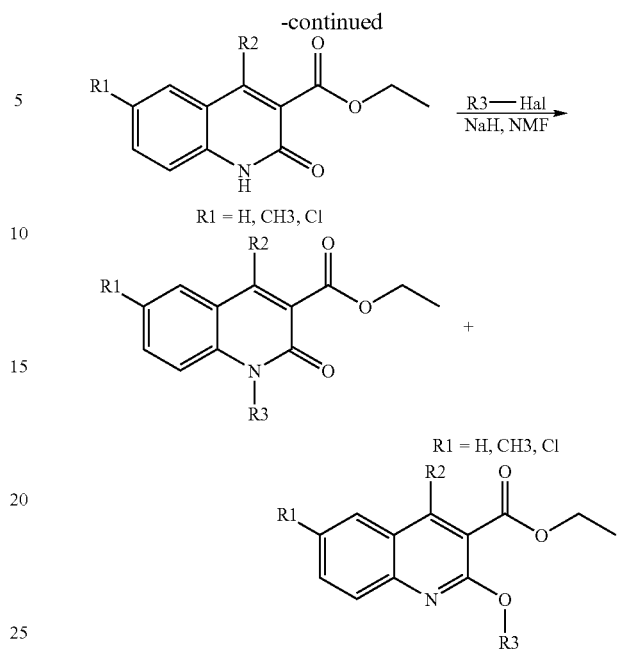

All of the following compounds were obtained using a similar or the same procedure: Compound 1M21: yield 176 mg, 56.56%; Compound 1M31: yield 64 mg, 20.60%; Compound 1M41: yield 110 mg, 35.48%; Compound 1M51: yield 139 mg, 44.18%; Compound 1M61: yield 88 mg, 28.37%; Compound 2M13 yield 144 mg, 38.09%; Compound 2M21: yield 113 mg, 36.73%; Compound 2M23: yield 137 mg, 36.16%; Compound 2M31: yield 27 mg, 8.67%; Compound 2M33: yield 141 mg, 37.45%; Compound 2M41: yield 72 mg, 23.30%; Compound 2M43: yield 117 mg, 31.54%; Compound 2M51: yield 65 mg, 21.20%; Compound 2M53 yield 91 mg, 24.87%; Compound 2M61: yield 113 mg, 36.94%; Compound 2M63: yield 127 mg, 33.99%; Compound 3M11: yield 58 mg, 19.00%; Compound 3M21: yield 134 mg, 43.32%; Compound 3M31: yield 117 mg, 37.50%; Compound 3M41: yield 141 mg, 45.83%; Compound 3M51 yield 119 mg, 38.42%; Compound 3M61: yield 142 mg, 45.85%; and Compound 3M63: yield 40 mg, 11.00%.

Reaction Scheme 22

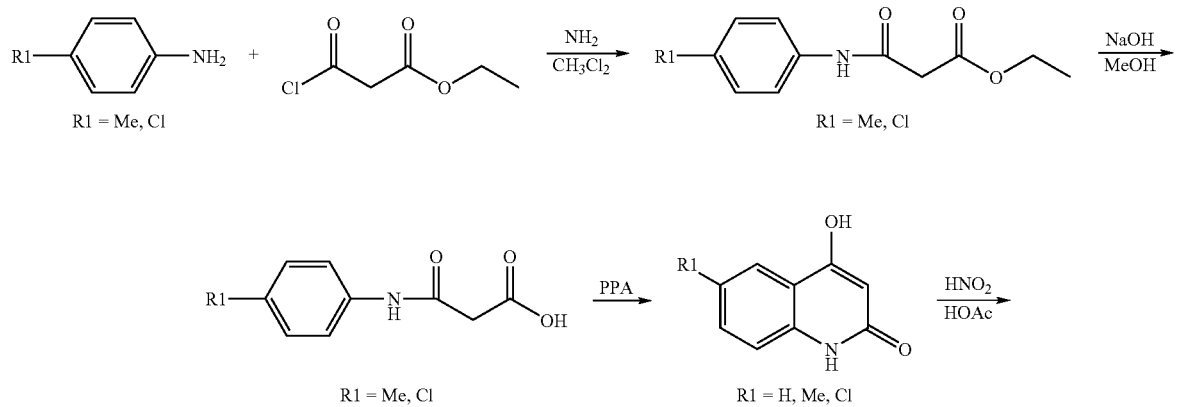

-continued
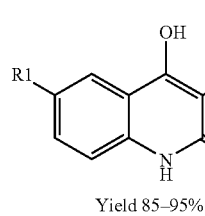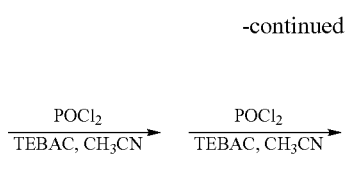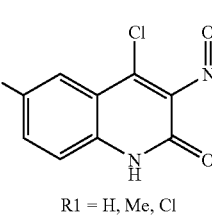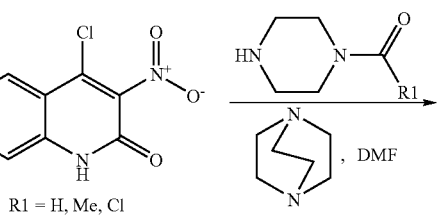
Yield 85–95%
R1 = H, Me, Cl
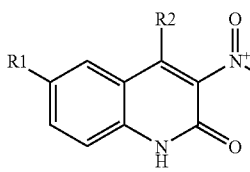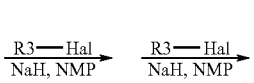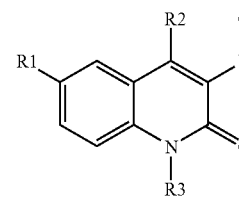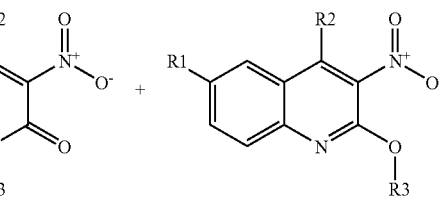
R1 = H, Me, Cl
R1 = H, CH3, Cl
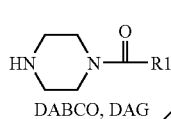
DABCO, DAG
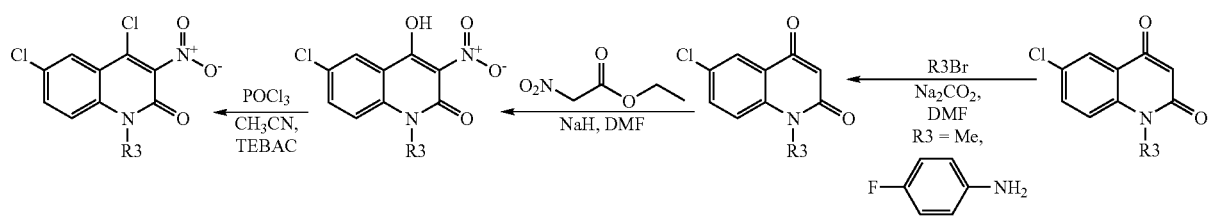
Example 21
Boc-derivatives of acids were prepared according to the following reaction scheme.
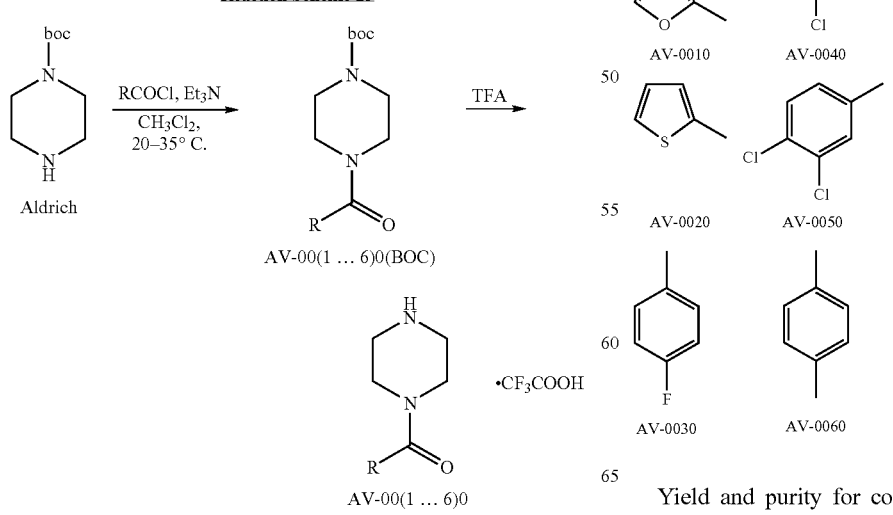
Yield and purity for compounds prepared according to Scheme 25 are provided in Table 13.

TABLE 13

| AV-0010 | Yield, g | Yield, % | Purity, % CMS |
|---|---|---|---|
| AV-0020 | 25.0 | 55 | >90 |
| AV-0030 | 42.0 | 52 | >90 |
| AV-0040 | 39.0 | 79 | >90 |
| AV-0050 | 49.0 | 86 | >90 |
| AV-0060 | 36.0 | 82 | >90 |
| AV-0070 | 43.0 | 88 | >90 |

Example 22

A series of MIF inhibitors was prepared according to the following reaction schemes. The reactants are abbreviated as follows: DCM=Dichloromethane; DMA=Dimethylacetamide; DMF=N-Dimethylformamide; HOAc=Acetic acid; MeCN=Acetonitrile; DABCO=Triethylenediamine; TEBAC=Benzyltriethylammonium chloride; NMP=1-Methyl-2-pyrrolidinone; BOC=tert-BuOCO; PPA=Polyphosphoric acid; TFA=Trifluoroacetic acid.

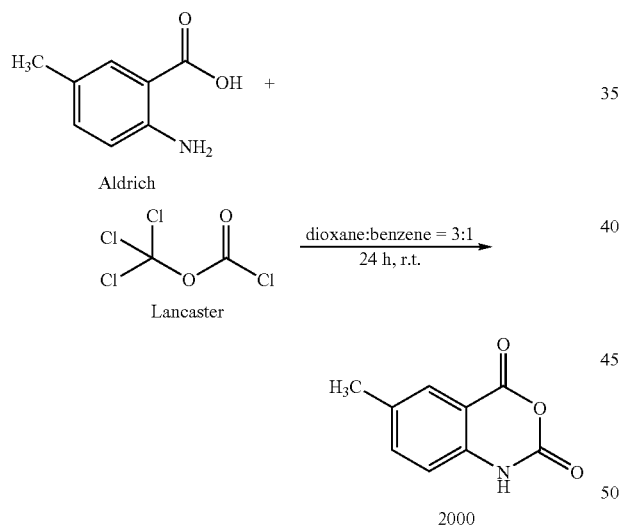

To a intensively stirred solution of 2-amino-5-methylbenzoic acid (67.7 g, 0.45 mole) in a mixture of 250 ml of dioxane and 150 ml of toluene, a solution of diphosgene (97.6 g, 0.49 mole) in 80 ml of dioxane was added dropwise. The reaction mixture was stirred for 12 hours and after that the precipitate was filtered off and washed with ether. The filtrate and ether fractions were combined and the solvent was removed under reduced pressure. The residue was titrated with hexane and the resulting precipitate was filtered off, washed with hexane and dried at room temperature overnight. Compound 2000: yield 66.5 g (84%), purity 93% (LCMS).

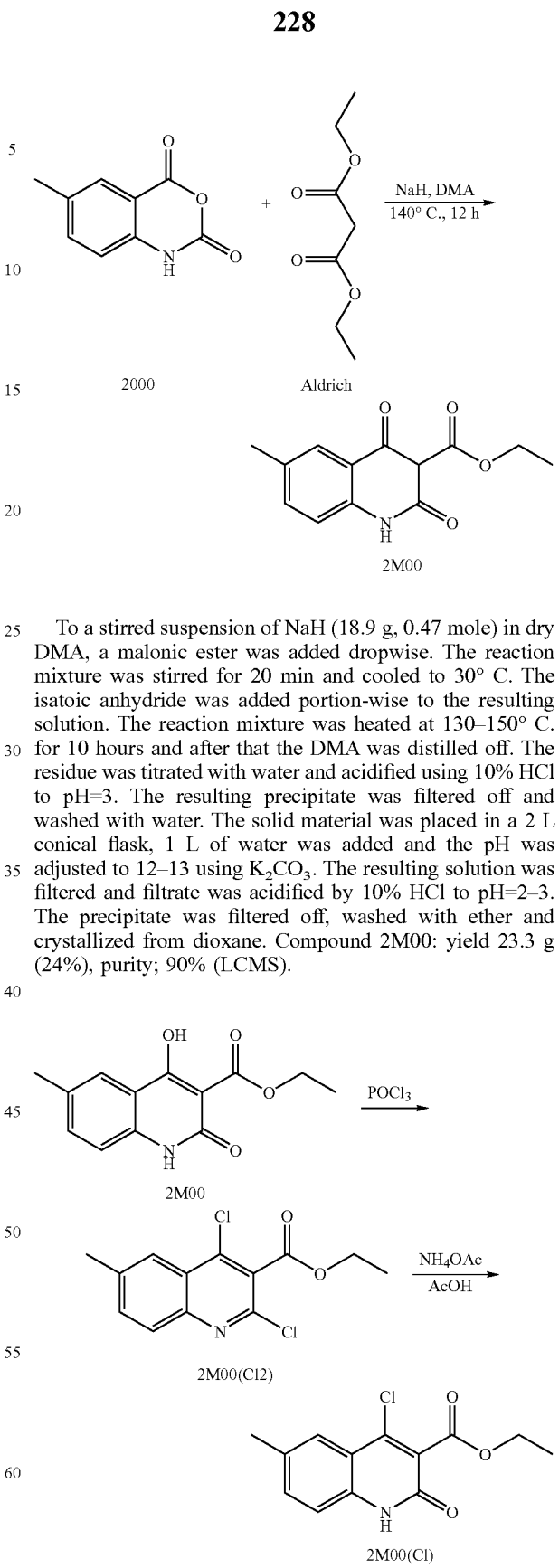

To a stirred suspension of NaH (18.9 g, 0.47 mole) in dry DMA, a malonic ester was added dropwise. The reaction mixture was stirred for 20 min and cooled to 30° C. The isatoic anhydride was added portion-wise to the resulting solution. The reaction mixture was heated at 130–150° C. for 10 hours and after that the DMA was distilled off. The residue was titrated with water and acidified using 10% HCl to pH=3. The resulting precipitate was filtered off and washed with water. The solid material was placed in a 2 L conical flask, 1 L of water was added and the pH was adjusted to 12–13 using $K_2CO_3$. The resulting solution was filtered and filtrate was acidified by 10% HCl to pH=2–3. The precipitate was filtered off, washed with ether and crystallized from dioxane. Compound 2M00: yield 23.3 g (24%), purity; 90% (LCMS).

To the suspension of 2M00 (23.0 g, 0.093 mole) in toluene (40 ml) was added 71.3 g of $POCl_3$ (43 ml, 0.465 mole). The resulting solution was heated under reflux for 1.5 hours. The solvent was distilled under reduced pressure and the residual oil was successively extracted with heptane (control by TLC). Combined heptane fractions were evaporated and the residue was heated with 200 ml of water and filtered off. After drying at room temperature for 18 hours, the dichloro compound obtained was transferred to a 250 ml round bottom flask and 90 ml of acetic acid and 8.0 g of ammonium acetate was added to it. The reaction mixture was heated under reflux for approx. 2 h (control by LCMS and TLC). When no starting material could be detected in the reaction mixture, the hot solution was poured in water and the resulting precipitate was filtered off. Yield and purity for compounds prepared according to the above scheme are provided in Table 14.

TABLE 14

| Compound | Yield, g | Yield, % | Purity, % LCMS |
|---|---|---|---|
| AV-1M00(Cl) | 50.00 | 70 | >90 |
| AV-2M00(Cl) | 10.96 | 44 | >90 |
| AV-3M00(Cl) | 30.00 | 70 | >90 | temperature under reduced pressure. The product was used in the next reaction without any further purification The yields of the obtained compounds are provided in Table 15.

TABLE 15

| Compound | Method | Yield, g | Yield, % | Purity, % CMS |
|---|---|---|---|---|
| 1M10 | A | 1.38 | 88 | >90 |
| 1M20 | A | 1.47 | 90 | >90 |
| 1M30 | A | 1.49 | 89 | >90 |
| 1M40 | A | 1.67 | 95 | >90 |
| 1M50 | A | 1.78 | 94 | >90 |
| 1M60 | A | 1.58 | 91 | >90 |
| 2M10 | A | 1.16 | 75 | >90 |
| 2M20 | A | 1.22 | 76 | >90 |
| 2M30 | A | 1.24 | 76 | >90 |
| 2M40 | A | 1.34 | 78 | >90 |
| 2M50 | B | 1.83 | 99 | >90 |
| 2M60 | A | 1.31 | 78 | >90 |
| 3M10 | A | 1.05 | 70 | >90 |
| 3M20 | A | 1.21 | 78 | >90 |
| 3M30 | A | 1.26 | 79 | >90 |
| 3M40 | A | 1.41 | 85 | >90 |
| 3M50 | A | 1.64 | 92 | >90 |
| 3M60 | A | 1.28 | 78 | >90 |

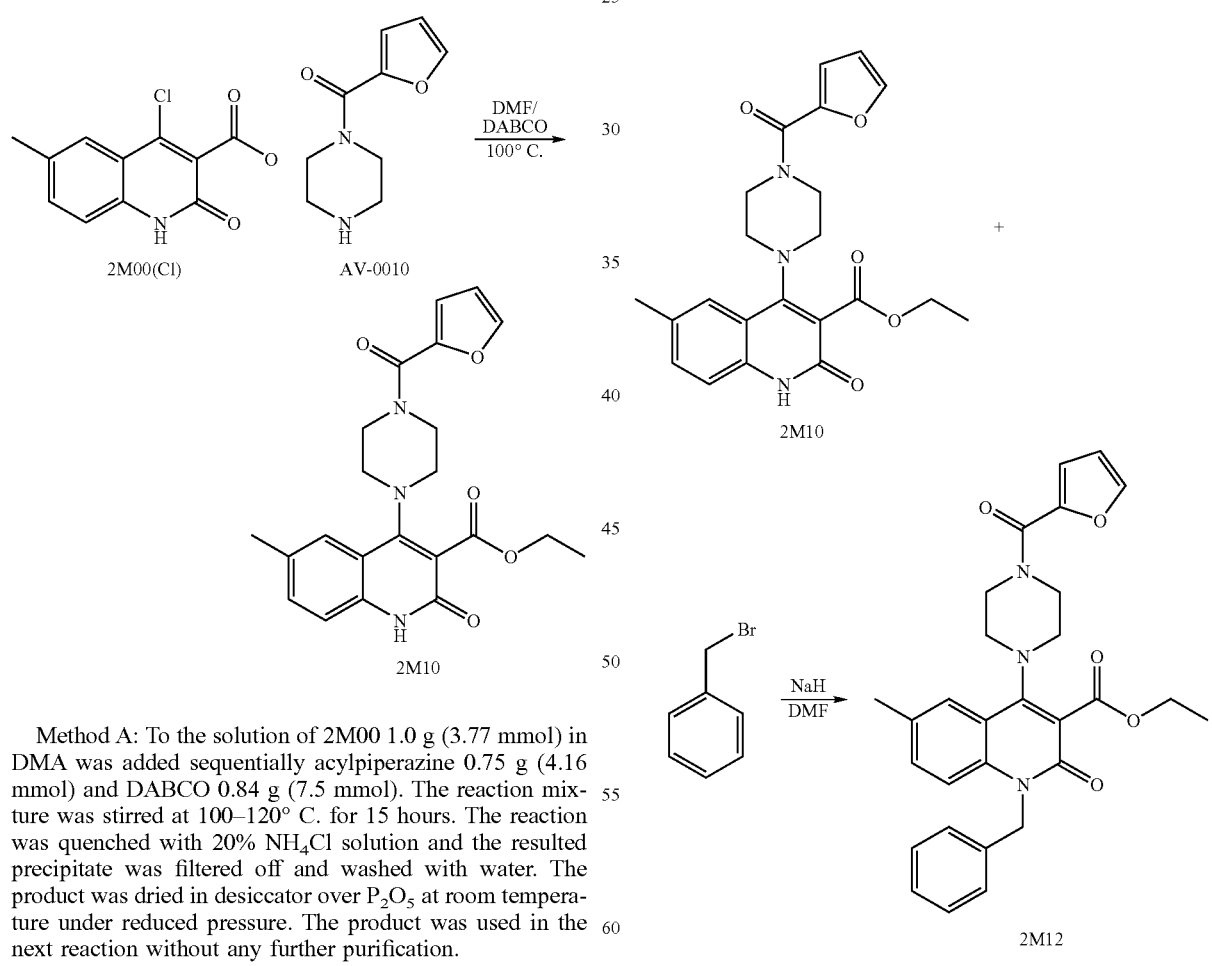

Method A: To the solution of 2M00 1.0 g (3.77 mmol) in DMA was added sequentially acylpiperazine 0.75 g (4.16 mmol) and DABCO 0.84 g (7.5 mmol). The reaction mixture was stirred at 100–120° C. for 15 hours. The reaction was quenched with 20% NH₄Cl solution and the resulted precipitate was filtered off and washed with water. The product was dried in desiccator over P₂O₅ at room temperature under reduced pressure. The product was used in the next reaction without any further purification.

Method B: A mixture of chloroquinolone 2M00 1.0 g (3.77 mmol), acylpiperazine trifluoroacetate, AV-0050 1.55 g (4.14 mmol) and DABCO 0.84 g (7.53 mmol) in DMF 3 ml was stirred at 101° C. overnight the mixture was poured in 50 ml of brine, the solid obtained was filtered of, washed with water, and dried in desiccator over P₂O₅ at room To the suspension of NaH 0.03 g (0.8 mmol) in dry DMF (1 ml) was added compound 2M10 0.30 g (0.7 mmol). After evolution of the gas ceased, the benzylbromide 0.19 g (1.1 mmol) was added. The reaction mixture was stirred until no traces of starting material could be detected (control by LCMS). The 20% solution of NH₄Cl (2 ml) was added to the reaction and resulted mixture was extracted with DCM. Compound 2M12 was isolated and purified by preparative HPLC (C-18 silica column, 150 mm×41 mm, 40 ml/min, gradient:water-acetonitrile=from 60:40 to 5:95, 20 min). Compound 2M12: yield 114 mg (31%), purity>99% (HPLC):

Method A: To the suspension of NaH 0.03 g (0.8 mmol) in dry DMF (2 ml) was added compound 1M60 300 mg (0.7 mmol). After evolution of the gas ceased (~30 min) the solution of dimethylamonoethyl chloride (2.1 mmol) in ether was added. The reaction mixture was heated at 100° C. (ether wad removed by distillation) for 12 h. The solution was cooled to room temperature and pH of the mixture was adjusted to pH 9 by 1% solution of AcOH in water. The mixture was extracted with DCM (3×3 ml) and combined DCM fractions were washed with brine and dried over MgSO₄. DCM was removed on a rotary evaporator and the product was purified by prep TLC (AnalTech silica gel GF, 1000 gm, eluent: CHCl₃:EtOH=4:1). Compound 1M64: yield 84 mg (24%), purity>99% (HPLC).

Method B: To a suspension of NaH 0.114 g (2.84 mmol; of 60% dispersion in mineral oil) in 3 ml NMP, the quinolone 2M50 0.33 g (0.676 mmol) was added portion-wise. After the evolution of the gas ceased (~30 min) the mixture was stirred for 30 min at room temperature and dimethylaminoethylchloride hydrochloride 0.195 g (1.35 mmol) was added. The resulting mixture was heated at 100° C. overnight. The reaction mixture was cooled and poured in water (25 ml) and the solid obtained was filtered off, washed with water and dried at 85° C. overnight. The target isomer was isolated by prep. TLC (AnalTech silica gel GF, 1500 gm, eluent: 10% of triethylamine in EtOAc, lower spot). Compound 2M54: yield 68 mg (18%).

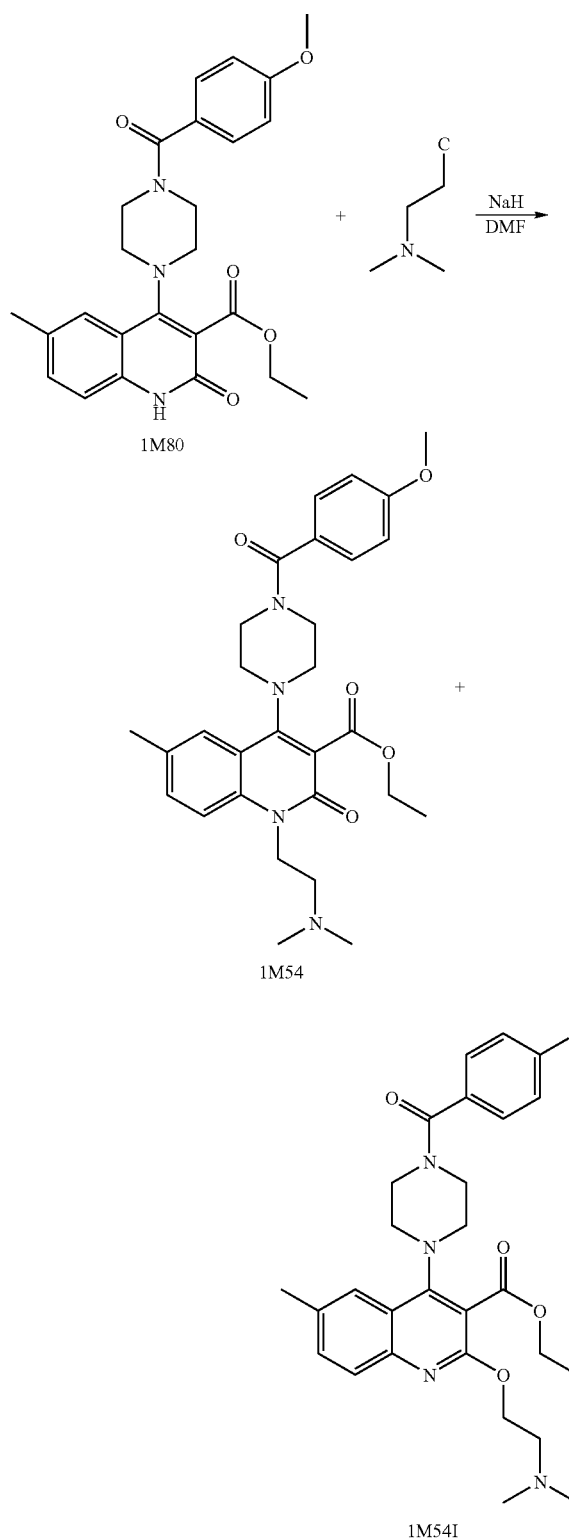

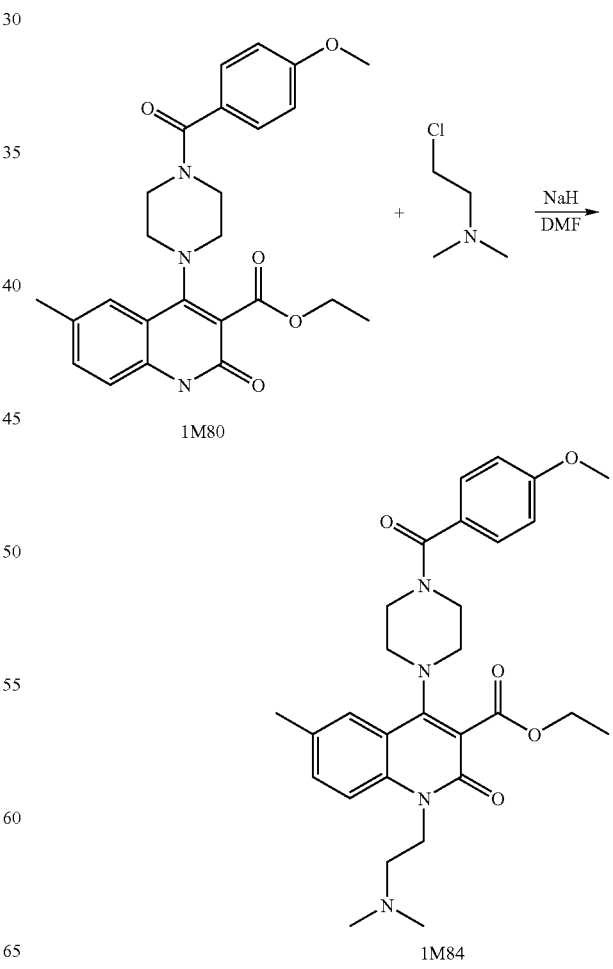

To the suspension of NaH (0.03 g, 0.8 mmol) in dry DMF (2 ml) was added compound 1 M60 (300 mg, 0.7 mmol). After evolution of the gas ceased (~30 min) the solution of dimethylaminoethyl chloride (2.1 mmol) in ether was added. The reaction mixture was heated at 100° C. (ether was removed by distillation) for 12 h. The solution was cooled to room temperature and the pH of the mixture was adjusted to pH=9 by a 1% solution of AcOH in water. The mixture was extracted with DCM (3×3 ml) and the combined DCM fraction was washed with brine and dried over MgSO$_4$. DCM was removed on a rotary evaporator and the product was purified by prep. TLC (AnalTech silica gel GF, 1000 gm, eluent: CHCl$_3$=EtOH=4:1). Compound 1M64: yield 57 mg, purity>99% (HPLC). All of the following compounds were obtained using similar or the same procedure: Compound 1M34: yield 77 mg, 22.00%; Compound 1M54: yield 58 mg, 16.88%; Compound 1M64: yield 84 mg, 24.00%; Compound 2M14: yield 57 mg, 16.25%; Compound 2M34: yield 63 mg, 17.95%; and Compound 2M64: yield 42 mg, 12.00%.

Reaction Scheme 24

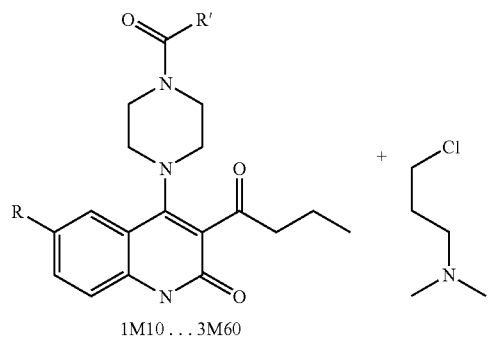

1M10 ... 3M60

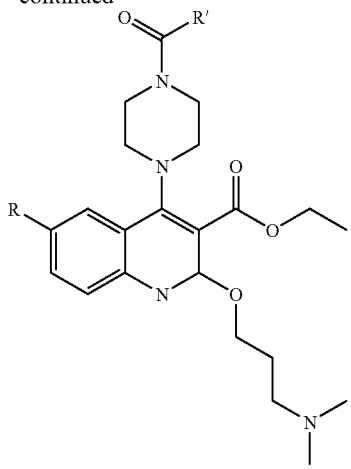

1M15i ... 3M65i (18 cmpds)

R':

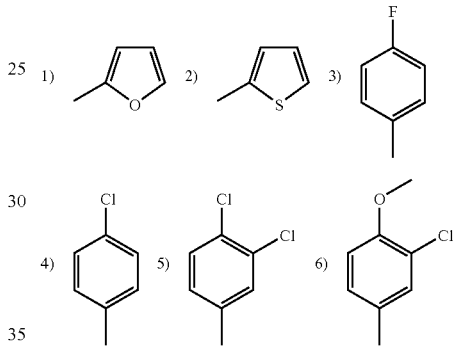

Compounds 1M15 ... 3M65: All compounds listed below were obtained using the procedure described above for compound 1M64: Compound 3M15: 36 mg; 13%; Compound 3M65: 5 mg; 1%; Compound 1M65: 31 mg; 9%; Compound 1M45: 34 mg; 10%; Compound 1M55: 51 mg; 15%; Compound 1M35: 51 mg; 14%; Compound 3M45: 52 mg; 15%; Compound 3M25: 24 mg; 7%; Compound 3M35: 71 mg; 20%; Compound 3M35i; 16 mg; 4%; Compound 3M15i; 22 mg; 8%; Compound 1M65i: 20 mg; 6%; Compound 1M45i: 27 mg; 8%; Compound 1M35i: 28 mg; 8%; Compound 3M65i: 23 mg; 6%.

Reaction Scheme 25

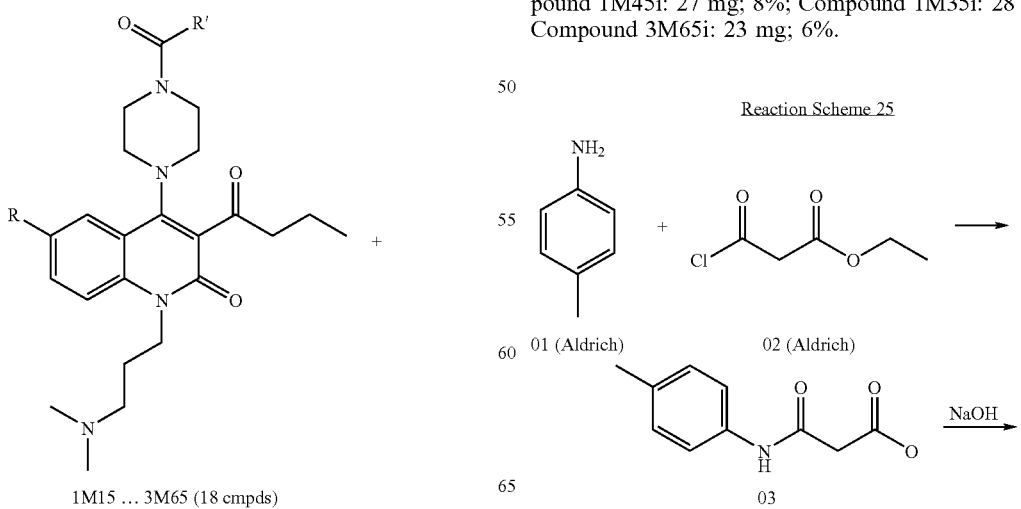

1M15 ... 3M65 (18 cmpds)

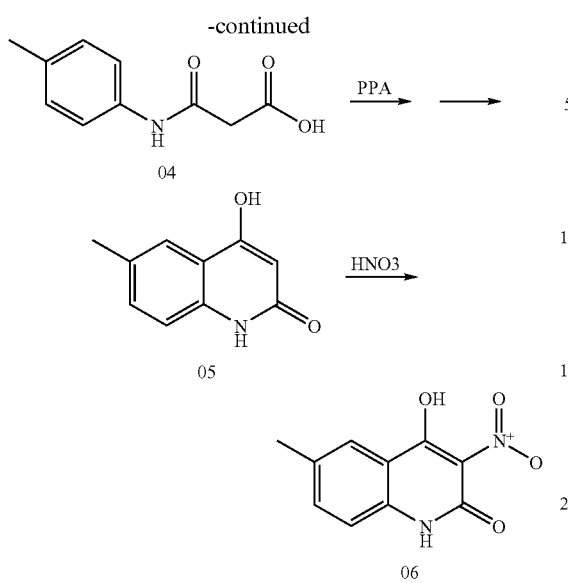

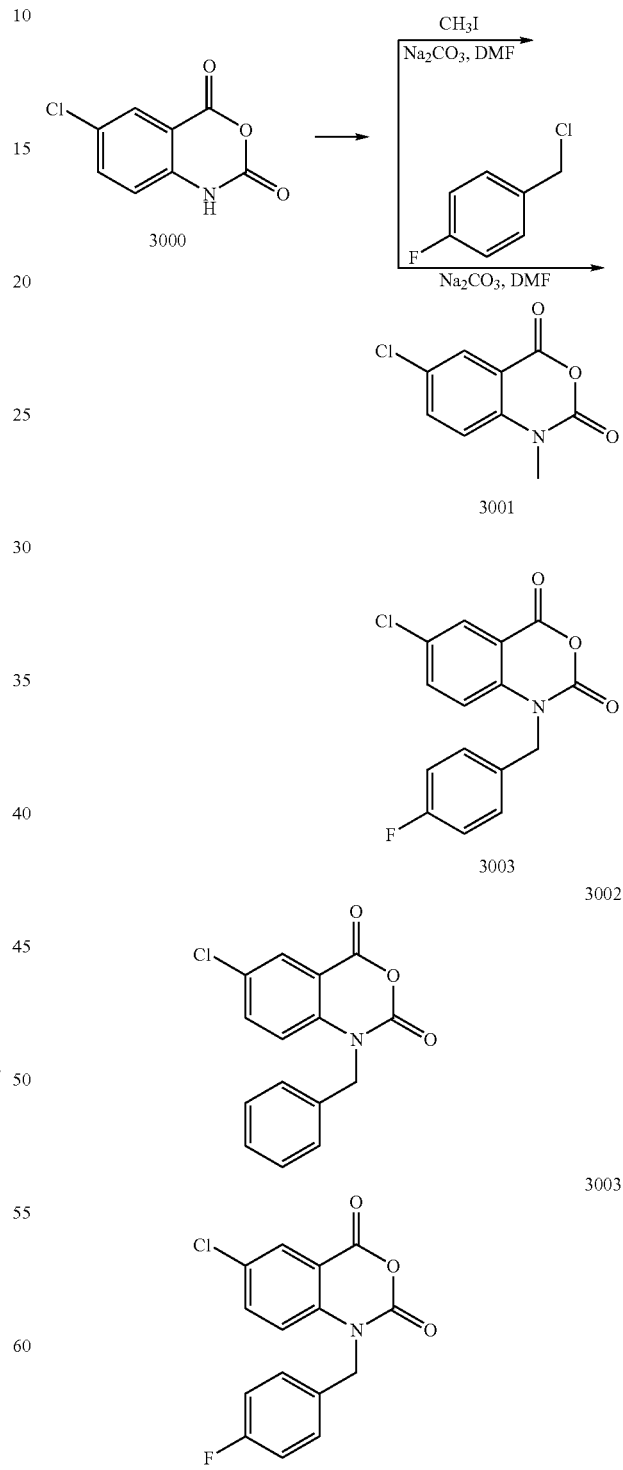

To the solution of p-toluidine 10 g (93.3 mmol) and Et₃N (13.6 ml) in DCM (100 ml) was added drop-wise monoethylmalonate chloride (17.72 ml) at 0–5° C. (ice-water bath). After the completion of the reaction (control by TLC) the reaction mixture was poured into water (300 ml) and pH was adjusted to 2 by HCl (c.). The organic layer was separated and the water phase was extracted by DCM (3×50 ml). Combined DCM extracts were washed with brine (50 ml) and dried over sodium sulfate. DCM was removed on rotary evaporator and a residue was dissolved in mixture of 600 ml of MeOH and 400 ml of 1 N NaOH. The reaction mixture was heated under reflux for 3 hours, cooled to room temperature and acidified by 2N HCl to pH 2. MeOH was removed under reduced pressure and water was extracted by EtOAc (3×100 ml). Organic phase was washed with brine, dried over sodium sulfate and solvent was removed under reduced pressure. To the residue was added 40 g of PPA and the mixture stirred on magnetic stirrer and heated at 170° C. for 3 hours. The reaction mixture was cooled to room temperature and was slowly diluted with 500 ml of 1 N HCl. The pH of the resulting solution was adjusted by a solution of 20% NaOH in water to pH 4. Formed precipitate was filtered off, washed with water and dried in a desiccator over NaOH overnight. The yield of 05 was 13.2 g (81%).

To the solution of 5-methyl-2,4-dihydroxyquinoline 13.2 g in glacial acetic acid (200 ml) was slowly added 25 ml of HNO₃ (63%). The reaction mixture was heated at 90° C. for 30 min, cooled to the room temperature and poured into water (700 ml). The formed precipitate was filtered off and washed with water. The obtained compound was dried over NaOH in desiccator overnight. The yield of 06 was 7.68 g (44%).

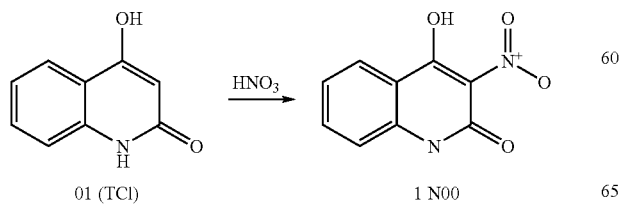

To the stirred suspension of dihydroxyquinolinone 01 (50 g) in glacial acetic acid (600 ml) was added 98 ml of HNO₃ (63%). The reaction mixture was heated at 90° C. for 30 min and cooled to room temperature. The formed precipitate was filtered off and washed with water (5×100 ml). The obtained compound was dried over P₂O₅ in a desiccator overnight. The yield of 1NOO was 52.7 g (82%).

Reaction Scheme 26

To a solution of 5-chloroisatoic anhydride 3000 15 g (75.91 mmol) in DMF (75 ml) was added potassium carbonate anhydrous (8.85 g) and methyl iodide 14.46 g (114 mmol). The reaction mixture was stirred at room temperature for 18 h. and poured into ice water. The precipitate was filtered off, washed with water and dried over P₂O₅ in a desiccator overnight. Compound 3001: yield 15.3 g (95%), purity>90% (LCMS). Compound 3003: yield 18.2 g (79%), purity>90% (LCMS). All of the following compounds were obtained using similar or the same procedure: Compound 3002: 16.1 g, 74% yield, purity>90% (LCMS); Compound 3003: 18.2 g, 78.5% yield, purity>90% (LCMS)

To the stirred solution of ethyl nitroacetate 7.5 ml (68 mmol) in 50 ml of DMF was added portion-wise to 2.85 g of NaH. After evolution of hydrogen ceased, the mixture was heated at 80° C. for 15 min. The solution of N-methyl isatoic anhydride 3001 15 g (71 mmol) in 60 ml of DMF was added over a period of 15 min. after which the reaction was heated at 120° C. for 18 h. The solvent was removed by distillation, the residue was dissolved in water and acidified with 6 N HCl to pH=4. The precipitate was collected, washed with water and dried in a desiccator over NaOH overnight. Compound 3N01: yield 16.6 g (92%), purity>90% (LCMS). Compound 3N03: yield 18.5 g (89%), purity>90% (LCMS). Compound 3N03: yield 18.5 g (89%) purity>90% (LCMS).

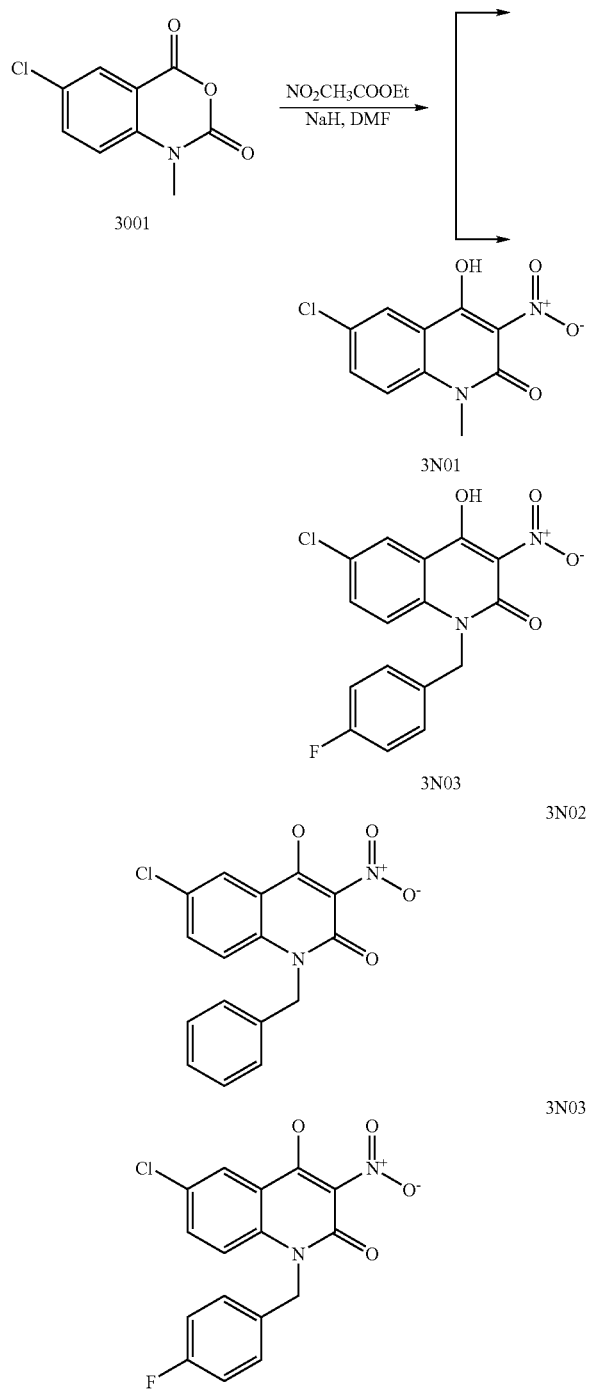

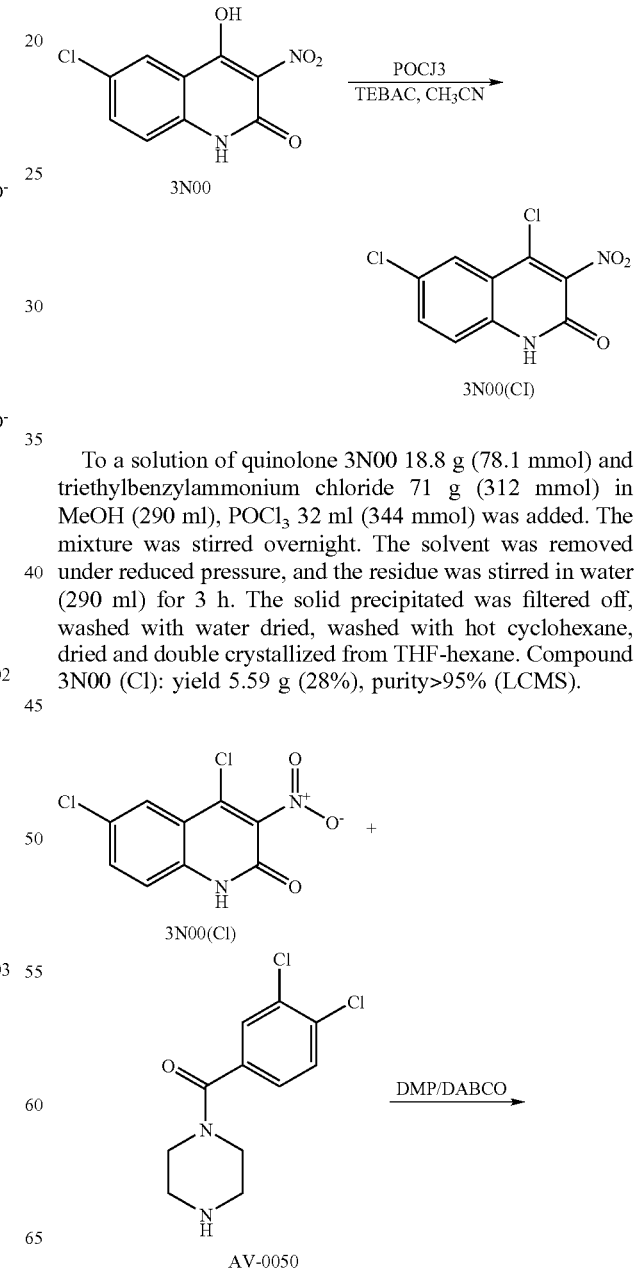

To a solution of quinolone 3N00 18.8 g (78.1 mmol) and triethylbenzylammonium chloride 71 g (312 mmol) in MeOH (290 ml), POCl₃ 32 ml (344 mmol) was added. The mixture was stirred overnight. The solvent was removed under reduced pressure, and the residue was stirred in water (290 ml) for 3 h. The solid precipitated was filtered off, washed with water dried, washed with hot cyclohexane, dried and double crystallized from THF-hexane. Compound 3N00 (Cl): yield 5.59 g (28%), purity>95% (LCMS).

-continued

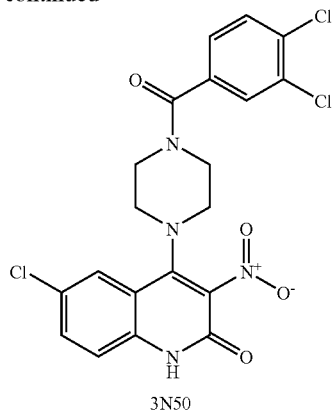

3N50

A mixture of chloroquinolone 3N00(Cl) 0.30 g (1.16 mmol), acylpiperazine trifluoroacetate AV-0050 0.45 g (1.22 mmol) and DABCO 0.26 g (2.32 mmol) in DMF 2 ml was stirred overnight. Then the mixture was poured in water (15 ml), the solid obtained was filtered off, washed with water and dried over $P_2O_5$ in desiccator overnight. The product was used in the next reaction without any further purification. Compound 3N50: yield 0.50 g (90%), purity>95% (LCMS).

The preferred embodiments have been described in connection with specific embodiments thereof. It will be understood that it is capable of further modification, and this application is intended to cover any variations, uses, or adaptations of the invention following, in general, the principles of the invention and including such departures from the present disclosure as come within known or customary practices in the art to which the invention pertains and as may be applied to the essential features hereinbefore set forth, and as fall within the scope of the invention and any equivalents thereof. All references cited herein, including but not limited to technical literature references, granted patents, and patent applications are incorporated herein by reference in their entireties.

What is claimed is:

1. A method for treating diabetes, the method comprising administering to a patient in need thereof a compound having a structure selected from the group consisting of:

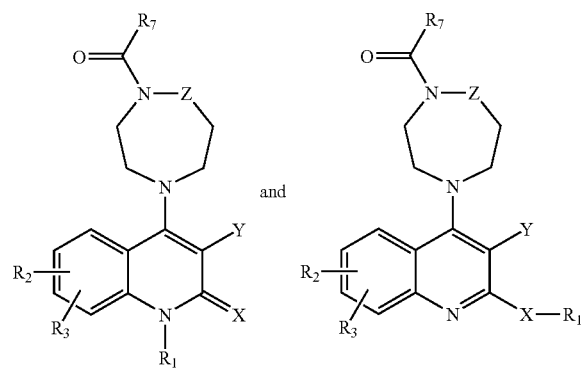

or a stereoisomer or a pharmaceutically acceptable salt thereof, wherein:

X is oxygen or sulfur;
Y is selected from the group consisting of $-NO_2$ and $-C(=O)OR_5$;
Z is $-CH_2-$ or $-C(=O)-$;
$R_1$ is selected from the group consisting of $C_{1-10}$ alkyl and aryl $C_{1-10}$ alkyl, wherein $R_1$ is unsubstituted or substituted with at least one substituent selected from the group consisting of halogen, alkoxy, alkylamino, dialkylamino, and keto;
$R_2$ and $R_3$ are independently selected from the group consisting of halogen, hydrogen, and $C_{1-6}$ alkyl;
$R_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofuranyl, thiazolidinyl, pyrazinyl, pyrrolidinyl, and piperidinyl, wherein $R_7$ is unsubstituted or substituted with at least one substituent selected from the group consisting of halogen, alkoxy, nitro, and alkylamino; and
$R_5$ is $C_{1-6}$ alkyl.

2. The method of claim 1, wherein Y is $-C(=O)OCH_2CH_3$.
3. The method of claim 1, wherein Y is $-NO_2$.
4. The method of claim 1, wherein X is oxygen.
5. The method of claim 1, wherein Z is $-CH_2-$.
6. The method of claim 1, wherein $R_7$ is

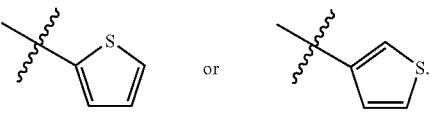

7. The method of claim 1, wherein $R_7$ is

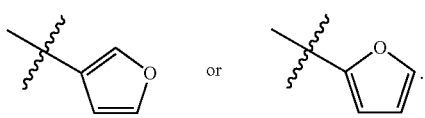

8. The method of claim 1, wherein $R_7$ is

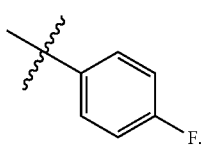

9. The method of claim 1, wherein $R_2$ and $R_3$ are independently selected from the group consisting of chlorine, hydrogen, and methyl.

10. The method of claim 1, wherein $R_1$ is selected from the group consisting

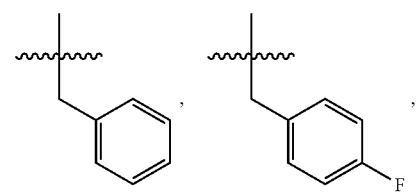

-continued

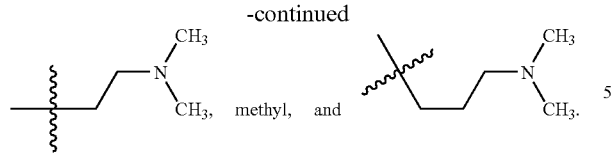

11. A method for treating endotoxic shock by inhibiting macrophage migration inhibitory factor activity, the method comprising administering to a patient in need thereof a compound having a structure selected from the group consisting of:

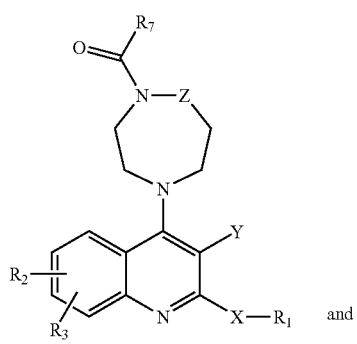

and

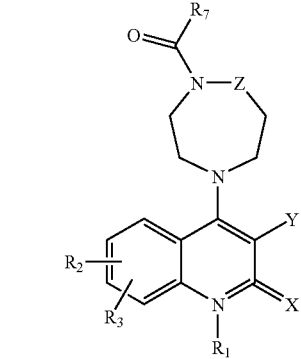

or a stereoisomer or a pharmaceutically acceptable salt thereof, wherein:

X is oxygen or sulfur;

Y is selected from the group consisting of —$NO_2$ and —C(=O)O$R_5$;

Z is —$CH_2$— or —C(=O)—;

$R_1$ is selected from the group consisting of $C_{1-10}$ alkyl and aryl $C_{1-10}$ alkyl, wherein $R_1$ is unsubstituted or substituted with at least one substituent selected from the group consisting of halogen, alkoxy, alkylamino, dialkylamino, and keto;

$R_2$ and $R_3$ are independently selected from the group consisting of halogen, hydrogen, and $C_{1-6}$ alkyl;

$R_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofuranyl, thiazolidinyl, pyrazinyl, pyrrolidinyl, and piperidinyl, wherein $R_7$ is unsubstituted or substituted with at least one substituent selected from the group consisting of halogen, alkoxy, nitro, and alkylamino; and $R_5$ is $C_{1-6}$ alkyl.

12. The method of claim 11, wherein Y is —C(=O)OCH$_2$CH$_3$.

13. The method of claim 11, wherein Y is —$NO_2$.

14. The method of claim 11, wherein X is oxygen.

15. The method of claim 11, wherein Z is —$CH_2$—.

16. The method of claim 11, wherein $R_7$ is

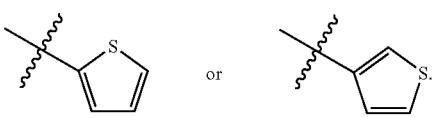

17. The method of claim 11, wherein $R_7$ is

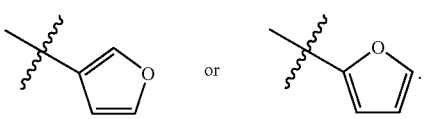

18. The method of claim 11, wherein $R_7$ is

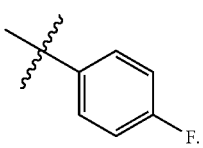

19. The method of claim 11, wherein $R_2$ and $R_3$ are independently selected from the group consisting of chlorine, hydrogen, and methyl.

20. The method of claim 11, wherein $R_1$ is selected from the group consisting

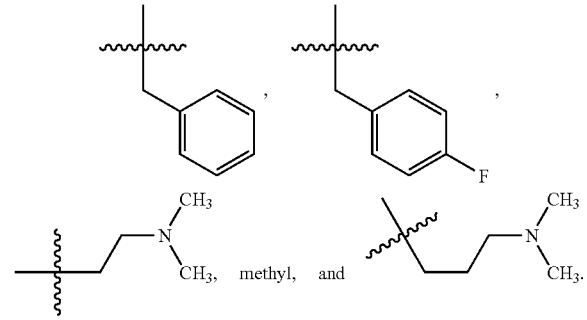

21. A method for treating arthritis, the method comprising administering to a patient in need thereof a compound having a structure selected from the group consisting of:

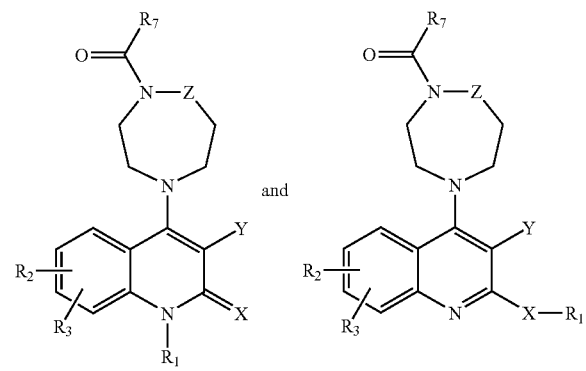

or a stereoisomer or a pharmaceutically acceptable salt thereof, wherein:

X is oxygen or sulfur;

Y is selected from the group consisting of —NO$_2$ and —C(=O)OR$_5$;

Z is —CH$_2$— or —C(=O)—;

R$_1$ is selected from the group consisting of C$_{1-10}$ alkyl and aryl C$_{1-10}$ alkyl, wherein R$_1$ is unsubstituted or substituted with at least one substituent selected from the group consisting of halogen, alkoxy, alkylamino, dialkylamino, and keto;

R$_2$ and R$_3$ are independently selected from the group consisting of halogen, hydrogen, and C$_{1-6}$ alkyl;

R$_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofuranyl, thiazolidinyl, pyrazinyl, pyrrolidinyl, and piperidinyl, wherein R$_7$ is unsubstituted or substituted with at least one substituent selected from the group consisting of halogen, alkoxy, nitro, and alkylamino; and R$_5$ is C$_{1-6}$ alkyl.

22. The method of claim 21, wherein the arthritis is rheumatoid arthritis.

23. The method of claim 21, wherein the arthritis is osteoarthritis.

24. The method of claim 21, wherein Y is —C(=O)OCH$_2$CH$_3$.

25. The method of claim 21, wherein Y is —NO$_2$.

26. The method of claim 21, wherein X is oxygen.

27. The method of claim 21, wherein Z is —CH$_2$—.

28. The method of claim 21, wherein R$_7$ is

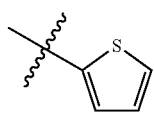 or 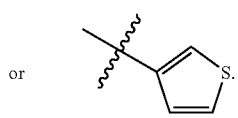

29. The method of claim 21, wherein R$_7$ is

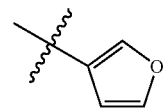 or 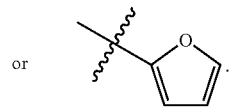

30. The method of claim 21, wherein R$_7$ is

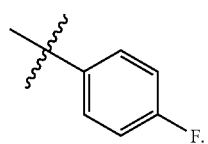

31. The method of claim 21, wherein R$_2$ and R$_3$ are independently selected from the group consisting of chlorine, hydrogen, and methyl.

32. The method of claim 21, wherein R$_1$ is selected from the group consisting of

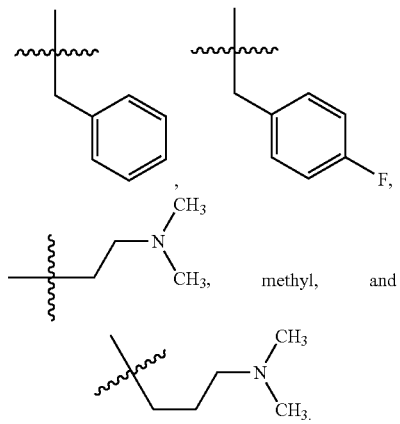

methyl, and

33. A method for treating glomerulonephritis, the method comprising administering to a patient in need thereof a compound having a structure selected from the group consisting of:

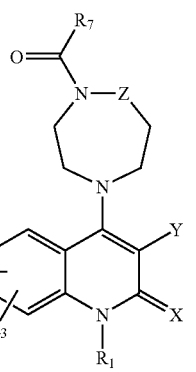 and 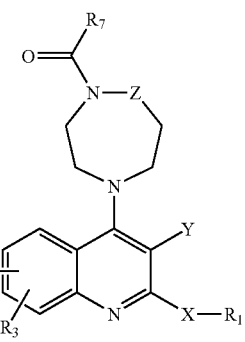

or a stereoisomer or a pharmaceutically acceptable salt thereof, wherein:

X is oxygen or sulfur;

Y is selected from the group consisting of —NO$_2$ and —C(=O)OR$_5$;

Z is —CH$_2$— or —C(=O)—;

R$_1$ is selected from the group consisting of C$_{1-10}$ alkyl and aryl C$_{1-10}$ alkyl, wherein R$_1$ is unsubstituted or substituted with at least one substituent selected from the group consisting of halogen, alkoxy, alkylamino, dialkylamino, and keto;

R$_2$ and R$_3$ are independently selected from the group consisting of halogen, hydrogen, and C$_{1-6}$ alkyl;

R$_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofuranyl, thiazolidinyl, pyrazinyl, pyrrolidinyl, and piperidinyl, wherein R$_7$ is unsubstituted or substituted with at least one substituent selected from the group consisting of halogen, alkoxy, nitro, and alkylamino; and R$_5$ is C$_{1-6}$ alkyl.

34. The method of claim 33, wherein Y is —C(=O)OCH$_2$CH$_3$.

35. The method of claim 33, wherein Y is —NO$_2$.

36. The method of claim 33, wherein X is oxygen.

37. The method of claim 33, wherein Z is —CH$_2$—.

38. The method of claim 33, wherein R$_7$ is

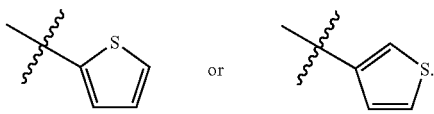

39. The method of claim 33, wherein R$_7$ is

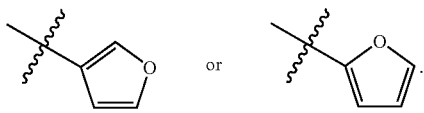

40. The method of claim 33, wherein R$_7$ is

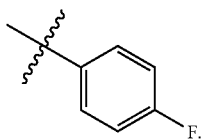

41. The method of claim 33, wherein R$_2$ and R$_3$ are independently selected from the group consisting of chlorine, hydrogen, and methyl.

42. The method of claim 33, wherein R$_1$ is selected from the group consisting of

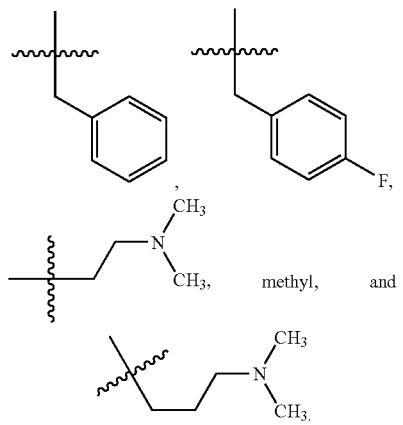

, methyl, and

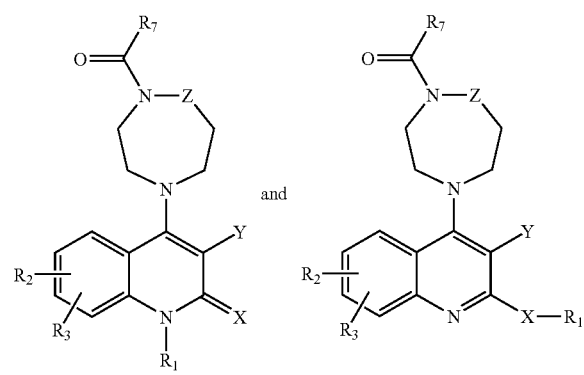

43. A method for treating psoriasis, the method comprising administering to a patient in need thereof a compound having a structure selected from the group consisting of:

and or a stereoisomer or a pharmaceutically acceptable salt thereof, wherein:

X is oxygen or sulfur;

Y is selected from the group consisting of —NO$_2$ and —C(=O)OR$_5$;

Z is —CH$_2$— or —C(=O)—;

R$_1$ is selected from the group consisting of C$_{1-10}$ alkyl and aryl C$_{1-10}$ alkyl, wherein R$_1$ is unsubstituted or substituted with at least one substituent selected from the group consisting of halogen, alkoxy, alkylamino, dialkylamino, and keto;

R$_2$ and R3 are independently selected from the group consisting of halogen, hydrogen, and C$_{1-6}$ alkyl;

R$_7$ is selected from the group consisting of cyclopentyl, phenyl, pyrazolyl, thiadiazolyl, isoxazolyl, imidazolyl, pyrrolyl, indolyl, isoquinolinyl, pyridinyl, tetrahydrothiophenyl, thienyl, furyl, tetrahydrofuranyl, thiazolidinyl, pyrazinyl, pyrrolidinyl, and piperidinyl, wherein R$_7$ is unsubstituted or substituted with at least one substituent selected from the group consisting of halogen, alkoxy, nitro, and alkylamino; and R$_5$ is C$_{1-6}$ alkyl.

44. The method of claim 43, wherein Y is —C(=O)OCH$_2$CH$_3$.

45. The method of claim 43, wherein Y is —NO$_2$.

46. The method of claim 43, wherein X is oxygen.

47. The method of claim 43, wherein Z is —CH$_2$—.

48. The method of claim 43, wherein R$_7$ is

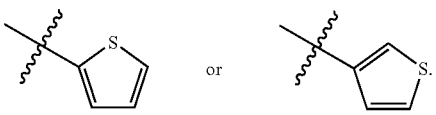

49. The method of claim 43, wherein R$_7$ is

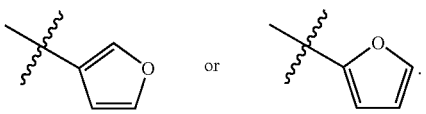

50. The method of claim 43, wherein R$_7$ is

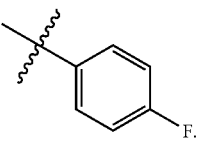

51. The method of claim 43, wherein R$_2$ and R$_3$ are independently selected from the group consisting of chlorine, hydrogen, and methyl.

52. The method of claim 43, wherein R$_1$ is selected from the group consisting of

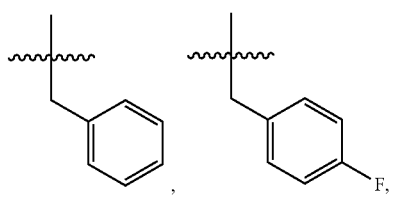

-continued
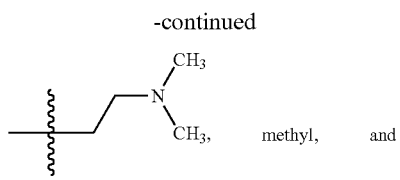 methyl, and
-continued
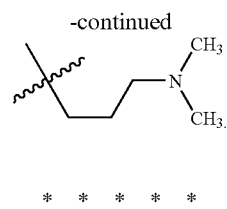
* * * * *